US007700316B2

(12) United States Patent
Schuh et al.

(10) Patent No.: US 7,700,316 B2
(45) Date of Patent: Apr. 20, 2010

(54) CD109 NUCLEIC ACID MOLECULES, POLYPEPTIDES AND METHODS OF USE

(76) Inventors: Andre Schuh, 359 Blythwood Road, Toronto, Ontario (CA) M4N 1A7; D. Robert Sutherland, 1327 Greeniaus Road, Oakville, Ontario (CA) L6J 6Y3

( * ) Notice: Subject to any disclaimer, the term of this patent is extended or adjusted under 35 U.S.C. 154(b) by 803 days.

(21) Appl. No.: 10/471,345

(22) PCT Filed: Mar. 7, 2002

(86) PCT No.: PCT/CA02/00292

§ 371 (c)(1),
(2), (4) Date: Aug. 9, 2004

(87) PCT Pub. No.: WO02/070696

PCT Pub. Date: Sep. 12, 2002

(65) Prior Publication Data

US 2004/0266990 A1  Dec. 30, 2004

Related U.S. Application Data

(60) Provisional application No. 60/273,814, filed on Mar. 7, 2001.

(51) Int. Cl.
*C12P 21/06* (2006.01)
*C12N 15/63* (2006.01)
*G01N 33/53* (2006.01)
*C07H 21/04* (2006.01)

(52) U.S. Cl. ...................... 435/69.1; 435/455; 435/810; 536/23.5

(58) Field of Classification Search ........................ None
See application file for complete search history.

(56) References Cited

FOREIGN PATENT DOCUMENTS

| WO | WO 91 03557 |   | 3/1991 |
|----|-------------|---|--------|
| WO | WO 91/03557 | * | 3/1991 |
| WO | WO 0029448  | * | 5/2000 |
| WO | WO 02 070696 |  | 9/2002 |
| WO | WO 02 085942 |  | 10/2002 |

OTHER PUBLICATIONS

Mountain TIBTECH (18:119-128 2000).*
Branch TIBS 1998; 23:45-50.*
J.O. Bordin et al. "Maternal immunization to Gov system alloantigens on human platelets." Transfusion, vol. 37, No. 8, Aug. 1997, pp. 823-828.
R.W.A.M. Kuijpers et al. "NH2-Terminal Globular Domain of Human Platelet Glycoprotein Ibalpha Has a Methionine 145/Threonine145 Amino Acid Polymorphism, Which Is Associated with the HPA-2 (Ko) Alloantigens." J. Clin. Invest., vol. 89, Feb. 1992, pp. 381-384.

T. Nakatani et al. "Functional Expression of Human Monoclonal Antibody Genes Directed Against Pseudomonal Exotoxin A in Mouse Myeloma Cells." Bio/Technology, vol. 7, Aug. 1989, pp. 805-810.
P.J. Newman et al. "Enzymatic Amplification of Platelet-specific Messenger RNA Using the Polymerase Chain Reaction." J. Clin. Invest., vol. 82, Aug. 1998, pp. 739-743.
P.J. Newman et al. "The Human Platelet Alloantigens, PlA1 and PlA2, Are Associated with a Leucine33/Proline33 Amino Acid Polymorphism in Membrane Glycoprotein IIIa, and Are Distinguishable by DNA Typing." J. Clin. Invest., vol. 83, May 1989, pp. 1778-1781.
W. Ouwehand & C. Navarrete. "The molecular basis of blood cell alloantigens." Molecular Haematology, Provan and Gribben (Eds), Blackwell Science (2000), Chapter 14, pp. 182-197.
R. Wang et al. "An Amino Acid Polymorphism within the RGD Binding Domain of Platelet Membrane Glycoprotein IIIa Is Responsible for the Formation of the Pena/Penb Alloantigen System." J. Clin. Invest., vol. 90, Nov. 1992, pp. 2038-2043.
E.S. Ward et al. "Binding activities of a repertoire of single immunoglobulin variable domains secreted from *Escherichia coli*." Nature, vol. 341, Oct. 12, 1989, pp. 544-546.
J.W. Smith et al. "Investigation of human platelet alloantigens and glycoproteins using non-radioactive immunoprecipitation." Journal of Immunological Methods, vol. 158, No. 1, 1993, pp. 77-85.
J.W. Smith et al. "Characterization and localization of the Gova/b alloantigens to the Glycosylphosphatidylinositol-Anchored Protein CDW109 on Human Platelets." Blood, vol. 86, No. 7, Oct. 1995, pp. 2807-2814.
J.E. Berry et al. "Detection of Gov system antibodies by MAIPA reveals an immunogenicity similar to the HPA-5 alloantigens." Brtish Journal of Haematology, vol. 110, No. 3, Sep. 2000, pp. 735-742.
J.G. Kelton et al. "Gova/b Alloantigen System on Human Platelets." Blood, vol. 75, No. 11, Jun. 1990, pp. 2172-2176.
S. Lyman et al. "Polymorphism of Human Platelet Membrane Glycoprotein IIb Associated With the Baka/Bakb Alloantigen System." Blood, vol. 75, No. 12, Jun. 1990, pp. 2343-2348.
J.G. Kelton et al. "ABH antigens on human platelets: Expression on the glycosyl phosphatidylinositol-anchored protein CD109." Journal of Laboratory and Clinical Medicine, vol. 132, No. 2, Aug. 1998, pp. 142-148.
Solomon KR, Mallory MA, Finberg RW. Determination of the nonionic detergent insolubility and phosphoprotein associations of glycosylphosphatidylinositol-anchored proteins expressed on T cells. Biochem J. 1998;334:325-333.
Totty NF, Waterfield MD, Hsuan JJ. Accelerated high-sensitivity microsequencing of proteins and peptides using a miniature reaction cartridge. Protein Sci. 1992;1:1215-1224.

(Continued)

*Primary Examiner*—Michail A Belyavskyi
(74) *Attorney, Agent, or Firm*—Ballard Spahr LLP

(57) ABSTRACT

The invention is a CD109 nucleic acid molecule and its corresponding polypeptide. The invention also includes biologically functional equivalent nucleic acid molecules and polypeptides. The invention also relates to methods of using these nucleic acid sequences and polypeptides in medical diagnosis and treatment and in drug screening.

16 Claims, 21 Drawing Sheets

OTHER PUBLICATIONS

H.M. DeLisser. "Epitope Mapping." Methods in Molecular Biology, vol. 96: Adhesion Protein Protocols, 1999, pp. 11-20.

C. Meier and J.W. Engels. "Peptide Nucleic Acids (PNAs)—Unusual Properties of Nonionic Oligonucleotide Analogues." Angew. Chem. Int. Ed. Engl. 1992, vol. 31, No. 8, pp. 1008-1010.

U. Englisch and D.H. Gauss. "Chemically Modified Oligonucleotides as Probes and Inhibitors." Angew. Chem. Int. Ed. Engl., vol. 30, No. 6, Jun. 1991, pp. 613-629.

F. Felici et al. "Peptide and protein display on the surface of filamentous bacteriophage." Biotechnology Annual Review, vol. 1, 1995, pp. 149-183.

W. Gish and D.J. States. "Identification of protein coding regions by database similarity search." Nature Genetics, vol. 3, Mar. 1993, pp. 266-272.

E.S. Kawasaki. "Amplification of RNA." PCR Protocols: A guide to Methods and Applications, Academic Press Inc., 1990, pp. 21-27.

M. Lin et al. "Cell surface antigen CD109 is a novel member of the $\alpha_2$ macroglobulin/C3, C4, C5 family of thioester-containing proteins." Blood, Mar. 2002, vol. 99, No. 5, pp. 1683-1691.

T.L. Madden et al. "Network BLAST Server Applications." Methods in Enzymology, vol. 266 (1996) pp. 131-141.

B.A. Morgan and J.A. Gainor. "Approaches to the Discovery of Non-Peptide Ligands for Peptide Receptors and Peptidases." Annual Reports in Medicinal Chemistry, Section VI-Topics in Chemistry and Drug Design, Chapter 26, 1989, pp. 243-252.

P.E. Nielsen et al. "Peptide nucleic acids (PNAs): Potential anti-sense and anti-gene agents." Anti-Cancer Drug Design (1993), vol. 8, pp. 53-63.

U. Reineke et al. "Antigen Sequence- and Library-Based Mapping of Linear and Discontinuous Protein-Protein-Interaction Sites by Spot Synthesis." Current Topics in Microbiology and Immunology, 243 (1999), pp. 23-36.

A.C. Schuh et. al. "A tyrosine703serine polymorphism of CD109 defines the Gov platelet alloantigens." Blood, Mar. 2002, vol. 99, No. 5, pp. 1692-1697.

A.C. Schuh et al. "Cell Surface Antigen CD109 Is a Novel Member of the a2 Macroglobulin/C3, C4, C5 Family of Thioester Containing Proteins." Blood 98 (11):50b (2001).

R. Steen and T. Egeland. "CD34 Molecule Epitope Distribution on Cells of Haematopoietic Origin." Leukemia and Lymphoma, 1998, vol. 30, pp. 23-30.

N. Suciu-Foca et al. "A late-differentiation antigen associated with the helper inducer function of human T cells." Nature, vol. 318, Dec. 1985, pp. 465-467.

D.R. Sutherland and E.L. Yeo. "CDw109 Cluster report." Leukocyte Typing V (Schlossman S. et al eds.), Oxford University Press, Oxford, pp. 1767-1769, 1995.

B. Westerlund-Wikstorm. "Peptide display on bacterial flagella: Principles and applications." Int. J. Med. Microbiol., 290, pp. 223-230 (2000).

Database EMBL Online, Feb. 2, 2001. "Hydrophobic domain protein isolated from HT-1080 cells." retrieved from EBI Database accession No. AAB12127.

J.F. Yu et al. "Comparison of the expression of CD109 and CD135 on CD34+ cells in human marrow, cord blood, and peripheral blood." Blood, vol. 94, No. 10, Suppl. 1, Part 2, Nov. 1999, p. 136b.

Database EMBL 'Online!, Feb 2, 2001. "Hydrophobic domain protein cDNA HP02837 isolated from HT-1080 cells." Retrieved from EBI, Database accession No. AAA62010.

S.F. Altschul et al. "Basic Local Alignment Search Tool." J. Mol. Biol. (1990) 215, pp. 403-410.

S.F. Altschul et al. "Gapped BLAST and PSI-BLAST: a new generation of protein database search programs." Nucleic Acids Research, 1997, vol. 25, No. 17, pp. 3389-3402.

C. Brashem-Stein et al. "Characterization of an Antigen Expressed on Activated Human T Cells and Platelets." The Journal of Immunology, vol. 140, Apr. 1988, pp. 2330-2333.

D. R. Burton. "Commentary Phage Display." Immunotechnology 1, (1995), pp. 87-94.

R. Cortese et al. "Selection of biologically active peptides by phage display of random peptide libraries." Current Opinion in Biotechnology, 1996, vol. 7, pp. 616-621.

J. M. Gershoni et al. "Combinatorial libraries, epitope structure and the prediction of protein conformation." Immunology Today, Mar. 1997, vol. 18, Issue 3, pp. 108-110.

J. Goodchild. "Conjugates of Oligonucleotides and Modified Oligonucleotides: A Review of Their Synthesis and Properties." Bioconjugate Chemistry, May/Jun. 1990, vol. 1, No. 3, pp. 165-187.

A. Haregewoin et al. "Cellular Expression of a GPI-Linked T Cell Activation Protein." Cellular Immunology, 1994, vol. 156, pp. 357-370.

E. Lesnik et al. "Oligodeoxynucleotides Containing 2'-O-Modified Adenosine: Synthesis and Effects on Stability of DNA:RNA Duplexes." Biochemistry, 1993, vol. 32, No. 30, pp. 7832-7838.

L. J. Murray et al. "CD109 is expressed on a subpopulation of CD34+ cells enriched in hematopoietic stem and progenitor cells." Experimental Hematology, 1999, vol. 27, 1282-1294.

D.R. Sutherland et al. Identification of a Cell-Surface Antigen Associated With Activated T Lymphoblasts and Activated Platelets. Blood, vol. 77, No. 1, Jan. 1991, pp. 84-93.

J. Tseng-Law et al. "Identification of a peptide directed against the anti-CD34 antibody, 9C5, by phage display and its use in hematopoietic stem cell selection." Experimental Hematology, 1999, vol. 27, 936-945.

J. Van de Water et al. "Detection of Molecular Determinants and Epitope Mapping Using Maldi-TOF Mass Spectrometry." Clinical Immunology and Immunopathology, vol. 85, No. 3, Dec. 1997, pp. 229-235.

M. H. V. Van Regenmortel et al. "Measurement of antigen-antibody interactions with biosensors." Journal of Molecular Recognition, 1998, vol. 11, pp. 163-167.

J. Zhang and T. L. Madden. PowerBLAST: A New Network BLAST Application for Interactive or Automated Sequence Analysis and Annotation. Genome Research, 1997, pp. 649-656.

* cited by examiner

```
CTAAACTCGAATTAAGAGGGAAAAAAAATCAGGGAGGAGGTGGCAAGCCA
CACCCCACGGTGCCCGCGAACTTCCCCGGCAGCGGACTGTAGCCCAGGCA
GACGCCGTCGAGATGCAGGGCCCACCGCTCCTGACCGCCGCCCACCTCCT
CTGCGTGTGCACCGCCGCGCTGGCCGTGGCTCCCGGGCCTCGGTTTCTGG
TGACAGCCCCAGGGATCATCAGGCCCGGAGGAAATGTGACTATTGGGGTG
GAGCTTCTGGAACACTGCCCTTCACAGGTGACTGTGAAGGCGGAGCTGCT
CAAGACAGCATCAAACCTCACTGTCTCTGTCCTGGAAGCAGAAGGAGTCT
TTGAAAAAGGCTCTTTTAAGACACTTACTCTTCCATCACTACCTCTGAAC
AGTGCAGATGAGATTTATGAGCTACGTGTAACCGGACGTACCCAGGATGA
GATTTTATTCTCTAATAGTACCCGCTTATCATTTGAGACCAAGAGAATAT
CTGTCTTCATTCAAACAGACAAGGCCTTATACAAGCCAAAGCAAGAAGTG
AAGTTTCGCATTGTTACACTCTTCTCAGATTTTAAGCCTTACAAAACCTC
TTTAAACATTCTCATTAAGGACCCCAAATCAAATTTGATCCAACAGTGGT
TGTCACAACAAAGTGATCTTGGAGTCATTTCCAAAACTTTTCAGCTATCT
TCCCATCCAATACTTGGTGACTGGTCTATTCAAGTTCAAGTGAATGACCA
GACATATTATCAATCATTTCAGGTTTCAGAATATGTATTACCAAAATTTG
AAGTGACTTTGCAGACACCATTATATTGTTCTATGAATTCTAAGCATTTA
AATGGTACCATCACGGCAAAGTATACATATGGGAAGCCAGTGAAAGGAGA
CGTAACGCTTACATTTTTACCTTTATCCTTTTGGGGAAAGAAGAAAAATA
TTACAAAAACATTTAAGATAAATGGATCTGCAAACTTCTCTTTTAATGAT
GAAGAGATGAAAAATGTAATGGATTCTTCAAATGGACTTTCTGAATACCT
GGATCTATCTTCCCCTGGACCAGTAGAAATTTTAACCACAGTGACAGAAT
CAGTTACAGGTATTTCAAGAAATGTAAGCACTAATGTGTTCTTCAAGCAA
CATGATTACATCATTGAGTTTTTTGATTATACTACTGTCTTGAAGCCATC
TCTCAACTTCACAGCCACTGTGAAGGTAACTCGTGCTGATGGCAACCAAC
TGACTCTTGAAGAAAGAAGAAATAATGTAGTCATAACAGTGACACAGAGA
AACTATACTGAGTACTGGAGCGGATCTAACAGTGGAAATCAGAAAATGGA
AGCTGTTCAGAAAATAAATTATACTGTCCCCCAAAGTGGAACTTTTAAGA
TTGAATTCCCAATCCTGGAGGATTCCAGTGAGCTACAGTTGAAGGCCTAT
TTCCTTGGTAGTAAAAGTAGCATGGCAGTTCATAGTCTGTTTAAGTCTCC
TAGTAAGACATACATCCAACTAAAAACAAGAGATGAAAATATAAAGGTGG
GATCGCCTTTTGAGTTGGTGGTTAGTGGCAACAAACGATTGAAGGAGTTA
AGCTATATGGTAGTATCCAGGGGACAGTTGGTGGCTGTAGGAAAACAAAA
TTCAACAATGTTCTCTTTAACACCAGAAAATTCTTGGACTCCAAAAGCCT
GTGTAATTGTGTATTATATTGAAGATGATGGGGAAATTATAAGTGATGTT
CTAAAAATTCCTGTTCAGCTTGTTTTTAAAAATAAGATAAAGCTATATTG
GAGTAAAGTGAAAGCTGAACCATCTGAGAAAGTCTCTCTTAGGATCTCTG
TGACACAGCCTGACTCCATAGTTGGGATTGTAGCTGTTGACAAAAGTGTG
AATCTGATGAATGCCTCTAATGATATTACAATGGAAATGTGGTCCATGA
GTTGGAACTTTATAACACAGGATATTATTTAGGCATGTTCATGAATTCTT
TTGCAGTCTTTCAGGAATGTGGACTCTGGGTATTGACAGATGCAAACCTC
ACGAAGGATTATATTGATGGTGTTTATGACAATGCAGAATATGCTGAGAG
GTTTATGGAGGAAAATGAAGGACATATTGTAGATATTCATGACTTTTCTT
TGGGTAGCAGTCCACATGTCCGAAAGCATTTTCCAGAGACTTGGATTTGG
CTAGACACCAACATGGGTTACAGGATTTACCAAGAATTTGAAGTAACTGT
ACCTGATTCTATCACTTCTTGGGTGGCTACTGGTTTTGTGATCTCTGAGG
```

Fig 1a (ctd. next pg.)

```
ACCTGGGTCTTGGACTAACAACTACTCCAGTGGAGCTCCAAGCCTTCCAA
CCATTTTTCATTTTTTTGAATCTTCCCTACTCTGTTATCAGAGGTGAAGA
ATTTGCTTTGGAAATAACTATATTCAATTATTTGAAAGATGCCACTGAGG
TTAAGGTAATCATTGAGAAAAGTGACAAATTTGATATTCTAATGACTTCA
AATGAAATAAATGCCACAGGCCACCAGCAGACCCTTCTGGTTCCCAGTGA
GGATGGGGCAACTGTTCTTTTTCCCATCAGGCCAACACATCTGGGAGAAA
TTCCTATCACAGTCACAGCTCTTTCACCCACTGCTTCTGATGCTGTCACC
CAGATGATTTTAGTAAAGGCTGAAGGAATAGAAAAATCATATTCACAATC
CATCTTATTAGACTTGACTGACAATAGGCTACAGAGTACCCTGAAAACTT
TGAGTTTCTCATTTCCTCCTAATACAGTGACTGGCAGTGAAAGAGTTCAG
ATCACTGCAATTGGAGATGTTCTTGGTCCTTCCATCAATGGCTTAGCCTC
ATTGATTCGGATGCCTTATGGCTGTGGTGAACAGAACATGATAAATTTTG
CTCCAAATATTTACATTTTGGATTATCTGACTAAAAGAAACAACTGACA
GATAATTTGAAAGAAAAAGCTCTTTCATTTATGAGGCAAGGTTACCAGAG
AGAACTTCTCTATCAGAGGGAAGATGGCTCTTTCAGTGCTTTTGGGAATT
ATGACCCTTCTGGGAGCACTTGGTTGTCAGCTTTTGTTTTAAGATGTTTC
CTTGAAGCCGATCCTTACATAGATATTGATCAGAATGTGTTACACAGAAC
ATACACTTGGCTTAAAGGACATCAGAAATCCAACGGTGAATTTTGGGATC
CAGGAAGAGTGATTCATAGTGAGCTTCAAGGTGGCAATAAAAGTCCAGTA
ACACTTACAGCCTATATTGTAACTTCTCTCCTGGGATATAGAAAGTATCA
GCCTAACATTGATGTGCAAGAGTCTATCCATTTTTTGGAGTCTGAATTCA
GTAGAGGAATTTCAGACAATTATACTCTAGCCCTTATAACTTATGCATTG
TCATCAGTGGGGAGTCCTAAAGCGAAGGAAGCTTTGAATATGCTGACTTG
GAGAGCAGAACAAGAAGGTGGCATGCAATTCTGGGTGTCATCAGAGTCCA
AACTTTCTGACTCCTGGCAGCCACGCTCCCTGGATATTGAAGTTGCAGCC
TATGCACTGCTCTCACACTTCTTACAATTTCAGACTTCTGAGGGAATCCC
AATTATGAGGTGGCTAAGCAGGCAAAGAAATAGCTTGGGTGGTTTTGCAT
CTACTCAGGATACCACTGTGGCTTTAAAGGCTCTGTCTGAATTTGCAGCC
CTAATGAATACAGAAAGGACAAATATCCAAGTGACCGTGACGGGGCCTAG
CTCACCAAGTCCTGTAAAGTTTCTGATTGACACACACAACCGCTTACTCC
TTCAGACAGCAGAGCTTGCTGTGGTACAGCCAATGGCAGTTAATATTTCC
GCAAATGGTTTTGGATTTGCTATTTGTCAGCTCAATGTTGTATATAATGT
GAAGGCTTCTGGGTCTTCTAGAAGACGAAGATCTATCCAAAATCAAGAAG
CCTTTGATTTAGATGTTGCTGTAAAAGAAAATAAAGATGATCTCAATCAT
GTGGATTTGAATGTGTGTACAAGCTTTTCGGGCCCGGGTAGGAGTGGCAT
GGCTCTTATGGAAGTTAACCTATTAAGTGGCTTTATGGTGCCTTCAGAAG
CAATTTCTCTGAGCGAGACAGTGAAGAAAGTGGAATATGATCATGGAAAA
CTCAACCTCTATTTAGATTCTGTAAATGAAACCCAGTTTTGTGTTAATAT
TCCTGCTGTGAGAAACTTTAAAGTTTCAAATACCCAAGATGCTTCAGTGT
CCATAGTGGATTACTATGAGCCAAGGAGACAGGCGGTGAGAAGTTACAAC
TCTGAAGTGAAGCTGTCCTCCTGTGACCTTTGCAGTGATGTCCAGGGCTG
CCGTCCTTGTGAGGATGGAGCTTCAGGCTCCCATCATCACTCTTCAGTCA
TTTTTATTTTCTGTTTCAAGCTTCTGTACTTTATGGAACTTTGGCTGTGA
TTTATTTTTAAAGGACTCTGTGTAACACTAACATTTCCAGTAGTCACATG
TGATTGTTTTGTTTTCGTAGAAGAATACTGCTTCTATTTTGAAAAAGAG
TTTTTTTTCTTTCTATGGGGTTGCAGGGATGGTGTACAACAGGTCCTAGC
ATGTATAGCTGCATAGATTTCTTCACCTGATCTTTGTGTGGAAGATCAGA
```

Figure 1a (continued on next pg)

ATGAATGCAGTTGTGTGTCTATATTTTCCCCTCACAAAATCTTTTAGAAT
TTTTTTGGAGGTGTTTGTTTTCTCCAGAATAAAGGTATTACTTTAGAAAA
AAAAAAAAAAA

Figure 1a.

```
CTAAACTCGAATTAAGAGGGAAAAAAAATCAGGGAGGAGGTGGCAAGCCA
CACCCCACGGTGCCCGCGAACTTCCCCGGCAGCGGACTGTAGCCCAGGCA
GACGCCGTCGAGATGCAGGGCCCACCGCTCCTGACCGCCGCCCACCTCCT
CTGCGTGTGCACCGCCGCGCTGGCCGTGGCTCCCGGGCCTCGGTTTCTGG
TGACAGCCCCAGGGATCATCAGGCCCGGAGGAAATGTGACTATTGGGGTG
GAGCTTCTGGAACACTGCCCTTCACAGGTGACTGTGAAGGCGGAGCTGCT
CAAGACAGCATCAAACCTCACTGTCTCTGTCCTGGAAGCAGAAGGAGTCT
TTGAAAAAGGCTCTTTTAAGACACTTACTCTTCCATCACTACCTCTGAAC
AGTGCAGATGAGATTTATGAGCTACGTGTAACCGGACGTACCCAGGATGA
GATTTTATTCTCTAATAGTACCCGCTTATCATTTGAGACCAAGAGAATAT
CTGTCTTCATTCAAACAGACAAGGCCTTATACAAGCCAAAGCAAGAAGTG
AAGTTTCGCATTGTTACACTCTTCTCAGATTTTAAGCCTTACAAAACCTC
TTTAAACATTCTCATTAAGGACCCCAAATCAAATTTGATCCAACAGTGGT
TGTCACAACAAAGTGATCTTGGAGTCATTTCCAAAACTTTTCAGCTATCT
TCCCATCCAATACTTGGTGACTGGTCTATTCAAGTTCAAGTGAATGACCA
GACATATTATCAATCATTTCAGGTTTCAGAATATGTATTACCAAAATTTG
AAGTGACTTTGCAGACACCATTATATTGTTCTATGAATTCTAAGCATTTA
AATGGTACCATCACGGCAAAGTATACATATGGGAAGCCAGTGAAAGGAGA
CGTAACGCTTACATTTTTACCTTTATCCTTTTGGGGAAAGAAGAAAAATA
TTACAAAAACATTTAAGATAAATGGATCTGCAAACTTCTCTTTTAATGAT
GAAGAGATGAAAAATGTAATGGATTCTTCAAATGGACTTTCTGAATACCT
GGATCTATCTTCCCCTGGACCAGTAGAAATTTTAACCACAGTGACAGAAT
CAGTTACAGGTATTTCAAGAAATGTAAGCACTAATGTGTTCTTCAAGCAA
CATGATTACATCATTGAGTTTTTTGATTATACTACTGTCTTGAAGCCATC
TCTCAACTTCACAGCCACTGTGAAGGTAACTCGTGCTGATGGCAACCAAC
TGACTCTTGAAGAAAGAAGAAATAATGTAGTCATAACAGTGACACAGAGA
AACTATACTGAGTACTGGAGCGGATCTAACAGTGGAAATCAGAAAATGGA
AGCTGTTCAGAAAATAAATTATACTGTCCCCAAAGTGGAACTTTTAAGA
TTGAATTCCCAATCCTGGAGGATTCCAGTGAGCTACAGTTGAAGGCCTAT
TTCCTTGGTAGTAAAAGTAGCATGGCAGTTCATAGTCTGTTTAAGTCTCC
TAGTAAGACATACATCCAACTAAAAACAAGAGATGAAAATATAAAGGTGG
GATCGCCTTTTGAGTTGGTGGTTAGTGGCAACAAACGATTGAAGGAGTTA
AGCTATATGGTAGTATCCAGGGGACAGTTGGTGGCTGTAGGAAAACAAAA
TTCAACAATGTTCTCTTTAACACCAGAAAATTCTTGGACTCCAAAAGCCT
GTGTAATTGTGTATTATATTGAAGATGATGGGGAAATTATAAGTGATGTT
CTAAAAATTCCTGTTCAGCTTGTTTTTAAAAATAAGATAAAGCTATATTG
GAGTAAAGTGAAAGCTGAACCATCTGAGAAAGTCTCTCTTAGGATCTCTG
TGACACAGCCTGACTCCATAGTTGGGATTGTAGCTGTTGACAAAAGTGTG
AATCTGATGAATGCCTCTAATGATATTACAATGGAAAATGTGGTCCATGA
GTTGGAACTTTATAACACAGGATATTATTTAGGCATGTTCATGAATTCTT
TTGCAGTCTTTCAGGAATGTGGACTCTGGGTATTGACAGATGCAAACCTC
ACGAAGGATTATATTGATGGTGTTTATGACAATGCAGAATATGCTGAGAG
GTTTATGGAGGAAAATGAAGGACATATTGTAGATATTCATGACTTTTCTT
TGGGTAGCAGTCCACATGTCCGAAAGCATTTTCCAGAGACTTGGATTTGG
CTAGACACCAACATGGGTTCCAGGATTTACCAAGAATTTGAAGTAACTGT
ACCTGATTCTATCACTTCTTGGGTGGCTACTGGTTTTGTGATCTCTGAGG
ACCTGGGTCTTGGACTAACAACTACTCCAGTGGAGCTCCAAGCCTTCCAA
```

Fig 1b (continued on next pg)

```
CCATTTTTCATTTTTTTGAATCTTCCCTACTCTGTTATCAGAGGTGAAGA
ATTTGCTTTGGAAATAACTATATTCAATTATTTGAAAGATGCCACTGAGG
TTAAGGTAATCATTGAGAAAAGTGACAAATTTGATATTCTAATGACTTCA
AATGAAATAAATGCCACAGGCCACCAGCAGACCCTTCTGGTTCCCAGTGA
GGATGGGGCAACTGTTCTTTTTCCCATCAGGCCAACACATCTGGGAGAAA
TTCCTATCACAGTCACAGCTCTTTCACCCACTGCTTCTGATGCTGTCACC
CAGATGATTTTAGTAAAGGCTGAAGGAATAGAAAAATCATATTCACAATC
CATCTTATTAGACTTGACTGACAATAGGCTACAGAGTACCCTGAAAACTT
TGAGTTTCTCATTTCCTCCTAATACAGTGACTGGCAGTGAAAGAGTTCAG
ATCACTGCAATTGGAGATGTTCTTGGTCCTTCCATCAATGGCTTAGCCTC
ATTGATTCGGATGCCTTATGGCTGTGGTGAACAGAACATGATAAATTTTG
CTCCAAATATTTACATTTTGGATTATCTGACTAAAAAGAAACAACTGACA
GATAATTTGAAAGAAAAGCTCTTTCATTTATGAGGCAAGGTTACCAGAG
AGAACTTCTCTATCAGAGGGAAGATGGCTCTTTCAGTGCTTTTGGGAATT
ATGACCCTTCTGGGAGCACTTGGTTGTCAGCTTTTGTTTTAAGATGTTTC
CTTGAAGCCGATCCTTACATAGATATTGATCAGAATGTGTTACACAGAAC
ATACACTTGGCTTAAAGGACATCAGAAATCCAACGGTGAATTTTGGGATC
CAGGAAGAGTGATTCATAGTGAGCTTCAAGGTGGCAATAAAAGTCCAGTA
ACACTTACAGCCTATATTGTAACTTCTCTCCTGGGATATAGAAAGTATCA
GCCTAACATTGATGTGCAAGAGTCTATCCATTTTTGGAGTCTGAATTCA
GTAGAGGAATTTCAGACAATTATACTCTAGCCCTTATAACTTATGCATTG
TCATCAGTGGGGAGTCCTAAAGCGAAGGAAGCTTTGAATATGCTGACTTG
GAGAGCAGAACAAGAAGGTGGCATGCAATTCTGGGTGTCATCAGAGTCCA
AACTTTCTGACTCCTGGCAGCCACGCTCCCTGGATATTGAAGTTGCAGCC
TATGCACTGCTCTCACACTTCTTACAATTTCAGACTTCTGAGGGAATCCC
AATTATGAGGTGGCTAAGCAGGCAAAGAAATAGCTTGGGTGGTTTTGCAT
CTACTCAGGATACCACTGTGGCTTTAAAGGCTCTGTCTGAATTTGCAGCC
CTAATGAATACAGAAAGGACAAATATCCAAGTGACCGTGACGGGGCCTAG
CTCACCAAGTCCTGTAAAGTTTCTGATTGACACACACAACCGCTTACTCC
TTCAGACAGCAGAGCTTGCTGTGGTACAGCCAATGGCAGTTAATATTTCC
GCAAATGGTTTTGGATTTGCTATTTGTCAGCTCAATGTTGTATATAATGT
GAAGGCTTCTGGGTCTTCTAGAAGACGAAGATCTATCCAAAATCAAGAAG
CCTTTGATTTAGATGTTGCTGTAAAAGAAAATAAAGATGATCTCAATCAT
GTGGATTTGAATGTGTGTACAAGCTTTTCGGGCCCGGGTAGGAGTGGCAT
GGCTCTTATGGAAGTTAACCTATTAAGTGGCTTTATGGTGCCTTCAGAAG
CAATTTCTCTGAGCGAGACAGTGAAGAAAGTGGAATATGATCATGGAAAA
CTCAACCTCTATTTAGATTCTGTAAATGAAACCCAGTTTTGTGTTAATAT
TCCTGCTGTGAGAAACTTTAAAGTTTCAAATACCCAAGATGCTTCAGTGT
CCATAGTGGATTACTATGAGCCAAGGAGACAGGCGGTGAGAAGTTACAAC
TCTGAAGTGAAGCTGTCCTCCTGTGACCTTTGCAGTGATGTCCAGGGCTG
CCGTCCTTGTGAGGATGGAGCTTCAGGCTCCCATCATCACTCTTCAGTCA
TTTTTATTTTCTGTTTCAAGCTTCTGTACTTTATGGAACTTTGGCTGTGA
TTTATTTTTAAAGGACTCTGTGTAACACTAACATTTCCAGTAGTCACATG
TGATTGTTTTGTTTCGTAGAAGAATACTGCTTCTATTTTGAAAAAAGAG
TTTTTTTTCTTTCTATGGGGTTGCAGGGATGGTGTACAACAGGTCCTAGC
ATGTATAGCTGCATAGATTTCTTCACCTGATCTTTGTGTGGAAGATCAGA
ATGAATGCAGTTGTGTGTCTATATTTTCCCCTCACAAAATCTTTTAGAAT
```

Figure 1b (continued on next page)

TTTTTTGGAGGTGTTTGTTTTCTCCAGAATAAAGGTATTACTTTAGAAAA
AAAAAAAAAAA

Figure 1b.

```
CTAAACTCGAATTAAGAGGGAAAAAAATCAGGGAGGAGGTGGCAAGCCA
CACCCCACGGTGCCCGCGAACTTCCCCGGCAGCGGACTGTAGCCCAGGCA
GACGCCGTCGAGATGCAGGGCCCACCGCTCCTGACCGCCGCCCACCTCCT
CTGCGTGTGCACCGCCGCGCTGGCCGTGGCTCCCGGGCCTCGGTTTCTGG
TGACAGCCCCAGGGATCATCAGGCCCGGAGGAAATGTGACTATTGGGGTG
GAGCTTCTGGAACACTGCCCTTCACAGGTGACTGTGAAGGCGGAGCTGCT
CAAGACAGCATCAAACCTCACTGTCTCTGTCCTGGAAGCAGAAGGAGTCT
TTGAAAAGGCTCTTTTAAGACACTTACTCTTCCATCACTACCTCTGAAC
AGTGCAGATGAGATTTATGAGCTACGTGTAACCGGACGTACCCAGGATGA
GATTTTATTCTCTAATAGTACCCGCTTATCATTTGAGACCAAGAGAATAT
CTGTCTTCATTCAAACAGACAAGGCCTTATACAAGCCAAAGCAAGAAGTG
AAGTTTCGCATTGTTACACTCTTCTCAGATTTTAAGCCTTACAAAACCTC
TTTAAACATTCTCATTAAGGACCCCAAATCAAATTTGATCCAACAGTGGT
TGTCACAACAAAGTGATCTTGGAGTCATTTCCAAAACTTTTCAGCTATCT
TCCCATCCAATACTTGGTGACTGGTCTATTCAAGTTCAAGTGAATGACCA
GACATATTATCAATCATTTCAGGTTTCAGAATATGTATTACCAAAATTTG
AAGTGACTTTGCAGACACCATTATATTGTTCTATGAATTCTAAGCATTTA
AATGGTACCATCACGGCAAAGTATACATATGGGAAGCCAGTGAAAGGAGA
CGTAACGCTTACATTTTTACCTTTATCCTTTTGGGGAAAGAAGAAAAATA
TTACAAAAACATTTAAGATAAATGGATCTGCAAACTTCTCTTTTAATGAT
GAAGAGATGAAAAATGTAATGGATTCTTCAAATGGACTTTCTGAATACCT
GGATCTATCTTCCCCTGGACCAGTAGAAATTTTAACCACAGTGACAGAAT
CAGTTACAGGTATTTCAAGAAATGTAAGCACTAATGTGTTCTTCAAGCAA
CATGATTACATCATTGAGTTTTTTGATTATACTACTGTCTTGAAGCCATC
TCTCAACTTCACAGCCACTGTGAAGGTAACTCGTGCTGATGGCAACCAAC
TGACTCTTGAAGAAGAAGAAATAATGTAGTCATAACAGTGACACAGAGA
AACTATACTGAGTACTGGAGCGGATCTAACAGTGGAAATCAGAAAATGGA
AGCTGTTCAGAAAATAAATTATACTGTCCCCAAAGTGGAACTTTTAAGA
TTGAATTCCCAATCCTGGAGGATTCCAGTGAGCTACAGTTGAAGGCCTAT
TTCCTTGGTAGTAAAAGTAGCATGGCAGTTCATAGTCTGTTTAAGTCTCC
TAGTAAGACATACATCCAACTAAAAACAAGAGATGAAAATATAAAGGTGG
GATCGCCTTTTGAGTTGGTGGTTAGTGGCAACAAACGATTGAAGGAGTTA
AGCTATATGGTAGTATCCAGGGGACAGTTGGTGGCTGTAGGAAAACAAAA
TTCAACAATGTTCTCTTTAACACCAGAAAATTCTTGGACTCCAAAAGCCT
GTGTAATTGTGTATTATATTGAAGATGATGGGGAAATTATAAGTGATGTT
CTAAAAATTCCTGTTCAGCTTGTTTTTAAAAATAAGATAAAGCTATATTG
GAGTAAAGTGAAAGCTGAACCATCTGAGAAAGTCTCTCTTAGGATCTCTG
TGACACAGCCTGACTCCATAGTTGGGATTGTAGCTGTTGACAAAAGTGTG
AATCTGATGAATGCCTCTAATGATATTACAATGGAAAATGTGGTCCATGA
GTTGGAACTTTATAACACAGGATATTATTTAGGCATGTTCATGAATTCTT
TTGCAGTCTTTCAGGAATGTGGACTCTGGGTATTGACAGATGCAAACCTC
ACGAAGGATTATATTGATGGTGTTTATGACAATGCAGAATATGCTGAGAG
GTTTATGGAGGAAAATGAAGGACATATTGTAGATATTCATGACTTTTCTT
TGGGTAGCAGTCCACATGTCCGAAAGCATTTTCCAGAGACTTGGATTTGG
CTAGACACCAACATGGGTTACAGGATTTACCAAGAATTTGAAGTAACTGT
ACCTGATTCTATCACTTCTTGGGTGGCTACTGGTTTTGTGATCTCTGAGG
```

Figure 2a (continued on next page)

```
ACCTGGGTCTTGGACTAACAACTACTCCAGTGGAGCTCCAAGCCTTCCAA
CCATTTTTCATTTTTTTGAATCTTCCCTACTCTGTTATCAGAGGTGAAGA
ATTTGCTTTGGAAATAACTATATTCAATTATTTGAAAGATGCCACTGAGG
TTAAGGTAATCATTGAGAAAAGTGACAAATTTGATATTCTAATGACTTCA
AATGAAATAAATGCCACAGGCCACCAGCAGACCCTTCTGGTTCCCAGTGA
GGATGGGGCAACTGTTCTTTTTCCCATCAGGCCAACACATCTGGGAGAAA
TTCCTATCACAGTCACAGCTCTTTCACCCACTGCTTCTGATGCTGTCACC
CAGATGATTTTAGTAAAGGCTGAAGGAATAGAAAAATCATATTCACAATC
CATCTTATTAGACTTGACTGACAATAGGCTACAGAGTACCCTGAAAACTT
TGAGTTTCTCATTTCCTCCTAATACAGTGACTGGCAGTGAAAGAGTTCAG
ATCACTGCAATTGGAGATGTTCTTGGTCCTTCCATCAATGGCTTAGCCTC
ATTGATTCGGATGCCTTATGGCTGTGGTGAACAGAACATGATAAATTTTG
CTCCAAATATTTACATTTTGGATTATCTGACTAAAAAGAAACAACTGACA
GATAATTTGAAAGAAAAAGCTCTTTCATTTATGAGGCAAGGTTACCAGAG
AGAACTTCTCTATCAGAGGGAAGATGGCTCTTTCAGTGCTTTTGGGAATT
ATGACCCTTCTGGGAGCACTTGGTTGTCAGCTTTTGTTTTAAGATGTTTC
CTTGAAGCCGATCCTTACATAGATATTGATCAGAATGTGTTACACAGAAC
ATACACTTGGCTTAAAGGACATCAGAAATCCAACGGTGAATTTTGGGATC
CAGGAAGAGTGATTCATAGTGAGCTTCAAGGTGGCAATAAAAGTCCAGTA
ACACTTACAGCCTATATTGTAACTTCTCTCCTGGGATATAGAAAGTATCA
GCCTAACATTGATGTGCAAGAGTCTATCCATTTTTTGGAGTCTGAATTCA
GTAGAGGAATTTCAGACAATTATACTCTAGCCCTTATAACTTATGCATTG
TCATCAGTGGGGAGTCCTAAAGCGAAGGAAGCTTTGAATATGCTGACTTG
GAGAGCAGAACAAGAAGGTGGCATGCAATTCTGGGTGTCATCAGAGTCCA
AACTTTCTGACTCCTGGCAGCCACGCTCCCTGGATATTGAAGTTGCAGCC
TATGCACTGCTCTCACACTTCTTACAATTTCAGACTTCTGAGGGAATCCC
AATTATGAGGTGGCTAAGCAGGCAAAGAAATAGCTTGGGTGGTTTTGCAT
CTACTCAGGATACCACTGTGGCTTTAAAGGCTCTGTCTGAATTTGCAGCC
CTAATGAATACAGAAAGGACAAATATCCAAGTGACCGTGACGGGGCCTAG
CTCACCAAGTCCTGTAAAGTTTCTGATTGACACACACAACCGCTTACTCC
TTCAGACAGCAGAGCTTGCTGTGGTACAGCCAATGGCAGTTAATATTTCC
GCAAATGGTTTTGGATTTGCTATTTGTCAGCTCAATGTTGTATATAATGT
GAAGGCTTCTGGGTCTTCTAGAAGACGAAGATCTATCCAAAATCAAGAAG
CCTTTGATTTAGATGTTGCTGTAAAAGAAAATAAAGATGATCTCAATCAT
GTGGATTTGAATGTGTGTACAAGCTTTTCGGGCCCGGGTAGGAGTGGCAT
GGCTCTTATGGAAGTTAACCTATTAAGTGGCTTTATGGTGCCTTCAGAAG
CAATTTCTCTGAGCGAGACAGTGAAGAAAGTGGAATATGATCATGGAAAA
CTCAACCTCTATTTAGATTCTGTAAATGAAACCCAGTTTTGTGTTAATAT
TCCTGCTGTGAGAAACTTTAAAGTTTCAAATACCCAAGATGCTTCAGTGT
CCATAGTGGATTACTATGAGCCAAGGAGACAGGCGGTGAGAAGTTACAAC
TCTGAAGTGAAGCTGTCCTCCTGTGACCTTTGCAGTGATGTCCAGGGCTG
CCGTCCTTGTGAGGATGGAGCTTCAGGCTCCCATCATCACTCTTCAGTCA
TTTTTATTTTCTGTTTCAAGCTTCTGTACTTTATGGAACTTTGGCTGTGA
TTTATTTTTAAAGGACTCTGTGTAACACTAACATTTCCAGTAGTCACATG
TGATTGTTTTGTTTTCGTAGAAGAATACTGCTTCTATTTTGAAAAAAGAG
TTTTTTTTCTTTCTATGGGGTTGCAGGGATGGTGTACAACAGGTCCTAGC
ATGTATAGCTGCATAGATTTCTTCACCTGATCTTTGTGTGGAAGATCAGA
```

Figure 2a (continued on next page)

ATGAATGCAGTTGTGTGTCTATATTTTCCCCTCACAAAATCTTTTAGAAT
TTTTTTGGAGGTGTTTGTTTTCTCCAGAATAAAGGTATTACTTTAGAAAT
AGGTATTCTCCTCATTTTGTGAAAGAAATGAACCTAGATTCTTAAGCATT
ATTACACATCCATGTTTGCTTAAAGATGGATTTCCCTGGGAATGGGAGAA
AACAGCCAGCAGGAGGAGCTTCATCTGTTCCCTTCCCACCTCCAACCTAG
CCCTACTGCCCACCCCACCCCAACCCACCCCATGCCCAGTGGTCTCAGTA
GATACTTCTTAACTGGAAATTCTTTCTTTTCAGAATCTAGGTGGTGAATT
TTTTTTAAGTGGCACGGTCTTTTTCTGCTTGAAATCTGATCACACCCCCC
AGCCATTGCCCTCCCTCTCTTTTTCCTCTGTAGAGAAATGTGAGGGGCAG
TACATTTACTGTGCTTTTCACACCATCTCAGAGGTTGAGGAGCATACTGA
AAATTGCCCTGGGGGGTGCTGGGTGTGCTGTCTCCTTCCCACATCCTCAG
CCCCACACCAGCTCTATTTCAGGGGTGAGAGTCAGAGAGCACTGCAATAT
GTGCTTCATGGGATTTCGATTCGAAGATCCTAGACCAGGGAGACACTGTG
AGCCAGGGATACAACAAAATACTAGGTAAGTCACTGCAGACCGACCTCCC
TGCAGTTTGGGAAAGAAGCTGGGTTTGTGGAGAATCAGAGCATCTTGACA
TGACTGCTGACCTAAAGATCCCTGGCATTGGCCAGGGATCCTGTGGAACC
TCTTCTAGTTCAGGGGTGTGAGCATTAGACTGCCAGTTGTCTAGTGACAT
CTGATGCTTGCTGTGAACTTTTAAGATCCCCGAATCCTGAGCACCTCAAT
CTTTAATTGCCCTGTATTCCGAAGGGTAATATAATTTATCTGGATGGAAA
TTTTAAAGATGAATCCCCCTTTTTTCTTTTCTTCTCTCTTTTCTTTCCTT
CTCCCTTTCTTCTTTGCCTTCTAAATATCTGAAATGATTTAGATATGTG
TCAACAATTAATGATCTTTTATTCAATCTAAGAAATGGTTTAGTTTTTCT
CTTTAGCTCTATGGCATTTCACTCAAGTGGACAGGGGAAAAAGTAATTGC
CATGGGCTCCAAAGAATTTGCTTTATGTTTTAGCTATTTAAAAATAAAT
CCATCAAAAATAAAGTATGCAAATGTATCTTTTAAAAAAAAAAAA

Figure 2a.

```
CTAAACTCGAATTAAGAGGGAAAAAAAATCAGGGAGGAGGTGGCAAGCCA
CACCCCACGGTGCCCGCGAACTTCCCCGGCAGCGGACTGTAGCCCAGGCA
GACGCCGTCGAGATGCAGGGCCCACCGCTCCTGACCGCCGCCCACCTCCT
CTGCGTGTGCACCGCCGCGCTGGCCGTGGCTCCCGGCCTCGGTTTCTGG
TGACAGCCCCAGGGATCATCAGGCCCGGAGGAAATGTGACTATTGGGGTG
GAGCTTCTGGAACACTGCCCTTCACAGGTGACTGTGAAGGCGGAGCTGCT
CAAGACAGCATCAAACCTCACTGTCTCTGTCCTGGAAGCAGAAGGAGTCT
TTGAAAAGGCTCTTTTAAGACACTTACTCTTCCATCACTACCTCTGAAC
AGTGCAGATGAGATTTATGAGCTACGTGTAACCGGACGTACCCAGGATGA
GATTTTATTCTCTAATAGTACCCGCTTATCATTTGAGACCAAGAGAATAT
CTGTCTTCATTCAAACAGACAAGGCCTTATACAAGCCAAAGCAAGAAGTG
AAGTTTCGCATTGTTACACTCTTCTCAGATTTTAAGCCTTACAAAACCTC
TTTAAACATTCTCATTAAGGACCCCAAATCAAATTTGATCCAACAGTGGT
TGTCACAACAAAGTGATCTTGGAGTCATTTCCAAAACTTTTCAGCTATCT
TCCCATCCAATACTTGGTGACTGGTCTATTCAAGTTCAAGTGAATGACCA
GACATATTATCAATCATTTCAGGTTTCAGAATATGTATTACCAAAATTTG
AAGTGACTTTGCAGACACCATTATATTGTTCTATGAATTCTAAGCATTTA
AATGGTACCATCACGGCAAAGTATACATATGGGAAGCCAGTGAAAGGAGA
CGTAACGCTTACATTTTTACCTTTATCCTTTTGGGGAAAGAAGAAAAATA
TTACAAAAACATTTAAGATAAATGGATCTGCAAACTTCTCTTTTAATGAT
GAAGAGATGAAAAATGTAATGGATTCTTCAAATGGACTTTCTGAATACCT
GGATCTATCTTCCCCTGGACCAGTAGAAATTTTAACCACAGTGACAGAAT
CAGTTACAGGTATTTCAAGAAATGTAAGCACTAATGTGTTCTTCAAGCAA
CATGATTACATCATTGAGTTTTTTGATTATACTACTGTCTTGAAGCCATC
TCTCAACTTCACAGCCACTGTGAAGGTAACTCGTGCTGATGGCAACCAAC
TGACTCTTGAAGAAAGAAGAAATAATGTAGTCATAACAGTGACACAGAGA
AACTATACTGAGTACTGGAGCGGATCTAACAGTGGAAATCAGAAAATGGA
AGCTGTTCAGAAAATAAATTATACTGTCCCCAAAGTGGAACTTTTAAGA
TTGAATTCCCAATCCTGGAGGATTCCAGTGAGCTACAGTTGAAGGCCTAT
TTCCTTGGTAGTAAAAGTAGCATGGCAGTTCATAGTCTGTTTAAGTCTCC
TAGTAAGACATACATCCAACTAAAAACAAGAGATGAAAATATAAAGGTGG
GATCGCCTTTTGAGTTGGTGGTTAGTGGCAACAAACGATTGAAGGAGTTA
AGCTATATGGTAGTATCCAGGGGACAGTTGGTGGCTGTAGGAAAACAAAA
TTCAACAATGTTCTCTTTAACACCAGAAAATTCTTGGACTCCAAAAGCCT
GTGTAATTGTGTATTATATTGAAGATGATGGGGAAATTATAAGTGATGTT
CTAAAAATTCCTGTTCAGCTTGTTTTTAAAAATAAGATAAAGCTATATTG
GAGTAAAGTGAAAGCTGAACCATCTGAGAAAGTCTCTCTTAGGATCTCTG
TGACACAGCCTGACTCCATAGTTGGGATTGTAGCTGTTGACAAAAGTGTG
AATCTGATGAATGCCTCTAATGATATTACAATGGAAATGTGGTCCATGA
GTTGGAACTTTATAACACAGGATATTATTTAGGCATGTTCATGAATTCTT
TTGCAGTCTTTCAGGAATGTGGACTCTGGGTATTGACAGATGCAAACCTC
ACGAAGGATTATATTGATGGTGTTTATGACAATGCAGAATATGCTGAGAG
GTTTATGGAGGAAAATGAAGGACATATTGTAGATATTCATGACTTTTCTT
TGGGTAGCAGTCCACATGTCCGAAAGCATTTTCCAGAGACTTGGATTTGG
CTAGACACCAACATGGGTTCCAGGATTTACCAAGAATTTGAAGTAACTGT
ACCTGATTCTATCACTTCTTGGGTGGCTACTGGTTTTGTGATCTCTGAGG
ACCTGGGTCTTGGACTAACAACTACTCCAGTGGAGCTCCAAGCCTTCCAA
```

Figure 2b (continued on next page)

```
CCATTTTTCATTTTTTTGAATCTTCCCTACTCTGTTATCAGAGGTGAAGA
ATTTGCTTTGGAAATAACTATATTCAATTATTTGAAAGATGCCACTGAGG
TTAAGGTAATCATTGAGAAAAGTGACAAATTTGATATTCTAATGACTTCA
AATGAAATAAATGCCACAGGCCACCAGCAGACCCTTCTGGTTCCCAGTGA
GGATGGGGCAACTGTTCTTTTTCCCATCAGGCCAACACATCTGGGAGAAA
TTCCTATCACAGTCACAGCTCTTTCACCCACTGCTTCTGATGCTGTCACC
CAGATGATTTTAGTAAAGGCTGAAGGAATAGAAAAATCATATTCACAATC
CATCTTATTAGACTTGACTGACAATAGGCTACAGAGTACCCTGAAAACTT
TGAGTTTCTCATTTCCTCCTAATACAGTGACTGGCAGTGAAAGAGTTCAG
ATCACTGCAATTGGAGATGTTCTTGGTCCTTCCATCAATGGCTTAGCCTC
ATTGATTCGGATGCCTTATGGCTGTGGTAACAGAACATGATAAATTTTG
CTCCAAATATTTACATTTTGGATTATCTGACTAAAAGAAACAACTGACA
GATAATTTGAAAGAAAAGCTCTTTCATTTATGAGGCAAGGTTACCAGAG
AGAACTTCTCTATCAGAGGGAAGATGGCTCTTTCAGTGCTTTTGGGAATT
ATGACCCTTCTGGGAGCACTTGGTTGTCAGCTTTTGTTTTAAGATGTTTC
CTTGAAGCCGATCCTTACATAGATATTGATCAGAATGTGTTACACAGAAC
ATACACTTGGCTTAAAGGACATCAGAAATCCAACGGTGAATTTTGGGATC
CAGGAAGAGTGATTCATAGTGAGCTTCAAGGTGGCAATAAAAGTCCAGTA
ACACTTACAGCCTATATTGTAACTTCTCCTGGGATATAGAAAGTATCA
GCCTAACATTGATGTGCAAGAGTCTATCCATTTTTGGAGTCTGAATTCA
GTAGAGGAATTTCAGACAATTATACTCTAGCCCTTATAACTTATGCATTG
TCATCAGTGGGGAGTCCTAAAGCGAAGGAAGCTTTGAATATGCTGACTTG
GAGAGCAGAACAAGAAGGTGGCATGCAATTCTGGGTGTCATCAGAGTCCA
AACTTTCTGACTCCTGGCAGCCACGCTCCCTGGATATTGAAGTTGCAGCC
TATGCACTGCTCTCACACTTCTTACAATTTCAGACTTCTGAGGGAATCCC
AATTATGAGGTGGCTAAGCAGGCAAGAAATAGCTTGGGTGGTTTTGCAT
CTACTCAGGATACCACTGTGGCTTTAAAGGCTCTGTCTGAATTTGCAGCC
CTAATGAATACAGAAAGGACAAATATCCAAGTGACCGTGACGGGGCCTAG
CTCACCAAGTCCTGTAAAGTTTCTGATTGACACACACAACCGCTTACTCC
TTCAGACAGCAGAGCTTGCTGTGGTACAGCCAATGGCAGTTAATATTTCC
GCAAATGGTTTTGGATTTGCTATTTGTCAGCTCAATGTTGTATATAATGT
GAAGGCTTCTGGGTCTTCTAGAAGACGAAGATCTATCCAAAATCAAGAAG
CCTTTGATTTAGATGTTGCTGTAAAAGAAAATAAAGATGATCTCAATCAT
GTGGATTTGAATGTGTGTACAAGCTTTTCGGGCCCGGGTAGGAGTGGCAT
GGCTCTTATGGAAGTTAACCTATTAAGTGGCTTTATGGTGCCTTCAGAAG
CAATTTCTCTGAGCGAGACAGTGAAGAAAGTGGAATATGATCATGGAAAA
CTCAACCTCTATTTAGATTCTGTAAATGAAACCCAGTTTTGTGTTAATAT
TCCTGCTGTGAGAAACTTTAAAGTTTCAAATACCCAAGATGCTTCAGTGT
CCATAGTGGATTACTATGAGCCAAGGAGACAGGCGGTGAGAAGTTACAAC
TCTGAAGTGAAGCTGTCCTCCTGTGACCTTTGCAGTGATGTCCAGGGCTG
CCGTCCTTGTGAGGATGGAGCTTCAGGCTCCCATCATCACTCTTCAGTCA
TTTTTATTTTCTGTTTCAAGCTTCTGTACTTTATGGAACTTTGGCTGTGA
TTTATTTTAAAGGACTCTGTGTAACACTAACATTTCCAGTAGTCACATG
TGATTGTTTTGTTTTCGTAGAAGAATACTGCTTCTATTTTGAAAAAAGAG
TTTTTTTTCTTTCTATGGGGTTGCAGGGATGGTGTACAACAGGTCCTAGC
ATGTATAGCTGCATAGATTTCTTCACCTGATCTTTGTGTGGAAGATCAGA
ATGAATGCAGTTGTGTGTCTATATTTTCCCCTCACAAAATCTTTTAGAAT
```

Figure 2b (continued on next page)

```
TTTTTTGGAGGTGTTTGTTTTCTCCAGAATAAAGGTATTACTTTAGAAAT
AGGTATTCTCCTCATTTTGTGAAAGAAATGAACCTAGATTCTTAAGCATT
ATTACACATCCATGTTTGCTTAAAGATGGATTTCCCTGGGAATGGGAGAA
AACAGCCAGCAGGAGGAGCTTCATCTGTTCCCTTCCCACCTCCAACCTAG
CCCTACTGCCCACCCCACCCCAACCCACCCCATGCCCAGTGGTCTCAGTA
GATACTTCTTAACTGGAATTCTTTCTTTTCAGAATCTAGGTGGTGAATT
TTTTTTAAGTGGCACGGTCTTTTCTGCTTGAAATCTGATCACACCCCCC
AGCCATTGCCCTCCCTCTCTTTTTCCTCTGTAGAGAAATGTGAGGGGCAG
TACATTACTGTGCTTTTCACACCATCTCAGAGGTTGAGGAGCATACTGA
AAATTGCCCTGGGGGGTGCTGGGTGTGCTGTCTCCTTCCCACATCCTCAG
CCCCACACCAGCTCTATTTCAGGGGTGAGAGTCAGAGAGCACTGCAATAT
GTGCTTCATGGATTTCGATTCGAAGATCCTAGACCAGGGAGACACTGTG
AGCCAGGGATACAACAAATACTAGGTAAGTCACTGCAGACCGACCTCCC
TGCAGTTTGGGAAGAAGCTGGGTTTGTGGAGAATCAGAGCATCTTGACA
TGACTGCTGACCTAAAGATCCCTGGCATTGGCCAGGGATCCTGTGGAACC
TCTTCTAGTTCAGGGGTGTGAGCATTAGACTGCCAGTTGTCTAGTGACAT
CTGATGCTTGCTGTGAACTTTTAAGATCCCCGAATCCTGAGCACCTCAAT
CTTTAATTGCCCTGTATTCCGAAGGGTAATATAATTTATCTGGATGGAAA
TTTTAAAGATGAATCCCCCTTTTTTCTTTTCTTCTCTCTTTTCTTTCCTT
CTCCCTTTCTTCTTTGCCTTCTAAATATACTGAAATGATTTAGATATGTG
TCAACAATTAATGATCTTTTATTCAATCTAAGAAATGGTTTAGTTTTTCT
CTTTAGCTCTATGGCATTTCACTCAAGTGGACAGGGGAAAAGTAATTGC
CATGGGCTCCAAGAATTTGCTTTATGTTTTAGCTATTTAAAAATAAAT
CCATCAAAAATAAAGTATGCAAATGTATCTTTTAAAAAAAAAAAA
```

Figure 2b.

```
MQGPPLLTAA HLLCVCTAAL AVAPGPRFLV TAPGIIRPGG NVTIGVELLE HCPSQVTVKA
ELLKTASNLT VSVLEAEGVF EKGSFKTLTL PSLPLNSADE IYELRVTGRT QDEILFSNST
RLSFETKRIS VFIQTDKALY KPKQEVKPRI VTLFSDFKPY KTSLNILIKD PKSNLIQQWL
SQQSDLGVIS KTFQLSSHPI LGDWSIQVQV NDQTYYQSFQ VSEYVLPKFE VTLQTPLYCS
MNSKHLNGTI TAKYTYGKPV KGDVTLTFLP LSFWGKKKNI TKTFKINGSA NFSFNDEEMK
NVMDSSNGLS EYLDLSSPGP VEILTTVTES VTGISRNVST NVFFKQHDYI IEFFDYTTVL
KPSLNFTATV KVTRADGNQL TLEERRNNVV ITVTQRNYTE YWSGSNSGNQ KMEAVQKINY
TVPQSGTFKI EFPILEDSSE LQLKAYPLGS KSSMAVHSLF KSPSKTYIQL KTRDENIKVG
SPFELVVSGN KRLKELSYMV VSRGQLVAVG KQNSTMFSLT PENSWTPKAC VIVYYIEDDG
EIISDVLKIP VQLVFKNKIK LYWSKVKAEP SEKVSLRISV TQPDSIVGIV AVDKSVNLMN
ASNDITMENV VHELELYNTG YYLGMFMNSF AVFQECGLWV LTDANLTKDY IDGVYDNAEY
AERFMEENEG HIVDIHDFSL GSSPHVRKHF PETWIWLDTN MGYRIYQEFE VTVPDSITSW
VATGFVISED LGLGLTTTPV ELQAFQPFFI FLNLPYSVIR GEEPALEITI FNYLKDATEV
KVIIEKSDKF DILMTSNEIN ATGHQQTLLV PSEDGATVLF PIRPTHLGEI PITVTALSPT
ASDAVTQMIL VKAEGIEKSY SQSILLDLTD NRLQSTLKTL SFSFPPNTVT GSERVQITAI
GDVLGPSING LASLIRMPYG CGEQNMINFA PNIYILDYLT KKKQLTDNLK EKALSFMRQG
YQRELLYQRE DGSFSAFGNY DPSGSTWLSA FVLRCFLEAD PYIDIDQNVL HRTYTWLKGH
QKSNGEFWDP GRVIHSELQG GNKSPVTLTA YIVTSLLGYR KYQPNIDVQE SIHFLESEFS
RGISDNYTLA LITYALSSVG SPKAKEALNM LTWRAEQEGG MQFWVSSESK LSDSWQPRSL
DIEVAAYALL SHFLQFQTSE GIPIMRWLSR QRNSLGGFAS TQDTTVALKA LSEFAALMNT
ERTNIQVTVT GPSSPSPVKF LIDTHNRLLL QTAELAVVQP MAVNISANGF GFAICQLNVV
YNVKASGSSR RRRSIQNQEA FDLDVAVKEN KDDLNHVDLN VCTSFSGPGR SGMALMEVNL
LSGFMVPSEA ISLSETVKKV EYDHGKLNLY LDSVNETQFC VNIPAVRNFK VSNTQDASVS
IVDYYEPRRQ AVRSYNSEVK LSSCDLCSDV QGCRPCEDGA SGSHHESSVI FIFCFKLLYF
MELWL
```

Figure 3a.

```
MQGPPLLTAA HLLCVCTAAL AVAPGPRFLV TAPGIIRPGG NVTIGVELLE HCPSQVTVKA
ELLKTASNLT VSVLEAEGVF EKGSFKTLTL PSLPLNSADE IYELRVTGRT QDEILFSNST
RLSFETKRIS VFIQTDKALY KPKQEVKFRI VTLFSDFKPY KTSLNILIKD PKSNLIQQWL
SQQSDLGVIS KTFQLSSHPI LGDWSIQVQV NDQTYYQSFQ VSEYVLPKFE VTLQTPLYCS
MNSKHLNGTI TAKYTYGKPV KGDVTLTFLP LSFWGKKKNI TKTPKINGSA NFSFNDEEMK
NVMDSSNGLS EYLDLSSPGP VEILTTVTES VTGISRNVST NVFFKQHDYI IEFFDYTTVL
KPSLNFTATV KVTRADGNQL TLEERRNNVV ITVTQRNYTE YWSGSNSGNQ KMEAVQKINY
TVPQSGTFKI EFPILEDSSE LQLKAYFLGS KSSMAVHSLF KSPSKTYIQL KTRDENIKVG
SPFELVVSGN KRLKELSYMV VSRGQLVAVG KQNSTMFSLT PENSWTPKAC VIVYYIEDDG
EIISDVLKIP VQLVFKNKIK LYWSKVKAEP SEKVSLRISV TQPDSIVGIV AVDKSVNLMN
ASNDITMENV VHELELYNTG YYLGMFMNSF AVFQECGLWV LTDANLTKDY IDGVYDNAEY
AERFMEENEG HIVDIHDFSL GSSPHVRKHF PETWIWLDTN MGSRIYQEFE VTVPDSITSW
VATGFVISED LGLGLTTTPV ELQAFQPFFI FLNLPYSVIR GEEFALEITI FNYLKDATEV
KVIIEKSDKF DILMTSNEIN ATGHQQTLLV PSEDGATVLF PIRPTHLGEI PITVTALSPT
ASDAVTQMIL VKAEGIEKSY SQSILLDLTD NRLQSTLKTL SFSFPPNTVT GSERVQITAI
GDVLGPSING LASLIRMPYG CGEQNMINFA PNIYILDYLT KKKQLTDNLK EKALSFMRQG
YQRELLYQRE DGSFSAFGNY DPSGSTWLSA FVLRCFLEAD PYIDIDQNVL HRTYTWLKGH
QKSNGEFWDP GRVIHSELQG GNKSPVTLTA YIVTSLLGYR KYQPNIDVQE SIHFLESEFS
RGISDNYTLA LITYALSSVG SPKAKEALNM LTWRAEQEGG MQFWVSSESK LSDSWQPRSL
DIEVAAYALL SHFLQFQTSE GIPIMRWLSR QRNSLGGFAS TQDTTVALKA LSEFAALMNT
ERTNIQVTVT GPSSPSPVKF LIDTHNRLLL QTAELAVVQP MAVNISANGF GFAICQLNVV
YNVKASGSSR RRRSIQNQEA FDLDVAVKEN KDDLNHVDLN VCTSFSGPGR SGMALMEVNL
LSGFMVPSEA ISLSETVKKV EYDHGKLNLY LDSVNETQFC VNIPAVRNFK VSNTQDASVS
IVDYYEPRRQ AVRSYNSEVK LSSCDLCSDV QGCRPCEDGA SGSHHHSSVI FIFCFKLLYF
MELWL
```

Figure 3b.

```
CTAAACTCGAATTAAGAGGGAAAAAAAATCAGGGAGGAGGTGGCAAGCCA
CACCCCACGGTGCCCGCGAACTTCCCCGGCAGCGGACTGTAGCCCAGGCA
GACGCCGTCGAGATGCAGGGCCCACCGCTCCTGACCGCCGCCCACCTCCT
CTGCGTGTGCACCGCCGCGCTGGCCGTGGCTCCCGGGCCTCGGTTTCTGG
TGACAGCCCCAGGGATCATCAGGCCCGGAGGAAATGTGACTATTGGGGTG
GAGCTTCTGGAACACTGCCCTTCACAGGTGACTGTGAAGGCGGAGCTGCT
CAAGACAGCATCAAACCTCACTGTCTCTGTCCTGGAAGCAGAAGGAGTCT
TTGAAAAGGCTCTTTTAAGACACTTACTCTTCCATCACTACCTCTGAAC
AGTGCAGATGAGATTTATGAGCTACGTGTAACCGGACGTACCCAGGATGA
GATTTTATTCTCTAATAGTACCCGCTTATCATTTGAGACCAAGAGAATAT
CTGTCTTCATTCAAACAGACAAGGCCTTATACAAGCCAAAGCAAGAAGTG
AAGTTTCGCATTGTTACACTCTTCTCAGATTTTAAGCCTTACAAAACCTC
TTTAAACATTCTCATTAAGGACCCCAAATCAAATTTGATCCAACAGTGGT
TGTCACAACAAAGTGATCTTGGAGTCATTTCCAAAACTTTTCAGCTATCT
TCCCATCCAATACTTGGTGACTGGTCTATTCAAGTTCAAGTGAATGACCA
GACATATTATCAATCATTTCAGGTTTCAGAATATGTATTACCAAAATTTG
AAGTGACTTTGCAGACACCATTATATTGTTCTATGAATTCTAAGCATTTA
AATGGTACCATCACGGCAAAGTATACATATGGGAAGCCAGTGAAAGGAGA
CGTAACGCTTACATTTTTACCTTTATCCTTTTGGGGAAAGAAGAAAAATA
TTACAAAAACATTTAAGATAAATGGATCTGCAAACTTCTCTTTTAATGAT
GAAGAGATGAAAAATGTAATGGATTCTTCAAATGGACTTTCTGAATACCT
GGATCTATCTTCCCCTGGACCAGTAGAAATTTTAACCACAGTGACAGAAT
CAGTTACAGGTATTTCAAGAAATGTAAGCACTAATGTGTTCTTCAAGCAA
CATGATTACATCATTGAGTTTTTTGATTATACTACTGTCTTGAAGCCATC
TCTCAACTTCACAGCCACTGTGAAGGTAACTCGTGCTGATGGCAACCAAC
TGACTCTTGAAGAAGAAGAAATAATGTAGTCATAACAGTGACACAGAGA
AACTATACTGAGTACTGGAGCGGATCTAACAGTGGAAATCAGAAAATGGA
AGCTGTTCAGAAAATAAATTATACTGTCCCCAAAGTGGAACTTTTAAGA
TTGAATTCCCAATCCTGGAGGATTCCAGTGAGCTACAGTTGAAGGCCTAT
TTCCTTGGTAGTAAAAGTAGCATGGCAGTTCATAGTCTGTTTAAGTCTCC
TAGTAAGACATACATCCAACTAAAAACAAGAGATGAAAATATAAAGGTGG
GATCGCCTTTTGAGTTGGTGGTTAGTGGCAACAAACGATTGAAGGAGTTA
AGCTATATGGTAGTATCCAGGGGACAGTTGGTGGCTGTAGGAAAACAAAA
TTCAACAATGTTCTCTTTAACACCAGAAAATTCTTGGACTCCAAAAGCCT
GTGTAATTGTGTATTATATTGAAGATGATGGGGAAATTATAAGTGATGTT
CTAAAAATTCCTGTTCAGCTTGTTTTTAAAAATAAGATAAAGCTATATTG
GAGTAAAGTGAAAGCTGAACCATCTGAGAAAGTCTCTCTTAGGATCTCTG
TGACACAGCCTGACTCCATAGTTGGGATTGTAGCTGTTGACAAAAGTGTG
AATCTGATGAATGCCTCTAATGATATTACAATGGAAAATGTGGTCCATGA
GTTGGAACTTTATAACACAGGATATTATTTAGGCATGTTCATGAATTCTT
TTGCAGTCTTTCAGGAATGTGGACTCTGGGTATTGACAGATGCAAACCTC
ACGAAGGATTATATTGATGGTGTTTATGACAATGCAGAATATGCTGAGAG
GTTTATGGAGGAAAATGAAGGACATATTGTAGATATTCATGACTTTTCTT
TGGGTAGCAGTCCACATGTCCGAAAGCATTTTCCAGAGACTTGGATTTGG
CTAGACACCAACATGGGTTACAGGATTTACCAAGAATTTGAAGTAACTGT
```

Figure 4a (continued on next page)

ACCTGATTCTATCACTTCTTGGGTGGCTACTGGTTTTGTGATCTCTGAGG
ACCTGGGTCTTGGACTAACAACTACTCCAGTGGAGCTCCAAGCCTTCCAA
CCATTTTTCATTTTTTTGAATCTTCCCTACTCTGTTATCAGAGGTGAAGA
ATTTGCTTTGGAAATAACTATATTCAATTATTTGAAAGATGCCACTGAGG
TTAAGGTAATCATTGAGAAAGTGACAAATTTGATATTCTAATGACTTCA
AATGAAATAAATGCCACAGGCCACCAGCAGACCCTTCTGGTTCCCAGTGA
GGATGGGGCAACTGTTCTTTTTCCCATCAGGCCAACACATCTGGGAGAAA
TTCCTATCACAGTCACAGCTCTTTCACCCACTGCTTCTGATGCTGTCACC
CAGATGATTTTAGTAAAGGCTGAAGGAATAGAAAATCATATTCACAATC
CATCTTATTAGACTTGACTGACAATAGGCTACAGAGTACCCTGAAAACTT
TGAGTTTCTCATTTCCTCCTAATACAGTGACTGGCAGTGAAAGAGTTCAG
ATCACTGCAATTGGAGATGTTCTTGGTCCTTCCATCAATGGCTTAGCCTC
ATTGATTCGGATGCCTTATGGCTGTGGTGAACAGAACATGATAAATTTTG
CTCCAAATATTTACATTTTGGATTATCTGACTAAAAGAAACAACTGACA
GATAATTTGAAAGAAAAGCTCTTTCATTTATGAGGCAAGGTTACCAGAG
AGAACTTCTCTATCAGAGGGAAGATGGCTCTTTCAGTGCTTTTGGGAATT
ATGACCCTTCTGGGAGCACTTGGTTGTCAGCTTTTGTTTAAGATGTTTC
CTTGAAGCCGATCCTTACATAGATATTGATCAGAATGTGTTACACAGAAC
ATACACTTGGCTTAAAGGACATCAGAAATCCAACGGTGAATTTGGGATC
CAGGAAGAGTGATTCATAGTGAGCTTCAAGGTGGCAATAAAAGTCCAGTA
ACACTTACAGCCTATATTGTAACTTCTCTCCTGGGATATAGAAAGTATCA
GGTATTTCGTATTTAATTTAATAAATGATAGATGGGAAATTCAAGGAAGG
TAGGTCTTAATGGGTCAAATATGTGTGTGGAAACTTAACAAGTTGCAGCT
TTACAACACATGTGAAATCTGAATTTGAGTACTCTTTTGCTTTGCATTTG
CAGCCATGTTCCAAAATCTGAGAATAAAACATTACCCACTCTTTCAGATA
ACTAAGAGATTCTAAAAAAAAAAAAAAAAAAAAAAA

Figure 4a.

```
CTAAACTCGAATTAAGAGGGAAAAAAAATCAGGGAGGAGGTGGCAAGCCA
CACCCCACGGTGCCCGCGAACTTCCCCGGCAGCGGACTGTAGCCCAGGCA
GACGCCGTCGAGATGCAGGGCCCACCGCTCCTGACCGCCGCCCACCTCCT
CTGCGTGTGCACCGCCGCGCTGGCCGTGGCTCCCGGGCCTCGGTTTCTGG
TGACAGCCCCAGGGATCATCAGGCCCGGAGGAAATGTGACTATTGGGGTG
GAGCTTCTGGAACACTGCCCTTCACAGGTGACTGTGAAGGCGGAGCTGCT
CAAGACAGCATCAAACCTCACTGTCTCTGTCCTGGAAGCAGAAGGAGTCT
TTGAAAAAGGCTCTTTTAAGACACTTACTCTTCCATCACTACCTCTGAAC
AGTGCAGATGAGATTTATGAGCTACGTGTAACCGGACGTACCCAGGATGA
GATTTATTCTCTAATAGTACCCGCTTATCATTTGAGACCAAGAGAATAT
CTGTCTTCATTCAAACAGACAAGGCCTTATACAAGCCAAAGCAAGAAGTG
AAGTTTCGCATTGTTACACTCTTCTCAGATTTTAAGCCTTACAAAACCTC
TTTAAACATTCTCATTAAGGACCCCAAATCAAATTTGATCCAACAGTGGT
TGTCACAACAAAGTGATCTTGGAGTCATTTCCAAAACTTTTCAGCTATCT
TCCCATCCAATACTTGGTGACTGGTCTATTCAAGTTCAAGTGAATGACCA
GACATATTATCAATCATTTCAGGTTTCAGAATATGTATTACCAAAATTTG
AAGTGACTTTGCAGACACCATTATATTGTTCTATGAATTCTAAGCATTTA
AATGGTACCATCACGGCAAAGTATACATATGGGAAGCCAGTGAAAGGAGA
CGTAACGCTTACATTTTACCTTTATCCTTTTGGGGAAAGAAGAAAAATA
TTACAAAAACATTTAAGATAAATGGATCTGCAAACTTCTCTTTTAATGAT
GAAGAGATGAAAAATGTAATGGATTCTTCAAATGGACTTTCTGAATACCT
GGATCTATCTTCCCTGGACCAGTAGAAATTTTAACCACAGTGACAGAAT
CAGTTACAGGTATTTCAAGAAATGTAAGCACTAATGTGTTCTTCAAGCAA
CATGATTACATCATTGAGTTTTTTGATTATACTACTGTCTTGAAGCCATC
TCTCAACTTCACAGCCACTGTGAAGGTAACTCGTGCTGATGGCAACCAAC
TGACTCTTGAAGAAGAAGAAATAATGTAGTCATAACAGTGACACAGAGA
AACTATACTGAGTACTGGAGCGGATCTAACAGTGGAAATCAGAAAATGGA
AGCTGTTCAGAAAATAAATTATACTGTCCCCCAAAGTGGAACTTTTAAGA
TTGAATTCCCAATCCTGGAGGATTCCAGTGAGCTACAGTTGAAGGCCTAT
TTCCTTGGTAGTAAAAGTAGCATGGCAGTTCATAGTCTGTTTAAGTCTCC
TAGTAAGACATACATCCAACTAAAAACAAGAGATGAAAATATAAAGGTGG
GATCGCCTTTTGAGTTGGTGGTTAGTGGCAACAAACGATTGAAGGAGTTA
AGCTATATGGTAGTATCCAGGGGACAGTTGGTGGCTGTAGGAAAACAAAA
TTCAACAATGTTCTCTTTAACACCAGAAAATTCTTGGACTCCAAAAGCCT
GTGTAATTGTGTATTATATTGAAGATGATGGGGAAATTATAAGTGATGTT
CTAAAAATTCCTGTTCAGCTTGTTTTTAAAAATAAGATAAAGCTATATTG
GAGTAAAGTGAAAGCTGAACCATCTGAGAAAGTCTCTCTTAGGATCTCTG
TGACACAGCCTGACTCCATAGTTGGGATTGTAGCTGTTGACAAAAGTGTG
AATCTGATGAATGCCTCTAATGATATTACAATGGAAAATGTGGTCCATGA
GTTGGAACTTTATAACACAGGATATTATTTAGGCATGTTCATGAATTCTT
TTGCAGTCTTTCAGGAATGTGGACTCTGGGTATTGACAGATGCAAACCTC
ACGAAGGATTATATTGATGGTGTTTATGACAATGCAGAATATGCTGAGAG
GTTTATGGAGGAAAATGAAGGACATATTGTAGATATTCATGACTTTTCTT
TGGGTAGCAGTCCACATGTCCGAAAGCATTTTCCAGAGACTTGGATTTGG
CTAGACACCAACATGGGTTCCAGGATTTACCAAGAATTTGAAGTAACTGT
ACCTGATTCTATCACTTCTTGGGTGGCTACTGGTTTTGTGATCTCTGAGG
```

Figure 4b (continued on next page)

```
ACCTGGGTCTTGGACTAACAACTACTCCAGTGGAGCTCCAAGCCTTCCAA
CCATTTTTCATTTTTTTGAATCTTCCCTACTCTGTTATCAGAGGTGAAGA
ATTTGCTTTGGAAATAACTATATTCAATTATTTGAAAGATGCCACTGAGG
TTAAGGTAATCATTGAGAAAAGTGACAAATTTGATATTCTAATGACTTCA
AATGAAATAAATGCCACAGGCCACCAGCAGACCCTTCTGGTTCCCAGTGA
GGATGGGGCAACTGTTCTTTTTCCCATCAGGCCAACACATCTGGGAGAAA
TTCCTATCACAGTCACAGCTCTTTCACCCACTGCTTCTGATGCTGTCACC
CAGATGATTTTAGTAAAGGCTGAAGGAATAGAAAATCATATTCACAATC
CATCTTATTAGACTTGACTGACAATAGGCTACAGAGTACCCTGAAAACTT
TGAGTTTCTCATTTCCTCCTAATACAGTGACTGGCAGTGAAAGAGTTCAG
ATCACTGCAATTGGAGATGTTCTTGGTCCTTCCATCAATGGCTTAGCCTC
ATTGATTCGGATGCCTTATGGCTGTGGTGAACAGAACATGATAAATTTTG
CTCCAAATATTTACATTTTGGATTATCTGACTAAAAAGAAACAACTGACA
GATAATTTGAAAGAAAAAGCTCTTTCATTTATGAGGCAAGGTTACCAGAG
AGAACTTCTCTATCAGAGGGAAGATGGCTCTTTCAGTGCTTTTGGGAATT
ATGACCCTTCTGGGAGCACTTGGTTGTCAGCTTTTGTTTTAAGATGTTTC
CTTGAAGCCGATCCTTACATAGATATTGATCAGAATGTGTTACACAGAAC
ATACACTTGGCTTAAAGGACATCAGAAATCCAACGGTGAATTTTGGGATC
CAGGAAGAGTGATTCATAGTGAGCTTCAAGGTGGCAATAAAAGTCCAGTA
ACACTTACAGCCTATATTGTAACTTCTCCTGGGATATAGAAAGTATCA
GGTATTTCGTATTTAATTTAATAAATGATAGATGGGAAATTCAAGGAAGG
TAGGTCTTAATGGGTCAAATATGTGTGTGGAAACTTAACAAGTTGCAGCT
TTACAACACATGTGAAATCTGATTTGAGTACTCTTTTGCTTTGCATTTG
CAGCCATGTTCCAAAATCTGAGAATAAAACATTACCCACTCTTTCAGATA
ACTAAGAGATTCTAAAAAAAAAAAAAAAAAAAAAAA
```

Figure 4b.

```
MQGPPLLTAA HLLCVCTAAL AVAPGPRFLV TAPGIIRPGG NVTIGVELLE HCPSQVTVKA
ELLKTASNLT VSVLEAEGVF EKGSFKTLTL PSLPLNSADE IYELRVTGRT QDEILFSNST
RLSFETKRIS VFIQTDKALY KPKQEVKFRI VTLFSDFKPY KTSLNILIKD PKSNLIQQWL
SQQSDLGVIS KTFQLSSHPI LGDWSIQVQV NDQTYYQSFQ VSEYVLPKFE VTLQTPLYCS
MNSKHLNGTI TAKYTYGKPV KGDVTLTFLP LSFWGKKKNI TKTFKINGSA NFSFNDEEMK
NVMDSSNGLS EYLDLSSPGP VEILTTVTES VTGISRNVST NVFFKQHDYI IEFFDYTTVL
KPSLNFTATV KVTRADGNQL TLEERRNNVV ITVTQRNYTE YWSGSNSGNQ KMEAVQKINY
TVPQSGTFKI EFPILEDSSE LQLKAYPLGS KSSMAVHSLF KSPSKTYIQL KTRDENIKVG
SPFELVVSGN KRLKELSYMV VSRGQLVAVG KQNSTMFSLT PENSWTPKAC VIVYYIEDDG
EIISDVLKIP VQLVFKNKIK LYWSKVKAEP SEKVSLRISV TQPDSIVGIV AVDKSVNLMN
ASNDITMENV VHELELYNTG YYLGMFMNSF AVFQECGLWV LTDANLTKDY IDGVYDNAEY
AERFMEENEG HIVDIHDFSL GSSPHVRKHF PETWIWLDTN MGYRIYQEFE VTVPDSITSW
VATGFVISED LGLGLTTTPV ELQAFQPFFI FLNLPYSVIR GEEFALEITI FNYLKDATEV
KVIIEKSDKF DILMTSNEIN ATGHQQTLLV PSEDGATVLF PIRPTHLGEI PITVTALSPT
ASDAVTQMIL VKAEGIEKSY SQSILLDLTD NRLQSTLKTL SFSFPPNTVT GSERVQITAI
GDVLGPSING LASLIRMPYG CGEQNMINFA PNIYILDYLT KKKQLTDNLK EKALSFMRQG
YQRELLYQRE DGSFSAFGNY DPSGSTWLSA FVLRCFLEAD PYIDIDQNVL HRTYTWLKGH
QKSNGEFWDP GRVIHSELQG GNKSPVTLTA YIVTSLLGYR KYQVFRI
```

Figure 5a.

```
MQGPPLLTAA HLLCVCTAAL AVAPGPRFLV TAPGIIRPGG NVTIGVELLE HCPSQVTVKA
ELLKTASNLT VSVLEAEGVF EKGSFKTLTL PSLPLNSADE IYELRVTGRT QDEILFSNST
RLSFETKRIS VFIQTDKALY KPKQEVKFRI VTLFSDFKPY RTSLNILIKD PKSNLIQQWL
SQQSDLGVIS KTFQLSSHPI LGDWSIQVQV NDQTYYQSPQ VSEYVLPKFE VTLQTPLYCS
MNSKHLNGTI TAKYTYGKPV KGDVTLTFLP LSFWGKKKNI TKTFKINGSA NFSFNDEEMK
NVMDSSNGLS EYLDLSSPGP VEILTTVTES VTGISRNVST NVFFKQHDYI IEFFDYTTVL
KPSLNFTATV KVTRADGNQL TLEERRNNVV ITVTQRNYTE YWSGSNSGNQ KMEAVQKINY
TVPQSGTFKI EFPILEDSSE LQLKAYFLGS KSSMAVHSLF KSPSKTYIQL KTRDENIKVG
SPFELVVSGN KRLKELSYMV VSRGQLVAVG KQNSTMFSLT PENSWTPKAC VIVYYIEDDG
EIISDVLKIP VQLVFKNKIK LYWSKVKAEP SEKVSLRISV TQPDSIVGIV AVDKSVNLMN
ASNDITMENV VHELELYNTG YYLGMFMNSF AVFQECGLWV LTDANLTKDY IDGVYDNAEY
AERFMEENEG HIVDIHDFSL GSSPHVRKHF PETWIWLDTN MGSRIYQEFE VTVPDSITSW
VATGFVISED LGLGLTTTPV ELQAFQPFFI FLNLPYSVIR GEEFALEITI PNYLKDATEV
KVIIEKSDKF DILMTSNEIN ATGHQQTLLV PSEDGATVLF PIRPTHLGEI PITVTALSPT
ASDAVTQMIL VKAEGIEKSY SQSILLDLTD NRLQSTLKTL SFSFPPNTVT GSERVQITAI
GDVLGPSING LASLIRMPYG CGEQNMINFA PNIYILDYLT KKKQLTDNLK EKALSFMRQG
YQRELLYQRE DGSFSAFGNY DPSGSTWLSA FVLRCFLEAD PYIDIDQNVL HRTYTWLKGH
QKSNGEFWDP GRVIHSELQG GNKSPVTLTA YIVTSLLGYR KYQVFRI
```

CD109 NUCLEIC ACID MOLECULES, POLYPEPTIDES AND METHODS OF USE

CROSS-REFERENCE TO RELATED APPLICATIONS

This application is a National Stage application based on International Application No. PCT/CA02/00292, filed Mar. 7, 2002, which claims priority to U.S. Provisional Application No. 60/273,814, filed Mar. 7, 2001, the disclosures of which are incorporated herein by reference.

FIELD OF THE INVENTION

The invention relates to isolated nucleic acid molecules encoding CD109 polypeptides, and the CD109 polypeptides themselves. The invention also includes methods of using the polypeptides and nucleic acid molecules and proteins for treatment of diseases, disorders and abnormal physical states.

BACKGROUND OF THE INVENTION

CD109 is a cell surface antigen that marks primitive progenitor and hematopoietic stem cells and activated platelets and T lymphocytes. To date, the function of CD109 in these cell types has remained largely unknown. While T cell CD109 has previously been implicated in the regulation of antibody inducing T helper cell function, but its role is poorly understood.

To date, no one has been able to isolate and sequence CD109 DNA or protein. There are many reasons for these problems including the very low levels of CD109 gene expression and the corresponding low level of protein expression and activity. Moreover the instability of CD109 in protein extracts, and its association with plasma membranes has contributed to the difficulties surrounding its isolation. Without the DNA and protein sequences, it is impossible to design rational strategies for the modulation of CD109 levels or activity, by modulating gene and protein expression. There is a need to identify these sequences in order to establish methods to modulate CD109 activity. Protein sequence information is important for the elucidation of protein structure and the ultimate design of chemical inhibitors that may modulate CD109 activity in vivo. There is also a need for cells which overexpress CD109 polypeptides or in which gene expression is reduced or blocked.

SUMMARY OF THE INVENTION

The invention relates to isolated and characterized human CD109 nucleic acid molecules and the corresponding polypeptides. CD109 is a novel member of the α2 macroglobulin (α2M)/C3, C4, C5 family of thioester-containing proteins. Analysis of sequences shows that specific proteolytic cleavage of CD109 results in activation of its thioester. The chemical reactivity of the activated CD109 thioester likely is similar to that of complement rather than that of α2M proteins, with reactivity being directed preferentially towards hydroxyl-containing carbohydrate and protein nucleophiles. Activated CD109 is capable of covalent binding to a variety of substrates, including cell membranes. In addition, the $t_{1/2}$, of the activated CD109 thioester is extremely short, so that CD109 action is spatially restricted to the site of its activation.

The invention relates to isolated nucleic acid molecules encoding CD109 polypeptides. The molecule preferably encodes a polypeptide including a thioester region which becomes reactive towards a nucleophile when the polypeptide is cleaved. Another aspect of the invention relates to an isolated nucleic acid molecule encoding a CD109 polypeptide, a fragment of a CD109 polypeptide having CD109 activity, or a polypeptide having CD109 activity, comprising a nucleic acid molecule selected from the group consisting of:

(a) a nucleic acid molecule that hybridizes to a nucleic acid molecule consisting of at least one of [SEQ ID NO:1, 3, 5, 7, 9 or 11], or a complement thereof under low, moderate or high stringency hybridization conditions wherein the nucleic acid molecule encodes a CD109 polypeptide or a polypeptide having CD109 activity;

(b) a nucleic acid molecule degenerate with respect to (a), wherein the nucleic molecule encodes a CD109 polypeptide or a polypeptide having CD109 activity.

The hybridization conditions optionally comprise low stringency conditions of 1×SSC, 0.1% SDS at 5000 or high stringency conditions of 0.1×SSC, 0.1% SDS at 65° C.

Another aspect of the invention relates to an isolated nucleic acid molecule encoding a CD109 polypeptide, a fragment of a CD109 polypeptide having CD109 activity, or a polypeptide having CD109 activity, comprising a nucleic acid molecule selected from the group consisting of:

(a) the nucleic acid molecule of the coding strand shown in [SEQ ID NO:1, 3, 5, 7, 9 or 11], or a complement thereof;

(b) a nucleic acid molecule encoding the same amino acid sequence as a nucleotide sequence of (a); and (c) a nucleic acid molecule having at least 17% identity with the nucleotide sequence of (a) and which encodes a CD109 polypeptide or a polypeptide having CD109 activity.

The CD109 polypeptide optionally comprises a K1 [SEQ ID NO:2], K1-H7 [SEQ ID NO:6] or K15 [SEQ ID NO:10] polypeptide or their variants [SEQ ID NO:4, 8 or 12]. The nucleic acid molecule of the invention, optionally comprises all or part of a nucleotide sequence shown in [SEQ ID NO:1, 3, 5, 7, 9 or 11] or a complement thereof. The nucleic acid molecule of the invention, optionally consist of the nucleotide sequence shown in [SEQ ID NO: 1, 3, 5, 7, 9, or 11] or a complement thereof. The CD109 nucleic acid molecule or a fragment thereof is optionally isolated from a human. The nucleic acid molecule of the invention optionally comprises genomic DNA, cDNA or RNA. The nucleic acid molecule of the invention, wherein the nucleic acid molecule is optionally chemically synthesized.

In another aspect, the invention relates to an isolated nucleic acid molecule comprising a nucleic acid molecule selected from the group consisting of 8 to 10 nucleotides of the nucleic acid molecule of the invention or a region shown in Table 1.1, 1.2 or 1.3. The nucleic acid molecule of the invention, optionally comprises at least 30 consecutive nucleotides of [SEQ ID NO: 1, 3, 5, 7, 9, or 11] or a complement thereof.

Another embodiment of the invention relates to a recombinant nucleic acid molecule comprising a nucleic acid molecule of the invention and a constitutive promoter sequence or an inducible promoter sequence operatively linked so that the promoter enhances transcription of the nucleic acid molecule in a host cell.

Another embodiment of the invention relates to a vector comprising a nucleic acid molecule of the invention. The vector optionally comprises a promoter selected from the group consisting of a vav promoter, a H2K promoter, a PF4 promoter, a GP1b promoter, a lck promoter, a CD2 promoter, a granzymeB promoter, a Beta actin promoter, a PGK promoter, a CMV promoter, a retroviral LTR, a metallothionein IIA promoter, an ecdysone promoter and a tetracycline inducible promoter.

Another embodiment of the invention relates to a host cell comprising the recombinant nucleic acid molecule of the invention, or progeny of the host cell. The host cell is optionally selected from the group consisting of a mammalian cell, a fungal cell, a yeast cell, a bacterial cell, a microorganism cell and a plant cell.

Another embodiment of the invention relates to an isolated polypeptide encoded by and/or produced from a nucleic acid molecule of the invention. The invention includes an isolated CD109 polypeptide or a fragment thereof having CD109 activity. The polypeptide of the invention optionally comprises all or part of an amino acid sequence in [SEQ ID NO:2, 4, 6, 8, 10 or 12]. The polypeptide optionally comprises ten or more, or ten or fewer consecutive residues of [SEQ ID NO:2, 4, 6, 8, 10 or 12].

The invention also includes an isolated immunogenic polypeptide, the amino acid sequence of which comprises ten or more, or ten or fewer consecutive residues of [SEQ ID NO:2, 4, 6, 8, 10 or 12]. The isolated polypeptide optionally comprises a region shown in Table 1a or Table 1b.

The invention includes a polypeptide fragment of a polypeptide of the invention or a peptide mimetic of said polypeptide. The polypeptide fragment optionally consists or comprises of 20 or more or 20 or fewer amino acids, which fragment has CD109 activity. The fragment or peptide mimetic is optionally capable of being bound by an antibody to the polypeptide of the invention. The polypeptide is optionally recombinantly produced.

The invention includes an isolated and purified polypeptide comprising the amino acid sequence of a CD109 polypeptide, wherein the polypeptide is encoded by a nucleic acid molecule that hybridizes under moderate or stringent conditions to a nucleic acid molecule in [SEQ ID NO:1, 3, 5, 7, 9, or 11], a degenerate form thereof or a complement.

The invention also includes a polypeptide comprising a sequence having greater than 20% sequence identity to a polypeptide of the invention. The polypeptide of the invention optionally comprises a CD109 polypeptide, such as a polypeptide isolated from a human cell. The polypeptide optionally comprises a region including at least 30% homology to a region shown in Table 1a or Table 1b. The invention includes an isolated nucleic acid molecule encoding a polypeptide of the invention.

The invention includes a CD109 specific antibody targeted to a region selected from the CD109 bait region, the CD109 thioester, or the CD109 thioester reactivity defining hexapeptide. The antibody optionally comprises a monoclonal antibody or a polyclonal antibody.

Another aspect of the invention relates to a pharmaceutical composition, comprising all or part of a polypeptide of the invention or a mimetic thereof, and a pharmaceutically acceptable carrier.

Another aspect of the invention relates to a pharmaceutical composition for use in gene therapy, comprising all or part of a nucleotide sequence of the invention, and a pharmaceutically acceptable carrier, auxiliary or excipient. Another variant of the invention relates to a pharmaceutical composition for use in gene therapy, comprising all or part of an antisense sequence to all or part of the nucleic acid sequence in [SEQ ID NO: 1, 3, 5, 7, 9, or 11].

Another aspect of the invention relates to a kit for the treatment or detection of a disease, disorder or abnormal physical state, comprising all or part of a nucleotide sequence of the invention. A kit for the treatment or detection of a disease, disorder or abnormal physical state, optionally comprises all or part of the polypeptide of the invention. A kit for the treatment or detection of a disease, disorder or abnormal physical state, optionally comprises an antibody to a polypeptide of the invention. The kit is useful in relation the disorder such as one selected from a group consisting of conditions associated with endothelial activation, platelet activation, activation of the coagulation or fibrinolytic systems, activation of T lymphocytes and of the complement system, cardiovascular disorders, stroke, myocardial infarction, thrombosis, embolism, peripheral vascular disease, disorders associated with quantitative or qualitative abnormalities of platelet function, thrombocytopenia, thrombocythemia, conditions associated with increased or impaired platelet aggregation and activation, conditions associated with increased or impaired activation of the coagulation and/or fibrinolytic systems, conditions associated with impaired or increased immune activation, autoimmune diseases, organ transplantation and bone marrow transplantation.

Another aspect of the invention relates to a method of medical treatment of a disease, disorder or abnormal physical state, characterized by excessive CD109 expression, concentration or activity, comprising administering a product that reduces or inhibits CD109 polypeptide expression, concentration or activity. The product is optionally an antisense nucleotide sequence to all or part of the nucleotide sequence of [SEQ ID NO. 1, 3, 5, 7, 9 or 11], the antisense nucleotide sequence being sufficient to reduce or inhibit CD109 polypeptide expression. The antisense DNA is optionally administered in a pharmaceutical composition comprising a carrier and a vector operably linked to the antisense DNA. The invention also relates to a method of medical treatment of a disease, disorder or abnormal physical state, characterized by inadequate CD109 expression, concentration or activity, comprising administering a product that increases CD109 polypeptide expression, concentration or activity. The product is optionally a nucleotide sequence comprising all or part of the nucleotide sequence of [SEQ ID NO. 1, 3, 5, 7, 9, or 11], the DNA being sufficient to increase CD109 polypeptide expression. The nucleotide sequence is optionally administered in a pharmaceutical composition comprising a carrier and a vector operably linked to the nucleotide sequence. The invention also includes a method of medical treatment of a disease, disorder or abnormal physical state having normal CD109 expression, concentration and activity, comprising administering a product that increases or reduces CD109 polypeptide expression, concentration or activity.

BRIEF DESCRIPTION OF THE DRAWINGS

Preferred embodiments of the invention will be described in relation to the drawings in which:

FIG. 1a. shows [SEQ ID NO:1]. In a preferred embodiment, the sequence is a CD109 K1 cDNA.

FIG. 1b. shows [SEQ ID NO:3]. In a preferred embodiment, the sequence is a variant of CD109 K1 cDNA.

FIG. 2a. shows [SEQ ID NO:5]. In a preferred embodiment, the sequence is called K1-H7 cDNA.

FIG. 2b. shows [SEQ ID NO:7]. In a preferred embodiment, the sequence is a variant of CD109 K1-H7 cDNA.

FIG. 3a. shows [SEQ ID NO:2 and SEQ ID NO:6]. In a preferred embodiment, these sequences are the 1445 aa protein sequences produced from K1 and K1-H7 CD109 cDNAs respectively.

FIG. 3b. shows [SEQ ID NO:4 and SEQ ID NO:8]. In a preferred embodiment, these sequences are variants of the 1445 aa protein sequences produced from K1 and K1-H7 variant CD109 cDNAs respectively.

FIG. 4a. shows [SEQ ID NO9]. In a preferred embodiment, the sequence is called the CD109 K15 cDNA.

FIG. 4b. shows [SEQ ID NO:11]. In a preferred embodiment, this sequence is variant of CD109 K15 cDNA.

FIG. 5a. shows [SEQ ID NO:10]. In a preferred embodiment, the sequence is the K15 amino acid sequence.

FIG. 5b. shows [SEQ ID NO:12] In a preferred embodiment, this sequence is a variant of the K15 amino acid sequence.

Figure 6:
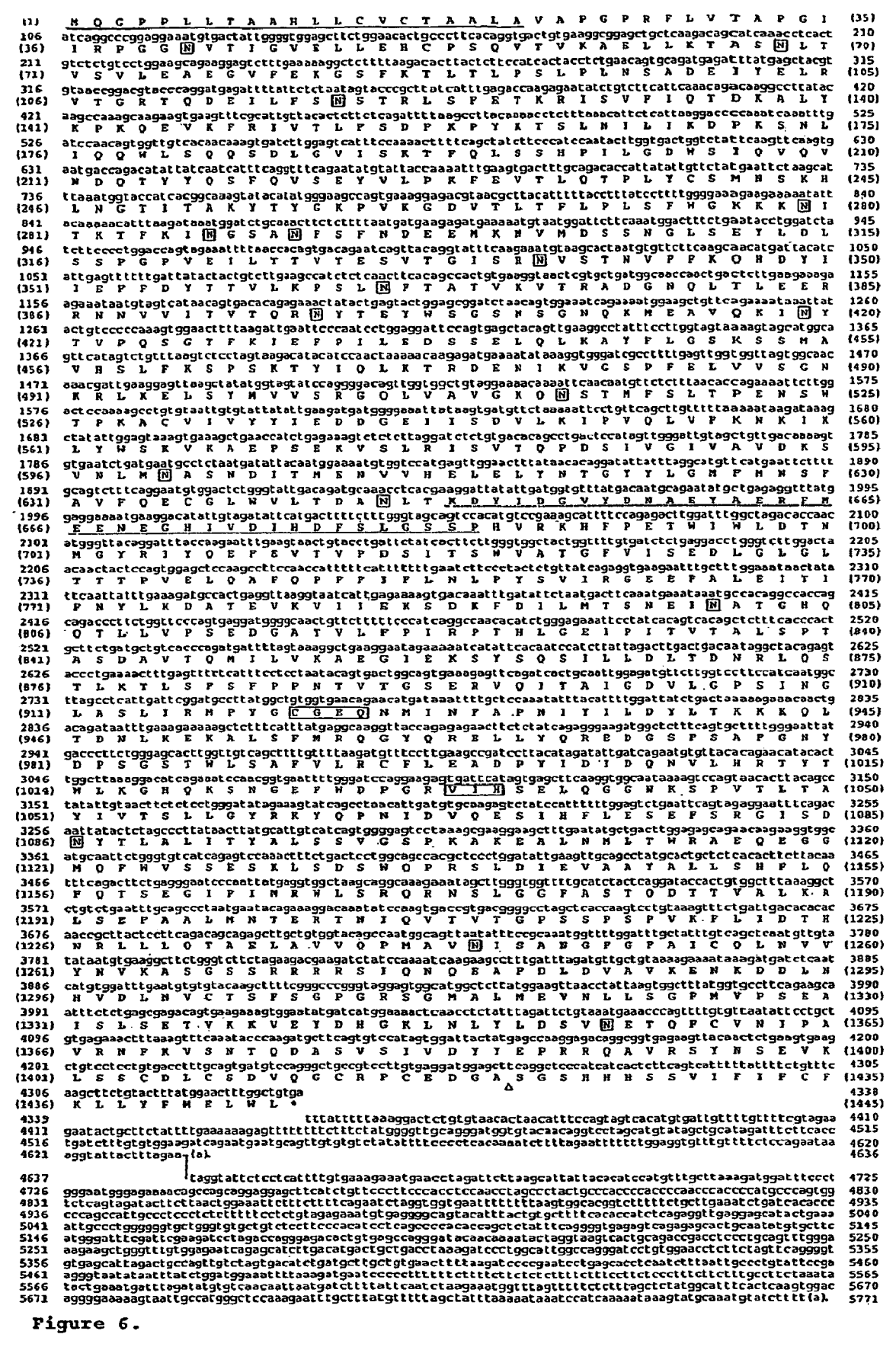

FIG. 6. shows K1, K1-H7, and the corresponding amino acid sequence (K1 and K1-H7 polypeptide sequences are identical). Nucleotides are numbered relative to the translation initiation codon, with the corresponding aa numbering shown in parentheses. Both K1 and K1-H7 3'UTRs, and the positions of the corresponding poly(A) tails [$(a)_n$)] are shown. Potential sites of N-linked glycosylation, the thioester signature sequence (aa residues 918-924), and the corresponding downstream thioester reactivity defining hexapeptide motif (aa residues 1039-1044) are marked by open boxes; solid underline, amino-terminal leader peptide; dotted underline, bait region; *, translation stop; open triangle, GPI anchor cleavage/addition site.

DETAILED DESCRIPTION OF THE INVENTION

"Nucleic acid molecule" includes DNA and RNA, whether single or double stranded. The term is also intended to include a strand that is a mixture of nucleic acid molecules and nucleic acid analogs and/or nucleotide analogs, or that is made entirely of nucleic acid analogs and/or nucleotide analogs.

"Nucleic acid analogue" refers to modified nucleic acids or species unrelated to nucleic acids that are capable of providing selective binding to nucleic acid molecules or other nucleic acid analogues. As used herein, the term "nucleotide analogues" includes nucleic acids where the internucleotide phosphodiester bond of DNA or RNA is modified to enhance bio-stability of the oligomer and "tune" the selectivity/specificity for target molecules (Ulhmann, et al., 1990, Angew. Chem. Int. Ed. Eng., 90: 543; Goodchild, 1990, J. Bioconjugate Chem., I: 165; Englisch et al., 1991, Angew, Chem. Int. Ed. Eng., 30: 613). Such modifications may include and are not limited to phosphorothioates, phosphotriesters, phosphoramidates or methylphosphonates. The 2'-O-methyl, allyl and 2'-deoxy-2'-fluoro RNA analogs, when incorporated into an oligomer show increased biostability and stabilization of the RNA/DNA duplex (Lesnik et al., 1993, Biochemistry, 32: 7832). As used herein, the term "nucleic acid analogues" also include alpha anomers (α-DNA), L-DNA (mirror image DNA), 2'-5' linked RNA, branched DNA/RNA or chimeras of natural DNA or RNA and the above-modified nucleic acids. For the purposes of the present invention, any nucleic acid molecule containing a "nucleotide analogue" shall be considered as a nucleic acid molecule. Backbone replaced nucleic acid analogues can also be adapted for use as immobilised selective moieties of the present invention. For purposes of the present invention, the peptide nucleic acids (PNAs) (Nielsen et al, 1993, Anti-Cancer Drug Design, 8: 53; Engels et al., 1992, Angew, Chem. Int. Ed. Eng., 31: 1008) and carbamate-bridged morpholino-type oligonucleotide analogs (Burger, D. R., 1993, J. Clinical Immunoassay, 16: 224; Uhlmann, et al., 1993, Methods in Molecular Biology, 20, "Protocols for Oligonucleotides and Analogs," ed. Sudhir Agarwal, Humana Press, NJ, U.S.A., pp. 335-389) are also embraced by the term "nucleic acid analogues". Both exhibit sequence-specific binding to DNA with the resulting duplexes being more thermally stable than the natural DNA/DNA duplex. Other backbone-replaced nucleic acids are well known to those skilled in the art and may also be used in the present invention (see e.g., Uhlmann et al 1993, Methods in Molecular Biology, 20, "Protocols for Oligonucleotides and Analogs," ed. Sudhir Agrawal, Humana Press, NJ, U.S.A., pp. 335).

Identification and Characterization of CD109

The invention includes isolated CD109 nucleic acid molecules and polypeptides. Three preferred sequences are K1 [SEQ ID NO:1 and 2], K1-H7 [SEQ ID NO:5 and 6] and K15 [(SEQ ID NO:9 and 10] and the K1 [SEQ ID NO:3 and 4], K1-H7 [SEQ ID NO:7 and 6], and K15 [SEQ ID NO:11 and 12] variants. The CD109 is preferably mammalian, and more preferably human. No isolated CD109 nucleic acid molecules or polypeptides were known prior to this invention. The invention also includes a host cell transformed with a CD109 recombinant nucleic acid molecule and a recombinant isolated CD109 protein. The invention includes the recombinant nucleic acid molecules as well as the vectors including these molecules.

The invention includes CD109 nucleic acid molecules and molecules having sequence identity or which hybridize to the CD109 sequences shown in the figures (preferred percentages for sequence identity are described below). The invention also includes CD109 or proteins having sequence identity (preferred percentages described below) to the sequence shown in the figures. The nucleic acid molecules and proteins of the invention may be isolated from a native source, or they may be synthetic or recombinant. The nucleic acid molecules and polypeptides are optionally purified so that they are suitable for administration to humans.

Characterization of Nucleic Acid Molecules and Polypeptides

In one variation, the invention includes DNA sequences including at least one of the sequences shown in the figures in a nucleic acid molecule of preferably about: less than 1000 base pairs, less than 1250 base pairs, less than 1500 base pairs, less than 1750 base pairs, less than 2000 base pairs, less than 2250 base pairs, less than 2500 base pairs, less than 2750 base pairs or less than 3000 base pairs.

Regions of the CD109 nucleic acid molecule are as follows:

TABLE 1a

Clones K1, K1-H7

| Nucleic Acid Molecule | Start Nucleotide [brackets show corresponding amino acid nos.] | End Nucleotide [brackets show corresponding amino acid nos.] |
|---|---|---|
| Coding region only | 1 (1) | 4335 (1445) |
| thioester signature sequence (aa residues 918-924) | 2752 (918) | 2772 (924) |
| thioester reactivity defining hexapeptide motif | 3088 (1030) | 3105 (1035) |
| Bait region | about 1942 (648) | about 2052 (684) |

TABLE 1b

| | Clone K15 | |
|---|---|---|
| Nucleic Acid Molecule | Start Nucleotide [brackets show corresponding amino acid nos.] | End Nucleotide [brackets show corresponding amino acid nos.] |
| Coding region only | 1 (1) | 3201 (1067) |
| thioester signature sequence (aa residues 918-924) | 2752 (918) | 2772 (924) |
| thioester reactivity defining hexapeptide motif | 3088 (1030) | 3105 (1035) |
| Bait region* | about 1942 (648) | about 2052 (684) |

*Note that the exact bait region coordinates are approximate

It will be apparent that these may be varied, for example, by shortening the 5' untranslated region or shortening the nucleic acid molecule so that the 3' end nucleotide is in a different position.

The discussion of the nucleic acid molecules, sequence identity, hybridization and other aspects of nucleic acid molecules included within the scope of the invention is intended to be applicable to either the entire nucleic acid molecule in the figure or its coding region. One may use the entire molecule or only the coding region. Other possible modifications to the sequence are apparent.

We have identified additional CD109 polymorphisms. Based on the numbering system of the CD109 patent, the 3 polymorphisms are as follows.

```
i. codon 792 of [SEQ ID NO:1]
   att to agt; Ile to Ser (isoleucine to serine)

ii. codon 797 of [SEQ ID NO:1]
    aat to agt; Asn to Ser (asparagine to serine)

iii. codon 845 of [SEQ ID NO:1]
     gtc to atc; Val to Ile (valine to isoleucine)
```

These polymorphisms optionally occur in each of the sequences of the invention. The polymorphisms would be expected to modify all of the cDNA and protein sequences (K1, K1 variant, K1-H7, K1-H7 variant, K15, K15 variant).

Functionally Equivalent Nucleic Acid Molecules

The term "isolated nucleic acid" refers to a nucleic acid the structure of which is not identical to that of any naturally occurring nucleic acid or to that of any fragment of a naturally occurring genomic nucleic acid spanning more than three separate genes. The term therefore covers, for example, (a) DNA which has the sequence of part of a naturally occurring genomic DNA molecule; (b) a nucleic acid incorporated into a vector or into the genomic DNA of a prokaryote or eukaryote, respectively, in a manner such that the resulting molecule is not identical to any naturally occurring vector or genomic DNA; (c) a separate molecule such as cDNA, a genomic fragment, a fragment produced by reverse transcription of polyA RNA which can be amplified by PCR, or a restriction fragment; and (c) a recombinant nucleotide sequence that is part of a hybrid gene, i.e., a gene encoding a fusion protein. Specifically excluded from this definition are nucleic acids present in mixtures of (i) DNA molecules, (ii) transfected cells, and (iii) cell clones, e.g., as these occur in a DNA library such as a cDNA or genomic DNA library.

Sequence Identity

This is the first isolation of a nucleic acid molecule encoding a CD109 polypeptide from a human. Nucleic acid sequences having sequence identity to the K1 [SEQ ID NO:1], K1-H7 [SEQ ID NO:2] or K15 [SEQ ID NO:9] sequence or their variants [SEQ ID NO:3, 7 and 11] are found in other mammals. The invention includes methods of isolating these nucleic acid molecules and polypeptides as well as methods of using these nucleic acid molecules and polypeptides according to the methods described in this application.

The invention includes the nucleic acid molecules from other species as well as methods of obtaining the nucleic acid molecules by, for example, screening a cDNA library or other DNA collection with a probe of the invention (such as a probe comprising at least about: 10 or preferably at least 15 or 30 nucleotides of K1 [SEQ ID NO:1], K1-H7 [SEQ ID NO:2] or K15 [SEQ ID NO:9] sequence or their variants [SEQ ID NO:3, 7 and 11] and detecting the presence of a CD109 nucleic acid molecule. Another method involves comparing the K1 [SEQ ID NO:1 to 4], K1-H7 [SEQ ID NO:5 to 8] or K15 [SEQ ID NO:9 to 12] sequence to other sequences, for example using bioinformatics techniques such as database searches or alignment strategies, and detecting the presence of a CD109 nucleic acid molecule or polypeptide. The invention includes the nucleic acid molecule and/or polypeptide obtained according to the methods of the invention. The invention also includes methods of using the nucleic acid molecules, for example to make probes, in research experiments or to transform host cells. These methods are as described below.

The polypeptides encoded by the CD109 nucleic acid molecules in other species will have amino acid sequence identity to the K1 [SEQ ID NO:2], K1-H7 [SEQ ID NO: 6] or K15 [SEQ ID NO:10] sequence or their variants [SEQ ID NO:4, 8 or 12]. Sequence identity may be at least about: >20%, >25%, >28%, >30%, >35%, >40%, >50% to an amino acid sequence shown in the figures (or a partial sequence thereof). Some polypeptides may have a sequence identity of at least about: >60%, >70%, >80% or >90%, more preferably at least about: >95%, >99% or >99.5% to an amino acid sequence in the figures (or a partial sequence thereof). Identity is calculated according to methods known in the art. Sequence identity (nucleic acid and protein) is most preferably assessed by the algorithm of BLAST version 2.1 advanced search. BLAST is a series of programs that are available online from the National Center for Biotechnology Information (NCBI) of the U.S. National Institutes of Health. The advanced blast search is set to default parameters. (ie Matrix BLOSUM62; Gap existence cost 11; Per residue gap cost 1; Lambda ratio 0.85 default).

References to BLAST Searches are:

Altschul, S. F., Gish, W., Miller, W., Myers, E. W. & Lipman, D. J. (1990) "Basic local alignment search tool." J. Mol. Biol. 215:403_410.

Gish, W. & States, D. J. (1993) "Identification of protein coding regions by database similarity search." Nature Genet. 3:266_272.

Madden, T. L., Tatusov, R. L. & Zhang, J. (1996) "Applications of network BLAST server" Meth. Enzymol. 266: 131_141.

Altschul, S. F., Madden, T. L., Schäffer, A. A., Zhang, J., Zhang, Z., Miller, W. & Lipman, D. J. (1997) "Gapped BLAST and PSI_BLAST: a new generation of protein database search programs." Nucleic Acids Res. 25:3389_3402.

Zhang, J. & Madden, T. L. (1997) "PowerBLAST: A new network BLAST application for interactive or automated sequence analysis and annotation." Genome Res. 7:649_656.

The invention also includes modified polypeptides which have sequence identity at least about: >20%, >25%, >28%, >30%, >35%, >40%, >50%, >60%, >70%, >80% or >90% more preferably at least about >95%, >99% or >99.5%, to a CD109 sequence in the figures (or a partial sequence thereof). Modified polypeptide molecules are discussed below. Preferably about: 1, 2, 3, 4, 5, 6 to 10, 10 to 25, 26 to 50 or 51 to 100, or 101 to 250 nucleotides or amino acids are modified.

Nucleic Acid Molecules and Polypeptides Similar to K1, K1-H7 or K15

Those skilled in the art will recognize that the nucleic acid molecule sequences in the figures are not the only sequences, which may be used to provide increased CD109 activity in cells. The genetic code is degenerate so other nucleic acid molecules, which encode a polypeptide identical to an amino acid sequence in the figures, may also be used. The sequences of the other nucleic acid molecules of this invention may also be varied without changing the polypeptide encoded by the sequence. Consequently, the nucleic acid molecule constructs described below and in the accompanying examples for the preferred nucleic acid molecules, vectors, and transformants of the invention are merely illustrative and are not intended to limit the scope of the invention.

The sequences of the invention can be prepared according to numerous techniques. The invention is not limited to any particular preparation means. For example, the nucleic acid molecules of the invention can be produced by cDNA cloning, genomic cloning, cDNA synthesis, polymerase chain reaction (PCR), or a combination of these approaches (Current Protocols in Molecular Biology (F. M. Ausbel et al., 1989)). Sequences may be synthesized using well-known methods and equipment, such as automated synthesizers.

In one variation, the similar sequences are as shown in [SEQ ID NO:3, 7 and 11]. The coding regions correspond to those shown in Table 1 a and 1 b.

Sequence Identity

The invention includes modified nucleic acid molecules with a sequence identity at least about: >17%, >20%, >30%, >40%, >50%, >60%, >70%, >80% or >90% more preferably at least about >95%, >99% or >99.5%, to a DNA sequence in the figures (or a partial sequence thereof). Preferably about 1, 2, 3, 4, 5, 6 to 10, 10 to 25, 26 to 50 or 51 to 100, or 101 to 250 nucleotides or amino acids are modified. Identity is calculated according to methods known in the art. Sequence identity is most preferably assessed by the algorithm of the BLAST version 2.1 program advanced search (parameters as above). For example, if a nucleotide sequence (called "Sequence A") has 90% identity to a portion of the nucleotide sequence in FIG. 1, then Sequence A will be identical to the referenced portion of the nucleotide sequence in FIG. 1, except that Sequence A may include up to 10 point mutations, such as substitutions with other nucleotides, per each 100 nucleotides of the referenced portion of the nucleotide sequence in FIG. 1. Nucleotide sequences functionally equivalent to the K1 [SEQ ID NO:1], K1-H7 [SEQ ID NO:5] or K15 [SEQ ID NO:9] sequence or their variants [SEQ ID NO:3, 7 and 11] can occur in a variety of forms as described below. Polypeptides having sequence identity may be similarly identified.

The polypeptides encoded by the homologous CD109 nucleic acid molecule in other species will have amino acid sequence identity at least about: >20%, >25%, >28%, >30%, >40% or >50% to an amino acid sequence shown in the figures (or a partial sequence thereof). Some species may have polypeptides with a sequence identity of at least about: >60%, >70%, >80% or >90%, more preferably at least about: >95%, >99% or >99.5% to all or part of an amino acid sequence in the figures (or a partial sequence thereof). Identity is calculated according to methods known in the art. Sequence identity is most preferably assessed by the BLAST version 2.1 program advanced search (parameters as above). Preferably about: 1, 2, 3, 4, 5, 6 to 10, 10 to 25, 26 to 50 or 51 to 100, or 101 to 250 nucleotides or amino acids are modified.

The invention includes nucleic acid molecules with mutations that cause an amino acid change in a portion of the polypeptide not involved in providing CD109 activity or an amino acid change in a portion of the polypeptide involved in providing CD109 activity so that the mutation increases or decreases the activity of the polypeptide.

Hybridization

Other functional equivalent forms of the CD109 nucleic acid molecules encoding nucleic acids can be isolated using conventional DNA-DNA or DNA-RNA hybridization techniques. These nucleic acid molecules and the CD109 sequences can be modified without significantly affecting their activity.

The present invention also includes nucleic acid molecules that hybridize to one or more of the sequences in the figures (or a partial sequence thereof) or their complementary sequences, and that encode peptides or polypeptides exhibiting substantially equivalent activity as that of a CD109 polypeptide produced by the DNA in the figures. Such nucleic acid molecules preferably hybridize to all or a portion of CD109 or its complement under low, moderate (intermediate), or high stringency conditions as defined herein (see Sambrook et al. (most recent edition) Molecular Cloning: A Laboratory Manual, Cold Spring Harbor Laboratory Press, Cold Spring Harbor, N.Y.; Ausubel et al. (eds.), 1995, Current Protocols in Molecular Biology, (John Wiley & Sons, NY)). The portion of the hybridizing nucleic acids is typically at least 15 (e.g. 20, 25, 30 or 50) nucleotides in length. The hybridizing portion of the hybridizing nucleic acid is at least 80% e.g. at least 95% or at least 98% identical to the sequence or a portion or all of a nucleic acid encoding a CD109 polypeptide, or its complement. Hybridizing nucleic acids of the type described herein can be used, for example, as a cloning probe, a primer (e.g. a PCR primer) or a diagnostic probe. Hybridization of the oligonucleotide probe to a nucleic acid sample typically is performed under stringent conditions. Nucleic acid duplex or hybrid stability is expressed as the melting temperature or Tm, which is the temperature at which a probe dissociates from a target DNA. This melting temperature is used to define the required stringency conditions. If sequences are to be identified that are related and substantially identical to the probe, rather than identical, then it is useful to first establish the lowest temperature at which only homologous hybridization occurs with a particular concentration of salt (e.g. SSC or SSPE). Then, assuming that 1% mismatching results in a 1 degree Celsius decrease in the Tm, the temperature of the final wash in the hybridization reaction is reduced accordingly (for example, if sequences having greater than 95% identity with the probe are sought, the final wash temperature is decreased by 5 degrees Celsius). In practice, the change in Tm can be between 0.5 degrees Celsius and 1.5 degrees Celsius per 1% mismatch. Low stringency conditions involve hybridizing at about: 1×SSC, 0.1% SDS at 50° C. High stringency conditions are: 0.1×SSC, 0.1% SDS at 65° C. Moderate stringency is about 1×SSC 0.1% SDS at 60 degrees Celsius. The parameters of salt concentration and temperature can be varied to achieve the optimal level of identity between the probe and the target nucleic acid.

The present invention also includes nucleic acid molecules from any source, whether modified or not, that hybridize to genomic DNA, cDNA, or synthetic DNA molecules that encode the amino acid sequence of a CD109 polypeptide, or genetically degenerate forms, under salt and temperature conditions equivalent to those described in this application, and that code for a peptide, or polypeptide that has CD109 activity. Preferably the polypeptide has the same or similar activity as that of a CD109 polypeptide. A nucleic acid molecule described above is considered to be functionally equivalent to a CD109 nucleic acid molecule (and thereby having CD109 activity) of the present invention if the polypeptide encoded by the nucleic acid molecule is recognized in a specific manner by a CD109-specific antibody, including—but not restricted to—the antibodies listed in this application.

The invention also includes nucleic acid molecules and polypeptides having sequence similarity taking into account conservative amino acid substitutions. Sequence similarity (and preferred percentages) is discussed below.

Modifications to Nucleic Acid Molecule or Polypeptide Sequence

Changes in the nucleotide sequence which result in production of a chemically equivalent or chemically similar amino acid sequences are included within the scope of the invention. Variants of the polypeptides of the invention may occur naturally, for example, by mutation, or may be made, for example, with polypeptide engineering techniques such as site directed mutagenesis, which are well known in the art for substitution of amino acids. For example, a hydrophobic residue, such as glycine can be substituted for another hydrophobic residue such as alanine. An alanine residue may be substituted with a more hydrophobic residue such as leucine, valine or isoleucine. A negatively charged amino acid such as aspartic acid may be substituted for glutamic acid. A positively charged amino acid such as lysine may be substituted for another positively charged amino acid such as arginine.

Therefore, the invention includes polypeptides having conservative changes or substitutions in amino acid sequences. Conservative substitutions insert one or more amino acids, which have similar chemical properties as the replaced amino acids. The invention includes sequences where conservative substitutions are made that do not destroy CD109 activity.

Polypeptides comprising one or more d-amino acids are contemplated within the invention. Also contemplated are polypeptides where one or more amino acids are acetylated at the N-terminus. Those of skill in the art recognize that a variety of techniques are available for constructing polypeptide mimetics with the same or similar desired CD109 activity as the corresponding polypeptide compound of the invention but with more favorable activity than the polypeptide with respect to solubility, stability, and/or susceptibility to hydrolysis and proteolysis. See, for example, Morgan and Gainor, Ann. Rep. Med. Chem., 24:243-252 (1989). Examples of polypeptide mimetics are described in U.S. Pat. No. 5,643,873. Other patents describing how to make and use mimetics include, for example in, U.S. Pat. No. 5,786,322, U.S. Pat. No. 5,767,075, U.S. Pat. No. 5,763,571, U.S. Pat. No. 5,753,226, U.S. Pat. No. 5,683,983, U.S. Pat. No. 5,677,280, U.S. Pat. No. 5,672,584, U.S. Pat. No. 5,668,110, U.S. Pat. No. 5,654,276, U.S. Pat. No. 5,643,873. Mimetics of the polypeptides of the invention may also be made according to other techniques known in the art. For example, by treating a polypeptide of the invention with an agent that chemically alters a side group by converting a hydrogen group to another group such as a hydroxy or amino group. Mimetics preferably include sequences that are either entirely made of amino acids or sequences that are hybrids including amino acids and modified amino acids or other organic molecules.

For example, one may modify the bait region to obtain variants with altered substrate specificity. One may also modify the hexapeptide region to alter thioester reactivity.

The invention also includes hybrid nucleic acid molecules and polypeptides, for example where a CD109 nucleotide sequence from one species is combined with a nucleotide sequence from a sequence of plant, mammal, bacteria or yeast to encode a fusion polypeptide. The invention includes a fusion protein having at least two components, wherein a first component of the fusion protein comprises a polypeptide of the invention, preferably a full length CD109 polypeptide (or a portion thereof, see below). The second component of the fusion protein preferably comprises a tag, for example GST, an epitope tag or an enzyme. The fusion protein may also comprise a histochemical or cytochemical marker such as lacZ, alkaline phosphatase, or horseradish perxidase, or a fluorescent marker such as GFP or one of its derivatives.

The invention also includes polypeptide fragments of the polypeptides of the invention which may be used to confer CD109 activity if the fragments retain activity. The invention also includes polypeptides fragments of the polypeptides of the invention which may be used as a research tool to characterize the polypeptide or its activity. Such polypeptides preferably consist of at least 5 amino acids. In preferred embodiments, they may consist of 6 to 10, 11 to 15, 16 to 25, 26 to 50, 51 to 75, 76 to 100 or 101 to 250 amino acids of the polypeptides of the invention (or longer amino acid sequences). The fragments preferably have CD109 activity. Fragments may include sequences with one or more amino acids removed, for example, C-terminus amino acids in a CD109 sequence.

The invention also includes a composition comprising all or part of an isolated nucleic acid molecule (preferably K1 [SEQ ID NO:1], K1-H7 [SEQ ID NO:5] or K15 [SEQ ID NO:9] sequence or their variants [SEQ ID NO:3, 7 and 11]) of the invention with or without a carrier, preferably in a composition for cell transformation. The invention also includes a composition comprising an isolated CD109 polypeptide (preferably K1 [SEQ ID NO:2], K1-H7 [SEQ ID NO: 6] or K15 [SEQ ID NO:10] or their variants [SEQ ID NO:4, 8 or 12] with or without a carrier, preferably for studying or modulating polypeptide activity.

Recombinant Nucleic Acid Molecules

The invention also includes recombinant nucleic acid molecules, preferably a K1 [SEQ ID NO:1], K1-H7 [SEQ ID NO:5] or K15 [SEQ ID NO:9] sequence or their variants [SEQ ID NO:3, 7, or 11] of the figures comprising a nucleic acid molecule of the invention and a promoter sequence, operatively linked so that the promoter enhances transcription of the nucleic acid molecule in a host cell (the nucleic acid molecules of the invention may be used in an isolated native gene or a chimeric gene, for example, where a nucleic acid molecule coding region is connected to one or more heterologous sequences to form a gene. The promoter sequence is preferably a constitutive promoter sequence or an inducible promoter sequence, operatively linked so that the promoter enhances transcription of the DNA molecule in a host cell. The promoter may be of a type not naturally associated with the cell such as a super promoter, a chemical or drug inducible promoter, a steroid-inducible promoter and a tissue specific promoter. The CMV and SV40 promoters are commonly used to express desired polypeptide in mammalian cells. Other promoters known in the art may also be used (many suitable promoters and vectors are described in the applications and patents referenced in this application). Tissue-specific promoters could include the vav or H2K promoters (all hematopoietic cells), PF4 or GP1b promoters (megakaryocytes and platelets), or the lck, CD2, or granzymeB promoters (T lymphocytes), and many others. Non-tissue specific promoters could include Beta actin, PGK, or CMV promoters, or retroviral LTRs, and many others. Inducible promoters could include the metallothionenin IIA promoter, or ecdysone inducible or tetracycline inducible or repressible promoters, among many others.

A recombinant nucleic acid molecule for conferring CD109 activity may also contain suitable transcriptional or translational regulatory elements. Suitable regulatory elements may be derived from a variety of sources, and they may be readily selected by one with ordinary skill in the art (Sambrook, J, Fritsch, E. E. & Maniatis, T. (most recent edition). Molecular Cloning: A laboratory manual. Cold Spring Harbor Laboratory Press. New York; Ausubel et al. (Most Recent Edition) Current Protocols in Molecular Biology, John Wiley & Sons, Inc.). For example, if one were to upregulate the expression of the nucleic acid molecule, one could insert a sense sequence and the appropriate promoter into the vector. If one were to downregulate the expression of the nucleic acid molecule, one could insert the antisense sequence and the appropriate promoter into the vehicle. Examples of regulatory elements include: an enhancer or RNA polymerase binding sequence, a terminator region, a ribosomal binding sequence, including a translation initiation signal. The regulatory elements described above may be from animal, plant, yeast, bacteria, fungus, virus or other sources, including synthetically produced elements and mutated elements. Additionally, depending on the vector employed, other genetic elements, such as selectable markers, may be incorporated into the recombinant molecule. Markers facilitate the selection of a transformed host cell. Such markers include genes associated with temperature sensitivity, drug resistance, or enzymes associated with phenotypic characteristics of the host organisms.

Methods of modifying DNA and polypeptides, preparing recombinant nucleic acid molecules and vectors, transformation of cells, expression of polypeptides are known in the art. For guidance, one may consult the following U.S. Pat. Nos. 5,840,537, 5,850,025, 5,858,719, 5,710,018, 5,792,851, 5,851,788, 5,759,788, 5,840,530, 5,789,202, 5,871,983, 5,821,096, 5,876,991, 5,422,108, 5,612,191, 5,804,693, 5,847,258, 5,880,328, 5,767,369, 5,756,684, 5,750,652, 5,824,864, 5,763,211, 5,767,375, 5,750,848, 5,859,337, 5,563,246, 5,346,815, and WO9713843. Many of these patents also provide guidance with respect to experimental assays, probes and antibodies, methods, transformation of host cells, which are described below. These patents, like all other patents, publications (such as articles and database publications) in this application, are incorporated by reference in their entirety.

Host Cells Including a CD109 Nucleic Acid Molecule

Levels of nucleic acid molecule expression may be controlled with nucleic acid molecules or nucleic acid molecule fragments that code for sense or anti-sense RNA. In a preferred embodiment of the invention, a cell (preferably a human cell) is transformed with a nucleic acid molecule of the invention or a fragment of a nucleic acid molecule inserted in a vector. The expression host may be any cell capable of expressing CD109, such as a cell selected from the group consisting of a mammalian cell, bacterium, yeast, fungus, protozoa or algae.

Another embodiment of the invention relates to the method of transforming a host cell with a nucleic acid molecule of the invention or a fragment of a nucleic acid molecule, inserted in a vector. The invention also includes the vector comprising a nucleic acid molecule of the invention. The nucleic acid molecules can be cloned into a variety of vectors by means that are well known in the art. The recombinant nucleic acid molecule may be inserted at a site in the vector created by restriction enzymes. A number of suitable vectors may be used, including cosmids, plasmids, bacteriophage, baculoviruses and viruses. Suitable vectors are capable of reproducing themselves and transforming a host cell. The invention also relates to a method of expressing polypeptides in the host cells.

Host cells may be cultured in conventional nutrient media. The media may be modified as appropriate for inducing promoters, amplifying genes or selecting transformants. The culture conditions, such as temperature, composition and pH will be apparent. After transformation, transformants may be identified on the basis of a selectable phenotype. A selectable marker in the vector can confer a selectable phenotype.

Methods known in the art, including but not limited to electroporation, calcium phosphate or chloroquine transfection, viral infection, microinjection, and the use of cationic lipid and lipid/amino acid complexes, or of liposomes, or a large variety of other commercially available, and readily synthesized transfection adjuvants, are useful to transfer a CD109 nucleic acid molecule into host cells. The invention also includes a method for constructing a host cell capable of expressing a nucleic acid molecule of the invention, the method comprising introducing into said host cell a vector of the invention. The genome of the host cell may or may not also include a functional CD109 gene. The invention also includes a method for expressing a CD109 polypeptide such as a K1 [(SEQ ID NO:2], K1-H7 [SEQ ID NO: 6] or K15 [SEQ ID NO:10] or their variants [SEQ ID NO:4, 8 or 12] in the host cell, the method comprising culturing the host cell in a culture medium under conditions suitable for gene expression so that the polypeptide is expressed. The process preferably further includes recovering the polypeptide from the cells or culture medium.

Antisense Technology for Inhibition of CD109

To reduce the abundance and thus the activity of the target protein, coding sequences typically obtained from cDNAs are expressed in the reverse orientation in transgenic cells so that the resultant RNA generated is complementary to the endogenous mRNA encoding the target protein. The binding of these two RNAs inhibits the translation of the target mRNA, thereby blocking or reducing the synthesis of the corresponding protein. Expression of the antisense RNA is usually accomplished using vectors that contain highly active promoter sequences, which synthesize an abundance of the antisense RNA. Patents that describe various uses and modifications of antisense technology include: U.S. Pat. Nos. 6,133, 246, 6,096,722, 6,040,296, 5,801,159 and 5,739,119.

The nucleotide sequence encoding the antisense RNA molecule can theoretically be of any length, providing that the antisense RNA molecule transcribable therefrom is sufficiently long so as to be able to form a complex with a sense mRNA molecule encoding a CD109 polypeptide. The antisense RNA molecule complexes with the mRNA encoding the polypeptide and thereby reduces the half-life of the CD109 mRNA, and/or inhibits or reduces the synthesis of CD109. As a consequence of this interference by the antisense RNA, the activity of the CD109 polypeptides is decreased. The antisense RNA preferably comprises a sequence that is complementary to a portion of the coding sequence for CD109 shown in the figures, or a portion thereof, or preferably comprises a sequence having at least 20%, 30%, 40%, 50%, 60%, 70%, 80%, 90% or 95% sequence identity to CD109 shown in the figures, or a portion thereof (sequence identity is determined as described above). The sequence may include the 5'-terminus, be downstream from the 5'-terminus, or may cover all or only a portion of the non-coding region, may bridge the non-coding and coding region, be complementary to all or part of the coding region, be complementary to the 3'-terminus of the coding region, or be complementary to the 3'-untranslated region of the mRNA. The particular site(s) to which the anti-sense sequence binds and the length of the anti-sense sequence will vary, for example, depending upon the degree of inhibition desired, the uniqueness of the sequence, and the stability of the anti-sense sequence.

The sequence may be a single sequence or a repetitive sequence having two or more repetitive sequences in tandem, where the single sequence may bind to a plurality of messenger RNAs. The antisense sequence may be complementary to a unique sequence or a repeated sequence, so as to enhance the probability of binding. The antisense sequence may be involved with the binding of a unique sequence, a single unit of a repetitive sequence or of a plurality of units of a repetitive sequence. In some instances, rather than providing for homoduplexing, heteroduplexing may be employed, where the same sequence may provide for inhibition of a plurality of messenger RNAs by having regions complementary to different messenger RNAs. The antisense sequence may also contain additional nucleotide sequence unrelated to the sequence encoding CD109. This unrelated sequence may be flanked on one or both sides by CD109-related sequence, or may be located at one or both ends of the CD109-related sequence. The transcriptional construct will preferably include, in the direction of transcription, a transcriptional initiation region, the sequence coding for the antisense RNA on the sense strand, and a transcriptional termination region.

The DNA encoding the antisense RNA can vary in length from less than 20 nucleotides in length, up to about the length of the corresponding mRNA produced by the cell. For example, the length of the DNA encoding the antisense RNA can be from less than 20 to 1500, 2000, 3000, or more, nucleotides in length. The anti-sense sequence complementary to a portion of the sequence of the messenger RNA will usually be at least about less than 20, 20, 30, 50, 75 or 100 nucleotides or more, and often being fewer than about 1000 nucleotides in length. The preferred source of antisense RNA for DNA constructs of the present invention is DNA that is complementary to a full length CD109, or fragments thereof. DNA showing substantial sequence identity to the complement of CD109 or fragments thereof is also useful, and is encompassed by this invention.

Suitable promoters are described elsewhere in this application and known in the art. The promoter gives rise to the transcription of a sufficient amount of the antisense RNA molecule at a rate sufficient to cause a reduction of CD109 protein in cells. The required amount of antisense RNA to be transcribed may vary from cell to cell. Other regulatory elements described in this application, such as enhancers and terminators may also be used. The invention also includes a vector, such as a plasmid or virus encompassing the antisense DNA.

The invention includes the cells (for example, the cells of the species listed above) containing the antisense sequence. The invention further provides tissues comprising such cells and the progeny of such cells, which contain the DNA sequence stably incorporated and hereditable.

The invention also includes the use of a sequence according to the invention, in the production of cells having a modified CD109 content. By "modified CD109 content" is meant a cell, which exhibits non wild-type levels of CD109 due to inhibited or reduced expression of CD109.

The invention still further provides a method of inhibiting or reducing expression of a CD109 polypeptide in cells, comprising introducing into such cells a nucleic acid molecule according to the invention, such as CD109 antisense DNA, or a vector containing such DNA. In one example, the invention includes a method for reducing expression of a nucleic acid molecule encoding a CD109 polypeptide, such as CD109, comprising: a) integrating into the genome of a cell, or expressing transiently within the cell without integration, a nucleic acid molecule complementary to all or part of endogenous CD109 mRNA; and b) growing the transformed cell, so that the complementary nucleic acid molecule is transcribed and binds to the CD109 mRNA, thereby reducing expression of the nucleic acid molecule encoding the CD109 polypeptide, and thereby resulting in reduced CD109 synthesis. Typically, the amount of RNA transcribed from the complementary strand is less than the amount of the mRNA endogenous to the cell.

The antisense DNA may also comprise a nucleic acid molecule encoding a marker polypeptide, the marker polypeptide also operably linked to a promoter.

Fragments/Probes

Preferable fragments include 10 to 50, 50 to 100, 100 to 250, 250 to 500, 500 to 1000, 1000 to 1500, or 1500 or more nucleotides of a nucleic acid molecule of the invention. A fragment may be generated by removing one or more nucleotides from a sequence in the figures (or a partial sequence thereof). Fragments may or may not encode a polypeptide having CD109 activity.

The nucleic acid molecules of the invention (including a fragment of a sequence in the figures (or a partial sequence thereof) can be used as probes to detect nucleic acid molecules according to techniques known in the art (for example, see U.S. Pat. Nos. 5,792,851 and 5,851,788; E. S. Kawasaki (1990), In Innis et al., Eds., PCR Protocols, Academic Press, San Diego, Chapter 3 re PCR and reverse transcriptase). The probes may be used to detect nucleic acid molecules that encode polypeptides similar to the polypeptides of the invention. For example, a probe having at least about 10 bases will hybridize to similar sequences under stringent hybridization conditions (Sambrook et al. 1989, Molecular Cloning, A Laboratory Manual, Cold Spring Harbor). Polypeptide fragments of K1 [SEQ ID NO:2], K1-H7 [SEQ ID NO: 6] or K15 [SEQ ID NO:10] or their variants [SEQ ID NO:4, 8 or 12] are preferably at least 8 amino acids in length and are useful, for example, as immunogens for raising antibodies that will bind to intact protein (immunogenic fragments). Typically the average length used for synthetic peptides is 8-16, 8 being the minimum, however 12 amino acids is commonly used. Cloning and expression of the DNA assess the activity of the polypeptide encoded by the nucleic acid molecule. After the expression product is isolated the polypeptide is assayed for activity as described in this application.

Enhancement of CD109 Polypeptide Activity

The activity of the CD109 polypeptide is increased or decreased by carrying out selective site-directed mutagenesis. Using protein modeling and other prediction methods, we characterize the binding domain and other critical amino acid residues in the polypeptide that are candidates for mutation, insertion and/or deletion. A DNA plasmid or expression vector containing the CD109 nucleic acid molecule or a nucleic acid molecule having sequence identity is preferably used for these studies using the U.S.E. (Unique site elimination) mutagenesis kit from Pharmacia Biotech or other mutagenesis kits that are commercially available, or using PCR. Once the mutation is created and confirmed by DNA sequence analysis, the mutant polypeptide is expressed using an expression system and its activity is monitored. This approach is useful not only to enhance activity, but also to engineer some functional domains for other properties useful in the purification or application of the polypeptides or the addition of other biological functions. It is also possible to synthesize a DNA fragment based on the sequence of the polypeptides that encodes smaller polypeptides that retain activity and are easier to express. It is also possible to modify the expression of the cDNA so that it is induced under desired environmental conditions or in response to different chemical inducers or hormones. It is also possible to modify the DNA sequence so that the polypeptide is targeted to a different location. All these modifications of the DNA sequences presented in this application and the polypeptides produced by the modified sequences are encompassed by the present invention.

Pharmaceutical Compositions

The CD109 nucleic acid molecule or its polypeptide and functional equivalent nucleic acid molecules or polypeptides are useful when used alone, but are also useful when combined with other components such as a carrier in a pharmaceutical composition.

CD109 is expressed on hematopoietic stem and progenitor cells, endothelial cells, and activated platelets and T cells, and s capable of covalent substrate binding and protease inhibition. CD109 is useful as a protease inhibitor. All or part of CD109 may be administered to a subject, such as a human, in soluble form as a therapeutic modulator of endothelial or of platelet function, of the blood coagulation (as an anticoagulant) or fibrinolytic systems, or of immune function, including T cell effector function, antigen presentation, and complement activation. Specifically, pharmaceutical compositions of this invention are used to treat patients having degenerative diseases, disorders or abnormal physical states, including but not limited to conditions associated with endothelial activation, platelet activation, activation of the coagulation or fibrinolytic systems, and activation of T lymphocytes, the complement system, and the immune system. Specifically, such disorders may include (but are not limited to) cardiovascular disorders including stroke, myocardial infarction, thrombosis, and embolism, and peripheral vascular disease; disorders associated with quantitative or qualitative abnormalities of platelet function, including thrombocytopenia, thrombocythemia, and conditions associated with increased or impaired platelet aggregation and activation; conditions associated with increased or impaired activation of the coagulation and/or fibrinolytic systems; and conditions associated with impaired or increased immune activation, including autoimmune diseases as well as organ and bone marrow transplantation. CD109 peptide and protein reagents may be used not only for the treatment of such conditions, but also for their diagnosis and prevention.

The CD109 compositions are useful when administered in methods of medical treatment, prevention, or diagnosis of a disease, disorder or abnormal physical state characterized by insufficient CD109 expression or inadequate levels or activity of CD109 polypeptide by increasing expression, concentration or activity. The invention also includes methods of medical treatment, prevention, diagnosis, of a disease, disorder or abnormal physical state characterized by excessive CD109 expression or levels or activity of CD109 polypeptide, for example by administering a pharmaceutical composition, possibly including a carrier and a vector, that expresses CD109 antisense DNA, or a vector that expresses an inactive mutant or variant form of CD109, or by the administration of CD109 specific antibodies that interfere with CD109 activity, or lead to decreased CD109 levels. The invention also includes measurement of cell associated or soluble CD109 levels for diagnostic follow up and risk assessment or prognostic information purposes. For example, one may monitor progression of autoimmune disease or responses to organ transplantation. The invention also includes methods of medical treatment, prevention, or diagnosis of a disease, disorder or abnormal physical state characterized by neither increased nor reduced CD109 expression or levels or activity of CD109 polypeptide, but in which the modulation of CD109 levels or activity may be of therapeutic, preventive, or of diagnostic value. An agent that upregulates CD109 gene expression or CD109 polypeptide activity may be combined with a carrier to form a pharmaceutical composition. An agent that downregulates CD109 expression or CD109 polypeptide activity may be combined with a carrier to form a pharmaceutical composition.

The pharmaceutical compositions can be administered to humans or animals by a variety of methods including, but not restricted to topical administration, oral administration, aerosol administration, intratracheal instillation, intraperitoneal injection, injection into the cerebrospinal fluid, and intravenous injection in methods of medical treatment involving upregulating or downregulating CD109 gene or polypeptide levels or activity. Dosages to be administered depend on patient needs, on the desired effect and on the chosen route of administration. Nucleic acid molecules and polypeptides may be introduced into cells using in vivo delivery vehicles such as liposomes. They may also be introduced into these cells using physical techniques such as microinjection and electroporation or chemical methods such as coprecipitation or using liposomes.

The pharmaceutical compositions can be prepared by known methods for the preparation of pharmaceutically acceptable compositions which can be administered to patients, and such that an effective quantity of the nucleic acid molecule or polypeptide is combined in a mixture with a pharmaceutically acceptable vehicle. Suitable vehicles are described, for example in Remington's Pharmaceutical Sciences (Remington's Pharmaceutical Sciences, Mack Publishing Company, Easton, Pa., USA).

On this basis, the pharmaceutical compositions could include an active compound or substance, such as a CD109 nucleic acid molecule or polypeptide, in association with one or more pharmaceutically acceptable vehicles or diluents, and contained in buffered solutions with a suitable pH and isoosmotic with the physiological fluids. The methods of combining the active molecules with the vehicles or combining them with diluents is well known to those skilled in the art. The composition could include a targeting agent for the transport of the active compound to specified sites within tissue.

Administration of CD109 Nucleic Acid Molecule by Gene Therapy

Since persons suffering from disease, disorder or abnormal physical state can be treated by either up or down regulation of CD109, gene therapy to increase or reduce CD109 expression is useful to modify the development/progression of disease. For example, to treat a hypercoagulable state, gene therapy (for example, targeting CD109 expression to endothelial or blood cells) could be used to enhance CD109 anticoagulant activity, thereby decreasing the propensity for blood clot formation.

The invention also includes methods and compositions for providing gene therapy for treatment of diseases, disorders or abnormal physical states characterized by insufficient CD109 expression or inadequate levels or activity of CD109 polypeptide (see the discussion of pharmaceutical compositions, above) involving administration of a pharmaceutical composition of the invention. The invention also includes methods and compositions for providing gene therapy for treatment of diseases, disorders or abnormal physical states characterized by excessive CD109 expression or levels of activity of CD109 polypeptide involving administration of a pharmaceutical composition.

The invention includes methods and compositions for providing a nucleic acid molecule encoding CD109 or functional equivalent nucleic acid molecule to the cells of an individual such that expression of CD109 in the cells provides the biological activity or phenotype of CD109 polypeptide to those cells. Sufficient amounts of the nucleic acid molecule are administered and expressed at sufficient levels to provide the biological activity or phenotype of CD109 polypeptide to the cells. For example, the method can preferably involve a method of delivering a nucleic acid molecule encoding CD109 to the cells of an individual having a disease, disorder or abnormal physical state, comprising administering to the individual a vector comprising DNA encoding CD109. The method may also relate to a method for providing an individual having a disease, disorder or abnormal physical state with biologically active CD109 polypeptide by administering DNA encoding CD109. The method may be performed ex vivo or in vivo. Methods and compositions for administering CD109 (including in gene therapy) are explained, for example, in U.S. Pat. Nos. 5,672,344, 5,645,829, 5,741,486, 5,656,465, 5,547,932, 5,529,774, 5,436,146, 5,399,346 and 5,670,488, 5,240,846 which are incorporated by reference in their entirety.

The method also relates to a method for producing a stock of recombinant virus by producing virus suitable for gene therapy comprising DNA encoding CD109. This method preferably involves transfecting cells permissive for virus replication (the virus containing the nucleic acid molecule) and collecting the virus produced.

The invention also includes methods and compositions for providing a nucleic acid molecule encoding an antisense sequence to CD109 such that expression of the sequence prevents CD109 biological activity or phenotype or reduces CD109. The methods and compositions can be used in vivo or in vitro. Sufficient amounts of the nucleic acid molecule are administered and expressed at sufficient levels to reduce the biological activity or phenotype of CD109 polypeptide in the cells. Similar methods as described in the preceding paragraph may be used with appropriate modifications.

The methods and compositions can be used in vivo or in vitro. The invention also includes compositions (preferably pharmaceutical compositions for gene therapy). The compositions include a vector containing CD109. The carrier may be a pharmaceutical carrier or a host cell transformant including the vector. Vectors known in the art include but are not restricted to retroviruses, adenoviruses, adeno associated virus (AAV), herpes virus vectors, such as vaccinia virus vectors, HIV and lentivirus-based vectors, and plasmids. The invention also includes packaging and helper cell lines that are required to produce the vector. Methods of producing the vector and methods of gene therapy using the vector are also included with the invention.

The invention also includes a transformed cell, such as a blood cell containing the vector and the recombinant CD109 nucleic acid molecule sense or antisense sequences.

Heterologous Expression of CD109

Expression vectors are useful to provide high levels of polypeptide expression. Cell cultures transformed with the nucleic acid molecules of the invention are useful as research tools particularly for studies of CD109. Cell cultures are used in overexpression and research according to numerous techniques known in the art. For example, a cell line (either an immortalized cell culture or a primary cell culture) may be transfected with a vector containing a CD109 nucleic acid molecule (or molecule having sequence identity) to measure levels of expression of the nucleic acid molecule and the activity of the nucleic acid molecule and polypeptide. A polypeptide of the invention may be used in an assay to identify compounds that bind the polypeptide (assays may be adopted, for example, from U.S. Pat. No. 5,851,788). Methods known in the art may be used to identify agonists and antagonists of the polypeptides. One may obtain cells that do not express CD109 endogenously and use them in experiments to assess CD109 nucleic acid molecule expression. Experimental groups of cells may be transfected with vectors containing different types of CD109 nucleic acid molecules (or nucleic acid molecules having sequence identity to CD109 or fragments of CD109 nucleic acid molecule) to assess the levels of polypeptide produced, its functionality and the phenotype of the cells produced. Other expression systems can also be utilized to overexpress the CD109 in recombinant systems. The polypeptides are also useful for in vitro analysis of CD109 activity. For example, the polypeptide produced can be used for microscopy or X-ray crystallography studies, and the tertiary structure of individual domains may be analyzed by NMR spectroscopy.

Experiments may be performed with cell cultures or in vivo to identify polypeptides that bind to different domains of CD109. One could also target thioester domains, such as the thioester signature sequence or the hexapeptide motif. For example, thioester activity could be blocked to study the effects on CD109. Another example is blocking the membrane domain to prevent membrane localization of CD109. Similar approaches could be taken to study other polypeptide domains or motifs.

Preparation of Antibodies

The invention includes an isolated antibody immunoreactive with a polypeptide of the invention. Antibodies are preferably generated against epitopes of native K1 [SEQ ID NO:2], K1-H7 [SEQ ID NO:6] or K15 [SEQ ID NO:10] or their variants [SEQ ID NO:4, 8 or 12] or synthetic peptides of K1 [SEQ ID NO:2], K1-H7 [SEQ ID NO:6] or K15 [SEQ ID NO:10] or their variants [SEQ ID NO:4, 8, or 12]. The antibody may be labeled with a detectable marker or unlabeled. The antibody is preferably a monoclonal antibody or a polyclonal antibody. CD109 antibodies can be employed to screen organisms containing CD109 polypeptides. The antibodies are also valuable for immuno-purification of polypeptides from crude extracts. For example, one may contact a biological sample with the antibody under conditions allowing the formation of an immunological complex between the antibody and a polypeptide recognized by the antibody and detecting the presence or absence of the immunological complex whereby the presence of CD109 or a similar polypeptide is detected in the sample. The invention also includes compositions preferably including the antibody, a medium suitable for the formation of an immunological complex between the antibody and a polypeptide recognized by the antibody and a reagent capable of detecting the immunological complex to ascertain the presence of CD109 or a similar polypeptide.

To recognize CD109, one may generate antibodies against a range of unique epitopes throughout the molecule. To block activity of CD109, one could generate antibodies that target the thioester signature sequence, or the thioester reactivity defining hexapeptide motif, to block thioester activity, or the bait region, to block initial proteolytic activation of CD109. In addition, these antibodies, or other antibodies directed against other CD109 epitopes could block CD109 activity by leading to enhanced. CD109 clearance/degradation, with a concomitant decrease in CD109 activity.

Monoclonal and polyclonal antibodies are prepared according to the description in this application and techniques known in the art. For examples of methods of the preparation and uses of monoclonal antibodies, see U.S. Pat. Nos. 5,688,681, 5,688,657, 5,683,693, 5,667,781, 5,665,356, 5,591,628, 5,510,241, 5,503,987, 5,501,988, 5,500,345 and 5,496,705 that are incorporated by reference in their entirety. Examples of the preparation and uses of polyclonal antibodies are disclosed in U.S. Pat. Nos. 5,512,282, 4,828,985, 5,225,331 and 5,124,147 which are incorporated by reference in their entirety.

The invention also includes methods of using the antibodies. For example, the invention includes a method for detecting the presence of a CD109 polypeptide such as K1 [SEQ ID NO:2], K1-H7 [SEQ ID NO:6] or K15 [SEQ ID NO:10] or their variants [SEQ ID NO:4, 8 or 12], by: a) contacting a sample containing one or more polypeptides with an antibody of the invention under conditions suitable for the binding of the antibody to polypeptides with which it is specifically reactive; b) separating unbound polypeptides from the antibody; and c) detecting antibody which remains bound to one or more of the polypeptides in the sample.

Identification of Epitopes and Purification of Hematopoietic Stem Cells

The sequences of the invention are used to map the epitopes recognized by anti-CD109 antibodies (see Table 3), including but not restricted to 8A3, 23/5F6, 39/6C3, TEA2/16, D2, LDA1, 7D1, 40B8, 1B3, 59D6, 8A1, 7C5, and B-E47. Identification of these epitopes allows the production of competing antibody-specific peptides that are useful for eluting CD109 selected cells from anti-CD109-based immuno-affinity matrices.

To date, existing CD109 antibodies are known to recognize at least five distinct epitopes that have been mapped as follows:

The simplest method demonstrates whether various antibodies recognize the same or distinct epitopes. This method determines whether unlabelled monoclonal antibodies available are able to block the binding of labelled antibodies. For example, an unlabelled antibody that recognizes the same epitope as a labelled antibody will block binding of the labelled antibody to the surface of a cell expressing the antigen of interest. Thus, decreased label will be found to bind to the cell. In contrast, an unlabelled antibody that does not bind to the same epitope will not inhibit the binding of the labelled antibody. A related method involves assessing whether the binding of distinct labelled antibodies to the target cell is additive. If the binding of two antibodies together (as determined by measuring cell-associated label) is greater than that of either antibody used individually, the two antibodies likely recognize distinct, non-overlapping epitopes. If the binding of two antibodies together (as determined by measuring cell-associated label) is greater than that of either antibody used individually, but is less than would be expected by adding the individual binding of the two antibodies together, then the two antibodies likely recognize distinct but closely apposed epitopes.

Using such techniques with biotinylated- or phycoerythrin-conjugated antibodies, we have performed epitope-mapping studies on several of the assigned CD109 antibodies.

We have determined that there exist at least five discrete CD109 epitopes recognized by different CD109 antibodies:

TABLE 2

| | Epitope | | | | |
|---|---|---|---|---|---|
| | I | II | III* | IV | V |
| clone | 7D1 | 8A3, 7C5 | 8A1 | 40B8 | 1B3 |

Additionally, clones LDA1, Tea2/16, and 59D6 recognize epitopes distinct from epitope II
*Epitope III is close to epitope II.

The invention includes methods of identifying such antibody-specific CD109 peptides for competitively binding to a CD109 antibody in the presence of CD109+ cells, including: (a) providing peptide fragments of [SEQ ID NO:2, 4, 6 or 8] (for example 5-10, 10-15 or 15-20 amino acid sequences); and (b) determining whether the fragments competitively bind to the CD109 antibody. Several approaches to defining such peptides are known according to techniques known in the art. Methods for identifying such peptides include, but are not restricted to, the following:

In one approach, polypeptides corresponding to overlapping CD109 cDNA subfragments are evaluated for antibody binding. Antibody specific peptides are identified by the sequential generation and expression of progressively smaller cDNA fragments, and ultimately by the synthesis of specific peptides. The ability of minimal binding peptides to block antibody binding to recombinant and native CD109 and CD109 expressing cells, and the ability of such peptides to elute CD109 and CD109 expressing cells from anti-CD109-based immuno-affinity matrices is then confirmed.

In an alternate approach, CD109 antibody specific peptides are identified by a phage-display, bacterial display or by an analogous CD109 cDNA expression library selection method, with the specificity of the resultant peptides evaluated as above. A phage display library is made from the cDNA encoding the molecule of choice such that each phage in the library expresses a cDNA fragment encoding a small peptide (6 amino acids, for example) portion of the molecule of interest. Overall, the entire library comprises a series of overlapping cDNA fragments such that the corresponding overlapping peptides represent the entire molecule. The phage library is then panned on a series of petri dishes, each pre-coated with one of the antibody clones. Phage expressing the appropriate hexapeptide recognised by the particular antibody clone become bound to the dish, while the rest can be washed away. After a series of similar panning/recloning steps, DNA from the cloned phage is sequenced to determine which fragment of the original cDNA it contains, and which amino acid sequence it encodes. By comparison with the overall cDNA, the precise location of the epitope can be mapped. In a related method, the phage library does not correspond directly to the cDNA of interest, but rather is composed of random cDNA fragments of defined size that encode random peptides. Screening and analysis is as above. Synthetic peptides are also screened directly by a similar approach. More recently, the ability to map antibody-specific epitopes by mass spectrography and with the use of biosensors has also been described.

References to Epitope Mapping:

Westerlund-Wikstrom B. et al. Peptide display on bacterial flagella: principles and applications. Int. J. Med. Microbiol. July 2000; 290(3):223-30.

Reineke U, et al. Antigen sequence- and library-based mapping of linear and discontinuous protein-protein-interaction sites by spot synthesis. Curr Top Microbiol. Immunol. 1999; 243:23-36.

DeLisser H M. Epitope mapping. Methods Mol Biol. 1999; 96:11-20.

Van Regenmortel M H, et al. Measurement of antigen-antibody interactions with biosensors. J Mol Recognit. 1998 Winter; 11(1-6):163-7.

Felici F, et al. Peptide and protein display on the surface of filamentous bacteriophage. Biotechnol Annu Rev. 1995; 1:149-83.

Steen R, et al. CD34 molecule epitope distribution on cells of haematopoietic origin. Leuk Lymphoma. June 1998; 30(1-2):23-30.

Van de Water J, et al. Detection of molecular determinants and epitope mapping using MALDI-TOF mass spectrometry. Clin Immunol Immunopathol. December 1997; 85(3):229-35.

Burton D R. Phage display. Immunotechnology. August 1995; 1(2):87-94.

Gershoni J M, et al. Combinatorial libraries, epitope structure and the prediction of protein conformations. Immunol Today. March 1997; 18(3): 108-10.

Cortese R, et al. Selection of biologically active peptides by phage display of random peptide libraries. Curr Opin Biotechnol. December 1996; 7(6):616-21.

Tseng-Law J, et al. Identification of a peptide directed against the anti-CD34 antibody, 9C5, by phage display and its use in hematopoietic stem cell selection studies. Exp Hematol 27:936-45, 1999.

CD109+ cells are preferably identified and purified by contacting a sample (such as bone marrow or peripheral blood mononuclear censor a fraction of such bone marrow or peripheral blood cells) with a CD109 antibody. A variety of methods are available for the subsequent purification of such antibody labelled cells.

When relatively few purified cells are required, the most efficient method involves the use of flow cytometry on a fluorescence activated cell sorter (FACS). Cells are stained as above with CD3/CD109. A sort gate delineating CD3+/CD109+ cells is established, and events contained within this gate are sorted (separated) by FACS.

Cells expressing a specific antigen can also be sorted by a variety of means involving antibodies immobilized on a support or matrix, such as dishes or beads. The latter can be used in suspension, or in the form of a column.

The antigen-specific antibody (antibody 8A3, for example) can be soluble, or directly conjugated to the beads. In the former case, a cell suspension containing CD109+ cells can be incubated with unlabelled CD109 antibodies for 30 minutes at 4 C. After removal of excess unbound antibody, the CD109+ cells can be fractionated (sorted or separated) using beads (magnetic or paramagnetic particles, for example) coated with antibodies recognizing murine immunoglobulins. CD109+ cells coated with CD109 antibody will bind to the anti-murine immunoglobulin coated beads. The cells adhering to the magnetic beads can then be captured by a magnet, or retained in a column, while CD109– cells will not. In the latter case, the CD109 antibodies are conjugated directly to the beads. In either case, the CD109+ cells must then be removed from the binding antibody before use. A number of methods for eluting the desired cells have been used, including competitive elution with a short polypeptide corresponding to the epitope recognized by the antibody used to select the CD109+ cells [This is the method of Baxter/Nexell to select marrow and peripheral blood CD34+ cells using their Isolex selection devices.]. CD109 is a marker of the earliest candidate hematopoietic stem and progenitor cells currently identifiable in humans. These primitive cells are capable of long-term hematopoietic reconstitution in vivo and therefore are ideal for bone marrow transplantation. In addition, CD109 expressing hematopoietic stem cells are highly suitable for a variety of gene therapy related ex vivo manipulations prior to bone marrow transplantation. In particular, this early population of cells is ideally suited for gene therapy applications involving long term expression of foreign DNA for the lifetime of the individual.

Purified CD109+ cells are thus useful for treatment of diseases requiring blood stem cell transplantation, including, but not restricted to, (i) hematopoietic malignancies, including leukemia, myelodysplasia, lymphoma, and myeloma; (ii) non-hematopoietic malignancies including breast cancer, malignant melanoma, and renal cell carcinoma; (iii) acquired hematopoietic diseases such as aplastic anemia and PNH [paroxysmal nocturnal hemoglobinuria]; (iv) a spectrum of acquired disorders characterised by autoimmunity, including SLE and rheumatoid arthritis; and (v) a variety of congenital, familial, and acquired conditions treatable by hematopoietic stem cell mediated gene therapy, including, but not restricted to the congenital anemias, thalassemias, and hemophilias, and other conditions such as Gaucher's disease.

Diagnostic Test

In many diseases, CD109 is aberrantly expressed or is mutated. Detection of CD109 expression is a useful screening tool for the presence of disease or to monitor its progression. For example, CD109 transcripts may be analyzed by DNA sequencing, SSCP analysis, or RFLP analysis, to determine if a CD109 mutation is present. Levels of CD109 expression may also be measured to determine whether CD109 expression is increased or decreased. The presence of a CD109 mutation, or of increased or decreased levels of CD109 expression are indicative of a disease state.

CD109 is a marker of platelet and T-cell activation. CD109 exists as both a cell surface (K1 [SEQ ID NO:2 and 4]) and a soluble (K15 [SEQ ID NO:10 and 12]) plasma molecule. As it is anchored to the cell membrane by a GPI linkage, the membrane bound (K1 [SEQ ID NO:2 and 4]) form of CD109 can be cleaved from the cell surface with phosphatidyl-specific phospholipase C (PI-PLC). Thus, conditions of platelet, endothelial, and T cell activation are associated both with increased levels of membrane-associated CD109, as well as with increased levels of soluble plasma CD109. The latter is derived from two sources: K15-type soluble CD109 secreted by cells following activation, and K1-type CD109 released from the cell surface by PI-PLC cleavage. Conditions associated with endothelial cell, platelet, or T cell activation, are associated with increased levels of membrane associated and soluble CD109. In addition, increased levels of membrane associated and soluble CD109 are found in subjects that are at risk of developing such diseases. Thus, the measurement of cell associated and soluble CD109 is used in the diagnosis of such disorders. The measurement of cell associated and soluble CD109 is also used to follow therapeutic response in patients with such disorders. The measurement of cell associated and soluble CD109 is also used to identify patients at risk of developing such disorders prior to the development of overt disease. The measurement of cell associated and soluble CD109 is also used to follow and assess the success of interventional disease preventive strategies in such patients at risk. The invention includes a method for assessing the levels of soluble and membrane associated CD109 in a subject comprising the following steps: (a) preparing a blood sample (such as whole blood or plasma, or purified blood cells) from a blood specimen collected from the subject; (b) testing for the presence of soluble CD109, and/or of membrane associated CD109 in the sample; and (c) correlating the presence or levels of CD109 in the sample with the presence (or risk) of disease such as cardiovascular disease in the subject.

Such measurement of soluble and membrane associated CD109 is useful in degenerative diseases, disorders or abnormal physical states associated with, but not limited to, conditions associated with endothelial activation, platelet activation, activation of the coagulation or fibrinolytic systems, and activation of T lymphocytes and of the complement system. Specifically, such disorders may include (but are not limited to) cardiovascular disorders including stroke, myocardial infarction, thrombosis, and embolism, and peripheral vascular disease; disorders associated with quantitative or qualitative abnormalities of platelet function, including thrombocytopenia, thrombocythemia, and conditions associated with increased or impaired platelet aggregation and activation; conditions associated with increased or impaired activation of the coagulation and/or fibrinolytic systems; and conditions associated with impaired or increased immune activation, including autoimmune diseases as well as organ and bone marrow transplantation. Measurement of soluble and membrane-associated CD109 may be used not only for the diagnosis of such conditions, but also to monitor therapeutic response, assess prognosis, assess patient disease risk, and to monitor the success of disease preventative interventions in patients at risk.

Cell surface CD109 can be measured by several well-known methods that include, but are not restricted to, Flow Cytometry and Radioimmunoassay:

a. Flow Cytometry

In one example, if activated T-lymphocytes (that express CD109 consequent to the activation process) are required, an anti-coagulated whole blood sample is collected from a healthy volunteer. In one example a fraction enriched in mononuclear cells is prepared by density gradient centrifugation using ficoll-hypaque density gradient centrifugation. Cells are then placed in culture using standard media supplemented with phytohemagglutinin (10 mcg/ml, Difco Detroit Mich.). After 24-36 hr, cells are washed and stained with a CD109-specific monoclonal antibody conjugated to the fluorescent dye phycoerythrin (CD109 PE) and with a CD3 specific antibody conjugated to fluorescein isothiocyanate (CD3 FITC; this stains all T cells). On a fluorescence activated flow cytometer, T cells and activated T lymphoblasts are then gated based on CD3 staining and CD3+ cells are analysed for CD109 PE staining. The amount of cell surface CD109 corresponds to the CD109-specific fluorescence per cell.

Similar methods are be used to sort CD109+ activated platelets. In one variation, fresh human blood is mixed 9:1 with 3.8% sodium citrate anti-coagulant. Platelet rich plasma is prepared by centrifugation of the citrated blood at 160×g for 15 minutes at 23EC. The plasma is decanted and incubated with 1 mmol/L prostaglandin 12 and 1 mmol/L acetylsalicylic acid for 30 min at 37EC. Gel-filtered platelets are prepared by passing 7 ml plasma over a 50 ml column of sepharose 2B (Pharmacia) pre-equilibrated with hepes-tyrode buffer (HTB) at pH 7.4. Fresh gel-filtered platelets are activated by addition of thrombin to a final concentration of 0.2 U/ml. Activated and non-activated platelets are analyzed by flow cytometry after staining with fluorescently conjugated CD109 antibodies as above.

b. Radioimmunoassay

Gel-filtered platelets or other CD109 expressing cells are incubated with varying concentrations of a CD109 antibody mixed with a fixed amount of radioiodinated CD109 antibody. After 20 min of incubation, the cell bound and unbound antibodies are separated by centrifugation and counted on a gamma counter. The data is analyzed using the method of Scatchard, which gives a direct indication of the number of binding sites present on the target cell for CD109.

Soluble CD109, in contrast, can be measured by a variety of obvious immunological methods including, but not restricted to, the enzyme-linked immunosorbent assay (ELISA), which has been described in many variant forms. Typically, a "capture" monoclonal antibody (such as antibody 8A3 in the case of CD109) is immobilized on the surface of multiple wells of a plate or dish. After washing with buffer and blocking (with Bovine Serum Albumin [BSA], for example), serial dilutions of sample containing CD109 (plasma, serum, or cell supernatants, for example) are added. The CD109 in solution will become bound to the immobilized capture antibody. After incubation and washing, a "detection" antibody (such as antibody 1B3 in the case of CD109) will be added to each well and incubated. After removal of unbound capture antibody by washing, capture antibody binding will be quantified spectrophotometrically following the addition of an enzyme-linked (alkaline phosphatase, for example) goat-anti-mouse antibody reagent. The amount of soluble antigen can then be determined by comparison of the signal obtained from various sample dilutions with that derived from a standard curve established using serial dilutions of known concentrations of native or recombinant CD109. Variations of this general approach use different "capture" antibody immobilization techniques and different "detection" antibody signal detection techniques.

Kits

The invention also includes a kit for conferring increased CD109 activity to a host cell including a nucleic acid molecule of the invention (preferably in a composition of the invention) and preferably reagents for transforming the host cell.

The invention also includes a kit for detecting the presence of CD109 nucleic acid molecule (e.g. a molecule in the figures), comprising at least one probe of the invention. Kits may be prepared according to known techniques, for example, see U.S. Pat. Nos. 5,851,788 and 5,750,653. The kit preferably includes an antibody, a medium suitable for the formation of an immunological complex between the antibody and a polypeptide recognized by the antibody and a reagent capable of detecting the immunological complex to ascertain the presence of CD109 or a similar polypeptide in a biological sample. Further background on the use of antibodies is provided, for example in U.S. Pat. Nos. 5,695,931 and 5,837,472 which are incorporated by reference in their entirety.

Screening for Agonists and Antagonists of CD109 Nucleic Add Molecule and Enhancers and Inhibitors of CD109 Polypeptide.

Inhibitors are preferably directed towards specific domains of CD109 to block CD109 activation. To achieve specificity, inhibitors should target the unique sequences of CD109. For example, they could block the thioester signature sequence or the defining hexapeptide motif of CD109. A similar approach can be used to search for compounds that may enhance CD109 activation.

Screening for Agonists and Antagonists of CD109 Nucleic Acid Molecule and Enhancers and Inhibitors of CD109 Polypeptide Inhibitors are preferably directed towards specific domains of CD109 to block CD109 activation or substrate binding. To achieve specificity, inhibitors should target the unique sequences of CD109 in Table 1a and 1b. A similar approach can be used to search for compounds that enhance CD109 activation.

A method of identifying a compound which modulates the activity of CD109, can include:

a) contacting (i) CD109, a fragment of CD109 or a derivative of either of the foregoing with (ii) a CD109-binding carbohydrate or protein containing substrate (such as a mammalian, preferably human, cell membrane) in the presence of the compound; and b) determining whether the interaction between (i) and (ii) is modulated, thereby indicating that the compound modulates the interaction of CD109 and the substrate. The method preferably involves determining whether the compound increases or decreases proteolytic cleavage of CD109 (and thus the activation of its thioester). One preferably determines whether the compound causes CD109 to become more or less reactive towards nucleophiles and more or less likely to form ester or amide bonds with the substrate.

Modulation can include increasing or decreasing the interaction between (i) and (ii). A CD109 inhibitor inhibits the interaction between (i) and (ii) while an enhancer increases the interaction.

The method preferably includes identifying a compound that blocks the bait region of CD109. The method may alternatively include identifying a compound that interferes with a CD109 domain involved in targeting the polypeptide to the plasma membrane. The method may alternatively include identifying a compound that interferes with the thioester signature sequence or thioester reactivity defining hexapeptide motif. A similar approach can be used to search for compounds that may enhance CD109 activation.

In a preferred embodiment, the invention includes an assay for evaluating whether test compounds are capable of acting as agonists or antagonists for CD109, or a polypeptide having CD109 functional activity, including culturing cells containing DNA which expresses CD109, or a polypeptide having CD109 activity so that the culturing is carried out in the presence of at least one compound whose ability to modulate CD109 activity is sought to be determined and thereafter monitoring the cells for either an increase or decrease in the level of CD109 or CD109 activity.

Other assays (as well as variations of the above assay) will be apparent from the description of this invention and techniques such as those disclosed in U.S. Pat. No. 5,851,788, 5,736,337 and 5,767,075 which are incorporated by reference in their entirety. For example, the test compound levels may be either fixed or increase.

Isolation of a CD109 cDNA

The restricted pattern of expression of CD109 within hematopoietic cells—CD109 is expressed by a subset of early progenitor and candidate HSCs, and by activated platelets and T cells, but not by their resting counterparts—shows that it plays a role in hematopoiesis, and in cell-mediated immunity and in hemostasis. We have used an immuno-purification/microsequencing strategy to isolate a human CD109 cDNA. Several lines of evidence show that this cDNA has been correctly identified: Not only did this clone encode 16 of 17 CD109-specific peptides originally identified by immunoaffinity purification of CD109 with the antibody 8A3, but expression of this cDNA resulted in the expression of a protein that could be detected by CD109-specific mAbs, both in vitro and in vivo. However, the presence of multiple CD109 transcripts by Northern analysis, as well as the presence of an additional CD109-related peptide that cannot be accounted for by our cDNA, shows that there exist additional or alternative CD109 variants as well.

CD109 is a Novel Member of the α2M/C3, C4, C5 Family of Thioester-Containing Proteins Consistent with the known size and biochemical features of CD109, cDNA clone K1 encodes a 1445 aa protein containing multiple N-linked glycosylation sites, an amino-terminal leader peptide, and a consensus C-terminal GPI anchor cleavage/addition site. And by virtue of high sequence similarity throughout the entire molecule, and in particular, the presence of a typical thioester motif, CD109 is defined as a new member of the α2M/C3, C4, C5 superfamily of thioester-containing proteins[50].

The α2M/C3, C4, C5 family comprises two general divisions—the α2M-like protease inhibitors, and the complement proteins—that are believed to have arisen from a common, ancestral α2M-like molecule.[50] By sequence similarity, CD109 is closely related to the α2M inhibitors, and much more distantly to C3 and C4 complement proteins. The overall organization and size of CD109 is more typical of α2M inhibitors as well: A unique bait region (residues ~651-683) with no homology to known proteins, lies in the middle of the ~162 kD chain, and a typical thioester motif (residues 918-924) lies about two-thirds of the way along the molecule. In addition, a hexapeptide motif (residues 1030-1035) that defines the chemical reactivity of the thioester (by protein folding, this domain interacts with, and modulates the reactivity of the thioester) is found, as expected, about 100 aa further downstream.

CD109 differs from typical α2M inhibitors in several respects, however First, while most α2M protease inhibitors exist as oligomers of a ~180 kD subunit[50] (for example, human α2 macroglobulin occurs in plasma as a ~720 kD tetramer), CD109 exists as a monomer.[3,5,6] To date, monomeric α2M protease inhibitors have been characterized primarily in rodents[50], although they are believed to exist in other vertebrates as well.[54] Second, CD109 is membrane-bound via a GPI anchor. Membrane bound α2M/C3, C4, C5 proteins have not been described previously. Third, while a variety of activated human and rodent α2M inhibitors have been shown to interact with two cellular receptors—the low density lipoprotein receptor-related protein/α2M receptor (LRP-α2MR) on macrophages (and a variety of other cell types) that mediates the clearance of inhibitor/protease complexes from the circulation[56] and the α2-macroglobulin signalling receptor (α2MSR) that is coupled to a pertussis toxin-insensitive G protein, thereby mediating a variety of α2M activation-dependent signals[57-66]—the carboxyl end of CD109 does not contain the KPTVK motif[59,67-75] required for receptor binding. And fourth, although CD109 bears much greater overall sequence similarity to α2M proteins than it does to complement, its reactivity-defining hexapeptide does not end in LLN as in other α2M proteins, but rather ends in the $^{1033}$VIH$^{1035}$ triplet characteristic of complement proteins (see below). Overall, therefore, CD109 defines a new member of the α2M family, but one with unusual features.

The Thioester Specificity of Activated CD109 Likely Resembles That of Complement C3 and C4

The defining structural feature of this family—the intrachain thioester bond—is typically unreactive in the native molecule (except with small nucleophiles such as methylamine). Upon proteolytic cleavage of the molecule, however—by specific activating enzymes in the case of the complement proteins, or by a wide range of proteases in the case of the protease inhibitors—a conformational change occurs, and the thioester becomes highly reactive towards nucleophiles, such that the proteins become covalently bound to nearby macromolecules via ester or amide bonds.[50] In the case of complement, this leads to the covalent deposition of C3 and C4 on the target cell and on immune aggregates. In the case of the protease inhibitors, covalent binding of the activating protease may similarly occur. CD109 becomes activated by proteolytic cleavage as well.

Curiously, while α2M proteins preferentially bind to substrate molecules by forming ester bonds with hydroxyl groups on carbohydrates or proteins, C3 and C4 generally form amide bonds with proteins[50,78]. As alluded above, this differential specificity is determined by the presence or absence of His or Asn in the terminal position of a conserved hexapeptide lying ~100 amino acids C-terminal to the thioester bond[77,78] (by protein folding, this domain interacts with, and modulates the reactivity of the thioester[79]). In the case of the complement proteins, this hexapeptide usually ends in a V-I-H triplet; the corresponding α2M inhibitor triplet is usually L-L-N. As has recently been elucidated,[50,80,81] proteolytically activated Asn-containing molecules undergo direct nucleophilic attack of the thioester carbonyl in an uncatalyzed reaction. In contrast, proteolytic activation of His-containing molecules results in a catalysed transacylation reaction that involves the initial intramolecular transacylation of the thioester carbonyl to the imidazole ring of His, forming a covalent intramolecular acyl imidazole intermediate. The liberated thioester cysteinyl sulfhydryl then acts as a general base to deprotonate hydroxyl nucleophiles for attack on the acyl imidazole intermediate. The catalysed (His) reaction thus facilitates transacylation to hydroxyl-containing carbohydrate or protein targets, while in the uncatalyzed (Asn) reaction, only primary amine groups of protein targets are sufficiently nucleophilic to attack the thioester bond directly. In addition, the $t_{1/2}$ of the reactive thioester is known to be much shorter if His is substituted for Asn, as the intermediate in the catalyzed reaction will react quickly with the most common hydroxyl-containing nucleophile, water.[50,80-82] Thus, α2M proteins bearing a carboxyl-terminal His residue can react with both carbohydrate and protein targets, but by virtue of the short half-life of the reactive thioester, such binding is believed to be tightly restricted spatially to the initial site of activation. As the CD109 regulatory motif ends in the VIH triplet usually associated with complement, it is likely not only that proteolytically activated CD109 forms ester bonds with hydroxyl groups on carbohydrates or proteins, rather than amide bonds, but also that this reactivity is short lived and highly restricted spatially to the site of activation, defining activated CD109 as a locally-acting molecule.

Mechanism(s) of Action of CD109

The identification of CD109 as a novel, monomeric α2M-type inhibitor with "complement-like" thioester reactivity, allows several functional conclusions:

CD109 becomes activated by proteolytic cleavage. While complement proteins are cleaved by specific activating proteases during complement activation, α2M inhibitors are able to interact with a variety of proteases. Indeed, α2M inhibitors have the unique ability to inhibit proteinases of all four mechanistic classes.[50,83] This promiscuous activity is defined by the "bait region", a stretch of ~30 amino acids unique to each α2M inhibitor, and that lies about half way along the protein, and contains cleavage sites for proteases of all mechanistic classes and with diverse specificities. Thus, typical α2M inhibitors do not function as specific inhibitors, but rather are believed to inhibit proteases for which no specific inhibitors are present, and proteases, which are released in excess of their specific inhibitors.

Second, proteolytic cleavage of CD109 results in a conformational change that leads to the covalent crosslinking CD109 to adjacent molecules. Such covalent crosslinking activity is essential for the action of C3 and C4 (leading to complement deposition on immune complexes and cell membranes), as well as for the protease inhibitory action of monomeric α2M inhibitors (leading to the binding/inhibition of the activating protease). In contrast, while activated multimeric α2M proteins are capable of covalent binding as well, this activity is not essential for protease inhibition. Rather, multimeric α2M inhibitors are believed to "entrap" proteases non-covalently after undergoing a bait region cleavage-induced conformational change, such that the protease is prevented from accessing substrates in a size-restricted manner[50,51,83]. CD109 functions as a protease inhibitor, and this activity would likely require covalent binding to the activating protease, resulting in the formation of a CD109/protease complex.

Third, the covalent binding of activated CD109 may not be restricted to proteases. Proteolytically activated α2M is able to bind other proteins and peptides as well, by both non-covalent "trapping" and by covalent thioester-mediated binding mechanisms. These interactions are believed to regulate the plasma stability, transport, and clearance of a variety of molecules including small proteases,[84] other proteins including antimicrobial defensins,[85] apolipoprotein E,[86] and amyloid beta[87-90] (indeed, specific allelic variants of α2M are reportedly associated with Alzheimer's disease[91,92]), a wide spectrum of hormones, growth factors, and cytokines (including insulin, TNFα, IL-1β, IL-2, IL-6, IL-8, bFGF, βNGF, PDGF, TGFβ, VEGF, EGF[93-97] and leptin[98]), as well as a variety of peptide antigens.[96,99-102] While proteolytically activated monomeric α2M family proteins such as CD109 would not be expected to be able to "trap" other molecules non-covalently as are their multimeric counterparts, they likely are capable of covalent binding to other non-protease substrates. Indeed, in view of the "complement-like" spatially restricted thioester reactivity of activated CD109, and its location as a cell surface molecule, that such non-protease substrates should include cell membranes.

And fourth, activated CD109/substrate complexes would not be expected to interact with LRP-α2MR and α2MSR receptors in the manner of other α2M family proteins. Thus, the route(s) by which putative activated CD109/substrate complexes released from the cell surface by GPI anchor cleavage, would be cleared from the circulation, remain(s) undefined. Similarly, it is unlikely that such complexes would signal via α2MSR. It is possible, however, that GPI-anchored substrate/CD109 complexes could be internalized directly, and could transduce intracellular signals, as has been described for a variety of other GPI-linked proteins[103-108].

Biological Role(s) of CD109

CD109 is a marker of specific hematopoietic stem/progenitor cell subsets, and a target antigen in alloimmune platelet destruction. The identification of CD109 as an atypical member of the α2M/C3, C4, C5 protein superfamily indicates a role for CD109 in hematopoiesis and in platelet and T cell activation. Following proteolytic cleavage, CD109 becomes capable of covalent binding to carbohydrate and protein containing substrates, including cell membranes. These interactions function to modulate and regulate these cellular processes. For example, CD109 functions as a locally acting membrane-bound α2M-type antiprotease.

Immunoaffinity Purification and Partial Amino Acid Sequencing of CD109

When analysed by SDS-PAGE/silver staining, the eluate from the mAb 8A3/Protein A Sepharose column yielded two ~150 and 170 kD bands characteristic of CD109[3,15,16]. Previous data have indicated that the ~150 kD form is likely derived proteolytically from the ~170 kD species[3,6]. The eluate was subsequently purified further by preparative SDS-PAGE, and the larger band was excised and digested with endoproteinase Lys-C or Asp-N. Purification and sequence analysis of the resultant peptide fragments yielded 20 peptide sequences ranging in size from 7-20 amino acids (aa). As shown in Table 1, after overlapping sequences were combined, 17 independent CD109-derived peptide sequences were obtained.

cDNA Cloning and Analysis

BLAST analysis[36,37] using these 17 CD109 peptide sequences identified a rat incisor EST—R47123[38]—that encoded the CD109-specific peptide fr76/60. A ~4 kb EcoRI/XhoI fragment from R47123 was subsequently used to probe a λ phage Uni-ZAP human umbilical vein endothelial cell (HUVEC) cDNA library (Stratagene), yielding 8 independent clones that were rescued into pBS SK$^+$ by in vivo excision. Restriction enzyme analysis and confirmatory DNA sequencing assigned these clones to two overlapping groups: The first comprised 7 clones that were progressive 5' truncations of the longest example—clone H6—a ~3 kb clone containing a ~2.7 kb open reading frame (ORF), followed by a 300 bp 3' untranslated region (UTR) ending with a poly(A) tract. The second—consisting of clone H7 (~2 kb)—was contiguous with the H6 series cDNAs, but contained a longer 3'UTR that extended an additional 1,132 bp prior to the appearance of a poly(A) tract. As clone H6 was not full-length, we endeavored unsuccessfully to obtain additional more 5' CD109 cDNA sequence by rescreening the HUVEC library with H6 itself. The screening of a variety of additional commercial cDNA libraries was similarly unrewarding.

Two human erythroleukemia (HEL) cDNA libraries—L12 and L13—were screened by nested PCR using two adjacent CD109-specific antisense oligonucleotide primers lying at the 5' end of clone H6, together with library-specific hEF-1 (sense) and supF (antisense) primers. This approach yielded one PCR product (clone E2) that overlapped with H6 and extended the CD109 sequence 450 bp in the 5' direction. Rescreening of L12 and L13 using more 5' clone E2-derived antisense oligonucleotides did not yield additional sequence.

Finally, a new ZAP Express KG1a cDNA library was screened using a clone H6 probe, yielding 9 independent clones that were rescued into pBK-CMV by in vivo excision. Restriction enzyme analysis and confirmatory DNA sequencing demonstrated that these clones comprised a series of progressive 5' deletions of the longest example—clone K1 [SEQ ID NO:1 and 3] (~4.7 kb)—that encompassed clones H6 and E2 in their entirety, and additionally contained ~1.3 kb of additional 5' cDNA sequence.

The nucleotide sequences of the 4 overlapping clones H6, H7, E2, and K1 were determined in their entirety for both strands, and were found to be in agreement in all cases. Clone K1 [SEQ ID NO:1 and 3] contains a 4,335 bp ORF flanked by 112 bp 5' and 300 bp 3' UTRs, respectively. The putative translation start, while not comprising an optimal Kozak consensus sequence, is preceded by stop codons in all three frames (In addition [see below], the first 20 codons downstream of this start are predicted to encode a cleavable signal peptide.) The K1 3' UTR contains a canonical polyadenylation signal—AATAAA—15 bp upstream of the poly(A) tail. The clone H7 3' UTR is contiguous with that of clones K1 and H6, but extends an additional 1,132 bp in the 5' direction. Two polyadenylation signals are found 34 and 19 bp, respectively, upstream of the H7 poly(A) tail.

Clone K1 Encodes CD109

To show that cDNA clone K1 [SEQ ID NO:1 and 3] did encode CD109, we initially examined the predicted K1 [SEQ ID NO:2 and 4] protein sequence: Notably, the clone K1 ORF was found to contain 16 of the 17 CD109-derived peptide sequences described above. Next, we confirmed that the protein encoded by K1 [SEQ ID NO:2 and 4] could be detected by CD109-specific mAbs. When transcribed and translated in vitro, K1 yielded a protein of ~160 kD that was recognized by mAb 1B3[15]. In addition, stable expression of done K1 was able to confer mAb 8A3 binding to transfected CHO cells. Clone K1 represents a CD109 cDNA.

CD109 is Predicted to be a GPI-Linked Thioester-Containing Protein

Consistent with the known size of CD109, the translated K1 sequence (FIG. 3A) predicts a 1445 aa protein of ~162 kD bearing a cleavable 21 aa N-terminal leader peptide[42] and containing 17 N-linked glycosylation sites. And as expected, the presence of a C-terminal hydrophobic tail preceded by a short hydrophilic stretch and a cluster of non-bulky amino acids defines a GPI anchor cleavage/addition site, with cleavage predicted to occur after aa 1420[43-45]. Notably, the presence of a thioester signature sequence[46,47]—$^{918}$PYGCGEQ$^{924}$—defines CD109 as a member of the α2 macroglobulin (α2M)/C3, C4, C5 superfamily of thioester-containing protease inhibitor and complement proteins. Indeed, as assessed by Blast[36,37] analysis, CD109 bears ~45-50% overall sequence similarity to other vertebrate and invertebrate α2M proteins (and is more distantly related to vertebrate complement C3 and C4 proteins), and shares the overall domain structure of the α2M family, with particularly high similarity in the region of the thioester and in 11 additional α2M family-specific conserved sequence blocks[48,49], including a hexapeptide motif[50] (residues 1030-1035) that lies ~100 aa downstream of the thioester and is believed to define its chemical reactivity (see below). In addition to these highly conserved regions, each α2M protein also contains a unique "bait region" that defines substrate specificity[50]. Consistent with this, CD109 also contains a putative "bait region" (~ residues 651-683; FIGS. 3A and 5A) that, as expected, is unrelated to the corresponding regions of other family members.

Native CD109 Contains an Intact Thioester

The defining structural feature of the α2M/C3, C4, C5 family—an intrachain thioester bond—is typically situated about two thirds of the way along the pro-molecule. In the native molecule, this bond—formed between a cysteinyl side chain sulfhydryl and a glutamine side chain carbonyl in the sequence CGEQ—is unreactive, except with small nucleophiles such as methylamine, which can therefore be used to disrupt the thioester[50,51].

In addition, under experimental conditions of heat or chemical denaturation (preparing a sample for SDS-PAGE, for example), both complement and α2M inhibitors may undergo internal nucleophilic attack on the thioester, resulting in the autolytic cleavage of the protein[52,53]. Although not of physiological significance, this autolytic reaction is useful diagnostically to indicate the presence of an intact thioester bond. We showed whether native CD109 could undergo high temperature autolytic cleavage that could be prevented by pretreatment with methylamine. Thioester-dependent cleavage would be abrogated by disruption of the thioester bond with methylamine. When KG1a-derived mAb 8A3/CD109 immune complexes were treated with 400 mM methylamine prior to boiling, only a single 170 kD CD109 band was subsequently observed. In the absence of methylamine treatment, however, boiling resulted in the appearance of the typical 150 kform, and of an associated ~20 kD fragment. In contrast, and consistent with the known inability of standard cell-free systems to support intramolecular thioester formation (XX), only a single band was observed when CD109 synthesized in vitro was boiled in the absence of methylamine. These observations demonstrate that native CD109 does indeed contain an intact thioester. The 150 kD CD109 band is derived from the 170 kD form by autolytic rather than by proteolytic cleavage.

Expression Pattern of CD109

As noted above, two distinct CD109 3' UTRs were isolated by library screening. To confirm that both cDNA variants were produced, and to discern the relative prevalence of these two forms, we assessed their expression in KG1a cells by semi-quantitative RT-PCR. Both variants were detected readily in KG1a RNA. Consistent with these data, multiple KG1a CD109 transcripts were detectable as well by Northern analysis. While the smallest ~5.4 kb transcript may correspond to the K1 cDNA, the identity of the two larger transcripts and their relationship to the H7 cDNA remain obscure. In any case, the existence of multiple CD109 transcripts shows that there exist additional CD109 variants that have not yet been identified. All CD109 variants are included within the scope of this invention. A CD109 probe was also used to evaluate the tissue range of expression of CD109 using a commercial multiple tissue blot bearing a series of human adult and fetal RNAs. CD109 transcripts were detected in a wide range of tissues, with highest levels being found in adult uterus, aorta, heart, lung, trachea, and placenta, and in fetal heart, kidney, liver, spleen and lung. Whether these data indicate true widespread expression, or merely reflect expression in endothelial cells (or both) is not known.

Chromosomal Mapping of the CD109 Locus

Using cDNA clone K1 [SEQ ID:NO1] as a probe, two positive genomic PAC clones—94J24 and 4L10—were identified. The chromosomal assignment of each of these clones was then determined by FISH analysis of 20 well-spread metaphases. Both PACs mapped to 6q12-13, with positive hybridization signals being observed in >90% of the cells, and on both homologues in >90% of the positive spreads. This chromosomal location was then confirmed by radiation hybrid mapping: Using both the Gene Bridge 4 and the Stanford G3 panels and a 3'UTR PCR probe, CD109 was mapped to within 11.09 cR and 6.9 cR of framework markers CHL-C.GATA 11F10 and SHGC-33186, respectively—a region that corresponds to 6q13.

Materials and Methods

Cell Culture

KG1a acute myeloblastic leukemia cells[1,2] were grown in RPMI 1640 medium supplemented with 10% heat-inactivated fetal calf serum (Hyclone), 2 mM L-glutamine, 100 U/ml penicillin, and 100 µg/ml streptomycin (Gibco Life Technologies). Chinese Hamster Ovary (CHO) cells were grown in F-12 (Ham) Nutrient Mixture (Gibco Life Technologies) supplemented as above, while 293 cells were cultured in similarly supplemented Dulbecco's Modified Eagle Medium (DMEM; Gibco Life Technologies). All cells were initially obtained from ATCC and were maintained at 37 C in a humidified atmosphere containing 5% $CO_2$.

Antibodies

CD109 MAbs 8A3, 7D1, 7C5 and 8A1 were raised against KG1a cells as described previously.[3] CD109 antibody 1B3[15] Other CD109 antibodies used in this study were obtained through the Endothelial Panel of the Vth and VIth HLDA Leukocyte Typing workshops.[5,6] The mAbs D51[28] (gift of H.-J. Gross) and KC4[29], which recognize CD71 and CD62P respectively, were used as immunoprecipitation and affinity purification controls, as appropriate.

Immunoaffinity Purification and Partial Amino Acid Sequencing of CD109

$1 \times 10^{10}$ KG1a cells were pelleted, washed three times in ice cold phosphate buffered saline (PBS; 140 mM NaCl, 2.7 mM KCl, 10 mM $Na_2HPO_4$, 1.8 mM $KH_2PO_4$) pH 7.4 supplemented with 0.2 mM EDTA. Pelleted cells were then resuspended vigorously in 300 ml ice cold lysis buffer (0.01M Tris-HCl, pH 8.1, 0.15 M NaCl and 0.5% Nonidet P-40 [NP40]) freshly supplemented with 2 mM PMSF, 1 mg/ml BSA, and 2 mM EDTA (Sigma) as described previously[30,31], and were kept on ice for 20 minutes with vigorous stirring. The lysate was clarified by centrifugation at 100,000×g for 30 minutes, and the supernatant was decanted and brought to 0.5 M NaCl. CD109 antigen was separated from the crude cell lysate by cross-linked immuno-affinity chromatography. Briefly, 10 mg of CD109 monoclonal antibody 8A3 were bound to 1 ml of Protein A Sepharose beads (Pharmacia) and linked covalently using the homobifunctional crosslinker dimethyl pimelimidate (Pierce). After loading the lysate, the column was washed extensively with lysis buffer containing 0.5 M NaCl, followed by lysis buffer containing 0.1% SDS. Bound CD109 was subsequently eluted with 0.05 M diethylamine (pH 11.5) containing 0.5% deoxycholate (DOC). The eluted material was adjusted to pH 8.1 by the careful addition of 0.1 N HCl[31,32] and its purity was assessed by SDS-PAGE and silver staining.[33]

The eluted CD109 preparation was further fractionated by preparative 7.5% SDS-PAGE, and the major band at 170 kD was visualized with RG 250 Coomassie blue. The band was excised and was digested overnight with either endoproteinase Lys-C or Asp-N (Boehringer). The resultant peptides were extracted and separated by tandem ion exchange and reverse phase chromatography. Fractions were collected manually into coated tubes, and were sequenced with an Applied Biosystems Procise sequencer using rapid cycle chemistry.[34]

Labeling of Cells and Immunoprecipitation of CD109

KG1a cells were labeled by lactoperoxidase-catalyzed radio-iodination as described previously[30], or by biotinylation using the water-soluble biotin derivative Sulfo-NHS-LC-LC-Biotin (Pierce). In the latter case, $2.5 \times 10^7$ KG1a cells were washed three times in ice cold PBS pH 8.0 and were resuspended in 1 ml of the same buffer at room temperature. 1 mg of Sulfo-NHS-LC-LC-Biotin was added to the cell suspension. After 20 minutes at room temperature, the reaction was terminated by washing the cells three times with ice cold PBS pH 7.4 containing 2 mM EDTA.

Labeled cells were lysed in ice cold lysis buffer (0.01 M Tris-HCl, pH 8.1; 0.15 M NaCl and 0.5% NP40) freshly supplemented with 2 mM PMSF, 1 mg/ml BSA, and 2 mM EDTA as described previously.[30,31] After 30 minutes on ice, the lysate was clarified by centrifugation at 14,000×g for 5 minutes. The supernatant was then decanted, brought to 0.5M NaCl by the addition of a 1/10 volume of 3.5M NaCl, and used for immunoprecipitation with specific antibodies as previously detailed.[30,31] Briefly, immune complexes were collected on protein A-Sepharose beads, or on rabbit anti-mouse immunoglobulin-coated protein A sepharose beads as appropriate. Immune complexes were then washed twice with lysis buffer containing 0.5M NaCl, and once with lysis buffer supplemented with 0.5% DOC/0.1% SDS.

Methylamine Treatment of Immunoprecipitates

Immunoprecipates prepared as above were washed further with 0.2 M Hepes, pH 8/0.1% NP40 and were then resuspended in 1 ml fresh 0.4 M methylamine (Sigma)/0.2 M Hepes, pH 8/0.1% NP40. After 30 minutes at 37° C., methylamine-treated immunoprecipitates were washed once with 0.2 M Hepes, pH 8/0.1% NP40 and once in lysis buffer containing 0.1% SDS/0.5% DOC as above, and were subsequently dissociated by incubation in SDS-gel sample buffer for 10 minutes at 37° C. Control, untreated immunoprecipitates were dissociated by boiling in SDS gel sample buffer for 30 minutes.

Analysis of Immune Complexes and Western Blotting

Immune complexes containing radio-iodinated cell surface antigens were analyzed by SDS-PAGE, and autoradiography, while biotinylated complexes were analyzed by SDS-PAGE and western blotting. Blots were blocked for at least 1 hour with 0.01 M Tris/0.15 M NaCl, pH 8.0 containing 5% w/v dried skim milk and developed using streptavidin-conjugated horseradish peroxidase (HRP)-coupled chemiluminescent detection (Pierce). In some experiments involving immune complexes from non-labeled cell lysates, CD109 was detected with the CD109 antibody 1B3, that detects a denaturation-resistant epitope of CD109 followed by either iodinated Protein A[32] or HRP-conjugated goat anti-mouse Ig-coupled chemiluminescence (Pierce).

cDNA Library Screening

BLAST analysis[36,37] identified a rat incisor EST-R47123[38]—that encoded a CD109-specific peptide. EST R47123 was obtained, the DNA sequence was confirmed, and a ~4 kb EcoRI/XhoI fragment was subsequently radiolabeled to high specific activity with α-$^{32}$P-dCTP using the random primer synthesis method[39] and used to screen a phage Uni-ZAP human umbilical vein endothelial cell (HUVEC) cDNA library (Stratagene):

The phage HUVEC cDNA library was plated and prepared for plaque hybridization. Duplicate supported nitrocellulose filters totalling 3.5×10$^6$ plaques were pre-hybridized in Quik-Hyb (Stratagene) for 4 hours at 65° C., hybridized with the EST probe in Quik-Hyb at 65° C. overnight, washed progressively to a final stringency of 0.1× standard saline citrate (SSC; 0.15 M NaCl, 0.015 M sodium citrate), 0.1% sodium dodecyl sulfate (SDS), 65° C., and exposed to X-ray film at −80° C. Positive plaques were picked into 500 µl SM buffer with 20 µl chloroform and eluted overnight at 4° C. After three further rounds of plaque purification, positive clones were rescued into pBS SK$^+$ by in vivo excision using the ExAssist/SOLR (Stratagene) system according to the manufacturer's instructions. Independent colonies were picked, grown overnight in LB-ampicillin, plasmid DNA was prepared by the alkaline lysis method, and inserts were evaluated by restriction endonuclease digestion and DNA sequence analysis.

Two pAX142-based[40] human erythroleukemia (HEL) cDNA libraries—L12 and L13—were screened by PCR using the CD109-specific nested antisense oligonucleotide primers 109-6-1-3 and 109-6-1-6 (which lie at the 5' end of clone H6, the largest of the HUVEC-derived cDNA clones above) and library-specific primers hEF-1 (5'-CCTCAGA-CAGTGGTTCAA-3') and supF (5'-CTTCGAACCTTCG-MTCC3'). Fifty µl "hot-start" PCR reactions (1× GIBCO PCR buffer, 1.5 mM MgCl2, 200 mM each dNTP (Boehringer), 1 mM each primer, 1.25 units Taq polymerase (GIBCO), 3 µl library cDNA) underwent 35 cycles of 94×45 s, 54×45 s, and 72×45–60 s. Resultant PCR products were cloned into pMAB1 (a pBS SK(−) derivative containing a PmeI recognition site within the polylinker) and analysed as above.

A KG1a cDNA library[41] constructed in ZAP Express was plated and 2×10$^7$ plaques were screened as above using a clone H6 probe that had been radiolabeled to high specific activity with $^{32}$P-dCTP by the random primer synthesis method. Positive plaques that survived tertiary screening were rescued into pBK-CMV by in vivo excision using the ExAssist/SOLR (Stratagene) system, and resultant plasmid clones were amplified and analysed by restriction endonuclease digestion and DNA sequence determination, as appropriate.

Restriction Endonuclease Analysis and DNA Sequencing

HUVEC- and KG1a-derived clones were digested singly (or in combination, as appropriate) with EcoRI, XhoI, KpnI, PstI, SmaI, BamHI, XbaI, NotI, and SacI, using the corresponding buffers supplied by the manufacturer (NEB). Digested samples were size-separated electrophoretically on 1%-2% agarose/TAE (40 mM Tris-acetate; 1 mM EDTA, pH 8.3) gels containing 0.5 µg/ml ethidium bromide, and were then analysed visually.

The nucleotide sequences of HUVEC-, KG1a-, and HEL-derived clones were determined either by i.) the dideoxy-nucleotide chain termination method using $^{35}$S dCTP (NEN) together with a T7 sequencing kit (Amersham Pharmacia Biotech), with reactions being size-separated electrophoretically on a 6% polyacrylamide/5 M urea gel that was then transferred to filter paper, dried by vacuum, and exposed to X-ray film overnight at room temperature, or ii.) using an ABI Prism dye terminator sequencing kit, together with a Perkin Elmer-Cetus 2400 thermocycler and an ABI Prism 310 Genetic Analyser (Perkin Elmer Applied Biosystems) as suggested by the manufacturer. Oligonucleotide primers used for sequencing reactions were synthesized by Gibco BRL and comprised standard T7 (5'-GTAATACGACTCACTAT-AGGGC-3') and T3 (5'-AATTAACCCTCACTAAAGGG-3') primers and a series of gene-specific CD109 primers. The HUVEC-derived H6 and H7, HEL-derived E2, and KG1a-derived K1 clones (FIG. 2A) were sequenced in their entirety on both strands.

Northern Blot Hybridization Analysis

Total RNA from KG1a cells was extracted by using TRIzol (Gibco BRL Life Technologies) as directed by the manufacturer. Poly(A) mRNA was purified from total KG1a RNA using an Oligotex mRNA kit (QIAGEN) according to the manufacturer's protocol. In either case, the final RNA pellet was dissolved in diethylpyrocarbonate (DEPC; Sigma)—treated water. Approximately 20 µg of total RNA and less than 1 µg of mRNA were size-separated electrophoretically in a 1% agarose/6.7% formaldehyde in MOPS (20 mM 3-(N-morpholino)propanesulphonic, 8 mM sodium acetate, 1 mM EDTA, pH 7) gel, transferred to a Hybond N nylon membrane (Amersham Pharmacia Biotech), crosslinked by baking in vacuo at 80° C. for 1 hour, and hybridized overnight in Quik-Hyb (Stratagene) with a CD109 K1 probe radiolabeled as above. The membrane was then washed to a final stringency of 1× SSC/0.1% SDS, and exposed to X-ray film with an intensifying screen at −80° C.

To determine the expression of CD109 in various human tissues, a human multiple tissue RNA nylon membrane (Human RNA Master Blot, Clontech) containing poly(A) RNAs from 50 human tissues was hybridized overnight at 65° C. with the same high specific activity radiolabeled CD109 K1 probe as above, but using ExpressHyb Hybridization Solution (Clontech) according to the manufacturer's instructions. Subsequently, the blot was washed progressively to a final stringency of 0.1× SSC/0.5% SDS at 55° C. and was exposed to X-ray film with an intensifying screen at −80° C.

RT-PCR

RNA prepared as above was treated for 15 minutes at 37° C. with 3 U/μg RQ1 RNAse-free DNAse (Promega) in 50 μl of 10 mM Tris-HCl, pH 8.3; 50 mM KCl; 1.5 mM $MgCl_2$, additionally containing 40 units of RNAse inhibitor (RNAguard, Amersham Pharmacia Biotech). RNA was then extracted sequentially with equal volumes of phenol-chloroform and chloroform alone, and after the addition of 0.1 volume of 3 M sodium acetate, pH 5.2, 20 μg of glycogen (Boehringer), and 40 U RNAse inhibitor, was precipitated overnight in absolute ethanol at −80° C. After centrifugation, the RNA pellet was washed with RNAse-free 75% ethanol, and resuspended in RNAse-free water.

cDNA was prepared from 5 μg KG1a RNA using SuperScript I reverse transcriptase (GIBCO BRL Life Technologies) in a 20 μl reaction volume containing 40-60 ng random hexameric oligodeoxyribonucleotides (Amersham Pharmacia Biotech) as recommended by the manufacturer, but also containing 40 U RNAse inhibitor, and 5 mM dithiothreitol (DTT; Sigma). Reactions were terminated by heat inactivation at 95° C. for 5 minutes.

Reverse transcription efficiency was initially tested by PCR using oligonucleotide primers HPRT-5' (5'-GAGGATTTGGAAAGGGTGTT-3') and HPRT-3' (5'-ACAATAGCTCTTCAGTCTGA-3'), which yield a 231 bp product specific to human hypoxanthine-guanine phosphoribosyl transferase (HPRT). Fifty μl PCR reactions (1× Gibco PCR buffer, 2 mM MgCl2, 200 mM each dNTP (Boehringer), 1 mM each primer, 1.0 units Taq polymerase (GIBCO), 2 μl reverse transcription reaction) underwent 35 cycles of "touchdown" PCR. Specifically, after a hot start at 94° C., the denaturation and extension steps remained at 94° C. and 72° C., respectively, for 60 s, but the annealing step (also 60 s) began at 65° C. for 2 cycles, and thereafter decreased in steps of 2 C/2 cycles until 47° C. The last 17 cycles continued at the annealing temperature of 47° C. The final extension was extended to 10 minutes. Finally, PCR-amplified products were size separated electrophoretically in 1% agarose/TAE gels containing 0.5 μg/ml ethidium bromide, and were inspected visually.

In Vitro Transcription/Translation

The KG1a-derived CD109 K1 clone in pBK-CMV was digested with NotI and SalI to liberate a cDNA fragment containing the entire open reading frame (ORF)—including the translation initiation codon—but missing the 5' and 3' UTRs, which was then inserted into NotI/SalI digested pBS II KS(−) such that the CD109 cDNA was placed downstream of the T7 promoter (pBS KS II T7/K1). Restriction enzyme digestion and DNA sequencing were used to confirm insert orientation.

The pBS KS II T7/K1 construct (1.2 μg) was then transcribed and translated in vitro using the T7/T3 TNT Coupled Reticulocyte Lysate System (Promega) and $^{35}$S-methionine (Amersham), in a 50 μl reaction following the manufacturer's protocol.

Following completion of the TNT reaction, 5 μl of the reaction mix were added to 195 μl of lysis buffer (50 mM Hepes, pH 7.5; 5 mM $MnCl_2$, 10 mM $MgCl_2$, 5 mM EGTA, 2 mM EDTA, 100 mM NaCl, 5 mM KCl, and 0.1% NP-40) supplemented with 50 μg/ml aminoethylbenzenesulfonylfluoride, 1 μg/ml antipain, 1 μg/ml leupeptin, 1 μg/ml pepstatin, and 1 μg/ml aprotinin (ICN Pharmaceuticals), 1.5 μg of the monoclonal CD109 antibody 1B3 or of the irrelevant CD71 mAb D51 were added, and the resultant mix was incubated on ice for 1 hour.

Protein A-Sepharose beads (Pharmacia) in lysis buffer (0.1 mg/ml) were initially precleared with KG1a cell lysate: $2×10^7$ KG1a cells were washed with PBS, were lysed in 500 μl of lysis buffer on ice for 20 minutes, and the supernatant was recovered by centrifugation (1000 g, 4° C., 1 minute). 100 μl of resuspended protein A-Sepharose beads were subsequently added to supernatant, incubated on ice for 30 minutes, were recovered by centrifugation (1000 g, 4° C., 5 minutes), and were washed twice (500 μl) and resuspended (100 μl) in cold lysis buffer.

To recover immune complexes, 20 μl of pre-cleared protein A-Sepharose beads were added to the TNT/antibody mixtures, rotated constantly at 4° C., for 45 minutes, and were then washed four times with 1 ml cold lysis buffer. Finally, the beads were resuspended in 2 μl 2× SDS sample buffer (100 mM Tris-HCl, pH 6.8; 4% SDS; 0.2% bromophenol blue; 20% glycerol) containing 200 mM DTT. After boiling for 3 minutes, and centrifugation, supernatants were size-separated electrophoretically on a 6% SDS-PAGE gel, and the gel was transferred to blotting paper and dried, and finally was exposed to X-ray film at room temperature.

Expression of CD109 cDNA in CHO Cells

The CD109 K1 cDNA ORF was excised from pBK-CMV as above, the SalI overhangs were made blunt with Klenow DNA polymerase (NEB), and the polished fragment was inserted downstream of the CMV promoter (but upstream of the IRES sequence) into EcoRV/NotI cut pIRES-EYFP (Clontech) to yield pK1/YFP. The orientation of the insert was subsequently verified by restriction enzyme analysis and DNA sequencing.

CHO cells were grown to ~75% confluency and seeded at a density of $2-3×10^5$ cells per well on a six-well plate before transfection. For transient expression of CD109, monolayers of CHO cells in a six-well plate were transfected with 20 μl of cesium chloride purified pK1/YFP fusion constructs (or with empty pIRES-EYFP control vector) using 20 μl SuperFect (QIAGEN) according to the manufacturer's protocol. Briefly, the DNA/SuperFect mixtures were incubated with the CHO cells at 37° C./5% $CO_2$. After 3 hours, this mixture was removed, fresh medium and serum were added, and the cells were grown without drug selection for another 24-72 hours at 37° C./5% $CO_2$. Cells were then lifted from the plates with citric saline (135 mM KCl, 15 mM sodium citrate), incubated with 3 μg PE-conjugated CD109 mAb 8A3 for 30 minutes on ice, rinsed twice in Tris-buffered saline (TBS; 25 mM Tris-HCl (pH 8.1), 140 mM NaCl, 2.7 mM KCl), and analysed flow cytometrically on a FACScan cytofluorimeter (Becton-Dickinson). Transfected CD109 expression was determined by assessing 8A3 binding to EYFP positive cells.

FISH Mapping of CD109 Locus

The ~4.5 kb CD109 cDNA (clone K1) was used to screen a P1 derived artificial chromosome (PAC) library in the Canadian Genome Analysis and Technologies (CGAT) Physical Mapping Resource Facility (Hospital for Sick Children, Toronto). The two resultant CD109-specific pCYPAC-1 clones—94J24 and 4L10—were then used for fluorescence in situ hybridization (FISH) analysis of normal human lymphocyte chromosomes counterstained with propidium iodide and 4',6-diamidin-2-phenylindol-dihydrochloride (DAPI). Following probe biotinylation by nick translation, and cot-1 suppression by preannealing, hybridization was detected with avidin-fluorescein isothiocyanate (FITC). Images of metaphase preparations were visualized by digital imaging microscopy using a thermoelectrically cooled charge coupled camera (Photometrics, Tucson, Ariz.). Hybridization signals and DAPI banded chromosome images were acquired, and pseudo coloured yellow (FITC) and blue (DAPI) signals were overlaid electronically and merged using Adobe Photoshop 3.0 software. Chromosomal band assignment was determined by measuring the fractional chromosome length and by analysing the banding pattern generated by the DAPI counterstained image.

Radiation Hybrid Mapping

Two PCR primers (K1UTRs, 5'-GTCACATGTGATTG-TATGTTTTCG-3'; K1UTRas, 5'-GGGGAAAATATAGA-CACACAACTGC-3') were designed to amplify a 189 bp fragment of the CD109 clone K1 3' UTR. PCR reactions were carried out in 25 µl reaction volumes with 25 ng of human genomic DNA; 12.5 pmol of each primer; 1.25 units of Taq polymerase; 200 pmol of each dNTP; 1.0 mM $MgCl_2$; 20 mM Tris-HCl, pH 8.4 and 50 mM KCl. A "hot start" was carried out with the addition of Taq polymerase and dNTP after an initial denaturation at 94° C. for 5 minutes followed by 30 cycles of 94° C.×30 s, 52° C.×30 s, 72° C.×30 s, followed by a single final extension at 72° C. for 15 minutes. All reactions were carried out in a DNA Thermocycler 480 (Perkin Elmer) with an overlay of two drops of mineral oil. At the completion of the PCR run, 5 µl of loading buffer were added to each reaction and a 10 µl aliquot was size-separated electrophoretically on a 2% agarose/TAE gel containing 0.5 µg/ml ethidium bromide, and inspected visually. Negative controls to check for cross contamination were negative, as was the homology control with hamster DNA (A3).

Both the GeneBridge 4 RH panel and Stanford G3 RH panel were screened using the K1UTRs/as primer pair. The GeneBridge 4 RH panel controls were HFL (human genomic DNA, positive) and A23 (hamster genomic DNA, negative), while the Stanford G3 RH panel controls were A3 (non-irradiated hamster genomic DNA, negative), and RM (non-irradiated human genomic DNA, positive). Panel results were scored independently.

The present invention has been described in detail and with particular reference to the preferred embodiments; however, it will be understood by one having ordinary skill in the art that changes can be made without departing from the spirit and scope thereof. For example, where the application refers to proteins, it is clear that peptides and polypeptides may often be used. Likewise, where a gene is described in the application, it is clear that nucleic acid molecules or gene fragments may often be used.

All publications (including Genbank entries), patents and patent applications are incorporated by reference in their entirety to the same extent as if each individual publication, patent or patent application was specifically and individually indicated to be incorporated by reference in its entirety.

TABLE 3

CD109 antibodies:
8A3, 23/5F639/6C3, TEA 2/16, D2, LDA1, 7D1, 40B8, 1B3, 59D6, 8A1, 7C5, B-E47

| Ab name | ref | Submitter | Department | Organisation | Address | Species | Subclass | Ascites/ Supernatant Purified |
|---|---|---|---|---|---|---|---|---|
| 8A3 | 1, 2 | Robert Sutherland | Oncology Research | Toronto Hospital | Room 407, 67 College St. Toronto, Ontario, M5G 2M1, Canada | M | IgG2aK | S/P |
| 23/5F6 | | Walter Knapp | Institute of Immunology | University of Vienna | Borschkegasse 8a, 1090 Vienna, Austria | M | IgG2a | ? |
| 39/6C3 | | Walter Knapp | Institute of Immunology | University of Vienna | Borschkegasse 8a, 1090 Vienna, Austria | M | IgG2a | ? |
| TEA 2/16 | | Francisco Sanchez-Madrid | Service Immunologia | Hospital de la Princesa | c/Diego de Leon 62, 28006 Madrid Spain | M | IgG1 | ? |
| D2 | 2, 3 | Robert Finberg | Division of Infectious Diseases | Dana-Faber Cancer Institute | 44 Binney Street, Boston MA 02115, USA | M | IgG1 | A/P |
| LDA1 | 2, 4 | Nicole Suclu-Foca | Dept. of Pathology | Columbia University | 630 West 168th Street, New York, NY 10032, USA | M | IgG2a | A/P |
| 7D1 | 1, 2 | Robert Sutherland | Oncology Research | Toronto Hospital | Room 407, 67 College St. Toronto, Ontario, M5G 2M1, Canada | M | IgG1K | S/P |
| 40B8 | 2 | Hans-Jorg Buhring | Medizinische Klinik und Poliklinik | Eberhard-Karis University of Tubingen | Dept II, Otfried-Muller-Str. 10, 72076 Tubingen, Germany | M | IgG1 | P |
| 1B3 | 2, 5 | Diane Nugent | | Childrens Hospital of Orange County | 455 Main St. Orange, CA 92668, USA | M | IgG2a | A/P |
| 59D6 | 2 | Hans-Jorg Buhring | Medizinische Klinik und Poliklinik | Eberhard-Karis University of Tubingen | Dept II, Otfried-Muller-Str. 10, 72076 Tubingen, Germany | M | IgM | S |
| 8A1 | 1, 2 | Robert Sutherland | Oncology Research | Toronto Hospital | Room 407, 67 College St. Toronto, Ontario, M5G 2M1, Canada | M | IgG1K | S/P |
| 7C5 | 1, 2 | Robert Sutherland | Oncology Research | Toronto Hospital | Room 407, 67 College St. Toronto, Ontario, M5G 2M1, Canada | M | IgG1K | S/P |
| B-E47 | | | | sold by EuroClone, Leinco, Diaclone | | M | IgG1 | S/P |

1. Sutherland D. R., Yeo E., Ryan A., Mills G. B., Bailey D. and Baker M. A. Blood 77 84-93 [1991].
2. Sutherland D. R. Yeo, E. L. Cluster report: CDw109. In: *Leukocyte Typing V* (ed. S. Schlossman et al.) pp. 1767-9. Oxford University Press, Oxford. [1995].
3. Haregewoin A., Solomon K., Hom R. C., Soman G., Bergelson J. M., Bhan A. K. and Finberg R. W. Cellular Immunology 156, 357-70 [1994].
4. Suciu-Foca N., Reed E., Rubenstein P., MacKenzie W., Ng A. and King D. W. Nature. 318, 465-7 [1985].
5. Brashem-Stein C., Nugent D. and Bernstein I. D. Journal of Immunology 140, 2330-3 [1988].

We claim:

1. An isolated nucleic acid molecule comprising the nucleic acid molecule of the coding strand shown in SEQ ID NO:1.

2. The molecule of claim 1, wherein the molecule encodes a polypeptide including a thioester region which becomes reactive towards a nucleophile when the polypeptide is cleaved.

3. An isolated nucleic acid molecule, comprising
a nucleic acid molecule encoding the same amino acid sequence as a nucleotide sequence of claim 1.

4. The nucleic acid molecule of claim 1, wherein the polypeptide activity comprises a K1 polypeptide SEQ ID NO:2.

5. The nucleic acid molecule of claim 1, consisting of the nucleotide sequence shown in SEQ ID NO: 1.

6. An isolated nucleic acid molecule comprising SEQ ID NO:1 isolated from a human.

7. The nucleic acid molecule of claim 1, wherein the molecule comprises genomic DNA, cDNA or RNA.

8. The nucleic acid molecule of claim 7, wherein the nucleic acid molecule is chemically synthesized.

9. A recombinant nucleic acid molecule comprising the nucleic acid molecule of claim 1 and a constitutive promoter sequence or an inducible promoter sequence operatively linked so that the promoter enhances transcription of the nucleic acid molecule in a host cell.

10. A vector comprising the nucleic acid molecule of claim 1.

11. The vector of claim 10, comprising a promoter selected from the group consisting of a vav promoter, a H2K promoter, a PF4 promoter, a GP1b promoter, a lck promoter, a CD2 promoter, a granzymeB promoter, a Beta actin promoter, a PGK promoter, a CMV promoter, a retroviral LTR, a metallothionenin IIA promoter, an ecdysone promoter and a tetracycline inducible promoter.

12. A host cell comprising the recombinant nucleic acid molecule of claim 9, or progeny of the host cell.

13. The host cell of claim 12, selected from the group consisting of a mammalian cell, a fungal cell, a yeast cell, a bacterial cell, a microorganism cell and a plant cell.

14. An isolated nucleic acid molecule encoding a polypeptide comprising the same amino acid sequence as the polypeptide encoded by SEQ ID NO:1.

15. A pharmaceutical composition comprising the nucleotide sequence of claim 1.

16. A kit for the treatment or detection of a disease, disorder or abnormal physical state, comprising the nucleotide sequence of claim 1.

* * * * *

SEQUENCE LISTING

<160> NUMBER OF SEQ ID NOS: 22

<210> SEQ ID NO 1
<211> LENGTH: 4761
<212> TYPE: DNA
<213> ORGANISM: HUMAN
<220> FEATURE:
<221> NAME/KEY: CDS
<222> LOCATION: (113)..(4447)

<400> SEQUENCE: 1

```
ctaaactcga attaagaggg aaaaaaaatc agggaggagg tggcaagcca caccccacgg        60
tgcccgcgaa cttccccggc agcggactgt agcccaggca gacgccgtcg ag atg cag     118
                                                          Met Gln
                                                            1 ggc cca ccg ctc ctg acc gcc gcc cac ctc ctc tgc gtg tgc acc gcc       166
Gly Pro Pro Leu Leu Thr Ala Ala His Leu Leu Cys Val Cys Thr Ala
         5                  10                  15 gcg ctg gcc gtg gct ccc ggg cct cgg ttt ctg gtg aca gcc cca ggg       214
Ala Leu Ala Val Ala Pro Gly Pro Arg Phe Leu Val Thr Ala Pro Gly
    20                  25                  30 atc atc agg ccc gga gga aat gtg act att ggg gtg gag ctc ctg gaa       262
Ile Ile Arg Pro Gly Gly Asn Val Thr Ile Gly Val Glu Leu Leu Glu
35                  40                  45                  50 cac tgc cct tca cag gtg act gtg aag gcg gag ctc ctc aag aca gca       310
His Cys Pro Ser Gln Val Thr Val Lys Ala Glu Leu Leu Lys Thr Ala
                55                  60                  65 tca aac ctc act gtc tct gtc ctg gaa gca gaa gga gtc ttt gaa aaa       358
Ser Asn Leu Thr Val Ser Val Leu Glu Ala Glu Gly Val Phe Glu Lys
            70                  75                  80 ggc tct ttt aag aca ctt act ctt cca tca cta cct ctg aac agt gca       406
Gly Ser Phe Lys Thr Leu Thr Leu Pro Ser Leu Pro Leu Asn Ser Ala
        85                  90                  95 gat gag att tat gag cta cgt gta acc gga cgt acc cag gat gag att       454
Asp Glu Ile Tyr Glu Leu Arg Val Thr Gly Arg Thr Gln Asp Glu Ile
    100                 105                 110 tta ttc tct aat agt acc cgc tta tca ttt gag acc aag aga ata tct       502
Leu Phe Ser Asn Ser Thr Arg Leu Ser Phe Glu Thr Lys Arg Ile Ser
115                 120                 125                 130 gtc ttc att caa aca gac aag gcc tta tac aag cca aag caa gaa gtg       550
Val Phe Ile Gln Thr Asp Lys Ala Leu Tyr Lys Pro Lys Gln Glu Val
                135                 140                 145 aag ttt cgc att gtt aca ctc ttc tca gat ttt aag cct tac aaa acc       598
Lys Phe Arg Ile Val Thr Leu Phe Ser Asp Phe Lys Pro Tyr Lys Thr
            150                 155                 160 tct tta aac att ctc att aag gac ccc aaa tca aat ttg atc caa cag       646
Ser Leu Asn Ile Leu Ile Lys Asp Pro Lys Ser Asn Leu Ile Gln Gln
        165                 170                 175 tgg ttg tca caa caa agt gat ctt gga gtc att tcc aaa act ttt cag       694
Trp Leu Ser Gln Gln Ser Asp Leu Gly Val Ile Ser Lys Thr Phe Gln
    180                 185                 190
```

-continued

| | |
|---|---|
| cta tct tcc cat cca ata ctt ggt gac tgg tct att caa gtt caa gtg<br>Leu Ser Ser His Pro Ile Leu Gly Asp Trp Ser Ile Gln Val Gln Val<br>195                    200                 205                   210 | 742 |
| aat gac cag aca tat tat caa tca ttt cag gtt tca gaa tat gta tta<br>Asn Asp Gln Thr Tyr Tyr Gln Ser Phe Gln Val Ser Glu Tyr Val Leu<br>                       215                 220                   225 | 790 |
| cca aaa ttt gaa gtg act ttg cag aca cca tta tat tgt tct atg aat<br>Pro Lys Phe Glu Val Thr Leu Gln Thr Pro Leu Tyr Cys Ser Met Asn<br>            230                 235                 240 | 838 |
| tct aag cat tta aat ggt acc atc acg gca aag tat aca tat ggg aag<br>Ser Lys His Leu Asn Gly Thr Ile Thr Ala Lys Tyr Thr Tyr Gly Lys<br>      245                 250                 255 | 886 |
| cca gtg aaa gga gac gta acg ctt aca ttt tta cct tta tcc ttt tgg<br>Pro Val Lys Gly Asp Val Thr Leu Thr Phe Leu Pro Leu Ser Phe Trp<br>260                    265                 270 | 934 |
| gga aag aag aaa aat att aca aaa aca ttt aag ata aat gga tct gca<br>Gly Lys Lys Lys Asn Ile Thr Lys Thr Phe Lys Ile Asn Gly Ser Ala<br>275                    280                 285                 290 | 982 |
| aac ttc tct ttt aat gat gaa gag atg aaa aat gta atg gat tct tca<br>Asn Phe Ser Phe Asn Asp Glu Glu Met Lys Asn Val Met Asp Ser Ser<br>                     295                 300                 305 | 1030 |
| aat gga ctt tct gaa tac ctg gat cta tct tcc cct gga cca gta gaa<br>Asn Gly Leu Ser Glu Tyr Leu Asp Leu Ser Ser Pro Gly Pro Val Glu<br>            310                 315                 320 | 1078 |
| att tta acc aca gtg aca gaa tca gtt aca ggt att tca aga aat gta<br>Ile Leu Thr Thr Val Thr Glu Ser Val Thr Gly Ile Ser Arg Asn Val<br>      325                 330                 335 | 1126 |
| agc act aat gtg ttc ttc aag caa cat gat tac atc att gag ttt ttt<br>Ser Thr Asn Val Phe Phe Lys Gln His Asp Tyr Ile Ile Glu Phe Phe<br>340                     345                 350 | 1174 |
| gat tat act act gtc ttg aag cca tct ctc aac ttc aca gcc act gtg<br>Asp Tyr Thr Thr Val Leu Lys Pro Ser Leu Asn Phe Thr Ala Thr Val<br>355                     360                 365                 370 | 1222 |
| aag gta act cgt gct gat ggc aac caa ctg act ctt gaa gaa aga aga<br>Lys Val Thr Arg Ala Asp Gly Asn Gln Leu Thr Leu Glu Glu Arg Arg<br>                     375                 380                 385 | 1270 |
| aat aat gta gtc ata aca gtg aca cag aga aac tat act gag tac tgg<br>Asn Asn Val Val Ile Thr Val Thr Gln Arg Asn Tyr Thr Glu Tyr Trp<br>            390                 395                 400 | 1318 |
| agc gga tct aac agt gga aat cag aaa atg gaa gct gtt cag aaa ata<br>Ser Gly Ser Asn Ser Gly Asn Gln Lys Met Glu Ala Val Gln Lys Ile<br>      405                 410                 415 | 1366 |
| aat tat act gtc ccc caa agt gga act ttt aag att gaa ttc cca atc<br>Asn Tyr Thr Val Pro Gln Ser Gly Thr Phe Lys Ile Glu Phe Pro Ile<br>420                     425                 430 | 1414 |
| ctg gag gat tcc agt gag cta cag ttg aag gcc tat ttc ctt ggt agt<br>Leu Glu Asp Ser Ser Glu Leu Gln Leu Lys Ala Tyr Phe Leu Gly Ser<br>435                     440                 445                 450 | 1462 |
| aaa agt agc atg gca gtt cat agt ctg ttt aag tct cct agt aag aca<br>Lys Ser Ser Met Ala Val His Ser Leu Phe Lys Ser Pro Ser Lys Thr<br>                     455                 460                 465 | 1510 |
| tac atc caa cta aaa aca aga gat gaa aat ata aag gtg gga tcg cct<br>Tyr Ile Gln Leu Lys Thr Arg Asp Glu Asn Ile Lys Val Gly Ser Pro<br>470                     475                 480 | 1558 |
| ttt gag ttg gtg gtt agt ggc aac aaa cga ttg aag gag tta agc tat<br>Phe Glu Leu Val Val Ser Gly Asn Lys Arg Leu Lys Glu Leu Ser Tyr<br>            485                 490                 495 | 1606 |
| atg gta gta tcc agg gga cag ttg gtg gct gta gga aaa caa aat tca<br>Met Val Val Ser Arg Gly Gln Leu Val Ala Val Gly Lys Gln Asn Ser | 1654 |

```
                                -continued
        500                 505                 510
aca atg ttc tct tta aca cca gaa aat tct tgg act cca aaa gcc tgt     1702
Thr Met Phe Ser Leu Thr Pro Glu Asn Ser Trp Thr Pro Lys Ala Cys
515                 520                 525                 530 gta att gtg tat tat att gaa gat gat ggg gaa att ata agt gat gtt     1750
Val Ile Val Tyr Tyr Ile Glu Asp Asp Gly Glu Ile Ile Ser Asp Val
                535                 540                 545 cta aaa att cct gtt cag ctt gtt ttt aaa aat aag ata aag cta tat     1798
Leu Lys Ile Pro Val Gln Leu Val Phe Lys Asn Lys Ile Lys Leu Tyr
            550                 555                 560 tgg agt aaa gtg aaa gct gaa cca tct gag aaa gtc tct ctt agg atc     1846
Trp Ser Lys Val Lys Ala Glu Pro Ser Glu Lys Val Ser Leu Arg Ile
        565                 570                 575 tct gtg aca cag cct gac tcc ata gtt ggg att gta gct gtt gac aaa     1894
Ser Val Thr Gln Pro Asp Ser Ile Val Gly Ile Val Ala Val Asp Lys
    580                 585                 590 agt gtg aat ctg atg aat gcc tct aat gat att aca atg gaa aat gtg     1942
Ser Val Asn Leu Met Asn Ala Ser Asn Asp Ile Thr Met Glu Asn Val
595                 600                 605                 610 gtc cat gag ttg gaa ctt tat aac aca gga tat tat tta ggc atg ttc     1990
Val His Glu Leu Glu Leu Tyr Asn Thr Gly Tyr Tyr Leu Gly Met Phe
                615                 620                 625 atg aat tct ttt gca gtc ttt cag gaa tgt gga ctc tgg gta ttg aca     2038
Met Asn Ser Phe Ala Val Phe Gln Glu Cys Gly Leu Trp Val Leu Thr
            630                 635                 640 gat gca aac ctc acg aag gat tat att gat ggt gtt tat gac aat gca     2086
Asp Ala Asn Leu Thr Lys Asp Tyr Ile Asp Gly Val Tyr Asp Asn Ala
        645                 650                 655 gaa tat gct gag agg ttt atg gag gaa aat gaa gga cat att gta gat     2134
Glu Tyr Ala Glu Arg Phe Met Glu Glu Asn Glu Gly His Ile Val Asp
    660                 665                 670 att cat gac ttt tct ttg ggt agc agt cca cat gtc cga aag cat ttt     2182
Ile His Asp Phe Ser Leu Gly Ser Ser Pro His Val Arg Lys His Phe
675                 680                 685                 690 cca gag act tgg att tgg cta gac acc aac atg ggt tac agg att tac     2230
Pro Glu Thr Trp Ile Trp Leu Asp Thr Asn Met Gly Tyr Arg Ile Tyr
                695                 700                 705 caa gaa ttt gaa gta act gta cct gat tct atc act tct tgg gtg gct     2278
Gln Glu Phe Glu Val Thr Val Pro Asp Ser Ile Thr Ser Trp Val Ala
            710                 715                 720 act ggt ttt gtg atc tct gag gac ctg ggt ctt gga cta aca act act     2326
Thr Gly Phe Val Ile Ser Glu Asp Leu Gly Leu Gly Leu Thr Thr Thr
        725                 730                 735 cca gtg gag ctc caa gcc ttc caa cca ttt ttc att ttt ttg aat ctt     2374
Pro Val Glu Leu Gln Ala Phe Gln Pro Phe Phe Ile Phe Leu Asn Leu
    740                 745                 750 ccc tac tct gtt atc aga ggt gaa gaa ttt gct ttg gaa ata act ata     2422
Pro Tyr Ser Val Ile Arg Gly Glu Glu Phe Ala Leu Glu Ile Thr Ile
755                 760                 765                 770 ttc aat tat ttg aaa gat gcc act gag gtt aag gta atc att gag aaa     2470
Phe Asn Tyr Leu Lys Asp Ala Thr Glu Val Lys Val Ile Ile Glu Lys
                775                 780                 785 agt gac aaa ttt gat att cta atg act tca aat gaa ata aat gcc aca     2518
Ser Asp Lys Phe Asp Ile Leu Met Thr Ser Asn Glu Ile Asn Ala Thr
            790                 795                 800 ggc cac cag cag acc ctt ctg gtt ccc agt gag gat ggg gca act gtt     2566
Gly His Gln Gln Thr Leu Leu Val Pro Ser Glu Asp Gly Ala Thr Val
        805                 810                 815 ctt ttt ccc atc agg cca aca cat ctg gga gaa att cct atc aca gtc     2614
```

```
                    Leu Phe Pro Ile Arg Pro Thr His Leu Gly Glu Ile Pro Ile Thr Val
                        820                 825                 830 aca gct ctt tca ccc act gct tct gat gct gtc acc cag atg att tta       2662
Thr Ala Leu Ser Pro Thr Ala Ser Asp Ala Val Thr Gln Met Ile Leu
835                 840                 845                 850 gta aag gct gaa gga ata gaa aaa tca tat tca caa tcc atc tta tta       2710
Val Lys Ala Glu Gly Ile Glu Lys Ser Tyr Ser Gln Ser Ile Leu Leu
                855                 860                 865 gac ttg act gac aat agg cta cag agt acc ctg aaa act ttg agt ttc       2758
Asp Leu Thr Asp Asn Arg Leu Gln Ser Thr Leu Lys Thr Leu Ser Phe
            870                 875                 880 tca ttt cct cct aat aca gtg act ggc agt gaa aga gtt cag atc act       2806
Ser Phe Pro Pro Asn Thr Val Thr Gly Ser Glu Arg Val Gln Ile Thr
                    885                 890                 895 gca att gga gat gtt ctt ggt cct tcc atc aat ggc tta gcc tca ttg       2854
Ala Ile Gly Asp Val Leu Gly Pro Ser Ile Asn Gly Leu Ala Ser Leu
900                 905                 910 att cgg atg cct tat ggc tgt ggt gaa cag aac atg ata aat ttt gct       2902
Ile Arg Met Pro Tyr Gly Cys Gly Glu Gln Asn Met Ile Asn Phe Ala
915                 920                 925                 930 cca aat att tac att ttg gat tat ctg act aaa aag aaa caa ctg aca       2950
Pro Asn Ile Tyr Ile Leu Asp Tyr Leu Thr Lys Lys Lys Gln Leu Thr
                935                 940                 945 gat aat ttg aaa gaa aaa gct ctt tca ttt atg agg caa ggt tac cag       2998
Asp Asn Leu Lys Glu Lys Ala Leu Ser Phe Met Arg Gln Gly Tyr Gln
            950                 955                 960 aga gaa ctt ctc tat cag agg gaa gat ggc tct ttc agt gct ttt ggg       3046
Arg Glu Leu Leu Tyr Gln Arg Glu Asp Gly Ser Phe Ser Ala Phe Gly
                965                 970                 975 aat tat gac cct tct ggg agc act tgg ttg tca gct ttt gtt tta aga       3094
Asn Tyr Asp Pro Ser Gly Ser Thr Trp Leu Ser Ala Phe Val Leu Arg
            980                 985                 990 tgt ttc ctt gaa gcc gat     cct tac ata gat att     gat cag aat gtg   3139
Cys Phe Leu Glu Ala Asp     Pro Tyr Ile Asp Ile     Asp Gln Asn Val
995                         1000                    1005 tta cac aga aca tac act     tgg ctt aaa gga cat     cag aaa tcc aac   3184
Leu His Arg Thr Tyr Thr     Trp Leu Lys Gly His     Gln Lys Ser Asn
1010                        1015                    1020 ggt gaa ttt tgg gat cca     gga aga gtg att cat     agt gag ctt caa   3229
Gly Glu Phe Trp Asp Pro     Gly Arg Val Ile His     Ser Glu Leu Gln
1025                        1030                    1035 ggt ggc aat aaa agt cca     gta aca ctt aca gcc     tat att gta act   3274
Gly Gly Asn Lys Ser Pro     Val Thr Leu Thr Ala     Tyr Ile Val Thr
1040                        1045                    1050 tct ctc ctg gga tat aga     aag tat cag cct aac     att gat gtg caa   3319
Ser Leu Leu Gly Tyr Arg     Lys Tyr Gln Pro Asn     Ile Asp Val Gln
1055                        1060                    1065 gag tct atc cat ttt ttg     gag tct gaa ttc agt     aga gga att tca   3364
Glu Ser Ile His Phe Leu     Glu Ser Glu Phe Ser     Arg Gly Ile Ser
1070                        1075                    1080 gac aat tat act cta gcc     ctt ata act tat gca     ttg tca tca gtg   3409
Asp Asn Tyr Thr Leu Ala     Leu Ile Thr Tyr Ala     Leu Ser Ser Val
1085                        1090                    1095 ggg agt cct aaa gcg aag     gaa gct ttg aat atg     ctg act tgg aga   3454
Gly Ser Pro Lys Ala Lys     Glu Ala Leu Asn Met     Leu Thr Trp Arg
1100                        1105                    1110 gca gaa caa gaa ggt ggc     atg caa ttc tgg gtg     tca tca gag tcc   3499
Ala Glu Gln Glu Gly Gly     Met Gln Phe Trp Val     Ser Ser Glu Ser
1115                        1120                    1125
```

| | | | | | | | | | | | | | |
|---|---|---|---|---|---|---|---|---|---|---|---|---|---|
| aaa | ctt | tct | gac | tcc | tgg | cag | cca | cgc | tcc | ctg | gat | att | gaa | gtt | 3544 |
| Lys | Leu | Ser | Asp | Ser | Trp | Gln | Pro | Arg | Ser | Leu | Asp | Ile | Glu | Val |
| 1130 | | | | 1135 | | | | | 1140 | | | | |

| gca | gcc | tat | gca | ctg | ctc | tca | cac | ttc | tta | caa | ttt | cag | act | tct | 3589 |
| Ala | Ala | Tyr | Ala | Leu | Leu | Ser | His | Phe | Leu | Gln | Phe | Gln | Thr | Ser |
| 1145 | | | | 1150 | | | | | 1155 | | | | |

| gag | gga | atc | cca | att | atg | agg | tgg | cta | agc | agg | caa | aga | aat | agc | 3634 |
| Glu | Gly | Ile | Pro | Ile | Met | Arg | Trp | Leu | Ser | Arg | Gln | Arg | Asn | Ser |
| 1160 | | | | 1165 | | | | | 1170 | | | | |

| ttg | ggt | ggt | ttt | gca | tct | act | cag | gat | acc | act | gtg | gct | tta | aag | 3679 |
| Leu | Gly | Gly | Phe | Ala | Ser | Thr | Gln | Asp | Thr | Thr | Val | Ala | Leu | Lys |
| 1175 | | | | 1180 | | | | | 1185 | | | | |

| gct | ctg | tct | gaa | ttt | gca | gcc | cta | atg | aat | aca | gaa | agg | aca | aat | 3724 |
| Ala | Leu | Ser | Glu | Phe | Ala | Ala | Leu | Met | Asn | Thr | Glu | Arg | Thr | Asn |
| 1190 | | | | 1195 | | | | | 1200 | | | | |

| atc | caa | gtg | acc | gtg | acg | ggg | cct | agc | tca | cca | agt | cct | gta | aag | 3769 |
| Ile | Gln | Val | Thr | Val | Thr | Gly | Pro | Ser | Ser | Pro | Ser | Pro | Val | Lys |
| 1205 | | | | 1210 | | | | | 1215 | | | | |

| ttt | ctg | att | gac | aca | cac | aac | cgc | tta | ctc | ctt | cag | aca | gca | gag | 3814 |
| Phe | Leu | Ile | Asp | Thr | His | Asn | Arg | Leu | Leu | Leu | Gln | Thr | Ala | Glu |
| 1220 | | | | 1225 | | | | | 1230 | | | | |

| ctt | gct | gtg | gta | cag | cca | atg | gca | gtt | aat | att | tcc | gca | aat | ggt | 3859 |
| Leu | Ala | Val | Val | Gln | Pro | Met | Ala | Val | Asn | Ile | Ser | Ala | Asn | Gly |
| 1235 | | | | 1240 | | | | | 1245 | | | | |

| ttt | gga | ttt | gct | att | tgt | cag | ctc | aat | gtt | gta | tat | aat | gtg | aag | 3904 |
| Phe | Gly | Phe | Ala | Ile | Cys | Gln | Leu | Asn | Val | Val | Tyr | Asn | Val | Lys |
| 1250 | | | | 1255 | | | | | 1260 | | | | |

| gct | tct | ggg | tct | tct | aga | aga | cga | aga | tct | atc | caa | aat | caa | gaa | 3949 |
| Ala | Ser | Gly | Ser | Ser | Arg | Arg | Arg | Arg | Ser | Ile | Gln | Asn | Gln | Glu |
| 1265 | | | | 1270 | | | | | 1275 | | | | |

| gcc | ttt | gat | tta | gat | gtt | gct | gta | aaa | gaa | aat | aaa | gat | gat | ctc | 3994 |
| Ala | Phe | Asp | Leu | Asp | Val | Ala | Val | Lys | Glu | Asn | Lys | Asp | Asp | Leu |
| 1280 | | | | 1285 | | | | | 1290 | | | | |

| aat | cat | gtg | gat | ttg | aat | gtg | tgt | aca | agc | ttt | tcg | ggc | ccg | ggt | 4039 |
| Asn | His | Val | Asp | Leu | Asn | Val | Cys | Thr | Ser | Phe | Ser | Gly | Pro | Gly |
| 1295 | | | | 1300 | | | | | 1305 | | | | |

| agg | agt | ggc | atg | gct | ctt | atg | gaa | gtt | aac | cta | tta | agt | ggc | ttt | 4084 |
| Arg | Ser | Gly | Met | Ala | Leu | Met | Glu | Val | Asn | Leu | Leu | Ser | Gly | Phe |
| 1310 | | | | 1315 | | | | | 1320 | | | | |

| atg | gtg | cct | tca | gaa | gca | att | tct | ctg | agc | gag | aca | gtg | aag | aaa | 4129 |
| Met | Val | Pro | Ser | Glu | Ala | Ile | Ser | Leu | Ser | Glu | Thr | Val | Lys | Lys |
| 1325 | | | | 1330 | | | | | 1335 | | | | |

| gtg | gaa | tat | gat | cat | gga | aaa | ctc | aac | ctc | tat | tta | gat | tct | gta | 4174 |
| Val | Glu | Tyr | Asp | His | Gly | Lys | Leu | Asn | Leu | Tyr | Leu | Asp | Ser | Val |
| 1340 | | | | 1345 | | | | | 1350 | | | | |

| aat | gaa | acc | cag | ttt | tgt | gtt | aat | att | cct | gct | gtg | aga | aac | ttt | 4219 |
| Asn | Glu | Thr | Gln | Phe | Cys | Val | Asn | Ile | Pro | Ala | Val | Arg | Asn | Phe |
| 1355 | | | | 1360 | | | | | 1365 | | | | |

| aaa | gtt | tca | aat | acc | caa | gat | gct | tca | gtg | tcc | ata | gtg | gat | tac | 4264 |
| Lys | Val | Ser | Asn | Thr | Gln | Asp | Ala | Ser | Val | Ser | Ile | Val | Asp | Tyr |
| 1370 | | | | 1375 | | | | | 1380 | | | | |

| tat | gag | cca | agg | aga | cag | gcg | gtg | aga | agt | tac | aac | tct | gaa | gtg | 4309 |
| Tyr | Glu | Pro | Arg | Arg | Gln | Ala | Val | Arg | Ser | Tyr | Asn | Ser | Glu | Val |
| 1385 | | | | 1390 | | | | | 1395 | | | | |

| aag | ctg | tcc | tcc | tgt | gac | ctt | tgc | agt | gat | gtc | cag | ggc | tgc | cgt | 4354 |
| Lys | Leu | Ser | Ser | Cys | Asp | Leu | Cys | Ser | Asp | Val | Gln | Gly | Cys | Arg |
| 1400 | | | | 1405 | | | | | 1410 | | | | |

| cct | tgt | gag | gat | gga | gct | tca | ggc | tcc | cat | cat | cac | tct | tca | gtc | 4399 |
| Pro | Cys | Glu | Asp | Gly | Ala | Ser | Gly | Ser | His | His | His | Ser | Ser | Val |
| 1415 | | | | 1420 | | | | | 1425 | | | | |

```
att ttt att ttc tgt ttc aag ctt ctg tac ttt atg gaa ctt tgg      4444
Ile Phe Ile Phe Cys Phe Lys Leu Leu Tyr Phe Met Glu Leu Trp
1430                1435                1440 ctg tgatttattt ttaaaggact ctgtgtaaca ctaacatttc cagtagtcac        4497
Leu
1445 atgtgattgt tttgttttcg tagaagaata ctgcttctat tttgaaaaaa gagttttttt  4557 tctttctatg gggttgcagg gatggtgtac aacaggtcct agcatgtata gctgcataga 4617 tttcttcacc tgatctttgt gtggaagatc agaatgaatg cagttgtgtg tctatatttt 4677 cccctcacaa aatcttttag aattttttg gaggtgtttg ttttctccag aataaaggta 4737 ttactttaga aaaaaaaaaa aaaa                                        4761

<210> SEQ ID NO 2
<211> LENGTH: 1445
<212> TYPE: PRT
<213> ORGANISM: HUMAN

<400> SEQUENCE: 2

Met Gln Gly Pro Pro Leu Leu Thr Ala Ala His Leu Leu Cys Val Cys
1               5                   10                  15

Thr Ala Ala Leu Ala Val Ala Pro Gly Pro Arg Phe Leu Val Thr Ala
                20                  25                  30

Pro Gly Ile Ile Arg Pro Gly Gly Asn Val Thr Ile Gly Val Glu Leu
            35                  40                  45

Leu Glu His Cys Pro Ser Gln Val Thr Val Lys Ala Glu Leu Leu Lys
        50                  55                  60

Thr Ala Ser Asn Leu Thr Val Ser Val Leu Glu Ala Glu Gly Val Phe
65                  70                  75                  80

Glu Lys Gly Ser Phe Lys Thr Leu Thr Leu Pro Ser Leu Pro Leu Asn
                85                  90                  95

Ser Ala Asp Glu Ile Tyr Glu Leu Arg Val Thr Gly Arg Thr Gln Asp
            100                 105                 110

Glu Ile Leu Phe Ser Asn Ser Thr Arg Leu Ser Phe Glu Thr Lys Arg
        115                 120                 125

Ile Ser Val Phe Ile Gln Thr Asp Lys Ala Leu Tyr Lys Pro Lys Gln
    130                 135                 140

Glu Val Lys Phe Arg Ile Val Thr Leu Phe Ser Asp Phe Lys Pro Tyr
145                 150                 155                 160

Lys Thr Ser Leu Asn Ile Leu Ile Lys Asp Pro Lys Ser Asn Leu Ile
                165                 170                 175

Gln Gln Trp Leu Ser Gln Ser Asp Leu Gly Val Ile Ser Lys Thr
            180                 185                 190

Phe Gln Leu Ser Ser His Pro Ile Leu Gly Asp Trp Ser Ile Gln Val
        195                 200                 205

Gln Val Asn Asp Gln Thr Tyr Tyr Gln Ser Phe Gln Val Ser Glu Tyr
    210                 215                 220

Val Leu Pro Lys Phe Glu Val Thr Leu Gln Thr Pro Leu Tyr Cys Ser
225                 230                 235                 240

Met Asn Ser Lys His Leu Asn Gly Thr Ile Thr Ala Lys Tyr Thr Tyr
                245                 250                 255

Gly Lys Pro Val Lys Gly Asp Val Thr Leu Thr Phe Leu Pro Leu Ser
            260                 265                 270

Phe Trp Gly Lys Lys Lys Asn Ile Thr Lys Thr Phe Lys Ile Asn Gly
```

-continued

```
                275                 280                 285
Ser Ala Asn Phe Ser Phe Asn Asp Glu Glu Met Lys Asn Val Met Asp
    290                 295                 300
Ser Ser Asn Gly Leu Ser Glu Tyr Leu Asp Leu Ser Ser Pro Gly Pro
305                 310                 315                 320
Val Glu Ile Leu Thr Thr Val Thr Glu Ser Val Thr Gly Ile Ser Arg
                325                 330                 335
Asn Val Ser Thr Asn Val Phe Phe Lys Gln His Asp Tyr Ile Ile Glu
            340                 345                 350
Phe Phe Asp Tyr Thr Thr Val Leu Lys Pro Ser Leu Asn Phe Thr Ala
            355                 360                 365
Thr Val Lys Val Thr Arg Ala Asp Gly Asn Gln Leu Thr Leu Glu Glu
        370                 375                 380
Arg Arg Asn Asn Val Val Ile Thr Val Thr Gln Arg Asn Tyr Thr Glu
385                 390                 395                 400
Tyr Trp Ser Gly Ser Asn Ser Gly Asn Gln Lys Met Glu Ala Val Gln
                405                 410                 415
Lys Ile Asn Tyr Thr Val Pro Gln Ser Gly Thr Phe Lys Ile Glu Phe
            420                 425                 430
Pro Ile Leu Glu Asp Ser Ser Glu Leu Gln Leu Lys Ala Tyr Phe Leu
        435                 440                 445
Gly Ser Lys Ser Ser Met Ala Val His Ser Leu Phe Lys Ser Pro Ser
    450                 455                 460
Lys Thr Tyr Ile Gln Leu Lys Thr Arg Asp Glu Asn Ile Lys Val Gly
465                 470                 475                 480
Ser Pro Phe Glu Leu Val Val Ser Gly Asn Lys Arg Leu Lys Glu Leu
                485                 490                 495
Ser Tyr Met Val Val Ser Arg Gly Gln Leu Val Ala Val Gly Lys Gln
            500                 505                 510
Asn Ser Thr Met Phe Ser Leu Thr Pro Glu Asn Ser Trp Thr Pro Lys
        515                 520                 525
Ala Cys Val Ile Val Tyr Tyr Ile Glu Asp Asp Gly Glu Ile Ile Ser
    530                 535                 540
Asp Val Leu Lys Ile Pro Val Gln Leu Val Phe Lys Asn Lys Ile Lys
545                 550                 555                 560
Leu Tyr Trp Ser Lys Val Lys Ala Glu Pro Ser Glu Lys Val Ser Leu
                565                 570                 575
Arg Ile Ser Val Thr Gln Pro Asp Ser Ile Val Gly Ile Val Ala Val
            580                 585                 590
Asp Lys Ser Val Asn Leu Met Asn Ala Ser Asn Asp Ile Thr Met Glu
        595                 600                 605
Asn Val Val His Glu Leu Glu Leu Tyr Asn Thr Gly Tyr Tyr Leu Gly
    610                 615                 620
Met Phe Met Asn Ser Phe Ala Val Phe Gln Glu Cys Gly Leu Trp Val
625                 630                 635                 640
Leu Thr Asp Ala Asn Leu Thr Lys Asp Tyr Ile Asp Gly Val Tyr Asp
                645                 650                 655
Asn Ala Glu Tyr Ala Glu Arg Phe Met Glu Glu Asn Glu Gly His Ile
            660                 665                 670
Val Asp Ile His Asp Phe Ser Leu Gly Ser Ser Pro His Val Arg Lys
        675                 680                 685
His Phe Pro Glu Thr Trp Ile Trp Leu Asp Thr Asn Met Gly Tyr Arg
    690                 695                 700
```

```
Ile Tyr Gln Glu Phe Glu Val Thr Val Pro Asp Ser Ile Thr Ser Trp
705                 710                 715                 720

Val Ala Thr Gly Phe Val Ile Ser Glu Asp Leu Gly Leu Gly Leu Thr
            725                 730                 735

Thr Thr Pro Val Glu Leu Gln Ala Phe Gln Pro Phe Phe Ile Phe Leu
            740                 745                 750

Asn Leu Pro Tyr Ser Val Arg Gly Glu Gly Phe Ala Leu Glu Ile
            755                 760                 765

Thr Ile Phe Asn Tyr Leu Lys Asp Ala Thr Glu Val Lys Val Ile Ile
770                 775                 780

Glu Lys Ser Asp Lys Phe Asp Ile Leu Met Thr Ser Asn Glu Ile Asn
785                 790                 795                 800

Ala Thr Gly His Gln Gln Thr Leu Leu Val Pro Ser Glu Asp Gly Ala
            805                 810                 815

Thr Val Leu Phe Pro Ile Arg Pro Thr His Leu Gly Glu Ile Pro Ile
            820                 825                 830

Thr Val Thr Ala Leu Ser Pro Thr Ala Ser Asp Ala Val Thr Gln Met
835                 840                 845

Ile Leu Val Lys Ala Glu Gly Ile Glu Lys Ser Tyr Ser Gln Ser Ile
850                 855                 860

Leu Leu Asp Leu Thr Asp Asn Arg Leu Gln Ser Thr Leu Lys Thr Leu
865                 870                 875                 880

Ser Phe Ser Phe Pro Pro Asn Thr Val Thr Gly Ser Glu Arg Val Gln
            885                 890                 895

Ile Thr Ala Ile Gly Asp Val Leu Gly Pro Ser Ile Asn Gly Leu Ala
            900                 905                 910

Ser Leu Ile Arg Met Pro Tyr Gly Cys Gly Glu Gln Asn Met Ile Asn
            915                 920                 925

Phe Ala Pro Asn Ile Tyr Ile Leu Asp Tyr Leu Thr Lys Lys Gln
            930                 935                 940

Leu Thr Asp Asn Leu Lys Glu Lys Ala Leu Ser Phe Met Arg Gln Gly
945                 950                 955                 960

Tyr Gln Arg Glu Leu Leu Tyr Gln Arg Glu Asp Gly Ser Phe Ser Ala
            965                 970                 975

Phe Gly Asn Tyr Asp Pro Ser Gly Ser Thr Trp Leu Ser Ala Phe Val
            980                 985                 990

Leu Arg Cys Phe Leu Glu Ala Asp Pro Tyr Ile Asp Ile Asp Gln Asn
            995                 1000                1005

Val Leu His Arg Thr Tyr Thr Trp Leu Lys Gly His Gln Lys Ser
    1010                1015                1020

Asn Gly Glu Phe Trp Asp Pro Gly Arg Val Ile His Ser Glu Leu
    1025                1030                1035

Gln Gly Gly Asn Lys Ser Pro Val Thr Leu Thr Ala Tyr Ile Val
    1040                1045                1050

Thr Ser Leu Leu Gly Tyr Arg Lys Tyr Gln Pro Asn Ile Asp Val
    1055                1060                1065

Gln Glu Ser Ile His Phe Leu Glu Ser Glu Phe Ser Arg Gly Ile
    1070                1075                1080

Ser Asp Asn Tyr Thr Leu Ala Leu Ile Thr Tyr Ala Leu Ser Ser
    1085                1090                1095

Val Gly Ser Pro Lys Ala Lys Glu Ala Leu Asn Met Leu Thr Trp
    1100                1105                1110
```

| Arg | Ala | Glu | Gln | Glu | Gly | Gly | Met | Gln | Phe | Trp | Val | Ser | Ser | Glu |
| 1115 | | | | | 1120 | | | | | 1125 | | | | |

| Ser | Lys | Leu | Ser | Asp | Ser | Trp | Gln | Pro | Arg | Ser | Leu | Asp | Ile | Glu |
| 1130 | | | | | 1135 | | | | | 1140 | | | | |

| Val | Ala | Ala | Tyr | Ala | Leu | Leu | Ser | His | Phe | Leu | Gln | Phe | Gln | Thr |
| 1145 | | | | | 1150 | | | | | 1155 | | | | |

| Ser | Glu | Gly | Ile | Pro | Ile | Met | Arg | Trp | Leu | Ser | Arg | Gln | Arg | Asn |
| 1160 | | | | | 1165 | | | | | 1170 | | | | |

| Ser | Leu | Gly | Gly | Phe | Ala | Ser | Thr | Gln | Asp | Thr | Thr | Val | Ala | Leu |
| 1175 | | | | | 1180 | | | | | 1185 | | | | |

| Lys | Ala | Leu | Ser | Glu | Phe | Ala | Ala | Leu | Met | Asn | Thr | Glu | Arg | Thr |
| 1190 | | | | | 1195 | | | | | 1200 | | | | |

| Asn | Ile | Gln | Val | Thr | Val | Thr | Gly | Pro | Ser | Ser | Pro | Ser | Pro | Val |
| 1205 | | | | | 1210 | | | | | 1215 | | | | |

| Lys | Phe | Leu | Ile | Asp | Thr | His | Asn | Arg | Leu | Leu | Leu | Gln | Thr | Ala |
| 1220 | | | | | 1225 | | | | | 1230 | | | | |

| Glu | Leu | Ala | Val | Val | Gln | Pro | Met | Ala | Val | Asn | Ile | Ser | Ala | Asn |
| 1235 | | | | | 1240 | | | | | 1245 | | | | |

| Gly | Phe | Gly | Phe | Ala | Ile | Cys | Gln | Leu | Asn | Val | Val | Tyr | Asn | Val |
| 1250 | | | | | 1255 | | | | | 1260 | | | | |

| Lys | Ala | Ser | Gly | Ser | Ser | Arg | Arg | Arg | Arg | Ser | Ile | Gln | Asn | Gln |
| 1265 | | | | | 1270 | | | | | 1275 | | | | |

| Glu | Ala | Phe | Asp | Leu | Asp | Val | Ala | Val | Lys | Glu | Asn | Lys | Asp | Asp |
| 1280 | | | | | 1285 | | | | | 1290 | | | | |

| Leu | Asn | His | Val | Asp | Leu | Asn | Val | Cys | Thr | Ser | Phe | Ser | Gly | Pro |
| 1295 | | | | | 1300 | | | | | 1305 | | | | |

| Gly | Arg | Ser | Gly | Met | Ala | Leu | Met | Glu | Val | Asn | Leu | Leu | Ser | Gly |
| 1310 | | | | | 1315 | | | | | 1320 | | | | |

| Phe | Met | Val | Pro | Ser | Glu | Ala | Ile | Ser | Leu | Ser | Glu | Thr | Val | Lys |
| 1325 | | | | | 1330 | | | | | 1335 | | | | |

| Lys | Val | Glu | Tyr | Asp | His | Gly | Lys | Leu | Asn | Leu | Tyr | Leu | Asp | Ser |
| 1340 | | | | | 1345 | | | | | 1350 | | | | |

| Val | Asn | Glu | Thr | Gln | Phe | Cys | Val | Asn | Ile | Pro | Ala | Val | Arg | Asn |
| 1355 | | | | | 1360 | | | | | 1365 | | | | |

| Phe | Lys | Val | Ser | Asn | Thr | Gln | Asp | Ala | Ser | Val | Ser | Ile | Val | Asp |
| 1370 | | | | | 1375 | | | | | 1380 | | | | |

| Tyr | Tyr | Glu | Pro | Arg | Arg | Gln | Ala | Val | Arg | Ser | Tyr | Asn | Ser | Glu |
| 1385 | | | | | 1390 | | | | | 1395 | | | | |

| Val | Lys | Leu | Ser | Ser | Cys | Asp | Leu | Cys | Ser | Asp | Val | Gln | Gly | Cys |
| 1400 | | | | | 1405 | | | | | 1410 | | | | |

| Arg | Pro | Cys | Glu | Asp | Gly | Ala | Ser | Gly | Ser | His | His | His | Ser | Ser |
| 1415 | | | | | 1420 | | | | | 1425 | | | | |

| Val | Ile | Phe | Ile | Phe | Cys | Phe | Lys | Leu | Leu | Tyr | Phe | Met | Glu | Leu |
| 1430 | | | | | 1435 | | | | | 1440 | | | | |

| Trp | Leu |
| 1445 | |

```
<210> SEQ ID NO 3
<211> LENGTH: 4761
<212> TYPE: DNA
<213> ORGANISM: HUMAN
<220> FEATURE:
<221> NAME/KEY: CDS
<222> LOCATION: (113)..(4447)

<400> SEQUENCE: 3
```

-continued

```
ctaaactcga attaagaggg aaaaaaaatc agggaggagg tggcaagcca caccccacgg         60
tgcccgcgaa cttccccggc agcggactgt agcccaggca gacgccgtcg ag atg cag       118
                                                        Met Gln
                                                          1 ggc cca ccg ctc ctg acc gcc gcc cac ctc ctc tgc gtg tgc acc gcc         166
Gly Pro Pro Leu Leu Thr Ala Ala His Leu Leu Cys Val Cys Thr Ala
        5                  10                  15 gcg ctg gcc gtg gct ccc ggg cct cgg ttt ctg gta aca gcc cca ggg         214
Ala Leu Ala Val Ala Pro Gly Pro Arg Phe Leu Val Thr Ala Pro Gly
 20                  25                  30 atc atc agg ccc gga gga aat gtg act att ggg gtg gag ctt ctg gaa         262
Ile Ile Arg Pro Gly Gly Asn Val Thr Ile Gly Val Glu Leu Leu Glu
 35                  40                  45                  50 cac tgc cct tca cag gtg act gtg aag gcg gag ctg ctc aag aca gca         310
His Cys Pro Ser Gln Val Thr Val Lys Ala Glu Leu Leu Lys Thr Ala
                 55                  60                  65 tca aac ctc act gtc tct gtc ctg gaa gca gaa gga gtc ttt gaa aaa         358
Ser Asn Leu Thr Val Ser Val Leu Glu Ala Glu Gly Val Phe Glu Lys
         70                  75                  80 ggc tct ttt aag aca ctt act ctt cca tca cta cct ctg aac agt gca         406
Gly Ser Phe Lys Thr Leu Thr Leu Pro Ser Leu Pro Leu Asn Ser Ala
     85                  90                  95 gat gag att tat gag cta cgt gta acc gga cgt acc cag gat gag att         454
Asp Glu Ile Tyr Glu Leu Arg Val Thr Gly Arg Thr Gln Asp Glu Ile
100                 105                 110 tta ttc tct aat agt acc cgc tta tca ttt gag acc aag aga ata tct         502
Leu Phe Ser Asn Ser Thr Arg Leu Ser Phe Glu Thr Lys Arg Ile Ser
115                 120                 125                 130 gtc ttc att caa aca gac aag gcc tta tac aag cca aag caa gaa gtg         550
Val Phe Ile Gln Thr Asp Lys Ala Leu Tyr Lys Pro Lys Gln Glu Val
                135                 140                 145 aag ttt cgc att gtt aca ctc ttc tca gat ttt aag cct tac aaa acc         598
Lys Phe Arg Ile Val Thr Leu Phe Ser Asp Phe Lys Pro Tyr Lys Thr
            150                 155                 160 tct tta aac att ctc att aag gac ccc aaa tca aat ttg atc caa cag         646
Ser Leu Asn Ile Leu Ile Lys Asp Pro Lys Ser Asn Leu Ile Gln Gln
        165                 170                 175 tgg ttg tca caa caa agt gat ctt gga gtc att tcc aaa act ttt cag         694
Trp Leu Ser Gln Gln Ser Asp Leu Gly Val Ile Ser Lys Thr Phe Gln
    180                 185                 190 cta tct tcc cat cca ata ctt ggt gac tgg tct att caa gtt caa gtg         742
Leu Ser Ser His Pro Ile Leu Gly Asp Trp Ser Ile Gln Val Gln Val
195                 200                 205                 210 aat gac cag aca tat tat caa tca ttt cag gtt tca gaa tat gta tta         790
Asn Asp Gln Thr Tyr Tyr Gln Ser Phe Gln Val Ser Glu Tyr Val Leu
                215                 220                 225 cca aaa ttt gaa gtg act ttg cag aca cca tta tat tgt tct atg aat         838
Pro Lys Phe Glu Val Thr Leu Gln Thr Pro Leu Tyr Cys Ser Met Asn
            230                 235                 240 tct aag cat tta aat ggt acc atc acg gca aag tat aca tat ggg aag         886
Ser Lys His Leu Asn Gly Thr Ile Thr Ala Lys Tyr Thr Tyr Gly Lys
        245                 250                 255 cca gtg aaa gga gac gta acg ctt aca ttt tta cct tta tcc ttt tgg         934
Pro Val Lys Gly Asp Val Thr Leu Thr Phe Leu Pro Leu Ser Phe Trp
    260                 265                 270 gga aag aag aaa aat att aca aaa aca ttt aag ata aat gga tct gca         982
Gly Lys Lys Lys Asn Ile Thr Lys Thr Phe Lys Ile Asn Gly Ser Ala
275                 280                 285                 290
```

```
aac ttc tct ttt aat gat gaa gag atg aaa aat gta atg gat tct tca    1030
Asn Phe Ser Phe Asn Asp Glu Glu Met Lys Asn Val Met Asp Ser Ser
            295                 300                 305 aat gga ctt tct gaa tac ctg gat cta tct tcc cct gga cca gta gaa    1078
Asn Gly Leu Ser Glu Tyr Leu Asp Leu Ser Ser Pro Gly Pro Val Glu
            310                 315                 320 att tta acc aca gtg aca gaa tca gtt aca ggt att tca aga aat gta    1126
Ile Leu Thr Thr Val Thr Glu Ser Val Thr Gly Ile Ser Arg Asn Val
            325                 330                 335 agc act aat gtg ttc ttc aag caa cat gat tac atc att gag ttt ttt    1174
Ser Thr Asn Val Phe Phe Lys Gln His Asp Tyr Ile Ile Glu Phe Phe
            340                 345                 350 gat tat act act gtc ttg aag cca tct ctc aac ttc aca gcc act gtg    1222
Asp Tyr Thr Thr Val Leu Lys Pro Ser Leu Asn Phe Thr Ala Thr Val
355                 360                 365                 370 aag gta act cgt gct gat ggc aac caa ctg act ctt gaa gaa aga aga    1270
Lys Val Thr Arg Ala Asp Gly Asn Gln Leu Thr Leu Glu Glu Arg Arg
                375                 380                 385 aat aat gta gtc ata aca gtg aca cag aga aac tat act gag tac tgg    1318
Asn Asn Val Val Ile Thr Val Thr Gln Arg Asn Tyr Thr Glu Tyr Trp
                390                 395                 400 agc gga tct aac agt gga aat cag aaa atg gaa gct gtt cag aaa ata    1366
Ser Gly Ser Asn Ser Gly Asn Gln Lys Met Glu Ala Val Gln Lys Ile
                405                 410                 415 aat tat act gtc ccc caa agt gga act ttt aag att gaa ttc cca atc    1414
Asn Tyr Thr Val Pro Gln Ser Gly Thr Phe Lys Ile Glu Phe Pro Ile
            420                 425                 430 ctg gag gat tcc agt gag cta cag ttg aag gcc tat ttc ctt ggt agt    1462
Leu Glu Asp Ser Ser Glu Leu Gln Leu Lys Ala Tyr Phe Leu Gly Ser
435                 440                 445                 450 aaa agt agc atg gca gtt cat agt ctg ttt aag tct cct agt aag aca    1510
Lys Ser Ser Met Ala Val His Ser Leu Phe Lys Ser Pro Ser Lys Thr
                455                 460                 465 tac atc caa cta aaa aca aga gat gaa aat ata aag gtg gga tcg cct    1558
Tyr Ile Gln Leu Lys Thr Arg Asp Glu Asn Ile Lys Val Gly Ser Pro
                470                 475                 480 ttt gag ttg gtg gtt agt ggc aac aaa cga ttg aag gag tta agc tat    1606
Phe Glu Leu Val Val Ser Gly Asn Lys Arg Leu Lys Glu Leu Ser Tyr
            485                 490                 495 atg gta gta tcc agg gga cag ttg gtg gct gta gga aaa caa aat tca    1654
Met Val Val Ser Arg Gly Gln Leu Val Ala Val Gly Lys Gln Asn Ser
            500                 505                 510 aca atg ttc tct tta aca cca gaa aat tct tgg act cca aaa gcc tgt    1702
Thr Met Phe Ser Leu Thr Pro Glu Asn Ser Trp Thr Pro Lys Ala Cys
515                 520                 525                 530 gta att gtg tat tat att gaa gat gat ggg gaa att ata agt gat gtt    1750
Val Ile Val Tyr Tyr Ile Glu Asp Asp Gly Glu Ile Ile Ser Asp Val
                535                 540                 545 cta aaa att cct gtt cag ctt gtt ttt aaa aat aag ata aag cta tat    1798
Leu Lys Ile Pro Val Gln Leu Val Phe Lys Asn Lys Ile Lys Leu Tyr
            550                 555                 560 tgg agt aaa gtg aaa gct gaa cca tct gag aaa gtc tct ctt agg atc    1846
Trp Ser Lys Val Lys Ala Glu Pro Ser Glu Lys Val Ser Leu Arg Ile
            565                 570                 575 tct gtg aca cag cct gac tcc ata gtt ggg att gta gct gtt gac aaa    1894
Ser Val Thr Gln Pro Asp Ser Ile Val Gly Ile Val Ala Val Asp Lys
            580                 585                 590 agt gtg aat ctg atg aat gcc tct aat gat att aca atg gaa aat gtg    1942
Ser Val Asn Leu Met Asn Ala Ser Asn Asp Ile Thr Met Glu Asn Val
595                 600                 605                 610
```

-continued

| | |
|---|---|
| gtc cat gag ttg gaa ctt tat aac aca gga tat tat tta ggc atg ttc<br>Val His Glu Leu Glu Leu Tyr Asn Thr Gly Tyr Tyr Leu Gly Met Phe<br>615　　　　　　　　620　　　　　　　　625 | 1990 |
| atg aat tct ttt gca gtc ttt cag gaa tgt gga ctc tgg gta ttg aca<br>Met Asn Ser Phe Ala Val Phe Gln Glu Cys Gly Leu Trp Val Leu Thr<br>　　　630　　　　　　　　635　　　　　　　　640 | 2038 |
| gat gca aac ctc acg aag gat tat att gat ggt gtt tat gac aat gca<br>Asp Ala Asn Leu Thr Lys Asp Tyr Ile Asp Gly Val Tyr Asp Asn Ala<br>645　　　　　　　　650　　　　　　　　655 | 2086 |
| gaa tat gct gag agg ttt atg gag gaa aat gaa gga cat att gta gat<br>Glu Tyr Ala Glu Arg Phe Met Glu Glu Asn Glu Gly His Ile Val Asp<br>　　660　　　　　　　　665　　　　　　　　670 | 2134 |
| att cat gac ttt tct ttg ggt agc agt cca cat gtc cga aag cat ttt<br>Ile His Asp Phe Ser Leu Gly Ser Ser Pro His Val Arg Lys His Phe<br>675　　　　　　　　680　　　　　　　　685　　　　　　　　690 | 2182 |
| cca gag act tgg att tgg cta gac acc aac atg ggt tcc agg att tac<br>Pro Glu Thr Trp Ile Trp Leu Asp Thr Asn Met Gly Ser Arg Ile Tyr<br>　　　695　　　　　　　　700　　　　　　　　705 | 2230 |
| caa gaa ttt gaa gta act gta cct gat tct atc act tct tgg gtg gct<br>Gln Glu Phe Glu Val Thr Val Pro Asp Ser Ile Thr Ser Trp Val Ala<br>　　710　　　　　　　　715　　　　　　　　720 | 2278 |
| act ggt ttt gtg atc tct gag gac ctg ggt ctt gga cta aca act act<br>Thr Gly Phe Val Ile Ser Glu Asp Leu Gly Leu Gly Leu Thr Thr Thr<br>725　　　　　　　　730　　　　　　　　735 | 2326 |
| cca gtg gag ctc caa gcc ttc caa cca ttt ttc att ttt ttg aat ctt<br>Pro Val Glu Leu Gln Ala Phe Gln Pro Phe Phe Ile Phe Leu Asn Leu<br>　　　740　　　　　　　　745　　　　　　　　750 | 2374 |
| ccc tac tct gtt atc aga ggt gaa gaa ttt gct ttg gaa ata act ata<br>Pro Tyr Ser Val Ile Arg Gly Glu Glu Phe Ala Leu Glu Ile Thr Ile<br>755　　　　　　　　760　　　　　　　　765　　　　　　　　770 | 2422 |
| ttc aat tat ttg aaa gat gcc act gag gtt aag gta atc att gag aaa<br>Phe Asn Tyr Leu Lys Asp Ala Thr Glu Val Lys Val Ile Ile Glu Lys<br>　　　775　　　　　　　　780　　　　　　　　785 | 2470 |
| agt gac aaa ttt gat att cta atg act tca aat gaa ata aat gcc aca<br>Ser Asp Lys Phe Asp Ile Leu Met Thr Ser Asn Glu Ile Asn Ala Thr<br>　　790　　　　　　　　795　　　　　　　　800 | 2518 |
| ggc cac cag cag acc ctt ctg gtt ccc agt gag gat ggg gca act gtt<br>Gly His Gln Gln Thr Leu Leu Val Pro Ser Glu Asp Gly Ala Thr Val<br>805　　　　　　　　810　　　　　　　　815 | 2566 |
| ctt ttt ccc atc agg cca aca cat ctg gga gaa att cct atc aca gtc<br>Leu Phe Pro Ile Arg Pro Thr His Leu Gly Glu Ile Pro Ile Thr Val<br>820　　　　　　　　825　　　　　　　　830 | 2614 |
| aca gct ctt tca ccc act gct tct gat gct gtc acc cag atg att tta<br>Thr Ala Leu Ser Pro Thr Ala Ser Asp Ala Val Thr Gln Met Ile Leu<br>835　　　　　　　　840　　　　　　　　845　　　　　　　　850 | 2662 |
| gta aag gct gaa gga ata gaa aaa tca tat tca caa tcc atc tta tta<br>Val Lys Ala Glu Gly Ile Glu Lys Ser Tyr Ser Gln Ser Ile Leu Leu<br>　　　855　　　　　　　　860　　　　　　　　865 | 2710 |
| gac ttg act gac aat agg cta cag agt acc ctg aaa act ttg agt ttc<br>Asp Leu Thr Asp Asn Arg Leu Gln Ser Thr Leu Lys Thr Leu Ser Phe<br>　　870　　　　　　　　875　　　　　　　　880 | 2758 |
| tca ttt cct cct aat aca gtg act ggc agt gaa aga gtt cag atc act<br>Ser Phe Pro Pro Asn Thr Val Thr Gly Ser Glu Arg Val Gln Ile Thr<br>885　　　　　　　　890　　　　　　　　895 | 2806 |
| gca att gga gat gtt ctt ggt cct tcc atc aat ggc tta gcc tca ttg<br>Ala Ile Gly Asp Val Leu Gly Pro Ser Ile Asn Gly Leu Ala Ser Leu<br>900　　　　　　　　905　　　　　　　　910 | 2854 |
| att cgg atg cct tat ggc tgt ggt gaa cag aac atg ata aat ttt gct<br>Ile Arg Met Pro Tyr Gly Cys Gly Glu Gln Asn Met Ile Asn Phe Ala | 2902 |

```
                          -continued
      915            920            925            930 cca aat att tac att ttg gat tat ctg act aaa aag aaa caa ctg aca    2950
Pro Asn Ile Tyr Ile Leu Asp Tyr Leu Thr Lys Lys Lys Gln Leu Thr
                    935                 940                 945 gat aat ttg aaa gaa aaa gct ctt tca ttt atg agg caa ggt tac cag    2998
Asp Asn Leu Lys Glu Lys Ala Leu Ser Phe Met Arg Gln Gly Tyr Gln
            950                 955                 960 aga gaa ctt ctc tat cag agg gaa gat ggc tct ttc agt gct ttt ggg    3046
Arg Glu Leu Leu Tyr Gln Arg Glu Asp Gly Ser Phe Ser Ala Phe Gly
        965                 970                 975 aat tat gac cct tct ggg agc act tgg ttg tca gct ttt gtt tta aga    3094
Asn Tyr Asp Pro Ser Gly Ser Thr Trp Leu Ser Ala Phe Val Leu Arg
    980                 985                 990 tgt ttc ctt gaa gcc gat cct tac ata gat att gat cag aat gtg        3139
Cys Phe Leu Glu Ala Asp Pro Tyr Ile Asp Ile Asp Gln Asn Val
995                 1000                1005 tta cac aga aca tac act tgg ctt aaa gga cat cag aaa tcc aac        3184
Leu His Arg Thr Tyr Thr Trp Leu Lys Gly His Gln Lys Ser Asn
1010                1015                1020 ggt gaa ttt tgg gat cca gga aga gtg att cat agt gag ctt caa        3229
Gly Glu Phe Trp Asp Pro Gly Arg Val Ile His Ser Glu Leu Gln
1025                1030                1035 ggt ggc aat aaa agt cca gta aca ctt aca gcc tat att gta act        3274
Gly Gly Asn Lys Ser Pro Val Thr Leu Thr Ala Tyr Ile Val Thr
1040                1045                1050 tct ctc ctg gga tat aga aag tat cag cct aac att gat gtg caa        3319
Ser Leu Leu Gly Tyr Arg Lys Tyr Gln Pro Asn Ile Asp Val Gln
1055                1060                1065 gag tct atc cat ttt ttg gag tct gaa ttc agt aga gga att tca        3364
Glu Ser Ile His Phe Leu Glu Ser Glu Phe Ser Arg Gly Ile Ser
1070                1075                1080 gac aat tat act cta gcc ctt ata act tat gca ttg tca tca gtg        3409
Asp Asn Tyr Thr Leu Ala Leu Ile Thr Tyr Ala Leu Ser Ser Val
1085                1090                1095 ggg agt cct aaa gcg aag gaa gct ttg aat atg ctg act tgg aga        3454
Gly Ser Pro Lys Ala Lys Glu Ala Leu Asn Met Leu Thr Trp Arg
1100                1105                1110 gca gaa caa gaa ggt ggc atg caa ttc tgg gtg tca tca gag tcc        3499
Ala Glu Gln Glu Gly Gly Met Gln Phe Trp Val Ser Ser Glu Ser
1115                1120                1125 aaa ctt tct gac tcc tgg cag cca cgc tcc ctg gat att gaa gtt        3544
Lys Leu Ser Asp Ser Trp Gln Pro Arg Ser Leu Asp Ile Glu Val
1130                1135                1140 gca gcc tat gca ctg ctc tca cac ttc tta caa ttt cag act tct        3589
Ala Ala Tyr Ala Leu Leu Ser His Phe Leu Gln Phe Gln Thr Ser
1145                1150                1155 gag gga atc cca att atg agg tgg cta agc agg caa aga aat agc        3634
Glu Gly Ile Pro Ile Met Arg Trp Leu Ser Arg Gln Arg Asn Ser
1160                1165                1170 ttg ggt ggt ttt gca tct act cag gat acc act gtg gct tta aag        3679
Leu Gly Gly Phe Ala Ser Thr Gln Asp Thr Thr Val Ala Leu Lys
1175                1180                1185 gct ctg tct gaa ttt gca gcc cta atg aat aca gaa agg aca aat        3724
Ala Leu Ser Glu Phe Ala Ala Leu Met Asn Thr Glu Arg Thr Asn
1190                1195                1200 atc caa gtg acc gtg acg ggg cct agc tca cca agt cct gta aag        3769
Ile Gln Val Thr Val Thr Gly Pro Ser Ser Pro Ser Pro Val Lys
1205                1210                1215 ttt ctg att gac aca cac aac cgc tta ctc ctt cag aca gca gag        3814
```

|     |     |     |     |     |     |     |     |     |     |     |
|-----|-----|-----|-----|-----|-----|-----|-----|-----|-----|-----|
| Phe | Leu | Ile | Asp | Thr | His | Asn | Arg | Leu | Leu | |
| 1220 | | | | | 1225 | | | | 1230 | |

| ctt | gct | gtg | gta | cag | cca | atg | gca | gtt | aat | att | tcc | gca | aat | ggt | 3859 |
|-----|-----|-----|-----|-----|-----|-----|-----|-----|-----|-----|-----|-----|-----|-----|------|
| Leu | Ala | Val | Val | Gln | Pro | Met | Ala | Val | Asn | Ile | Ser | Ala | Asn | Gly | |
| 1235 | | | | 1240 | | | | | 1245 | | | | | | |

| ttt | gga | ttt | gct | att | tgt | cag | ctc | aat | gtt | gta | tat | aat | gtg | aag | 3904 |
|-----|-----|-----|-----|-----|-----|-----|-----|-----|-----|-----|-----|-----|-----|-----|------|
| Phe | Gly | Phe | Ala | Ile | Cys | Gln | Leu | Asn | Val | Val | Tyr | Asn | Val | Lys | |
| 1250 | | | | | 1255 | | | | 1260 | | | | | | |

| gct | tct | ggg | tct | tct | aga | aga | cga | aga | tct | atc | caa | aat | caa | gaa | 3949 |
|-----|-----|-----|-----|-----|-----|-----|-----|-----|-----|-----|-----|-----|-----|-----|------|
| Ala | Ser | Gly | Ser | Ser | Arg | Arg | Arg | Arg | Ser | Ile | Gln | Asn | Gln | Glu | |
| 1265 | | | | | 1270 | | | | 1275 | | | | | | |

| gcc | ttt | gat | tta | gat | gtt | gct | gta | aaa | gaa | aat | aaa | gat | gat | ctc | 3994 |
|-----|-----|-----|-----|-----|-----|-----|-----|-----|-----|-----|-----|-----|-----|-----|------|
| Ala | Phe | Asp | Leu | Asp | Val | Ala | Val | Lys | Glu | Asn | Lys | Asp | Asp | Leu | |
| 1280 | | | | 1285 | | | | | 1290 | | | | | | |

| aat | cat | gtg | gat | ttg | aat | gtg | tgt | aca | agc | ttt | tcg | ggc | ccg | ggt | 4039 |
|-----|-----|-----|-----|-----|-----|-----|-----|-----|-----|-----|-----|-----|-----|-----|------|
| Asn | His | Val | Asp | Leu | Asn | Val | Cys | Thr | Ser | Phe | Ser | Gly | Pro | Gly | |
| 1295 | | | | 1300 | | | | | 1305 | | | | | | |

| agg | agt | ggc | atg | gct | ctt | atg | gaa | gtt | aac | cta | tta | agt | ggc | ttt | 4084 |
|-----|-----|-----|-----|-----|-----|-----|-----|-----|-----|-----|-----|-----|-----|-----|------|
| Arg | Ser | Gly | Met | Ala | Leu | Met | Glu | Val | Asn | Leu | Leu | Ser | Gly | Phe | |
| 1310 | | | | 1315 | | | | | 1320 | | | | | | |

| atg | gtg | cct | tca | gaa | gca | att | tct | ctg | agc | gag | aca | gtg | aag | aaa | 4129 |
|-----|-----|-----|-----|-----|-----|-----|-----|-----|-----|-----|-----|-----|-----|-----|------|
| Met | Val | Pro | Ser | Glu | Ala | Ile | Ser | Leu | Ser | Glu | Thr | Val | Lys | Lys | |
| 1325 | | | | 1330 | | | | | 1335 | | | | | | |

| gtg | gaa | tat | gat | cat | gga | aaa | ctc | aac | ctc | tat | tta | gat | tct | gta | 4174 |
|-----|-----|-----|-----|-----|-----|-----|-----|-----|-----|-----|-----|-----|-----|-----|------|
| Val | Glu | Tyr | Asp | His | Gly | Lys | Leu | Asn | Leu | Tyr | Leu | Asp | Ser | Val | |
| 1340 | | | | 1345 | | | | | 1350 | | | | | | |

| aat | gaa | acc | cag | ttt | tgt | gtt | aat | att | cct | gct | gtg | aga | aac | ttt | 4219 |
|-----|-----|-----|-----|-----|-----|-----|-----|-----|-----|-----|-----|-----|-----|-----|------|
| Asn | Glu | Thr | Gln | Phe | Cys | Val | Asn | Ile | Pro | Ala | Val | Arg | Asn | Phe | |
| 1355 | | | | 1360 | | | | | 1365 | | | | | | |

| aaa | gtt | tca | aat | acc | caa | gat | gct | tca | gtg | tcc | ata | gtg | gat | tac | 4264 |
|-----|-----|-----|-----|-----|-----|-----|-----|-----|-----|-----|-----|-----|-----|-----|------|
| Lys | Val | Ser | Asn | Thr | Gln | Asp | Ala | Ser | Val | Ser | Ile | Val | Asp | Tyr | |
| 1370 | | | | 1375 | | | | | 1380 | | | | | | |

| tat | gag | cca | agg | aga | cag | gcg | gtg | aga | agt | tac | aac | tct | gaa | gtg | 4309 |
|-----|-----|-----|-----|-----|-----|-----|-----|-----|-----|-----|-----|-----|-----|-----|------|
| Tyr | Glu | Pro | Arg | Arg | Gln | Ala | Val | Arg | Ser | Tyr | Asn | Ser | Glu | Val | |
| 1385 | | | | 1390 | | | | | 1395 | | | | | | |

| aag | ctg | tcc | tcc | tgt | gac | ctt | tgc | agt | gat | gtc | cag | ggc | tgc | cgt | 4354 |
|-----|-----|-----|-----|-----|-----|-----|-----|-----|-----|-----|-----|-----|-----|-----|------|
| Lys | Leu | Ser | Ser | Cys | Asp | Leu | Cys | Ser | Asp | Val | Gln | Gly | Cys | Arg | |
| 1400 | | | | 1405 | | | | | 1410 | | | | | | |

| cct | tgt | gag | gat | gga | gct | tca | ggc | tcc | cat | cat | cac | tct | tca | gtc | 4399 |
|-----|-----|-----|-----|-----|-----|-----|-----|-----|-----|-----|-----|-----|-----|-----|------|
| Pro | Cys | Glu | Asp | Gly | Ala | Ser | Gly | Ser | His | His | His | Ser | Ser | Val | |
| 1415 | | | | 1420 | | | | | 1425 | | | | | | |

| att | ttt | att | ttc | tgt | ttc | aag | ctt | ctg | tac | ttt | atg | gaa | ctt | tgg | 4444 |
|-----|-----|-----|-----|-----|-----|-----|-----|-----|-----|-----|-----|-----|-----|-----|------|
| Ile | Phe | Ile | Phe | Cys | Phe | Lys | Leu | Leu | Tyr | Phe | Met | Glu | Leu | Trp | |
| 1430 | | | | 1435 | | | | | 1440 | | | | | | |

| ctg | tgatttattt | ttaaaggact | ctgtgtaaca | ctaacatttc | cagtagtcac | 4497 |
|-----|------------|------------|------------|------------|------------|------|
| Leu | | | | | | |
| 1445 | | | | | | |

| atgtgattgt | tttgtttttcg | tagaagaata | ctgcttctat | tttgaaaaaa | gagtttttt | 4557 |
|------------|-------------|------------|------------|------------|-----------|------|

| tctttctatg | gggttgcagg | gatggtgtac | aacaggtcct | agcatgtata | gctgcataga | 4617 |

| tttcttcacc | tgatctttgt | gtggaagatc | agaatgaatg | cagttgtgtg | tctatatttt | 4677 |

| cccctcacaa | aatcttttag | aatttttttg | gaggtgtttg | ttttctccag | aataaaggta | 4737 |

| ttactttaga | aaaaaaaaaa | aaaa | | | | 4761 |

<210> SEQ ID NO 4
<211> LENGTH: 1445
<212> TYPE: PRT
<213> ORGANISM: HUMAN

<400> SEQUENCE: 4

```
Met Gln Gly Pro Pro Leu Leu Thr Ala Ala His Leu Leu Cys Val Cys
  1               5                  10                  15

Thr Ala Ala Leu Ala Val Ala Pro Gly Pro Arg Phe Leu Val Thr Ala
                 20                  25                  30

Pro Gly Ile Ile Arg Pro Gly Gly Asn Val Thr Ile Gly Val Glu Leu
             35                  40                  45

Leu Glu His Cys Pro Ser Gln Val Thr Val Lys Ala Glu Leu Leu Lys
         50                  55                  60

Thr Ala Ser Asn Leu Thr Val Ser Val Leu Glu Ala Glu Gly Val Phe
 65                  70                  75                  80

Glu Lys Gly Ser Phe Lys Thr Leu Thr Leu Pro Ser Leu Pro Leu Asn
                 85                  90                  95

Ser Ala Asp Glu Ile Tyr Glu Leu Arg Val Thr Gly Arg Thr Gln Asp
            100                 105                 110

Glu Ile Leu Phe Ser Asn Ser Thr Arg Leu Ser Phe Glu Thr Lys Arg
        115                 120                 125

Ile Ser Val Phe Ile Gln Thr Asp Lys Ala Leu Tyr Lys Pro Lys Gln
130                 135                 140

Glu Val Lys Phe Arg Ile Val Thr Leu Phe Ser Asp Phe Lys Pro Tyr
145                 150                 155                 160

Lys Thr Ser Leu Asn Ile Leu Ile Lys Asp Pro Lys Ser Asn Leu Ile
                165                 170                 175

Gln Gln Trp Leu Ser Gln Ser Asp Leu Gly Val Ile Ser Lys Thr
            180                 185                 190

Phe Gln Leu Ser Ser His Pro Ile Leu Gly Asp Trp Ser Ile Gln Val
        195                 200                 205

Gln Val Asn Asp Gln Thr Tyr Tyr Gln Ser Phe Gln Val Ser Glu Tyr
    210                 215                 220

Val Leu Pro Lys Phe Glu Val Thr Leu Gln Thr Pro Leu Tyr Cys Ser
225                 230                 235                 240

Met Asn Ser Lys His Leu Asn Gly Thr Ile Thr Ala Lys Tyr Thr Tyr
                245                 250                 255

Gly Lys Pro Val Lys Gly Asp Val Thr Leu Thr Phe Leu Pro Leu Ser
            260                 265                 270

Phe Trp Gly Lys Lys Asn Ile Thr Lys Thr Phe Lys Ile Asn Gly
        275                 280                 285

Ser Ala Asn Phe Ser Phe Asn Asp Glu Glu Met Lys Asn Val Met Asp
    290                 295                 300

Ser Ser Asn Gly Leu Ser Glu Tyr Leu Asp Leu Ser Ser Pro Gly Pro
305                 310                 315                 320

Val Glu Ile Leu Thr Thr Val Thr Glu Ser Val Thr Gly Ile Ser Arg
                325                 330                 335

Asn Val Ser Thr Asn Val Phe Phe Lys Gln His Asp Tyr Ile Ile Glu
            340                 345                 350

Phe Phe Asp Tyr Thr Thr Val Leu Lys Pro Ser Leu Asn Phe Thr Ala
        355                 360                 365

Thr Val Lys Val Thr Arg Ala Asp Gly Asn Gln Leu Thr Leu Glu Glu
    370                 375                 380

Arg Arg Asn Asn Val Val Ile Thr Val Thr Gln Arg Asn Tyr Thr Glu
385                 390                 395                 400

Tyr Trp Ser Gly Ser Asn Ser Gly Asn Gln Lys Met Glu Ala Val Gln
                405                 410                 415
```

-continued

```
Lys Ile Asn Tyr Thr Val Pro Gln Ser Gly Thr Phe Lys Ile Glu Phe
            420                 425                 430

Pro Ile Leu Glu Asp Ser Ser Glu Leu Gln Leu Lys Ala Tyr Phe Leu
            435                 440                 445

Gly Ser Lys Ser Ser Met Ala Val His Ser Leu Phe Lys Ser Pro Ser
            450                 455                 460

Lys Thr Tyr Ile Gln Leu Lys Thr Arg Asp Glu Asn Ile Lys Val Gly
465                 470                 475                 480

Ser Pro Phe Glu Leu Val Val Ser Gly Asn Lys Arg Leu Lys Glu Leu
                485                 490                 495

Ser Tyr Met Val Val Ser Arg Gly Gln Leu Val Ala Val Gly Lys Gln
                500                 505                 510

Asn Ser Thr Met Phe Ser Leu Thr Pro Glu Asn Ser Trp Thr Pro Lys
            515                 520                 525

Ala Cys Val Ile Val Tyr Tyr Ile Glu Asp Asp Gly Glu Ile Ile Ser
            530                 535                 540

Asp Val Leu Lys Ile Pro Val Gln Leu Val Phe Lys Asn Lys Ile Lys
545                 550                 555                 560

Leu Tyr Trp Ser Lys Val Lys Ala Glu Pro Ser Glu Lys Val Ser Leu
                565                 570                 575

Arg Ile Ser Val Thr Gln Pro Asp Ser Ile Val Gly Ile Val Ala Val
                580                 585                 590

Asp Lys Ser Val Asn Leu Met Asn Ala Ser Asn Asp Ile Thr Met Glu
            595                 600                 605

Asn Val Val His Glu Leu Glu Leu Tyr Asn Thr Gly Tyr Tyr Leu Gly
            610                 615                 620

Met Phe Met Asn Ser Phe Ala Val Phe Gln Glu Cys Gly Leu Trp Val
625                 630                 635                 640

Leu Thr Asp Ala Asn Leu Thr Lys Asp Tyr Ile Asp Gly Val Tyr Asp
                645                 650                 655

Asn Ala Glu Tyr Ala Glu Arg Phe Met Glu Glu Asn Glu Gly His Ile
                660                 665                 670

Val Asp Ile His Asp Phe Ser Leu Gly Ser Ser Pro His Val Arg Lys
            675                 680                 685

His Phe Pro Glu Thr Trp Ile Trp Leu Asp Thr Asn Met Gly Ser Arg
            690                 695                 700

Ile Tyr Gln Glu Phe Glu Val Thr Val Pro Asp Ser Ile Thr Ser Trp
705                 710                 715                 720

Val Ala Thr Gly Phe Val Ile Ser Glu Asp Leu Gly Leu Gly Leu Thr
                725                 730                 735

Thr Thr Pro Val Glu Leu Gln Ala Phe Gln Pro Phe Phe Ile Phe Leu
            740                 745                 750

Asn Leu Pro Tyr Ser Val Ile Arg Gly Glu Glu Phe Ala Leu Glu Ile
            755                 760                 765

Thr Ile Phe Asn Tyr Leu Lys Asp Ala Thr Glu Val Lys Val Ile Ile
            770                 775                 780

Glu Lys Ser Asp Lys Phe Asp Ile Leu Met Thr Ser Asn Glu Ile Asn
785                 790                 795                 800

Ala Thr Gly His Gln Gln Thr Leu Leu Val Pro Ser Glu Asp Gly Ala
                805                 810                 815

Thr Val Leu Phe Pro Ile Arg Pro Thr His Leu Gly Glu Ile Pro Ile
            820                 825                 830
```

-continued

```
Thr Val Thr Ala Leu Ser Pro Thr Ala Ser Asp Ala Val Thr Gln Met
        835                 840                 845
Ile Leu Val Lys Ala Glu Gly Ile Glu Lys Ser Tyr Ser Gln Ser Ile
850                 855                 860
Leu Leu Asp Leu Thr Asp Asn Arg Leu Gln Ser Thr Leu Lys Thr Leu
865                 870                 875                 880
Ser Phe Ser Phe Pro Pro Asn Thr Val Thr Gly Ser Glu Arg Val Gln
                885                 890                 895
Ile Thr Ala Ile Gly Asp Val Leu Gly Pro Ser Ile Asn Gly Leu Ala
            900                 905                 910
Ser Leu Ile Arg Met Pro Tyr Gly Cys Gly Glu Gln Asn Met Ile Asn
            915                 920                 925
Phe Ala Pro Asn Ile Tyr Ile Leu Asp Tyr Leu Thr Lys Lys Lys Gln
        930                 935                 940
Leu Thr Asp Asn Leu Lys Glu Lys Ala Leu Ser Phe Met Arg Gln Gly
945                 950                 955                 960
Tyr Gln Arg Glu Leu Leu Tyr Gln Arg Glu Asp Gly Ser Phe Ser Ala
                965                 970                 975
Phe Gly Asn Tyr Asp Pro Ser Gly Ser Thr Trp Leu Ser Ala Phe Val
            980                 985                 990
Leu Arg Cys Phe Leu Glu Ala Asp Pro Tyr Ile Asp Ile Asp Gln Asn
        995                 1000                1005
Val Leu His Arg Thr Tyr Thr Trp Leu Lys Gly His Gln Lys Ser
    1010                1015                1020
Asn Gly Glu Phe Trp Asp Pro Gly Arg Val Ile His Ser Glu Leu
    1025                1030                1035
Gln Gly Gly Asn Lys Ser Pro Val Thr Leu Thr Ala Tyr Ile Val
    1040                1045                1050
Thr Ser Leu Leu Gly Tyr Arg Lys Tyr Gln Pro Asn Ile Asp Val
    1055                1060                1065
Gln Glu Ser Ile His Phe Leu Glu Ser Glu Phe Ser Arg Gly Ile
    1070                1075                1080
Ser Asp Asn Tyr Thr Leu Ala Leu Ile Thr Tyr Ala Leu Ser Ser
    1085                1090                1095
Val Gly Ser Pro Lys Ala Lys Glu Ala Leu Asn Met Leu Thr Trp
    1100                1105                1110
Arg Ala Glu Gln Glu Gly Gly Met Gln Phe Trp Val Ser Ser Glu
    1115                1120                1125
Ser Lys Leu Ser Asp Ser Trp Gln Pro Arg Ser Leu Asp Ile Glu
    1130                1135                1140
Val Ala Ala Tyr Ala Leu Leu Ser His Phe Leu Gln Phe Gln Thr
    1145                1150                1155
Ser Glu Gly Ile Pro Ile Met Arg Trp Leu Ser Arg Gln Arg Asn
    1160                1165                1170
Ser Leu Gly Gly Phe Ala Ser Thr Gln Asp Thr Thr Val Ala Leu
    1175                1180                1185
Lys Ala Leu Ser Glu Phe Ala Ala Leu Met Asn Thr Glu Arg Thr
    1190                1195                1200
Asn Ile Gln Val Thr Val Thr Gly Pro Ser Ser Pro Ser Pro Val
    1205                1210                1215
Lys Phe Leu Ile Asp Thr His Asn Arg Leu Leu Leu Gln Thr Ala
    1220                1225                1230
Glu Leu Ala Val Val Gln Pro Met Ala Val Asn Ile Ser Ala Asn
```

-continued

```
                    1235                1240                1245

Gly Phe  Gly Phe Ala Ile Cys  Gln Leu Asn Val Val  Tyr Asn Val
    1250                1255                1260

Lys Ala  Ser Gly Ser Ser Arg  Arg Arg Arg Ser Ile  Gln Asn Gln
    1265                1270                1275

Glu Ala  Phe Asp Leu Asp Val  Ala Val Lys Glu Asn  Lys Asp Asp
    1280                1285                1290

Leu Asn  His Val Asp Leu Asn  Val Cys Thr Ser Phe  Ser Gly Pro
    1295                1300                1305

Gly Arg  Ser Gly Met Ala Leu  Met Glu Val Asn Leu  Leu Ser Gly
    1310                1315                1320

Phe Met  Val Pro Ser Glu Ala  Ile Ser Leu Ser Glu  Thr Val Lys
    1325                1330                1335

Lys Val  Glu Tyr Asp His Gly  Lys Leu Asn Leu Tyr  Leu Asp Ser
    1340                1345                1350

Val Asn  Glu Thr Gln Phe Cys  Val Asn Ile Pro Ala  Val Arg Asn
    1355                1360                1365

Phe Lys  Val Ser Asn Thr Gln  Asp Ala Ser Val Ser  Ile Val Asp
    1370                1375                1380

Tyr Tyr  Glu Pro Arg Arg Gln  Ala Val Arg Ser Tyr  Asn Ser Glu
    1385                1390                1395

Val Lys  Leu Ser Ser Cys Asp  Leu Cys Ser Asp Val  Gln Gly Cys
    1400                1405                1410

Arg Pro  Cys Glu Asp Gly Ala  Ser Gly Ser His His  His Ser Ser
    1415                1420                1425

Val Ile  Phe Ile Phe Cys Phe  Lys Leu Leu Tyr Phe  Met Glu Leu
    1430                1435                1440

Trp Leu
    1445

<210> SEQ ID NO 5
<211> LENGTH: 5895
<212> TYPE: DNA
<213> ORGANISM: HUMAN
<220> FEATURE:
<221> NAME/KEY: CDS
<222> LOCATION: (113)..(4447)

<400> SEQUENCE: 5
ctaaactcga attaagaggg aaaaaaaatc agggaggagg tggcaagcca caccccacgg        60
tgcccgcgaa cttccccggc agcggactgt agcccaggca gacgccgtcg ag atg cag      118
                                                            Met Gln
                                                              1 ggc cca ccg ctc ctg acc gcc gcc cac ctc ctc tgc gtg tgc acc gcc        166
Gly Pro Pro Leu Leu Thr Ala Ala His Leu Leu Cys Val Cys Thr Ala
        5                   10                  15 gcg ctg gcc gtg gct ccc ggg cct cgg ttt ctg gtg aca gcc cca ggg        214
Ala Leu Ala Val Ala Pro Gly Pro Arg Phe Leu Val Thr Ala Pro Gly
     20                  25                  30 atc atc agg ccc gga gga aat gtg act att ggg gtg gag ctt ctg gaa        262
Ile Ile Arg Pro Gly Gly Asn Val Thr Ile Gly Val Glu Leu Leu Glu
 35                  40                  45                  50 cac tgc cct tca cag gtg act gtg aag gcg gag ctg ctc aag aca gca        310
His Cys Pro Ser Gln Val Thr Val Lys Ala Glu Leu Leu Lys Thr Ala
                 55                  60                  65 tca aac ctc act gtc tct gtc ctg gaa gca gaa gga gtc ttt gaa aaa        358
Ser Asn Leu Thr Val Ser Val Leu Glu Ala Glu Gly Val Phe Glu Lys
```

-continued

```
                        70                        75                        80
ggc tct ttt aag aca ctt act ctt cca tca cta cct ctg aac agt gca      406
Gly Ser Phe Lys Thr Leu Thr Leu Pro Ser Leu Pro Leu Asn Ser Ala
             85                    90                    95 gat gag att tat gag cta cgt gta acc gga cgt acc cag gat gag att      454
Asp Glu Ile Tyr Glu Leu Arg Val Thr Gly Arg Thr Gln Asp Glu Ile
        100                   105                   110 tta ttc tct aat agt acc cgc tta tca ttt gag acc aag aga ata tct      502
Leu Phe Ser Asn Ser Thr Arg Leu Ser Phe Glu Thr Lys Arg Ile Ser
115                   120                   125                   130 gtc ttc att caa aca gac aag gcc tta tac aag cca aag caa gaa gtg      550
Val Phe Ile Gln Thr Asp Lys Ala Leu Tyr Lys Pro Lys Gln Glu Val
                  135                   140                   145 aag ttt cgc att gtt aca ctc ttc tca gat ttt aag cct tac aaa acc      598
Lys Phe Arg Ile Val Thr Leu Phe Ser Asp Phe Lys Pro Tyr Lys Thr
             150                   155                   160 tct tta aac att ctc att aag gac ccc aaa tca aat ttg atc caa cag      646
Ser Leu Asn Ile Leu Ile Lys Asp Pro Lys Ser Asn Leu Ile Gln Gln
        165                   170                   175 tgg ttg tca caa caa agt gat ctt gga gtc att tcc aaa act ttt cag      694
Trp Leu Ser Gln Gln Ser Asp Leu Gly Val Ile Ser Lys Thr Phe Gln
180                   185                   190 cta tct tcc cat cca ata ctt ggt gac tgg tct att caa gtt caa gtg      742
Leu Ser Ser His Pro Ile Leu Gly Asp Trp Ser Ile Gln Val Gln Val
195                   200                   205                   210 aat gac cag aca tat tat caa tca ttt cag gtt tca gaa tat gta tta      790
Asn Asp Gln Thr Tyr Tyr Gln Ser Phe Gln Val Ser Glu Tyr Val Leu
                  215                   220                   225 cca aaa ttt gaa gtg act ttg cag aca cca tta tat tgt tct atg aat      838
Pro Lys Phe Glu Val Thr Leu Gln Thr Pro Leu Tyr Cys Ser Met Asn
             230                   235                   240 tct aag cat tta aat ggt acc atc acg gca aag tat aca tat ggg aag      886
Ser Lys His Leu Asn Gly Thr Ile Thr Ala Lys Tyr Thr Tyr Gly Lys
        245                   250                   255 cca gtg aaa gga gac gta acg ctt aca ttt tta cct tta tcc ttt tgg      934
Pro Val Lys Gly Asp Val Thr Leu Thr Phe Leu Pro Leu Ser Phe Trp
260                   265                   270 gga aag aag aaa aat att aca aaa aca ttt aag ata aat gga tct gca      982
Gly Lys Lys Lys Asn Ile Thr Lys Thr Phe Lys Ile Asn Gly Ser Ala
275                   280                   285                   290 aac ttc tct ttt aat gat gaa gag atg aaa aat gta atg gat tct tca     1030
Asn Phe Ser Phe Asn Asp Glu Glu Met Lys Asn Val Met Asp Ser Ser
                  295                   300                   305 aat gga ctt tct gaa tac ctg gat cta tct tcc cct gga cca gta gaa     1078
Asn Gly Leu Ser Glu Tyr Leu Asp Leu Ser Ser Pro Gly Pro Val Glu
             310                   315                   320 att tta acc aca gtg aca gaa tca gtt aca ggt att tca aga aat gta     1126
Ile Leu Thr Thr Val Thr Glu Ser Val Thr Gly Ile Ser Arg Asn Val
        325                   330                   335 agc act aat gtg ttc ttc aag caa cat gat tac atc att gag ttt ttt     1174
Ser Thr Asn Val Phe Phe Lys Gln His Asp Tyr Ile Ile Glu Phe Phe
340                   345                   350 gat tat act act gtc ttg aag cca tct ctc aac ttc aca gcc act gtg     1222
Asp Tyr Thr Thr Val Leu Lys Pro Ser Leu Asn Phe Thr Ala Thr Val
355                   360                   365                   370 aag gta act cgt gct gat ggc aac caa ctg act ctt gaa gaa aga aga     1270
Lys Val Thr Arg Ala Asp Gly Asn Gln Leu Thr Leu Glu Glu Arg Arg
                  375                   380                   385 aat aat gta gtc ata aca gtg aca cag aga aac tat act gag tac tgg     1318
```

```
                                                             -continued

Asn Asn Val Val Ile Thr Val Thr Gln Arg Asn Tyr Thr Glu Tyr Trp
            390                 395                 400 agc gga tct aac agt gga aat cag aaa atg gaa gct gtt cag aaa ata      1366
Ser Gly Ser Asn Ser Gly Asn Gln Lys Met Glu Ala Val Gln Lys Ile
        405                 410                 415 aat tat act gtc ccc caa agt gga act ttt aag att gaa ttc cca atc      1414
Asn Tyr Thr Val Pro Gln Ser Gly Thr Phe Lys Ile Glu Phe Pro Ile
    420                 425                 430 ctg gag gat tcc agt gag cta cag ttg aag gcc tat ttc ctt ggt agt      1462
Leu Glu Asp Ser Ser Glu Leu Gln Leu Lys Ala Tyr Phe Leu Gly Ser
435                 440                 445                 450 aaa agc agc atg gca gtt cat agt ctg ttt aag tct cct agt aag aca      1510
Lys Ser Ser Met Ala Val His Ser Leu Phe Lys Ser Pro Ser Lys Thr
                455                 460                 465 tac atc caa cta aaa aca aga gat gaa aat ata aag gtg gga tcg cct      1558
Tyr Ile Gln Leu Lys Thr Arg Asp Glu Asn Ile Lys Val Gly Ser Pro
            470                 475                 480 ttt gag ttg gtg gtt agt ggc aac aaa cga ttg aag gag tta agc tat      1606
Phe Glu Leu Val Val Ser Gly Asn Lys Arg Leu Lys Glu Leu Ser Tyr
        485                 490                 495 atg gta gta tcc agg gga cag ttg gtg gct gta gga aaa caa aat tca      1654
Met Val Val Ser Arg Gly Gln Leu Val Ala Val Gly Lys Gln Asn Ser
    500                 505                 510 aca atg ttc tct tta aca cca gaa aat tct tgg act cca aaa gcc tgt      1702
Thr Met Phe Ser Leu Thr Pro Glu Asn Ser Trp Thr Pro Lys Ala Cys
515                 520                 525                 530 gta att gtg tat tat att gaa gat gat ggg gaa att ata agt gat gtt      1750
Val Ile Val Tyr Tyr Ile Glu Asp Asp Gly Glu Ile Ile Ser Asp Val
                535                 540                 545 cta aaa att cct gtt cag ctt gtt ttt aaa aat aag ata aag cta tat      1798
Leu Lys Ile Pro Val Gln Leu Val Phe Lys Asn Lys Ile Lys Leu Tyr
            550                 555                 560 tgg agt aaa gtg aaa gct gaa cca tct gag aaa gtc tct ctt agg atc      1846
Trp Ser Lys Val Lys Ala Glu Pro Ser Glu Lys Val Ser Leu Arg Ile
        565                 570                 575 tct gtg aca cag cct gac tcc ata gtt ggg att gta gct gtt gac aaa      1894
Ser Val Thr Gln Pro Asp Ser Ile Val Gly Ile Val Ala Val Asp Lys
    580                 585                 590 agt gtg aat ctg atg aat gcc tct aat gat att aca atg gaa aat gtg      1942
Ser Val Asn Leu Met Asn Ala Ser Asn Asp Ile Thr Met Glu Asn Val
595                 600                 605                 610 gtc cat gag ttg gaa ctt tat aac aca gga tat tat tta ggc atg ttc      1990
Val His Glu Leu Glu Leu Tyr Asn Thr Gly Tyr Tyr Leu Gly Met Phe
                615                 620                 625 atg aat tct ttt gca gtc ttt cag gaa tgt gga ctc tgg gta ttg aca      2038
Met Asn Ser Phe Ala Val Phe Gln Glu Cys Gly Leu Trp Val Leu Thr
            630                 635                 640 gat gca aac ctc acg aag gat tat att gat ggt gtt tat gac aat gca      2086
Asp Ala Asn Leu Thr Lys Asp Tyr Ile Asp Gly Val Tyr Asp Asn Ala
        645                 650                 655 gaa tat gct gag agg ttt atg gag gaa aat gaa gga cat att gta gat      2134
Glu Tyr Ala Glu Arg Phe Met Glu Glu Asn Glu Gly His Ile Val Asp
    660                 665                 670 att cat gac ttt tct ttg ggt agc agt cca cat gtc cga aag cat ttt      2182
Ile His Asp Phe Ser Leu Gly Ser Ser Pro His Val Arg Lys His Phe
675                 680                 685                 690 cca gag act tgg att tgg cta gac acc aac atg ggt tac agg att tac      2230
Pro Glu Thr Trp Ile Trp Leu Asp Thr Asn Met Gly Tyr Arg Ile Tyr
                695                 700                 705
```

-continued

| | | |
|---|---|---|
| caa gaa ttt gaa gta act gta cct gat tct atc act tct tgg gtg gct<br>Gln Glu Phe Glu Val Thr Val Pro Asp Ser Ile Thr Ser Trp Val Ala<br>           710                 715                720 | | 2278 |
| act ggt ttt gtg atc tct gag gac ctg ggt ctt gga cta aca act act<br>Thr Gly Phe Val Ile Ser Glu Asp Leu Gly Leu Gly Leu Thr Thr Thr<br>       725                   730               735 | | 2326 |
| cca gtg gag ctc caa gcc ttc caa cca ttt ttc att ttt ttg aat ctt<br>Pro Val Glu Leu Gln Ala Phe Gln Pro Phe Phe Ile Phe Leu Asn Leu<br>740                   745               750 | | 2374 |
| ccc tac tct gtt atc aga ggt gaa gaa ttt gct ttg gaa ata act ata<br>Pro Tyr Ser Val Ile Arg Gly Glu Glu Phe Ala Leu Glu Ile Thr Ile<br>755                   760               765              770 | | 2422 |
| ttc aat tat ttg aaa gat gcc act gag gtt aag gta atc att gag aaa<br>Phe Asn Tyr Leu Lys Asp Ala Thr Glu Val Lys Val Ile Ile Glu Lys<br>           775                 780               785 | | 2470 |
| agt gac aaa ttt gat att cta atg act tca aat gaa ata aat gcc aca<br>Ser Asp Lys Phe Asp Ile Leu Met Thr Ser Asn Glu Ile Asn Ala Thr<br>              790               795               800 | | 2518 |
| ggc cac cag cag acc ctt ctg gtt ccc agt gag gat ggg gca act gtt<br>Gly His Gln Gln Thr Leu Leu Val Pro Ser Glu Asp Gly Ala Thr Val<br>           805                 810               815 | | 2566 |
| ctt ttt ccc atc agg cca aca cat ctg gga gaa att cct atc aca gtc<br>Leu Phe Pro Ile Arg Pro Thr His Leu Gly Glu Ile Pro Ile Thr Val<br>820                   825               830 | | 2614 |
| aca gct ctt tca ccc act gct tct gat gct gtc acc cag atg att tta<br>Thr Ala Leu Ser Pro Thr Ala Ser Asp Ala Val Thr Gln Met Ile Leu<br>835                   840               845              850 | | 2662 |
| gta aag gct gaa gga ata gaa aaa tca tat tca caa tcc atc tta tta<br>Val Lys Ala Glu Gly Ile Glu Lys Ser Tyr Ser Gln Ser Ile Leu Leu<br>              855               860               865 | | 2710 |
| gac ttg act gac aat agg cta cag agt acc ctg aaa act ttg agt ttc<br>Asp Leu Thr Asp Asn Arg Leu Gln Ser Thr Leu Lys Thr Leu Ser Phe<br>                 870               875               880 | | 2758 |
| tca ttt cct cct aat aca gtg act ggc agt gaa aga gtt cag atc act<br>Ser Phe Pro Pro Asn Thr Val Thr Gly Ser Glu Arg Val Gln Ile Thr<br>           885                 890               895 | | 2806 |
| gca att gga gat gtt ctt ggt cct tcc atc aat ggc tta gcc tca ttg<br>Ala Ile Gly Asp Val Leu Gly Pro Ser Ile Asn Gly Leu Ala Ser Leu<br>900                   905               910 | | 2854 |
| att cgg atg cct tat ggc tgt ggt gaa cag aac atg ata aat ttt gct<br>Ile Arg Met Pro Tyr Gly Cys Gly Glu Gln Asn Met Ile Asn Phe Ala<br>915                   920               925              930 | | 2902 |
| cca aat att tac att ttg gat tat ctg act aaa aag aaa caa ctg aca<br>Pro Asn Ile Tyr Ile Leu Asp Tyr Leu Thr Lys Lys Lys Gln Leu Thr<br>              935               940               945 | | 2950 |
| gat aat ttg aaa gaa aaa gct ctt tca ttt atg agg caa ggt tac cag<br>Asp Asn Leu Lys Glu Lys Ala Leu Ser Phe Met Arg Gln Gly Tyr Gln<br>           950                 955               960 | | 2998 |
| aga gaa ctt ctc tat cag agg gaa gat ggc tct ttc agt gct ttt ggg<br>Arg Glu Leu Leu Tyr Gln Arg Glu Asp Gly Ser Phe Ser Ala Phe Gly<br>       965                   970               975 | | 3046 |
| aat tat gac cct tct ggg agc act tgg ttg tca gct ttt gtt tta aga<br>Asn Tyr Asp Pro Ser Gly Ser Thr Trp Leu Ser Ala Phe Val Leu Arg<br>980                   985               990 | | 3094 |
| tgt ttc ctt gaa gcc gat  cct tac ata gat att  gat cag aat gtg<br>Cys Phe Leu Glu Ala Asp  Pro Tyr Ile Asp Ile  Asp Gln Asn Val<br>995                   1000              1005 | | 3139 |
| tta  cac aga aca tac act  tgg ctt aaa gga cat  cag aaa tcc aac<br>Leu  His Arg Thr Tyr Thr  Trp Leu Lys Gly His  Gln Lys Ser Asn<br>1010                   1015              1020 | | 3184 |

```
ggt gaa ttt tgg gat cca gga aga gtg att cat agt gag ctt caa      3229
Gly Glu Phe Trp Asp Pro Gly Arg Val Ile His Ser Glu Leu Gln
1025                1030                1035 ggt ggc aat aaa agt cca gta aca ctt aca gcc tat att gta act      3274
Gly Gly Asn Lys Ser Pro Val Thr Leu Thr Ala Tyr Ile Val Thr
1040                1045                1050 tct ctc ctg gga tat aga aag tat cag cct aac att gat gtg caa      3319
Ser Leu Leu Gly Tyr Arg Lys Tyr Gln Pro Asn Ile Asp Val Gln
1055                1060                1065 gag tct atc cat ttt ttg gag tct gaa ttc agt aga gga att tca      3364
Glu Ser Ile His Phe Leu Glu Ser Glu Phe Ser Arg Gly Ile Ser
1070                1075                1080 gac aat tat act cta gcc ctt ata act tat gca ttg tca tca gtg      3409
Asp Asn Tyr Thr Leu Ala Leu Ile Thr Tyr Ala Leu Ser Ser Val
1085                1090                1095 ggg agt cct aaa gcg aag gaa gct ttg aat atg ctg act tgg aga      3454
Gly Ser Pro Lys Ala Lys Glu Ala Leu Asn Met Leu Thr Trp Arg
1100                1105                1110 gca gaa caa gaa ggt ggc atg caa ttc tgg gtg tca tca gag tcc      3499
Ala Glu Gln Glu Gly Gly Met Gln Phe Trp Val Ser Ser Glu Ser
1115                1120                1125 aaa ctt tct gac tcc tgg cag cca cgc tcc ctg gat att gaa gtt      3544
Lys Leu Ser Asp Ser Trp Gln Pro Arg Ser Leu Asp Ile Glu Val
1130                1135                1140 gca gcc tat gca ctg ctc tca cac ttc tta caa ttt cag act tct      3589
Ala Ala Tyr Ala Leu Leu Ser His Phe Leu Gln Phe Gln Thr Ser
1145                1150                1155 gag gga atc cca att atg agg tgg cta agc agg caa aga aat agc      3634
Glu Gly Ile Pro Ile Met Arg Trp Leu Ser Arg Gln Arg Asn Ser
1160                1165                1170 ttg ggt ggt ttt gca tct act cag gat acc act gtg gct tta aag      3679
Leu Gly Gly Phe Ala Ser Thr Gln Asp Thr Thr Val Ala Leu Lys
1175                1180                1185 gct ctg tct gaa ttt gca gcc cta atg aat aca gaa agg aca aat      3724
Ala Leu Ser Glu Phe Ala Ala Leu Met Asn Thr Glu Arg Thr Asn
1190                1195                1200 atc caa gtg acc gtg acg ggg cct agc tca cca agt cct gta aag      3769
Ile Gln Val Thr Val Thr Gly Pro Ser Ser Pro Ser Pro Val Lys
1205                1210                1215 ttt ctg att gac aca cac aac cgc tta ctc ctt cag aca gca gag      3814
Phe Leu Ile Asp Thr His Asn Arg Leu Leu Leu Gln Thr Ala Glu
1220                1225                1230 ctt gct gtg gta cag cca atg gca gtt aat att tcc gca aat ggt      3859
Leu Ala Val Val Gln Pro Met Ala Val Asn Ile Ser Ala Asn Gly
1235                1240                1245 ttt gga ttt gct att tgt cag ctc aat gtt gta tat aat gtg aag      3904
Phe Gly Phe Ala Ile Cys Gln Leu Asn Val Val Tyr Asn Val Lys
1250                1255                1260 gct tct ggg tct tct aga aga cga aga tct atc caa aat caa gaa      3949
Ala Ser Gly Ser Ser Arg Arg Arg Arg Ser Ile Gln Asn Gln Glu
1265                1270                1275 gcc ttt gat tta gat gtt gct gta aaa gaa aat aaa gat gat ctc      3994
Ala Phe Asp Leu Asp Val Ala Val Lys Glu Asn Lys Asp Asp Leu
1280                1285                1290 aat cat gtg gat ttg aat gtg tgt aca agc ttt tcg ggc ccg ggt      4039
Asn His Val Asp Leu Asn Val Cys Thr Ser Phe Ser Gly Pro Gly
1295                1300                1305 agg agt ggc atg gct ctt atg gaa gtt aac cta tta agt ggc ttt      4084
Arg Ser Gly Met Ala Leu Met Glu Val Asn Leu Leu Ser Gly Phe
```

| | | | | | | | | | | |
|---|---|---|---|---|---|---|---|---|---|---|
| | | 1310 | | | 1315 | | | 1320 | | |
| atg | gtg | cct | tca | gaa | gca | att | tct | ctg | agc | gag | aca | gtg | aag | aaa | 4129 |
| Met | Val | Pro | Ser | Glu | Ala | Ile | Ser | Leu | Ser | Glu | Thr | Val | Lys | Lys | |
| 1325 | | | | 1330 | | | | | 1335 | | | | | | |
| gtg | gaa | tat | gat | cat | gga | aaa | ctc | aac | ctc | tat | tta | gat | tct | gta | 4174 |
| Val | Glu | Tyr | Asp | His | Gly | Lys | Leu | Asn | Leu | Tyr | Leu | Asp | Ser | Val | |
| 1340 | | | | | 1345 | | | | | 1350 | | | | | |
| aat | gaa | acc | cag | ttt | tgt | gtt | aat | att | cct | gct | gtg | aga | aac | ttt | 4219 |
| Asn | Glu | Thr | Gln | Phe | Cys | Val | Asn | Ile | Pro | Ala | Val | Arg | Asn | Phe | |
| 1355 | | | | | 1360 | | | | | 1365 | | | | | |
| aaa | gtt | tca | aat | acc | caa | gat | gct | tca | gtg | tcc | ata | gtg | gat | tac | 4264 |
| Lys | Val | Ser | Asn | Thr | Gln | Asp | Ala | Ser | Val | Ser | Ile | Val | Asp | Tyr | |
| 1370 | | | | | 1375 | | | | | 1380 | | | | | |
| tat | gag | cca | agg | aga | cag | gcg | gtg | aga | agt | tac | aac | tct | gaa | gtg | 4309 |
| Tyr | Glu | Pro | Arg | Arg | Gln | Ala | Val | Arg | Ser | Tyr | Asn | Ser | Glu | Val | |
| 1385 | | | | | 1390 | | | | | 1395 | | | | | |
| aag | ctg | tcc | tcc | tgt | gac | ctt | tgc | agt | gat | gtc | cag | ggc | tgc | cgt | 4354 |
| Lys | Leu | Ser | Ser | Cys | Asp | Leu | Cys | Ser | Asp | Val | Gln | Gly | Cys | Arg | |
| 1400 | | | | | 1405 | | | | | 1410 | | | | | |
| cct | tgt | gag | gat | gga | gct | tca | ggc | tcc | cat | cat | cac | tct | tca | gtc | 4399 |
| Pro | Cys | Glu | Asp | Gly | Ala | Ser | Gly | Ser | His | His | His | Ser | Ser | Val | |
| 1415 | | | | | 1420 | | | | | 1425 | | | | | |
| att | ttt | att | ttc | tgt | ttc | aag | ctt | ctg | tac | ttt | atg | gaa | ctt | tgg | 4444 |
| Ile | Phe | Ile | Phe | Cys | Phe | Lys | Leu | Leu | Tyr | Phe | Met | Glu | Leu | Trp | |
| 1430 | | | | | 1435 | | | | | 1440 | | | | | |
| ctg | tgatttattt | ttaaaggact | ctgtgtaaca | ctaacatttc | cagtagtcac | 4497 |
| Leu | | | | | | |
| 1445 | | | | | | |

| | |
|---|---|
| atgtgattgt tttgttttcg tagaagaata ctgcttctat tttgaaaaaa gagtttttt | 4557 |
| tctttctatg gggttgcagg gatggtgtac aacaggtcct agcatgtata gctgcataga | 4617 |
| tttcttcacc tgatctttgt gtggaagatc agaatgaatg cagttgtgtg tctatatttt | 4677 |
| cccctcacaa aatcttttag aattttttg gaggtgtttg ttttctccag aataaaggta | 4737 |
| ttactttaga aataggtatt ctcctcattt tgtgaaagaa atgaacctag attcttaagc | 4797 |
| attattacac atccatgttt gcttaaagat ggatttccct gggaatggga gaaaacagcc | 4857 |
| agcaggagga gcttcatctg ttcccttccc acctccaacc tagccctact gcccacccca | 4917 |
| ccccaaccca ccccatgccc agtggtctca gtagatactt cttaactgga aattcttcct | 4977 |
| tttcagaatc taggtggtga atttttttta agtggcacgg tcttttttctg cttgaaatct | 5037 |
| gatcacaccc cccagccatt gccctccctc tctttttcct ctgtagagaa atgtgagggg | 5097 |
| cagtacattt actgtgcttt tcacaccatc tcagaggttg aggagcatac tgaaaattgc | 5157 |
| cctgggggt gctgggtgtg ctgtctcctt cccacatcct cagccccaca ccagctctat | 5217 |
| ttcagggtg agagtcagag agcactgcaa tatgtgcttc atgggatttc gattcgaaga | 5277 |
| tcctagacca gggagacact gtgagccagg atacaacaa atactaggt aagtcactgc | 5337 |
| agaccgacct ccctgcagtt tgggaagaa gctgggtttg tggagaatca gagcatcttg | 5397 |
| acatgactgc tgacctaaag atccctggca ttggccaggg atcctgtgga acctcttcta | 5457 |
| gttcaggggt gtgagcatta gactgccagt tgtctagtga catctgatgc ttgctgtgaa | 5517 |
| cttttaagat ccccgaatcc tgagcacctc aatctttaat tgccctgtat tccgaagggt | 5577 |
| aatataattt atctggatgg aaattttaaa gatgaatccc cctttttct tttcttctct | 5637 |
| cttttctttc cttctccctt tcttctttgc cttctaaata tactgaaatg atttagatat | 5697 |
| gtgtcaacaa ttaatgatct tttattcaat ctaagaaatg gtttagtttt tctcttttagc | 5757 |

-continued

```
tctatggcat tcactcaag tggacagggg aaaaagtaat tgccatgggc tccaaagaat    5817
ttgctttatg tttttagcta tttaaaaata aatccatcaa aaataaagta tgcaaatgta    5877
tcttttaaaa aaaaaaaa                                                   5895
```

<210> SEQ ID NO 6
<211> LENGTH: 1445
<212> TYPE: PRT
<213> ORGANISM: HUMAN

<400> SEQUENCE: 6

```
Met Gln Gly Pro Pro Leu Leu Thr Ala Ala His Leu Leu Cys Val Cys
1               5                   10                  15

Thr Ala Ala Leu Ala Val Ala Pro Gly Pro Arg Phe Leu Val Thr Ala
            20                  25                  30

Pro Gly Ile Ile Arg Pro Gly Gly Asn Val Thr Ile Gly Val Glu Leu
        35                  40                  45

Leu Glu His Cys Pro Ser Gln Val Thr Val Lys Ala Glu Leu Leu Lys
    50                  55                  60

Thr Ala Ser Asn Leu Thr Val Ser Val Leu Glu Ala Glu Gly Val Phe
65                  70                  75                  80

Glu Lys Gly Ser Phe Lys Thr Leu Thr Leu Pro Ser Leu Pro Leu Asn
                85                  90                  95

Ser Ala Asp Glu Ile Tyr Glu Leu Arg Val Thr Gly Arg Thr Gln Asp
            100                 105                 110

Glu Ile Leu Phe Ser Asn Ser Thr Arg Leu Ser Phe Glu Thr Lys Arg
        115                 120                 125

Ile Ser Val Phe Ile Gln Thr Asp Lys Ala Leu Tyr Lys Pro Lys Gln
    130                 135                 140

Glu Val Lys Phe Arg Ile Val Thr Leu Phe Ser Asp Phe Lys Pro Tyr
145                 150                 155                 160

Lys Thr Ser Leu Asn Ile Leu Ile Lys Asp Pro Lys Ser Asn Leu Ile
                165                 170                 175

Gln Gln Trp Leu Ser Gln Ser Asp Leu Gly Val Ile Ser Lys Thr
            180                 185                 190

Phe Gln Leu Ser Ser His Pro Ile Leu Gly Asp Trp Ser Ile Gln Val
        195                 200                 205

Gln Val Asn Asp Gln Thr Tyr Tyr Gln Ser Phe Gln Val Ser Glu Tyr
    210                 215                 220

Val Leu Pro Lys Phe Glu Val Thr Leu Gln Thr Pro Leu Tyr Cys Ser
225                 230                 235                 240

Met Asn Ser Lys His Leu Asn Gly Thr Ile Thr Ala Lys Tyr Thr Tyr
                245                 250                 255

Gly Lys Pro Val Lys Gly Asp Val Thr Leu Thr Phe Leu Pro Leu Ser
            260                 265                 270

Phe Trp Gly Lys Lys Asn Ile Thr Lys Thr Phe Lys Ile Asn Gly
        275                 280                 285

Ser Ala Asn Phe Ser Phe Asn Asp Glu Glu Met Lys Asn Val Met Asp
    290                 295                 300

Ser Ser Asn Gly Leu Ser Glu Tyr Leu Asp Leu Ser Ser Pro Gly Pro
305                 310                 315                 320

Val Glu Ile Leu Thr Thr Val Thr Glu Ser Val Thr Gly Ile Ser Arg
                325                 330                 335

Asn Val Ser Thr Asn Val Phe Phe Lys Gln His Asp Tyr Ile Ile Glu
```

-continued

```
                340                 345                 350
Phe Phe Asp Tyr Thr Thr Val Leu Lys Pro Ser Leu Asn Phe Thr Ala
            355                 360                 365
Thr Val Lys Val Thr Arg Ala Asp Gly Asn Gln Leu Thr Leu Glu Glu
        370                 375                 380
Arg Arg Asn Asn Val Val Ile Thr Val Thr Gln Arg Asn Tyr Thr Glu
385                 390                 395                 400
Tyr Trp Ser Gly Ser Asn Ser Gly Asn Gln Lys Met Glu Ala Val Gln
                405                 410                 415
Lys Ile Asn Tyr Thr Val Pro Gln Ser Gly Thr Phe Lys Ile Glu Phe
            420                 425                 430
Pro Ile Leu Glu Asp Ser Ser Glu Leu Gln Leu Lys Ala Tyr Phe Leu
        435                 440                 445
Gly Ser Lys Ser Ser Met Ala Val His Ser Leu Phe Lys Ser Pro Ser
    450                 455                 460
Lys Thr Tyr Ile Gln Leu Lys Thr Arg Asp Glu Asn Ile Lys Val Gly
465                 470                 475                 480
Ser Pro Phe Glu Leu Val Val Ser Gly Asn Lys Arg Leu Lys Glu Leu
                485                 490                 495
Ser Tyr Met Val Val Ser Arg Gly Gln Leu Val Ala Val Gly Lys Gln
            500                 505                 510
Asn Ser Thr Met Phe Ser Leu Thr Pro Glu Asn Ser Trp Thr Pro Lys
        515                 520                 525
Ala Cys Val Ile Val Tyr Tyr Ile Glu Asp Asp Gly Glu Ile Ile Ser
    530                 535                 540
Asp Val Leu Lys Ile Pro Val Gln Leu Val Phe Lys Asn Lys Ile Lys
545                 550                 555                 560
Leu Tyr Trp Ser Lys Val Lys Ala Glu Pro Ser Glu Lys Val Ser Leu
                565                 570                 575
Arg Ile Ser Val Thr Gln Pro Asp Ser Ile Val Gly Ile Val Ala Val
            580                 585                 590
Asp Lys Ser Val Asn Leu Met Asn Ala Ser Asn Asp Ile Thr Met Glu
        595                 600                 605
Asn Val Val His Glu Leu Glu Leu Tyr Asn Thr Gly Tyr Tyr Leu Gly
    610                 615                 620
Met Phe Met Asn Ser Phe Ala Val Phe Gln Glu Cys Gly Leu Trp Val
625                 630                 635                 640
Leu Thr Asp Ala Asn Leu Thr Lys Asp Tyr Ile Asp Gly Val Tyr Asp
                645                 650                 655
Asn Ala Glu Tyr Ala Glu Arg Phe Met Glu Glu Asn Glu Gly His Ile
            660                 665                 670
Val Asp Ile His Asp Phe Ser Leu Gly Ser Ser Pro His Val Arg Lys
        675                 680                 685
His Phe Pro Glu Thr Trp Ile Trp Leu Asp Thr Asn Met Gly Tyr Arg
    690                 695                 700
Ile Tyr Gln Glu Phe Glu Val Thr Val Pro Asp Ser Ile Thr Ser Trp
705                 710                 715                 720
Val Ala Thr Gly Phe Val Ile Ser Glu Asp Leu Gly Leu Gly Leu Thr
                725                 730                 735
Thr Thr Pro Val Glu Leu Gln Ala Phe Gln Pro Phe Ile Phe Leu
            740                 745                 750
Asn Leu Pro Tyr Ser Val Ile Arg Gly Glu Glu Phe Ala Leu Glu Ile
    755                 760                 765
```

-continued

```
Thr Ile Phe Asn Tyr Leu Lys Asp Ala Thr Glu Val Lys Val Ile Ile
770                 775                 780

Glu Lys Ser Asp Lys Phe Asp Ile Leu Met Thr Ser Asn Glu Ile Asn
785                 790                 795                 800

Ala Thr Gly His Gln Gln Thr Leu Leu Val Pro Ser Glu Asp Gly Ala
            805                 810                 815

Thr Val Leu Phe Pro Ile Arg Pro Thr His Leu Gly Ile Pro Ile
                820                 825                 830

Thr Val Thr Ala Leu Ser Pro Thr Ala Ser Asp Ala Val Thr Gln Met
            835                 840                 845

Ile Leu Val Lys Ala Glu Gly Ile Glu Lys Ser Tyr Ser Gln Ser Ile
850                 855                 860

Leu Leu Asp Leu Thr Asp Asn Arg Leu Gln Ser Thr Leu Lys Thr Leu
865                 870                 875                 880

Ser Phe Ser Phe Pro Pro Asn Thr Val Thr Gly Ser Glu Arg Val Gln
            885                 890                 895

Ile Thr Ala Ile Gly Asp Val Leu Gly Pro Ser Ile Asn Gly Leu Ala
            900                 905                 910

Ser Leu Ile Arg Met Pro Tyr Gly Cys Gly Glu Gln Asn Met Ile Asn
            915                 920                 925

Phe Ala Pro Asn Ile Tyr Ile Leu Asp Tyr Leu Thr Lys Lys Lys Gln
930                 935                 940

Leu Thr Asp Asn Leu Lys Glu Lys Ala Leu Ser Phe Met Arg Gln Gly
945                 950                 955                 960

Tyr Gln Arg Glu Leu Leu Tyr Gln Arg Glu Asp Gly Ser Phe Ser Ala
            965                 970                 975

Phe Gly Asn Tyr Asp Pro Ser Gly Ser Thr Trp Leu Ser Ala Phe Val
            980                 985                 990

Leu Arg Cys Phe Leu Glu Ala Asp Pro Tyr Ile Asp Ile Asp Gln Asn
            995                 1000                1005

Val Leu His Arg Thr Tyr Thr Trp Leu Lys Gly His Gln Lys Ser
    1010                1015                1020

Asn Gly Glu Phe Trp Asp Pro Gly Arg Val Ile His Ser Glu Leu
    1025                1030                1035

Gln Gly Gly Asn Lys Ser Pro Val Thr Leu Thr Ala Tyr Ile Val
    1040                1045                1050

Thr Ser Leu Leu Gly Tyr Arg Lys Tyr Gln Pro Asn Ile Asp Val
    1055                1060                1065

Gln Glu Ser Ile His Phe Leu Glu Ser Glu Phe Ser Arg Gly Ile
    1070                1075                1080

Ser Asp Asn Tyr Thr Leu Ala Leu Ile Thr Tyr Ala Leu Ser Ser
    1085                1090                1095

Val Gly Ser Pro Lys Ala Lys Glu Ala Leu Asn Met Leu Thr Trp
    1100                1105                1110

Arg Ala Glu Gln Glu Gly Gly Met Gln Phe Trp Val Ser Ser Glu
    1115                1120                1125

Ser Lys Leu Ser Asp Ser Trp Gln Pro Arg Ser Leu Asp Ile Glu
    1130                1135                1140

Val Ala Ala Tyr Ala Leu Leu Ser His Phe Leu Gln Phe Gln Thr
    1145                1150                1155

Ser Glu Gly Ile Pro Ile Met Arg Trp Leu Ser Arg Gln Arg Asn
    1160                1165                1170
```

```
Ser  Leu  Gly  Gly  Phe  Ala  Ser  Thr  Gln  Asp  Thr  Thr  Val  Ala  Leu
     1175                1180                1185

Lys  Ala  Leu  Ser  Glu  Phe  Ala  Ala  Leu  Met  Asn  Thr  Glu  Arg  Thr
     1190                1195                1200

Asn  Ile  Gln  Val  Thr  Val  Thr  Gly  Pro  Ser  Ser  Pro  Ser  Pro  Val
     1205                1210                1215

Lys  Phe  Leu  Ile  Asp  Thr  His  Asn  Arg  Leu  Leu  Leu  Gln  Thr  Ala
     1220                1225                1230

Glu  Leu  Ala  Val  Val  Gln  Pro  Met  Ala  Val  Asn  Ile  Ser  Ala  Asn
     1235                1240                1245

Gly  Phe  Gly  Phe  Ala  Ile  Cys  Gln  Leu  Asn  Val  Val  Tyr  Asn  Val
     1250                1255                1260

Lys  Ala  Ser  Gly  Ser  Ser  Arg  Arg  Arg  Arg  Ser  Ile  Gln  Asn  Gln
     1265                1270                1275

Glu  Ala  Phe  Asp  Leu  Asp  Val  Ala  Val  Lys  Glu  Asn  Lys  Asp  Asp
     1280                1285                1290

Leu  Asn  His  Val  Asp  Leu  Asn  Val  Cys  Thr  Ser  Phe  Ser  Gly  Pro
     1295                1300                1305

Gly  Arg  Ser  Gly  Met  Ala  Leu  Met  Glu  Val  Asn  Leu  Leu  Ser  Gly
     1310                1315                1320

Phe  Met  Val  Pro  Ser  Glu  Ala  Ile  Ser  Leu  Ser  Glu  Thr  Val  Lys
     1325                1330                1335

Lys  Val  Glu  Tyr  Asp  His  Gly  Lys  Leu  Asn  Leu  Tyr  Leu  Asp  Ser
     1340                1345                1350

Val  Asn  Glu  Thr  Gln  Phe  Cys  Val  Asn  Ile  Pro  Ala  Val  Arg  Asn
     1355                1360                1365

Phe  Lys  Val  Ser  Asn  Thr  Gln  Asp  Ala  Ser  Val  Ser  Ile  Val  Asp
     1370                1375                1380

Tyr  Tyr  Glu  Pro  Arg  Arg  Gln  Ala  Val  Arg  Ser  Tyr  Asn  Ser  Glu
     1385                1390                1395

Val  Lys  Leu  Ser  Ser  Cys  Asp  Leu  Cys  Ser  Asp  Val  Gln  Gly  Cys
     1400                1405                1410

Arg  Pro  Cys  Glu  Asp  Gly  Ala  Ser  Gly  Ser  His  His  His  Ser  Ser
     1415                1420                1425

Val  Ile  Phe  Ile  Phe  Cys  Phe  Lys  Leu  Leu  Tyr  Phe  Met  Glu  Leu
     1430                1435                1440

Trp  Leu
     1445

<210> SEQ ID NO 7
<211> LENGTH: 5895
<212> TYPE: DNA
<213> ORGANISM: HUMAN
<220> FEATURE:
<221> NAME/KEY: CDS
<222> LOCATION: (113)..(4447)

<400> SEQUENCE: 7
ctaaactcga attaagaggg aaaaaaaatc agggaggagg tggcaagcca caccccacgg      60
tgcccgcgaa cttccccggc agcggactgt agcccaggca gacgccgtcg ag atg cag     118
                                                          Met Gln
                                                            1 ggc cca ccg ctc ctg acc gcc gcc cac ctc ctc tgc gtg tgc acc gcc      166
Gly Pro Pro Leu Leu Thr Ala Ala His Leu Leu Cys Val Cys Thr Ala
        5                  10                  15 gcg ctg gcc gtg gct ccc ggg cct cgg ttt ctg gtg aca gcc cca ggg      214
```

```
Ala Leu Ala Val Ala Pro Gly Pro Arg Phe Leu Val Thr Ala Pro Gly
         20              25              30 atc atc agg ccc gga gga aat gtg act att ggg gtg gag ctt ctg gaa      262
Ile Ile Arg Pro Gly Gly Asn Val Thr Ile Gly Val Glu Leu Leu Glu
 35              40              45              50 cac tgc cct tca cag gtg act gtg aag gcg gag ctg ctc aag aca gca      310
His Cys Pro Ser Gln Val Thr Val Lys Ala Glu Leu Leu Lys Thr Ala
                 55              60              65 tca aac ctc act gtc tct gtc ctg gaa gca gaa gga gtc ttt gaa aaa      358
Ser Asn Leu Thr Val Ser Val Leu Glu Ala Glu Gly Val Phe Glu Lys
             70              75              80 ggc tct ttt aag aca ctt act ctt cca tca cta cct ctg aac agt gca      406
Gly Ser Phe Lys Thr Leu Thr Leu Pro Ser Leu Pro Leu Asn Ser Ala
         85              90              95 gat gag att tat gag cta cgt gta acc gga cgt acc cag gat gag att      454
Asp Glu Ile Tyr Glu Leu Arg Val Thr Gly Arg Thr Gln Asp Glu Ile
100             105             110 tta ttc tct aat agt acc cgc tta tca ttt gag acc aag aga ata tct      502
Leu Phe Ser Asn Ser Thr Arg Leu Ser Phe Glu Thr Lys Arg Ile Ser
115             120             125             130 gtc ttc att caa aca gac aag gcc tta tac aag cca aag caa gaa gtg      550
Val Phe Ile Gln Thr Asp Lys Ala Leu Tyr Lys Pro Lys Gln Glu Val
                 135             140             145 aag ttt cgc att gtt aca ctc ttc tca gat ttt aag cct tac aaa acc      598
Lys Phe Arg Ile Val Thr Leu Phe Ser Asp Phe Lys Pro Tyr Lys Thr
             150             155             160 tct tta aac att ctc att aag gac ccc aaa tca aat ttg atc caa cag      646
Ser Leu Asn Ile Leu Ile Lys Asp Pro Lys Ser Asn Leu Ile Gln Gln
         165             170             175 tgg ttg tca caa caa agt gat ctt gga gtc att tcc aaa act ttt cag      694
Trp Leu Ser Gln Gln Ser Asp Leu Gly Val Ile Ser Lys Thr Phe Gln
180             185             190 cta tct tcc cat cca ata ctt ggt gac tgg tct att caa gtt caa gtg      742
Leu Ser Ser His Pro Ile Leu Gly Asp Trp Ser Ile Gln Val Gln Val
195             200             205             210 aat gac cag aca tat tat caa tca ttt cag gtt tca gaa tat gta tta      790
Asn Asp Gln Thr Tyr Tyr Gln Ser Phe Gln Val Ser Glu Tyr Val Leu
                 215             220             225 cca aaa ttt gaa gtg act ttg cag aca cca tta tat tgt tct atg aat      838
Pro Lys Phe Glu Val Thr Leu Gln Thr Pro Leu Tyr Cys Ser Met Asn
             230             235             240 tct aag cat tta aat ggt acc atc acg gca aag tat aca tat ggg aag      886
Ser Lys His Leu Asn Gly Thr Ile Thr Ala Lys Tyr Thr Tyr Gly Lys
         245             250             255 cca gtg aaa gga gac gta acg ctt aca ttt tta cct tta tcc ttt tgg      934
Pro Val Lys Gly Asp Val Thr Leu Thr Phe Leu Pro Leu Ser Phe Trp
260             265             270 gga aag aag aaa aat att aca aaa aca ttt aag ata aat gga tct gca      982
Gly Lys Lys Lys Asn Ile Thr Lys Thr Phe Lys Ile Asn Gly Ser Ala
275             280             285             290 aac ttc tct ttt aat gat gaa gag atg aaa aat gta atg gat tct tca     1030
Asn Phe Ser Phe Asn Asp Glu Glu Met Lys Asn Val Met Asp Ser Ser
                 295             300             305 aat gga ctt tct gaa tac ctg gat cta tct tcc cct gga cca gta gaa     1078
Asn Gly Leu Ser Glu Tyr Leu Asp Leu Ser Ser Pro Gly Pro Val Glu
             310             315             320 att tta acc aca gtg aca gaa tca gtt aca ggt att tca aga aat gta     1126
Ile Leu Thr Thr Val Thr Glu Ser Val Thr Gly Ile Ser Arg Asn Val
         325             330             335
```

```
agc act aat gtg ttc ttc aag caa cat gat tac atc att gag ttt ttt    1174
Ser Thr Asn Val Phe Phe Lys Gln His Asp Tyr Ile Ile Glu Phe Phe
    340             345                 350 gat tat act act gtc ttg aag cca tct ctc aac ttc aca gcc act gtg    1222
Asp Tyr Thr Thr Val Leu Lys Pro Ser Leu Asn Phe Thr Ala Thr Val
355             360                 365                 370 aag gta act cgt gct gat ggc aac caa ctg act ctt gaa gaa aga aga    1270
Lys Val Thr Arg Ala Asp Gly Asn Gln Leu Thr Leu Glu Glu Arg Arg
                375                 380                 385 aat aat gta gtc ata aca gtg aca cag aga aac tat act gag tac tgg    1318
Asn Asn Val Val Ile Thr Val Thr Gln Arg Asn Tyr Thr Glu Tyr Trp
            390                 395                 400 agc gga tct aac agt gga aat cag aaa atg gaa gct gtt cag aaa ata    1366
Ser Gly Ser Asn Ser Gly Asn Gln Lys Met Glu Ala Val Gln Lys Ile
        405                 410                 415 aat tat act gtc ccc caa agt gga act ttt aag att gaa ttc cca atc    1414
Asn Tyr Thr Val Pro Gln Ser Gly Thr Phe Lys Ile Glu Phe Pro Ile
420                 425                 430 ctg gag gat tcc agt gag cta cag ttg aag gcc tat ttc ctt ggt agt    1462
Leu Glu Asp Ser Ser Glu Leu Gln Leu Lys Ala Tyr Phe Leu Gly Ser
435                 440                 445                 450 aaa agt agc atg gca gtt cat agt ctg ttt aag tct cct agt aag aca    1510
Lys Ser Ser Met Ala Val His Ser Leu Phe Lys Ser Pro Ser Lys Thr
                455                 460                 465 tac atc caa cta aaa aca aga gat gaa aat ata aag gtg gga tcg cct    1558
Tyr Ile Gln Leu Lys Thr Arg Asp Glu Asn Ile Lys Val Gly Ser Pro
            470                 475                 480 ttt gag ttg gtg gtt agt ggc aac aaa cga ttg aag gag tta agc tat    1606
Phe Glu Leu Val Val Ser Gly Asn Lys Arg Leu Lys Glu Leu Ser Tyr
        485                 490                 495 atg gta gta tcc agg gga cag ttg gtg gct gta gga aaa caa aat tca    1654
Met Val Val Ser Arg Gly Gln Leu Val Ala Val Gly Lys Gln Asn Ser
    500                 505                 510 aca atg ttc tct tta aca cca gaa aat tct tgg act cca aaa gcc tgt    1702
Thr Met Phe Ser Leu Thr Pro Glu Asn Ser Trp Thr Pro Lys Ala Cys
515                 520                 525                 530 gta att gtg tat tat att gaa gat gat ggg gaa att ata agt gat gtt    1750
Val Ile Val Tyr Tyr Ile Glu Asp Asp Gly Glu Ile Ile Ser Asp Val
                535                 540                 545 cta aaa att cct gtt cag ctt gtt ttt aaa aat aag ata aag cta tat    1798
Leu Lys Ile Pro Val Gln Leu Val Phe Lys Asn Lys Ile Lys Leu Tyr
            550                 555                 560 tgg agt aaa gtg aaa gct gaa cca tct gag aaa gtc tct ctt agg atc    1846
Trp Ser Lys Val Lys Ala Glu Pro Ser Glu Lys Val Ser Leu Arg Ile
        565                 570                 575 tct gtg aca cag cct gac tcc ata gtt ggg att gta gct gtt gac aaa    1894
Ser Val Thr Gln Pro Asp Ser Ile Val Gly Ile Val Ala Val Asp Lys
    580                 585                 590 agt gtg aat ctg atg aat gcc tct aat gat att aca atg gaa aat gtg    1942
Ser Val Asn Leu Met Asn Ala Ser Asn Asp Ile Thr Met Glu Asn Val
595                 600                 605                 610 gtc cat gag ttg gaa ctt tat aac aca gga tat tat tta ggc atg ttc    1990
Val His Glu Leu Glu Leu Tyr Asn Thr Gly Tyr Tyr Leu Gly Met Phe
                615                 620                 625 atg aat tct ttt gca gtc ttt cag gaa tgt gga ctc tgg gta ttg aca    2038
Met Asn Ser Phe Ala Val Phe Gln Glu Cys Gly Leu Trp Val Leu Thr
            630                 635                 640 gat gca aac ctc acg aag gat tat att gat ggt gtt tat gac aat gca    2086
Asp Ala Asn Leu Thr Lys Asp Tyr Ile Asp Gly Val Tyr Asp Asn Ala
        645                 650                 655
```

```
gaa tat gct gag agg ttt atg gag gaa aat gaa gga cat att gta gat    2134
Glu Tyr Ala Glu Arg Phe Met Glu Glu Asn Glu Gly His Ile Val Asp
    660                 665                 670 att cat gac ttt tct ttg ggt agc agt cca cat gtc cga aag cat ttt    2182
Ile His Asp Phe Ser Leu Gly Ser Ser Pro His Val Arg Lys His Phe
675                 680                 685                 690 cca gag act tgg att tgg cta gac acc aac atg ggt tcc agg att tac    2230
Pro Glu Thr Trp Ile Trp Leu Asp Thr Asn Met Gly Ser Arg Ile Tyr
                695                 700                 705 caa gaa ttt gaa gta act gta cct gat tct atc act tct tgg gtg gct    2278
Gln Glu Phe Glu Val Thr Val Pro Asp Ser Ile Thr Ser Trp Val Ala
        710                 715                 720 act ggt ttt gtg atc tct gag gac ctg ggt ctt gga cta aca act act    2326
Thr Gly Phe Val Ile Ser Glu Asp Leu Gly Leu Gly Leu Thr Thr Thr
            725                 730                 735 cca gtg gag ctc caa gcc ttc caa cca ttt ttc att ttt ttg aat ctt    2374
Pro Val Glu Leu Gln Ala Phe Gln Pro Phe Phe Ile Phe Leu Asn Leu
        740                 745                 750 ccc tac tct gtt atc aga ggt gaa gaa ttt gct ttg gaa ata act ata    2422
Pro Tyr Ser Val Ile Arg Gly Glu Glu Phe Ala Leu Glu Ile Thr Ile
755                 760                 765                 770 ttc aat tat ttg aaa gat gcc act gag gtt aag gta atc att gag aaa    2470
Phe Asn Tyr Leu Lys Asp Ala Thr Glu Val Lys Val Ile Ile Glu Lys
                775                 780                 785 agt gac aaa ttt gat att cta atg act tca aat gaa ata aat gcc aca    2518
Ser Asp Lys Phe Asp Ile Leu Met Thr Ser Asn Glu Ile Asn Ala Thr
        790                 795                 800 ggc cac cag cag acc ctt ctg gtt ccc agt gag gat ggg gca act gtt    2566
Gly His Gln Gln Thr Leu Leu Val Pro Ser Glu Asp Gly Ala Thr Val
            805                 810                 815 ctt ttt ccc atc agg cca aca cat ctg gga gaa att cct atc aca gtc    2614
Leu Phe Pro Ile Arg Pro Thr His Leu Gly Glu Ile Pro Ile Thr Val
820                 825                 830 aca gct ctt tca ccc act gct tct gat gct gtc acc cag atg att tta    2662
Thr Ala Leu Ser Pro Thr Ala Ser Asp Ala Val Thr Gln Met Ile Leu
835                 840                 845                 850 gta aag gct gaa gga ata gaa aaa tca tat tca caa tcc atc tta tta    2710
Val Lys Ala Glu Gly Ile Glu Lys Ser Tyr Ser Gln Ser Ile Leu Leu
                855                 860                 865 gac ttg act gac aat agg cta cag agt acc ctg aaa act ttg agt ttc    2758
Asp Leu Thr Asp Asn Arg Leu Gln Ser Thr Leu Lys Thr Leu Ser Phe
        870                 875                 880 tca ttt cct cct aat aca gtg act ggc agt gaa aga gtt cag atc act    2806
Ser Phe Pro Pro Asn Thr Val Thr Gly Ser Glu Arg Val Gln Ile Thr
            885                 890                 895 gca att gga gat gtt ctt ggt cct tcc atc aat ggc tta gcc tca ttg    2854
Ala Ile Gly Asp Val Leu Gly Pro Ser Ile Asn Gly Leu Ala Ser Leu
900                 905                 910 att cgg atg cct tat ggc tgt ggt gaa cag aac atg ata aat ttt gct    2902
Ile Arg Met Pro Tyr Gly Cys Gly Glu Gln Asn Met Ile Asn Phe Ala
915                 920                 925                 930 cca aat att tac att ttg gat tat ctg act aaa aag aaa caa ctg aca    2950
Pro Asn Ile Tyr Ile Leu Asp Tyr Leu Thr Lys Lys Lys Gln Leu Thr
                935                 940                 945 gat aat ttg aaa gaa aaa gct ctt tca ttt atg agg caa ggt tac cag    2998
Asp Asn Leu Lys Glu Lys Ala Leu Ser Phe Met Arg Gln Gly Tyr Gln
        950                 955                 960 aga gaa ctt ctc tat cag agg gaa gat ggc tct ttc agt gct ttt ggg    3046
Arg Glu Leu Leu Tyr Gln Arg Glu Asp Gly Ser Phe Ser Ala Phe Gly
```

-continued

```
       965             970             975
aat tat gac cct tct ggg agc act tgg ttg tca gct ttt gtt tta aga    3094
Asn Tyr Asp Pro Ser Gly Ser Thr Trp Leu Ser Ala Phe Val Leu Arg
980             985             990 tgt ttc ctt gaa gcc gat  cct tac ata gat att  gat cag aat gtg    3139
Cys Phe Leu Glu Ala Asp  Pro Tyr Ile Asp Ile  Asp Gln Asn Val
995             1000            1005 tta cac aga aca tac act tgg ctt aaa gga cat cag aaa tcc aac    3184
Leu His Arg Thr Tyr Thr Trp Leu Lys Gly His Gln Lys Ser Asn
1010            1015            1020 ggt gaa ttt tgg gat cca gga aga gtg att cat agt gag ctt caa    3229
Gly Glu Phe Trp Asp Pro Gly Arg Val Ile His Ser Glu Leu Gln
1025            1030            1035 ggt ggc aat aaa agt cca gta aca ctt aca gcc tat att gta act    3274
Gly Gly Asn Lys Ser Pro Val Thr Leu Thr Ala Tyr Ile Val Thr
1040            1045            1050 tct ctc ctg gga tat aga aag tat cag cct aac att gat gtg caa    3319
Ser Leu Leu Gly Tyr Arg Lys Tyr Gln Pro Asn Ile Asp Val Gln
1055            1060            1065 gag tct atc cat ttt ttg gag tct gaa ttc agt aga gga att tca    3364
Glu Ser Ile His Phe Leu Glu Ser Glu Phe Ser Arg Gly Ile Ser
1070            1075            1080 gac aat tat act cta gcc ctt ata act tat gca ttg tca tca gtg    3409
Asp Asn Tyr Thr Leu Ala Leu Ile Thr Tyr Ala Leu Ser Ser Val
1085            1090            1095 ggg agt cct aaa gcg aag gaa gct ttg aat atg ctg act tgg aga    3454
Gly Ser Pro Lys Ala Lys Glu Ala Leu Asn Met Leu Thr Trp Arg
1100            1105            1110 gca gaa caa gaa ggt ggc atg caa ttc tgg gtg tca tca gag tcc    3499
Ala Glu Gln Glu Gly Gly Met Gln Phe Trp Val Ser Ser Glu Ser
1115            1120            1125 aaa ctt tct gac tcc tgg cag cca cgc tcc ctg gat att gaa gtt    3544
Lys Leu Ser Asp Ser Trp Gln Pro Arg Ser Leu Asp Ile Glu Val
1130            1135            1140 gca gcc tat gca ctg ctc tca cac ttc tta caa ttt cag act tct    3589
Ala Ala Tyr Ala Leu Leu Ser His Phe Leu Gln Phe Gln Thr Ser
1145            1150            1155 gag gga atc cca att atg agg tgg cta agc agg caa aga aat agc    3634
Glu Gly Ile Pro Ile Met Arg Trp Leu Ser Arg Gln Arg Asn Ser
1160            1165            1170 ttg ggt ggt ttt gca tct act cag gat acc act gtg gct tta aag    3679
Leu Gly Gly Phe Ala Ser Thr Gln Asp Thr Thr Val Ala Leu Lys
1175            1180            1185 gct ctg tct gaa ttt gca gcc cta atg aat aca gaa agg aca aat    3724
Ala Leu Ser Glu Phe Ala Ala Leu Met Asn Thr Glu Arg Thr Asn
1190            1195            1200 atc caa gtg acc gtg acg ggg cct agc tca cca agt cct gta aag    3769
Ile Gln Val Thr Val Thr Gly Pro Ser Ser Pro Ser Pro Val Lys
1205            1210            1215 ttt ctg att gac aca cac aac cgc tta ctc ctt cag aca gca gag    3814
Phe Leu Ile Asp Thr His Asn Arg Leu Leu Leu Gln Thr Ala Glu
1220            1225            1230 ctt gct gtg gta cag cca atg gca gtt aat att tcc gca aat ggt    3859
Leu Ala Val Val Gln Pro Met Ala Val Asn Ile Ser Ala Asn Gly
1235            1240            1245 ttt gga ttt gct att tgt cag ctc aat gtt gta tat aat gtg aag    3904
Phe Gly Phe Ala Ile Cys Gln Leu Asn Val Val Tyr Asn Val Lys
1250            1255            1260 gct tct ggg tct tct aga aga cga aga tct atc caa aat caa gaa    3949
```

```
Ala Ser Gly Ser Ser Arg Arg Arg Ser Ile Gln Asn Gln Glu
1265                 1270                1275 gcc ttt gat tta gat gtt gct gta aaa gaa aat aaa gat gat ctc      3994
Ala Phe Asp Leu Asp Val Ala Val Lys Glu Asn Lys Asp Asp Leu
1280                 1285                1290 aat cat gtg gat ttg aat gtg tgt aca agc ttt tcg ggc ccg ggt      4039
Asn His Val Asp Leu Asn Val Cys Thr Ser Phe Ser Gly Pro Gly
1295                 1300                1305 agg agt ggc atg gct ctt atg gaa gtt aac cta tta agt ggc ttt      4084
Arg Ser Gly Met Ala Leu Met Glu Val Asn Leu Leu Ser Gly Phe
1310                 1315                1320 atg gtg cct tca gaa gca att tct ctg agc gag aca gtg aag aaa      4129
Met Val Pro Ser Glu Ala Ile Ser Leu Ser Glu Thr Val Lys Lys
1325                 1330                1335 gtg gaa tat gat cat gga aaa ctc aac ctc tat tta gat tct gta      4174
Val Glu Tyr Asp His Gly Lys Leu Asn Leu Tyr Leu Asp Ser Val
1340                 1345                1350 aat gaa acc cag ttt tgt gtt aat att cct gct gtg aga aac ttt      4219
Asn Glu Thr Gln Phe Cys Val Asn Ile Pro Ala Val Arg Asn Phe
1355                 1360                1365 aaa gtt tca aat acc caa gat gct tca gtg tcc ata gtg gat tac      4264
Lys Val Ser Asn Thr Gln Asp Ala Ser Val Ser Ile Val Asp Tyr
1370                 1375                1380 tat gag cca agg aga cag gcg gtg aga agt tac aac tct gaa gtg      4309
Tyr Glu Pro Arg Arg Gln Ala Val Arg Ser Tyr Asn Ser Glu Val
1385                 1390                1395 aag ctg tcc tcc tgt gac ctt tgc agt gat gtc cag ggc tgc cgt      4354
Lys Leu Ser Ser Cys Asp Leu Cys Ser Asp Val Gln Gly Cys Arg
1400                 1405                1410 cct tgt gag gat gga gct tca ggc tcc cat cat cac tct tca gtc      4399
Pro Cys Glu Asp Gly Ala Ser Gly Ser His His His Ser Ser Val
1415                 1420                1425 att ttt att ttc tgt ttc aag ctt ctg tac ttt atg gaa ctt tgg      4444
Ile Phe Ile Phe Cys Phe Lys Leu Leu Tyr Phe Met Glu Leu Trp
1430                 1435                1440 ctg tgatttattt ttaaaggact ctgtgtaaca ctaacatttc cagtagtcac        4497
Leu
1445 atgtgattgt tttgttttcg tagaagaata ctgcttctat tttgaaaaaa gagttttttt  4557 tctttctatg gggttgcagg gatggtgtac aacaggtcct agcatgtata gctgcataga  4617 tttcttcacc tgatctttgt gtggaagatc agaatgaatg cagttgtgtg tctatatttt  4677 cccctcacaa aatcttttag aatttttttg gaggtgtttg ttttctccag aataaaggta  4737 ttactttaga aataggtatt ctcctcattt tgtgaaagaa atgaacctag attcttaagc  4797 attattacac atccatgttt gcttaaagat ggatttccct gggaatggga gaaaacagcc  4857 agcaggagga gcttcatctg ttcccttccc acctccaacc tagccctact gcccacccca  4917 ccccaaccca ccccatgccc agtggtctca gtagatactt cttaactgga aattctttct  4977 tttcagaatc taggtggtga atttttttta agtggcacgg tcttttttctg cttgaaatct  5037 gatcacaccc cccagccatt gccctccctc tcttttcct ctgtagagaa atgtgagggg   5097 cagtacattt actgtgcttt tcacaccatc tcagaggttg aggagcatac tgaaaattgc  5157 cctgggggt gctgggtgtg ctgtctcctt cccacatcct cagccccaca ccagctctat    5217 ttcaggggtg agagtcagag agcactgcaa tatgtgcttc atgggatttc gattcgaaga  5277 tcctagacca gggagacact gtgagccagg gatacaacaa aatactaggt aagtcactgc  5337
```

-continued

```
agaccgacct ccctgcagtt tgggaaagaa gctgggtttg tggagaatca gagcatcttg      5397
acatgactgc tgacctaaag atccctggca ttggccaggg atcctgtgga acctcttcta      5457
gttcaggggt gtgagcatta gactgccagt tgtctagtga catctgatgc ttgctgtgaa      5517
cttttaagat ccccgaatcc tgagcacctc aatctttaat tgcccgtgta tccgaagggt      5577
aatataattt atctggatgg aaattttaaa gatgaatccc cctttttct tttcttctct       5637 cttttctttc cttctcccct tcttctttgc cttctaaata tactgaaatg atttagatat      5697
gtgtcaacaa ttaatgatct tttattcaat ctaagaaatg gtttagtttt tctctttagc      5757
tctatggcat ttcactcaag tggacagggg aaaaagtaat tgccatgggc tccaaagaat      5817
ttgctttatg tttttagcta tttaaaaata aatccatcaa aaataaagta tgcaaatgta      5877
tcttttaaaa aaaaaaaa                                                    5895
```

<210> SEQ ID NO 8
<211> LENGTH: 1445
<212> TYPE: PRT
<213> ORGANISM: HUMAN

<400> SEQUENCE: 8

```
Met Gln Gly Pro Pro Leu Leu Thr Ala Ala His Leu Leu Cys Val Cys
1               5                   10                  15

Thr Ala Ala Leu Ala Val Ala Pro Gly Pro Arg Phe Leu Val Thr Ala
            20                  25                  30

Pro Gly Ile Ile Arg Pro Gly Gly Asn Val Thr Ile Gly Val Glu Leu
        35                  40                  45

Leu Glu His Cys Pro Ser Gln Val Thr Val Lys Ala Glu Leu Leu Lys
    50                  55                  60

Thr Ala Ser Asn Leu Thr Val Ser Val Leu Glu Ala Glu Gly Val Phe
65                  70                  75                  80

Glu Lys Gly Ser Phe Lys Thr Leu Thr Leu Pro Ser Leu Pro Leu Asn
                85                  90                  95

Ser Ala Asp Glu Ile Tyr Glu Leu Arg Val Thr Gly Arg Thr Gln Asp
            100                 105                 110

Glu Ile Leu Phe Ser Asn Ser Thr Arg Leu Ser Phe Glu Thr Lys Arg
        115                 120                 125

Ile Ser Val Phe Ile Gln Thr Asp Lys Ala Leu Tyr Lys Pro Lys Gln
    130                 135                 140

Glu Val Lys Phe Arg Ile Val Thr Leu Phe Ser Asp Phe Lys Pro Tyr
145                 150                 155                 160

Lys Thr Ser Leu Asn Ile Leu Lys Asp Pro Lys Ser Asn Leu Ile
                165                 170                 175

Gln Gln Trp Leu Ser Gln Ser Asp Leu Gly Val Ile Ser Lys Thr
            180                 185                 190

Phe Gln Leu Ser Ser His Pro Ile Leu Gly Asp Trp Ser Ile Gln Val
        195                 200                 205

Gln Val Asn Asp Gln Thr Tyr Tyr Gln Ser Phe Gln Val Ser Glu Tyr
    210                 215                 220

Val Leu Pro Lys Phe Glu Val Thr Leu Gln Thr Pro Leu Tyr Cys Ser
225                 230                 235                 240

Met Asn Ser Lys His Leu Asn Gly Thr Ile Thr Ala Lys Tyr Thr Tyr
                245                 250                 255

Gly Lys Pro Val Lys Gly Asp Val Thr Leu Thr Phe Leu Pro Leu Ser
            260                 265                 270
```

-continued

```
Phe Trp Gly Lys Lys Lys Asn Ile Thr Lys Thr Phe Lys Ile Asn Gly
            275                 280                 285

Ser Ala Asn Phe Ser Phe Asn Asp Glu Glu Met Lys Asn Val Met Asp
            290                 295                 300

Ser Ser Asn Gly Leu Ser Glu Tyr Leu Asp Leu Ser Ser Pro Gly Pro
305                 310                 315                 320

Val Glu Ile Leu Thr Thr Val Thr Glu Ser Val Thr Gly Ile Ser Arg
                    325                 330                 335

Asn Val Ser Thr Asn Val Phe Phe Lys Gln His Asp Tyr Ile Ile Glu
            340                 345                 350

Phe Phe Asp Tyr Thr Thr Val Leu Lys Pro Ser Leu Asn Phe Thr Ala
            355                 360                 365

Thr Val Lys Val Thr Arg Ala Asp Gly Asn Gln Leu Thr Leu Glu Glu
            370                 375                 380

Arg Arg Asn Asn Val Val Ile Thr Val Thr Gln Arg Asn Tyr Thr Glu
385                 390                 395                 400

Tyr Trp Ser Gly Ser Asn Ser Gly Asn Gln Lys Met Glu Ala Val Gln
                    405                 410                 415

Lys Ile Asn Tyr Thr Val Pro Gln Ser Gly Thr Phe Lys Ile Glu Phe
            420                 425                 430

Pro Ile Leu Glu Asp Ser Ser Glu Leu Gln Leu Lys Ala Tyr Phe Leu
            435                 440                 445

Gly Ser Lys Ser Ser Met Ala Val His Ser Leu Phe Lys Ser Pro Ser
450                 455                 460

Lys Thr Tyr Ile Gln Leu Lys Thr Arg Asp Glu Asn Ile Lys Val Gly
465                 470                 475                 480

Ser Pro Phe Glu Leu Val Val Ser Gly Asn Lys Arg Leu Lys Glu Leu
                    485                 490                 495

Ser Tyr Met Val Val Ser Arg Gly Gln Leu Val Ala Val Gly Lys Gln
            500                 505                 510

Asn Ser Thr Met Phe Ser Leu Thr Pro Glu Asn Ser Trp Thr Pro Lys
            515                 520                 525

Ala Cys Val Ile Val Tyr Tyr Ile Glu Asp Asp Gly Glu Ile Ile Ser
            530                 535                 540

Asp Val Leu Lys Ile Pro Val Gln Leu Val Phe Lys Asn Lys Ile Lys
545                 550                 555                 560

Leu Tyr Trp Ser Lys Val Lys Ala Glu Pro Ser Glu Lys Val Ser Leu
                    565                 570                 575

Arg Ile Ser Val Thr Gln Pro Asp Ser Ile Val Gly Ile Val Ala Val
            580                 585                 590

Asp Lys Ser Val Asn Leu Met Asn Ala Ser Asn Asp Ile Thr Met Glu
            595                 600                 605

Asn Val Val His Glu Leu Glu Leu Tyr Asn Thr Gly Tyr Tyr Leu Gly
610                 615                 620

Met Phe Met Asn Ser Phe Ala Val Phe Gln Glu Cys Gly Leu Trp Val
625                 630                 635                 640

Leu Thr Asp Ala Asn Leu Thr Lys Asp Tyr Ile Asp Gly Val Tyr Asp
                    645                 650                 655

Asn Ala Glu Tyr Ala Glu Arg Phe Met Glu Asn Glu Gly His Ile
            660                 665                 670

Val Asp Ile His Asp Phe Ser Leu Gly Ser Ser Pro His Val Arg Lys
            675                 680                 685

His Phe Pro Glu Thr Trp Ile Trp Leu Asp Thr Asn Met Gly Ser Arg
```

-continued

```
            690                 695                 700
Ile Tyr Gln Glu Phe Glu Val Thr Val Pro Asp Ser Ile Thr Ser Trp
705                 710                 715                 720

Val Ala Thr Gly Phe Val Ile Ser Glu Asp Leu Gly Leu Gly Leu Thr
                725                 730                 735

Thr Thr Pro Val Glu Leu Gln Ala Phe Gln Pro Phe Ile Phe Leu
                740                 745                 750

Asn Leu Pro Tyr Ser Val Ile Arg Gly Glu Glu Phe Ala Leu Glu Ile
                755                 760                 765

Thr Ile Phe Asn Tyr Leu Lys Asp Ala Thr Glu Val Lys Val Ile Ile
770                 775                 780

Glu Lys Ser Asp Lys Phe Asp Ile Leu Met Thr Ser Asn Glu Ile Asn
785                 790                 795                 800

Ala Thr Gly His Gln Gln Thr Leu Leu Val Pro Ser Glu Asp Gly Ala
                805                 810                 815

Thr Val Leu Phe Pro Ile Arg Pro Thr His Leu Gly Glu Ile Pro Ile
                820                 825                 830

Thr Val Thr Ala Leu Ser Pro Thr Ala Ser Asp Ala Val Thr Gln Met
                835                 840                 845

Ile Leu Val Lys Ala Glu Gly Ile Glu Lys Ser Tyr Ser Gln Ser Ile
850                 855                 860

Leu Leu Asp Leu Thr Asp Asn Arg Leu Gln Ser Thr Leu Lys Thr Leu
865                 870                 875                 880

Ser Phe Ser Phe Pro Pro Asn Thr Val Thr Gly Ser Glu Arg Val Gln
                885                 890                 895

Ile Thr Ala Ile Gly Asp Val Leu Gly Pro Ser Ile Asn Gly Leu Ala
                900                 905                 910

Ser Leu Ile Arg Met Pro Tyr Gly Cys Gly Glu Gln Asn Met Ile Asn
                915                 920                 925

Phe Ala Pro Asn Ile Tyr Ile Leu Asp Tyr Leu Thr Lys Lys Lys Gln
                930                 935                 940

Leu Thr Asp Asn Leu Lys Glu Lys Ala Leu Ser Phe Met Arg Gln Gly
945                 950                 955                 960

Tyr Gln Arg Glu Leu Leu Tyr Gln Arg Glu Asp Gly Ser Phe Ser Ala
                965                 970                 975

Phe Gly Asn Tyr Asp Pro Ser Gly Ser Thr Trp Leu Ser Ala Phe Val
                980                 985                 990

Leu Arg Cys Phe Leu Glu Ala Asp Pro Tyr Ile Asp Ile Asp Gln Asn
                995                1000                1005

Val Leu His Arg Thr Tyr Thr Trp Leu Lys Gly His Gln Lys Ser
1010                1015                1020

Asn Gly Glu Phe Trp Asp Pro Gly Arg Val Ile His Ser Glu Leu
1025                1030                1035

Gln Gly Gly Asn Lys Ser Pro Val Thr Leu Thr Ala Tyr Ile Val
1040                1045                1050

Thr Ser Leu Leu Gly Tyr Arg Lys Tyr Gln Pro Asn Ile Asp Val
1055                1060                1065

Gln Glu Ser Ile His Phe Leu Glu Ser Glu Phe Ser Arg Gly Ile
1070                1075                1080

Ser Asp Asn Tyr Thr Leu Ala Leu Ile Thr Tyr Ala Leu Ser Ser
1085                1090                1095

Val Gly Ser Pro Lys Ala Lys Glu Ala Leu Asn Met Leu Thr Trp
1100                1105                1110
```

```
Arg Ala Glu Gln Glu Gly Gly Met Gln Phe Trp Val Ser Ser Glu
1115                1120                1125

Ser Lys Leu Ser Asp Ser Trp Gln Pro Arg Ser Leu Asp Ile Glu
1130                1135                1140

Val Ala Ala Tyr Ala Leu Leu Ser His Phe Leu Gln Phe Gln Thr
1145                1150                1155

Ser Glu Gly Ile Pro Ile Met Arg Trp Leu Ser Arg Gln Arg Asn
1160                1165                1170

Ser Leu Gly Gly Phe Ala Ser Thr Gln Asp Thr Thr Val Ala Leu
1175                1180                1185

Lys Ala Leu Ser Glu Phe Ala Ala Leu Met Asn Thr Glu Arg Thr
1190                1195                1200

Asn Ile Gln Val Thr Val Thr Gly Pro Ser Ser Pro Ser Pro Val
1205                1210                1215

Lys Phe Leu Ile Asp Thr His Asn Arg Leu Leu Leu Gln Thr Ala
1220                1225                1230

Glu Leu Ala Val Val Gln Pro Met Ala Val Asn Ile Ser Ala Asn
1235                1240                1245

Gly Phe Gly Phe Ala Ile Cys Gln Leu Asn Val Val Tyr Asn Val
1250                1255                1260

Lys Ala Ser Gly Ser Ser Arg Arg Arg Arg Ser Ile Gln Asn Gln
1265                1270                1275

Glu Ala Phe Asp Leu Asp Val Ala Val Lys Glu Asn Lys Asp Asp
1280                1285                1290

Leu Asn His Val Asp Leu Asn Val Cys Thr Ser Phe Ser Gly Pro
1295                1300                1305

Gly Arg Ser Gly Met Ala Leu Met Glu Val Asn Leu Leu Ser Gly
1310                1315                1320

Phe Met Val Pro Ser Glu Ala Ile Ser Leu Ser Glu Thr Val Lys
1325                1330                1335

Lys Val Glu Tyr Asp His Gly Lys Leu Asn Leu Tyr Leu Asp Ser
1340                1345                1350

Val Asn Glu Thr Gln Phe Cys Val Asn Ile Pro Ala Val Arg Asn
1355                1360                1365

Phe Lys Val Ser Asn Thr Gln Asp Ala Ser Val Ser Ile Val Asp
1370                1375                1380

Tyr Tyr Glu Pro Arg Arg Gln Ala Val Arg Ser Tyr Asn Ser Glu
1385                1390                1395

Val Lys Leu Ser Ser Cys Asp Leu Cys Ser Asp Val Gln Gly Cys
1400                1405                1410

Arg Pro Cys Glu Asp Gly Ala Ser Gly Ser His His His Ser Ser
1415                1420                1425

Val Ile Phe Ile Phe Cys Phe Lys Leu Leu Tyr Phe Met Glu Leu
1430                1435                1440

Trp Leu
1445

<210> SEQ ID NO 9
<211> LENGTH: 3535
<212> TYPE: DNA
<213> ORGANISM: HUMAN
<220> FEATURE:
<221> NAME/KEY: CDS
<222> LOCATION: (113)..(3316)
```

<400> SEQUENCE: 9

```
ctaaactcga attaagaggg aaaaaaaatc agggaggagg tggcaagcca caccccacgg         60
tgcccgcgaa cttccccggc agcggactgt agcccaggca gacgccgtcg ag atg cag        118
                                                         Met Gln
                                                          1 ggc cca ccg ctc ctg acc gcc gcc cac ctc ctc tgc gtg tgc acc gcc         166
Gly Pro Pro Leu Leu Thr Ala Ala His Leu Leu Cys Val Cys Thr Ala
        5                  10                  15 gcg ctg gcc gtg gct ccc ggg cct cgg ttt ctg gtg aca gcc cca ggg         214
Ala Leu Ala Val Ala Pro Gly Pro Arg Phe Leu Val Thr Ala Pro Gly
 20                  25                  30 atc atc agg ccc gga gga aat gtg act att ggg gtg gag ctt ctg gaa         262
Ile Ile Arg Pro Gly Gly Asn Val Thr Ile Gly Val Glu Leu Leu Glu
35                  40                  45                  50 cac tgc cct tca cag gtg act gtg aag gcg gag ctg ctc aag aca gca         310
His Cys Pro Ser Gln Val Thr Val Lys Ala Glu Leu Leu Lys Thr Ala
                55                  60                  65 tca aac ctc act gtc tct gtc ctg gaa gca gaa gga gtc ttt gaa aaa         358
Ser Asn Leu Thr Val Ser Val Leu Glu Ala Glu Gly Val Phe Glu Lys
            70                  75                  80 ggc tct ttt aag aca ctt act ctt cca tca cta cct ctg aac agt gca         406
Gly Ser Phe Lys Thr Leu Thr Leu Pro Ser Leu Pro Leu Asn Ser Ala
        85                  90                  95 gat gag att tat gag cta cgt gta acc gga cgt acc cag gat gag att         454
Asp Glu Ile Tyr Glu Leu Arg Val Thr Gly Arg Thr Gln Asp Glu Ile
    100                 105                 110 tta ttc tct aat agt acc cgc tta tca ttt gag acc aag aga ata tct         502
Leu Phe Ser Asn Ser Thr Arg Leu Ser Phe Glu Thr Lys Arg Ile Ser
115                 120                 125                 130 gtc ttc att caa aca gac aag gcc tta tac aag cca aag caa gaa gtg         550
Val Phe Ile Gln Thr Asp Lys Ala Leu Tyr Lys Pro Lys Gln Glu Val
                135                 140                 145 aag ttt cgc att gtt aca ctc ttc tca gat ttt aag cct tac aaa acc         598
Lys Phe Arg Ile Val Thr Leu Phe Ser Asp Phe Lys Pro Tyr Lys Thr
            150                 155                 160 tct tta aac att ctc att aag gac ccc aaa tca aat ttg atc caa cag         646
Ser Leu Asn Ile Leu Ile Lys Asp Pro Lys Ser Asn Leu Ile Gln Gln
        165                 170                 175 tgg ttg tca caa caa agt gat ctt gga gtc att tcc aaa act ttt cag         694
Trp Leu Ser Gln Gln Ser Asp Leu Gly Val Ile Ser Lys Thr Phe Gln
    180                 185                 190 cta tct tcc cat cca ata ctt ggt gac tgg tct att caa gtt caa gtg         742
Leu Ser Ser His Pro Ile Leu Gly Asp Trp Ser Ile Gln Val Gln Val
195                 200                 205                 210 aat gac cag aca tat tat caa tca ttt cag gtt tca gaa tat gta tta         790
Asn Asp Gln Thr Tyr Tyr Gln Ser Phe Gln Val Ser Glu Tyr Val Leu
                215                 220                 225 cca aaa ttt gaa gtg act ttg cag aca cca tta tat tgt tct atg aat         838
Pro Lys Phe Glu Val Thr Leu Gln Thr Pro Leu Tyr Cys Ser Met Asn
            230                 235                 240 tct aag cat tta aat ggt acc atc acg gca aag tat aca tat ggg aag         886
Ser Lys His Leu Asn Gly Thr Ile Thr Ala Lys Tyr Thr Tyr Gly Lys
        245                 250                 255 cca gtg aaa gga gac gta acg ctt aca ttt tta cct tta tcc ttt tgg         934
Pro Val Lys Gly Asp Val Thr Leu Thr Phe Leu Pro Leu Ser Phe Trp
    260                 265                 270 gga aag aag aaa aat att aca aaa aca ttt aag ata aat gga tct gca         982
Gly Lys Lys Lys Asn Ile Thr Lys Thr Phe Lys Ile Asn Gly Ser Ala
275                 280                 285                 290
```

```
aac ttc tct ttt aat gat gaa gag atg aaa aat gta atg gat tct tca    1030
Asn Phe Ser Phe Asn Asp Glu Glu Met Lys Asn Val Met Asp Ser Ser
                295                 300                 305 aat gga ctt tct gaa tac ctg gat cta tct tcc cct gga cca gta gaa    1078
Asn Gly Leu Ser Glu Tyr Leu Asp Leu Ser Ser Pro Gly Pro Val Glu
        310                 315                 320 att tta acc aca gtg aca gaa tca gtt aca ggt att tca aga aat gta    1126
Ile Leu Thr Thr Val Thr Glu Ser Val Thr Gly Ile Ser Arg Asn Val
            325                 330                 335 agc act aat gtg ttc ttc aag caa cat gat tac atc att gag ttt ttt    1174
Ser Thr Asn Val Phe Phe Lys Gln His Asp Tyr Ile Ile Glu Phe Phe
        340                 345                 350 gat tat act act gtc ttg aag cca tct ctc aac ttc aca gcc act gtg    1222
Asp Tyr Thr Thr Val Leu Lys Pro Ser Leu Asn Phe Thr Ala Thr Val
355                 360                 365                 370 aag gta act cgt gct gat ggc aac caa ctg act ctt gaa gaa aga aga    1270
Lys Val Thr Arg Ala Asp Gly Asn Gln Leu Thr Leu Glu Glu Arg Arg
                375                 380                 385 aat aat gta gtc ata aca gtg aca cag aga aac tat act gag tac tgg    1318
Asn Asn Val Val Ile Thr Val Thr Gln Arg Asn Tyr Thr Glu Tyr Trp
            390                 395                 400 agc gga tct aac agt gga aat cag aaa atg gaa gct gtt cag aaa ata    1366
Ser Gly Ser Asn Ser Gly Asn Gln Lys Met Glu Ala Val Gln Lys Ile
        405                 410                 415 aat tat act gtc ccc caa agt gga act ttt aag att gaa ttc cca atc    1414
Asn Tyr Thr Val Pro Gln Ser Gly Thr Phe Lys Ile Glu Phe Pro Ile
420                 425                 430 ctg gag gat tcc agt gag cta cag ttg aag gcc tat ttc ctt ggt agt    1462
Leu Glu Asp Ser Ser Glu Leu Gln Leu Lys Ala Tyr Phe Leu Gly Ser
435                 440                 445                 450 aaa agc agc atg gca gtt cat agt ctg ttt aag tct cct agt aag aca    1510
Lys Ser Ser Met Ala Val His Ser Leu Phe Lys Ser Pro Ser Lys Thr
                455                 460                 465 tac atc caa cta aaa aca aga gat gaa aat ata aag gtg gga tcg cct    1558
Tyr Ile Gln Leu Lys Thr Arg Asp Glu Asn Ile Lys Val Gly Ser Pro
            470                 475                 480 ttt gag ttg gtg gtt agt ggc aac aaa cga ttg aag gag tta agc tat    1606
Phe Glu Leu Val Val Ser Gly Asn Lys Arg Leu Lys Glu Leu Ser Tyr
        485                 490                 495 atg gta gta tcc agg gga cag ttg gtg gct gta gga aaa caa aat tca    1654
Met Val Val Ser Arg Gly Gln Leu Val Ala Val Gly Lys Gln Asn Ser
500                 505                 510 aca atg ttc tct tta aca cca gaa aat tct tgg act cca aaa gcc tgt    1702
Thr Met Phe Ser Leu Thr Pro Glu Asn Ser Trp Thr Pro Lys Ala Cys
515                 520                 525                 530 gta att gtg tat tat att gaa gat gat ggg gaa att ata agt gat gtt    1750
Val Ile Val Tyr Tyr Ile Glu Asp Asp Gly Glu Ile Ile Ser Asp Val
                535                 540                 545 cta aaa att cct gtt cag ctt gtt ttt aaa aat aag ata aag cta tat    1798
Leu Lys Ile Pro Val Gln Leu Val Phe Lys Asn Lys Ile Lys Leu Tyr
            550                 555                 560 tgg agt aaa gtg aaa gct gaa cca tct gag aaa gtc tct ctt agg atc    1846
Trp Ser Lys Val Lys Ala Glu Pro Ser Glu Lys Val Ser Leu Arg Ile
        565                 570                 575 tct gtg aca cag cct gac tcc ata gtt ggg att gta gct gtt gac aaa    1894
Ser Val Thr Gln Pro Asp Ser Ile Val Gly Ile Val Ala Val Asp Lys
580                 585                 590 agt gtg aat ctg atg aat gcc tct aat gat att aca atg gaa aat gtg    1942
Ser Val Asn Leu Met Asn Ala Ser Asn Asp Ile Thr Met Glu Asn Val
```

-continued

```
               595                 600                 605                 610
gtc cat gag ttg gaa ctt tat aac aca gga tat tat tta ggc atg ttc           1990
Val His Glu Leu Glu Leu Tyr Asn Thr Gly Tyr Tyr Leu Gly Met Phe
                    615                 620                 625 atg aat tct ttt gca gtc ttt cag gaa tgt gga ctc tgg gta ttg aca           2038
Met Asn Ser Phe Ala Val Phe Gln Glu Cys Gly Leu Trp Val Leu Thr
                630                 635                 640 gat gca aac ctc acg aag gat tat att gat ggt gtt tat gac aat gca           2086
Asp Ala Asn Leu Thr Lys Asp Tyr Ile Asp Gly Val Tyr Asp Asn Ala
            645                 650                 655 gaa tat gct gag agg ttt atg gag gaa aat gaa gga cat att gta gat           2134
Glu Tyr Ala Glu Arg Phe Met Glu Glu Asn Glu Gly His Ile Val Asp
        660                 665                 670 att cat gac ttt tct ttg ggt agc agt cca cat gtc cga aag cat ttt           2182
Ile His Asp Phe Ser Leu Gly Ser Ser Pro His Val Arg Lys His Phe
    675                 680                 685                 690 cca gag act tgg att tgg cta gac acc aac atg ggt tac agg att tac           2230
Pro Glu Thr Trp Ile Trp Leu Asp Thr Asn Met Gly Tyr Arg Ile Tyr
                695                 700                 705 caa gaa ttt gaa gta act gta cct gat tct atc act tct tgg gtg gct           2278
Gln Glu Phe Glu Val Thr Val Pro Asp Ser Ile Thr Ser Trp Val Ala
            710                 715                 720 act ggt ttt gtg atc tct gag gac ctg ggt ctt gga cta aca act act           2326
Thr Gly Phe Val Ile Ser Glu Asp Leu Gly Leu Gly Leu Thr Thr Thr
        725                 730                 735 cca gtg gag ctc caa gcc ttc caa cca ttt ttc att ttt ttg aat ctt           2374
Pro Val Glu Leu Gln Ala Phe Gln Pro Phe Phe Ile Phe Leu Asn Leu
    740                 745                 750 ccc tac tct gtt atc aga ggt gaa gaa ttt gct ttg gaa ata act ata           2422
Pro Tyr Ser Val Ile Arg Gly Glu Glu Phe Ala Leu Glu Ile Thr Ile
755                 760                 765                 770 ttc aat tat ttg aaa gat gcc act gag gtt aag gta atc att gag aaa           2470
Phe Asn Tyr Leu Lys Asp Ala Thr Glu Val Lys Val Ile Ile Glu Lys
                775                 780                 785 agt gac aaa ttt gat att cta atg act tca aat gaa ata aat gcc aca           2518
Ser Asp Lys Phe Asp Ile Leu Met Thr Ser Asn Glu Ile Asn Ala Thr
            790                 795                 800 ggc cac cag cag acc ctt ctg gtt ccc agt gag gat ggg gca act gtt           2566
Gly His Gln Gln Thr Leu Leu Val Pro Ser Glu Asp Gly Ala Thr Val
        805                 810                 815 ctt ttt ccc atc agg cca aca cat ctg gga gaa att cct atc aca gtc           2614
Leu Phe Pro Ile Arg Pro Thr His Leu Gly Glu Ile Pro Ile Thr Val
    820                 825                 830 aca gct ctt tca ccc act gct tct gat gct gtc acc cag atg att tta           2662
Thr Ala Leu Ser Pro Thr Ala Ser Asp Ala Val Thr Gln Met Ile Leu
835                 840                 845                 850 gta aag gct gaa gga ata gaa aaa tca tat tca caa tcc atc tta tta           2710
Val Lys Ala Glu Gly Ile Glu Lys Ser Tyr Ser Gln Ser Ile Leu Leu
                855                 860                 865 gac ttg act gac aat agg cta cag agt acc ctg aaa act ttg agt ttc           2758
Asp Leu Thr Asp Asn Arg Leu Gln Ser Thr Leu Lys Thr Leu Ser Phe
            870                 875                 880 tca ttt cct cct aat aca gtg act ggc agt gaa aga gtt cag atc act           2806
Ser Phe Pro Pro Asn Thr Val Thr Gly Ser Glu Arg Val Gln Ile Thr
        885                 890                 895 gca att gga gat gtt ctt ggt cct tcc atc aat ggc tta gcc tca ttg           2854
Ala Ile Gly Asp Val Leu Gly Pro Ser Ile Asn Gly Leu Ala Ser Leu
    900                 905                 910 att cgg atg cct tat ggc tgt ggt gaa cag aac atg ata aat ttt gct           2902
```

```
Ile Arg Met Pro Tyr Gly Cys Gly Glu Gln Asn Met Ile Asn Phe Ala
915                 920                 925                 930 cca aat att tac att ttg gat tat ctg act aaa aag aaa caa ctg aca    2950
Pro Asn Ile Tyr Ile Leu Asp Tyr Leu Thr Lys Lys Lys Gln Leu Thr
                935                 940                 945 gat aat ttg aaa gaa aaa gct ctt tca ttt atg agg caa ggt tac cag    2998
Asp Asn Leu Lys Glu Lys Ala Leu Ser Phe Met Arg Gln Gly Tyr Gln
            950                 955                 960 aga gaa ctt ctc tat cag agg gaa gat ggc tct ttc agt gct ttt ggg    3046
Arg Glu Leu Leu Tyr Gln Arg Glu Asp Gly Ser Phe Ser Ala Phe Gly
        965                 970                 975 aat tat gac cct tct ggg agc act tgg ttg tca gct ttt gtt tta aga    3094
Asn Tyr Asp Pro Ser Gly Ser Thr Trp Leu Ser Ala Phe Val Leu Arg
    980                 985                 990 tgt ttc ctt gaa gcc gat  cct tac ata gat att  gat cag aat gtg     3139
Cys Phe Leu Glu Ala Asp  Pro Tyr Ile Asp Ile  Asp Gln Asn Val
995                 1000                1005 tta cac aga aca tac act  tgg ctt aaa gga cat  cag aaa tcc aac     3184
Leu His Arg Thr Tyr Thr  Trp Leu Lys Gly His  Gln Lys Ser Asn
1010            1015                 1020 ggt gaa ttt tgg gat cca  gga aga gtg att cat  agt gag ctt caa     3229
Gly Glu Phe Trp Asp Pro  Gly Arg Val Ile His  Ser Glu Leu Gln
1025            1030                 1035 ggt ggc aat aaa agt cca  gta aca ctt aca gcc  tat att gta act     3274
Gly Gly Asn Lys Ser Pro  Val Thr Leu Thr Ala  Tyr Ile Val Thr
1040            1045                 1050 tct ctc ctg gga tat aga  aag tat cag gta ttt  cgt att taa         3316
Ser Leu Leu Gly Tyr Arg  Lys Tyr Gln Val Phe  Arg Ile
1055            1060                 1065 tttaataaat gatagatggg aaattcaagg aaggtaggtc ttaatgggtc aaatatgtgt  3376
gtggaaactt aacaagttgc agctttacaa cacatgtgaa atctgaattt gagtactctt  3436
ttgctttgca tttgcagcca tgttccaaaa tctgagaata aaacattacc cactctttca  3496
gataactaag agattctaaa aaaaaaaaaa aaaaaaaa                          3535

<210> SEQ ID NO 10
<211> LENGTH: 1067
<212> TYPE: PRT
<213> ORGANISM: HUMAN

<400> SEQUENCE: 10

Met Gln Gly Pro Pro Leu Leu Thr Ala Ala His Leu Leu Cys Val Cys
1               5                   10                  15

Thr Ala Ala Leu Ala Val Ala Pro Gly Pro Arg Phe Leu Val Thr Ala
                20                  25                  30

Pro Gly Ile Ile Arg Pro Gly Gly Asn Val Thr Ile Gly Val Glu Leu
            35                  40                  45

Leu Glu His Cys Pro Ser Gln Val Thr Val Lys Ala Glu Leu Leu Lys
        50                  55                  60

Thr Ala Ser Asn Leu Thr Val Ser Val Leu Glu Ala Glu Gly Val Phe
65                  70                  75                  80

Glu Lys Gly Ser Phe Lys Thr Leu Thr Leu Pro Ser Leu Pro Leu Asn
                85                  90                  95

Ser Ala Asp Glu Ile Tyr Glu Leu Arg Val Thr Gly Arg Thr Gln Asp
            100                 105                 110

Glu Ile Leu Phe Ser Asn Ser Thr Arg Leu Ser Phe Glu Thr Lys Arg
        115                 120                 125
```

-continued

```
Ile Ser Val Phe Ile Gln Thr Asp Lys Ala Leu Tyr Lys Pro Lys Gln
    130                 135                 140

Glu Val Lys Phe Arg Ile Val Thr Leu Phe Ser Asp Phe Lys Pro Tyr
145                 150                 155                 160

Lys Thr Ser Leu Asn Ile Leu Ile Lys Asp Pro Lys Ser Asn Leu Ile
                165                 170                 175

Gln Gln Trp Leu Ser Gln Ser Asp Leu Gly Val Ile Ser Lys Thr
                180                 185                 190

Phe Gln Leu Ser Ser His Pro Ile Leu Gly Asp Trp Ser Ile Gln Val
                195                 200                 205

Gln Val Asn Asp Gln Thr Tyr Tyr Gln Ser Phe Gln Val Ser Glu Tyr
210                 215                 220

Val Leu Pro Lys Phe Glu Val Thr Leu Gln Thr Pro Leu Tyr Cys Ser
225                 230                 235                 240

Met Asn Ser Lys His Leu Asn Gly Thr Ile Thr Ala Lys Tyr Thr Tyr
                245                 250                 255

Gly Lys Pro Val Lys Gly Asp Val Thr Leu Thr Phe Leu Pro Leu Ser
                260                 265                 270

Phe Trp Gly Lys Lys Asn Ile Thr Lys Thr Phe Lys Ile Asn Gly
                275                 280                 285

Ser Ala Asn Phe Ser Phe Asn Asp Glu Glu Met Lys Asn Val Met Asp
290                 295                 300

Ser Ser Asn Gly Leu Ser Glu Tyr Leu Asp Leu Ser Ser Pro Gly Pro
305                 310                 315                 320

Val Glu Ile Leu Thr Thr Val Thr Glu Ser Val Thr Gly Ile Ser Arg
                325                 330                 335

Asn Val Ser Thr Asn Val Phe Phe Lys Gln His Asp Tyr Ile Ile Glu
                340                 345                 350

Phe Phe Asp Tyr Thr Thr Val Leu Lys Pro Ser Leu Asn Phe Thr Ala
                355                 360                 365

Thr Val Lys Val Thr Arg Ala Asp Gly Asn Gln Leu Thr Leu Glu Glu
                370                 375                 380

Arg Arg Asn Asn Val Val Ile Thr Val Thr Gln Arg Asn Tyr Thr Glu
385                 390                 395                 400

Tyr Trp Ser Gly Ser Asn Ser Gly Asn Gln Lys Met Glu Ala Val Gln
                405                 410                 415

Lys Ile Asn Tyr Thr Val Pro Gln Ser Gly Thr Phe Lys Ile Glu Phe
                420                 425                 430

Pro Ile Leu Glu Asp Ser Ser Glu Leu Gln Leu Lys Ala Tyr Phe Leu
                435                 440                 445

Gly Ser Lys Ser Ser Met Ala Val His Ser Leu Phe Lys Ser Pro Ser
450                 455                 460

Lys Thr Tyr Ile Gln Leu Lys Thr Arg Asp Glu Asn Ile Lys Val Gly
465                 470                 475                 480

Ser Pro Phe Glu Leu Val Val Ser Gly Asn Lys Arg Leu Lys Glu Leu
                485                 490                 495

Ser Tyr Met Val Val Ser Arg Gly Gln Leu Val Ala Val Gly Lys Gln
                500                 505                 510

Asn Ser Thr Met Phe Ser Leu Thr Pro Glu Asn Ser Trp Thr Pro Lys
                515                 520                 525

Ala Cys Val Ile Val Tyr Tyr Ile Glu Asp Gly Glu Ile Ile Ser
530                 535                 540

Asp Val Leu Lys Ile Pro Val Gln Leu Val Phe Lys Asn Lys Ile Lys
```

-continued

```
            545                 550                 555                 560
        Leu Tyr Trp Ser Lys Val Lys Ala Glu Pro Ser Glu Lys Val Ser Leu
                        565                 570                 575

Arg Ile Ser Val Thr Gln Pro Asp Ser Ile Val Gly Ile Val Ala Val
                        580                 585                 590

Asp Lys Ser Val Asn Leu Met Asn Ala Ser Asn Asp Ile Thr Met Glu
                        595                 600                 605

Asn Val Val His Glu Leu Glu Leu Tyr Asn Thr Gly Tyr Tyr Leu Gly
                        610                 615                 620

Met Phe Met Asn Ser Phe Ala Val Phe Gln Glu Cys Gly Leu Trp Val
        625                 630                 635                 640

Leu Thr Asp Ala Asn Leu Thr Lys Asp Tyr Ile Asp Gly Val Tyr Asp
                        645                 650                 655

Asn Ala Glu Tyr Ala Glu Arg Phe Met Glu Glu Asn Glu Gly His Ile
                        660                 665                 670

Val Asp Ile His Asp Phe Ser Leu Gly Ser Ser Pro His Val Arg Lys
                        675                 680                 685

His Phe Pro Glu Thr Trp Ile Trp Leu Asp Thr Asn Met Gly Tyr Arg
                        690                 695                 700

Ile Tyr Gln Glu Phe Glu Val Thr Val Pro Asp Ser Ile Thr Ser Trp
        705                 710                 715                 720

Val Ala Thr Gly Phe Val Ile Ser Glu Asp Leu Gly Leu Gly Leu Thr
                        725                 730                 735

Thr Thr Pro Val Glu Leu Gln Ala Phe Gln Pro Phe Phe Ile Phe Leu
                        740                 745                 750

Asn Leu Pro Tyr Ser Val Ile Arg Gly Glu Glu Phe Ala Leu Glu Ile
                        755                 760                 765

Thr Ile Phe Asn Tyr Leu Lys Asp Ala Thr Glu Val Lys Val Ile Ile
                        770                 775                 780

Glu Lys Ser Asp Lys Phe Asp Ile Leu Met Thr Ser Asn Glu Ile Asn
        785                 790                 795                 800

Ala Thr Gly His Gln Gln Thr Leu Leu Val Pro Ser Glu Asp Gly Ala
                        805                 810                 815

Thr Val Leu Phe Pro Ile Arg Pro Thr His Leu Gly Glu Ile Pro Ile
                        820                 825                 830

Thr Val Thr Ala Leu Ser Pro Thr Ala Ser Asp Ala Val Thr Gln Met
                        835                 840                 845

Ile Leu Val Lys Ala Glu Gly Ile Glu Lys Ser Tyr Ser Gln Ser Ile
                        850                 855                 860

Leu Leu Asp Leu Thr Asp Asn Arg Leu Gln Ser Thr Leu Lys Thr Leu
        865                 870                 875                 880

Ser Phe Ser Phe Pro Pro Asn Thr Val Thr Gly Ser Glu Arg Val Gln
                        885                 890                 895

Ile Thr Ala Ile Gly Asp Val Leu Gly Pro Ser Ile Asn Gly Leu Ala
                        900                 905                 910

Ser Leu Ile Arg Met Pro Tyr Gly Cys Gly Glu Gln Asn Met Ile Asn
                        915                 920                 925

Phe Ala Pro Asn Ile Tyr Ile Leu Asp Tyr Leu Thr Lys Lys Lys Gln
                        930                 935                 940

Leu Thr Asp Asn Leu Lys Glu Lys Ala Leu Ser Phe Met Arg Gln Gly
        945                 950                 955                 960

Tyr Gln Arg Glu Leu Leu Tyr Gln Arg Glu Asp Gly Ser Phe Ser Ala
                        965                 970                 975
```

```
Phe Gly Asn Tyr Asp Pro Ser Gly Ser Thr Trp Leu Ser Ala Phe Val
            980                 985                 990

Leu Arg Cys Phe Leu Glu Ala Asp Pro Tyr Ile Asp Ile Asp Gln Asn
        995                1000                1005

Val Leu His Arg Thr Tyr Thr Trp Leu Lys Gly His Gln Lys Ser
   1010                1015                1020

Asn Gly Glu Phe Trp Asp Pro Gly Arg Val Ile His Ser Glu Leu
       1025                1030                1035

Gln Gly Gly Asn Lys Ser Pro Val Thr Leu Thr Ala Tyr Ile Val
       1040                1045                1050

Thr Ser Leu Leu Gly Tyr Arg Lys Tyr Gln Val Phe Arg Ile
       1055                1060                1065

<210> SEQ ID NO 11
<211> LENGTH: 3535
<212> TYPE: DNA
<213> ORGANISM: HUMAN
<220> FEATURE:
<221> NAME/KEY: CDS
<222> LOCATION: (113)..(3316)

<400> SEQUENCE: 11
ctaaactcga attaagaggg aaaaaaaatc agggaggagg tggcaagcca caccccacgg        60
tgcccgcgaa cttccccggc agcggactgt agcccaggca gacgccgtcg ag atg cag      118
                                                          Met Gln
                                                            1 ggc cca ccg ctc ctg acc gcc gcc cac ctc ctc tgc gtg tgc acc gcc        166
Gly Pro Pro Leu Leu Thr Ala Ala His Leu Leu Cys Val Cys Thr Ala
      5                  10                  15 gcg ctg gcc gtg gct ccc ggg cct cgg ttt ctg gtg aca gcc cca ggg        214
Ala Leu Ala Val Ala Pro Gly Pro Arg Phe Leu Val Thr Ala Pro Gly
 20                  25                  30 atc atc agg ccc gga gga aat gtg act att ggg gtg gag ctt ctg gaa        262
Ile Ile Arg Pro Gly Gly Asn Val Thr Ile Gly Val Glu Leu Leu Glu
35                  40                  45                  50 cac tgc cct tca cag gtg act gtg aag gcg gag ctg ctc aag aca gca        310
His Cys Pro Ser Gln Val Thr Val Lys Ala Glu Leu Leu Lys Thr Ala
                 55                  60                  65 tca aac ctc act gtc tct gtc ctg gaa gca gaa gga gtc ttt gaa aaa        358
Ser Asn Leu Thr Val Ser Val Leu Glu Ala Glu Gly Val Phe Glu Lys
             70                  75                  80 ggc tct ttt aag aca ctt act ctt cca tca cta cct ctg aac agt gca        406
Gly Ser Phe Lys Thr Leu Thr Leu Pro Ser Leu Pro Leu Asn Ser Ala
         85                  90                  95 gat gag att tat gag cta cgt gta acc gga cgt acc cag gat gag att        454
Asp Glu Ile Tyr Glu Leu Arg Val Thr Gly Arg Thr Gln Asp Glu Ile
    100                 105                 110 tta ttc tct aat agt acc cgc tta tca ttt gag acc aag aga ata tct        502
Leu Phe Ser Asn Ser Thr Arg Leu Ser Phe Glu Thr Lys Arg Ile Ser
115                 120                 125                 130 gtc ttc att caa aca gac aag gcc tta tac aag cca aag caa gaa gtg        550
Val Phe Ile Gln Thr Asp Lys Ala Leu Tyr Lys Pro Lys Gln Glu Val
                135                 140                 145 aag ttt cgc att gtt aca ctc ttc tca gat ttt aag cct tac aaa acc        598
Lys Phe Arg Ile Val Thr Leu Phe Ser Asp Phe Lys Pro Tyr Lys Thr
            150                 155                 160 tct tta aac att ctc att aag gac ccc aaa tca aat ttg atc caa cag        646
Ser Leu Asn Ile Leu Ile Lys Asp Pro Lys Ser Asn Leu Ile Gln Gln
        165                 170                 175
```

```
tgg ttg tca caa caa agt gat ctt gga gtc att tcc aaa act ttt cag    694
Trp Leu Ser Gln Gln Ser Asp Leu Gly Val Ile Ser Lys Thr Phe Gln
    180                 185                 190 cta tct tcc cat cca ata ctt ggt gac tgg tct att caa gtt caa gtg    742
Leu Ser Ser His Pro Ile Leu Gly Asp Trp Ser Ile Gln Val Gln Val
195                 200                 205                 210 aat gac cag aca tat tat caa tca ttt cag gtt tca gaa tat gta tta    790
Asn Asp Gln Thr Tyr Tyr Gln Ser Phe Gln Val Ser Glu Tyr Val Leu
                215                 220                 225 cca aaa ttt gaa gtg act ttg cag aca cca tta tat tgt tct atg aat    838
Pro Lys Phe Glu Val Thr Leu Gln Thr Pro Leu Tyr Cys Ser Met Asn
            230                 235                 240 tct aag cat tta aat ggt acc atc acg gca aag tat aca tat ggg aag    886
Ser Lys His Leu Asn Gly Thr Ile Thr Ala Lys Tyr Thr Tyr Gly Lys
        245                 250                 255 cca gtg aaa gga gac gta acg ctt aca ttt tta cct tta tcc ttt tgg    934
Pro Val Lys Gly Asp Val Thr Leu Thr Phe Leu Pro Leu Ser Phe Trp
    260                 265                 270 gga aag aag aaa aat att aca aaa aca ttt aag ata aat gga tct gca    982
Gly Lys Lys Lys Asn Ile Thr Lys Thr Phe Lys Ile Asn Gly Ser Ala
275                 280                 285                 290 aac ttc tct ttt aat gat gaa gag atg aaa aat gta atg gat tct tca   1030
Asn Phe Ser Phe Asn Asp Glu Glu Met Lys Asn Val Met Asp Ser Ser
                295                 300                 305 aat gga ctt tct gaa tac ctg gat cta tct tcc cct gga cca gta gaa   1078
Asn Gly Leu Ser Glu Tyr Leu Asp Leu Ser Ser Pro Gly Pro Val Glu
            310                 315                 320 att tta acc aca gtg aca gaa tca gtt aca ggt att tca aga aat gta   1126
Ile Leu Thr Thr Val Thr Glu Ser Val Thr Gly Ile Ser Arg Asn Val
        325                 330                 335 agc act aat gtg ttc ttc aag caa cat gat tac atc att gag ttt ttt   1174
Ser Thr Asn Val Phe Phe Lys Gln His Asp Tyr Ile Ile Glu Phe Phe
    340                 345                 350 gat tat act act gtc ttg aag cca tct ctc aac ttc aca gcc act gtg   1222
Asp Tyr Thr Thr Val Leu Lys Pro Ser Leu Asn Phe Thr Ala Thr Val
355                 360                 365                 370 aag gta act cgt gct gat ggc aac caa ctg act ctt gaa gaa aga aga   1270
Lys Val Thr Arg Ala Asp Gly Asn Gln Leu Thr Leu Glu Glu Arg Arg
                375                 380                 385 aat aat gta gtc ata aca gtg aca cag aga aac tat act gag tac tgg   1318
Asn Asn Val Val Ile Thr Val Thr Gln Arg Asn Tyr Thr Glu Tyr Trp
            390                 395                 400 agc gga tct aac agt gga aat cag aaa atg gaa gct gtt cag aaa ata   1366
Ser Gly Ser Asn Ser Gly Asn Gln Lys Met Glu Ala Val Gln Lys Ile
        405                 410                 415 aat tat act gtc ccc caa agt gga act ttt aag att gaa ttc cca atc   1414
Asn Tyr Thr Val Pro Gln Ser Gly Thr Phe Lys Ile Glu Phe Pro Ile
    420                 425                 430 ctg gag gat tcc agt gag cta cag ttg aag gcc tat ttc ctt ggt agt   1462
Leu Glu Asp Ser Ser Glu Leu Gln Leu Lys Ala Tyr Phe Leu Gly Ser
435                 440                 445                 450 aaa agt agc atg gca gtt cat agt ctg ttt aag tct cct agt aag aca   1510
Lys Ser Ser Met Ala Val His Ser Leu Phe Lys Ser Pro Ser Lys Thr
                455                 460                 465 tac atc caa cta aaa aca aga gat gaa aat ata aag gtg gga tcg cct   1558
Tyr Ile Gln Leu Lys Thr Arg Asp Glu Asn Ile Lys Val Gly Ser Pro
            470                 475                 480 ttt gag ttg gtg gtt agt ggc aac aaa cga ttg aag gag tta agc tat   1606
Phe Glu Leu Val Val Ser Gly Asn Lys Arg Leu Lys Glu Leu Ser Tyr
```

```
                485                 490                 495
atg gta gta tcc agg gga cag ttg gtg gct gta gga aaa caa aat tca    1654
Met Val Val Ser Arg Gly Gln Leu Val Ala Val Gly Lys Gln Asn Ser
    500                 505                 510 aca atg ttc tct tta aca cca gaa aat tct tgg act cca aaa gcc tgt    1702
Thr Met Phe Ser Leu Thr Pro Glu Asn Ser Trp Thr Pro Lys Ala Cys
515                 520                 525                 530 gta att gtg tat tat att gaa gat gat ggg gaa att ata agt gat gtt    1750
Val Ile Val Tyr Tyr Ile Glu Asp Asp Gly Glu Ile Ile Ser Asp Val
            535                 540                 545 cta aaa att cct gtt cag ctt gtt ttt aaa aat aag ata aag cta tat    1798
Leu Lys Ile Pro Val Gln Leu Val Phe Lys Asn Lys Ile Lys Leu Tyr
        550                 555                 560 tgg agt aaa gtg aaa gct gaa cca tct gag aaa gtc tct ctt agg atc    1846
Trp Ser Lys Val Lys Ala Glu Pro Ser Glu Lys Val Ser Leu Arg Ile
    565                 570                 575 tct gtg aca cag cct gac tcc ata gtt ggg att gta gct gtt gac aaa    1894
Ser Val Thr Gln Pro Asp Ser Ile Val Gly Ile Val Ala Val Asp Lys
580                 585                 590 agt gtg aat ctg atg aat gcc tct aat gat att aca atg gaa aat gtg    1942
Ser Val Asn Leu Met Asn Ala Ser Asn Asp Ile Thr Met Glu Asn Val
595                 600                 605                 610 gtc cat gag ttg gaa ctt tat aac aca gga tat tat tta ggc atg ttc    1990
Val His Glu Leu Glu Leu Tyr Asn Thr Gly Tyr Tyr Leu Gly Met Phe
            615                 620                 625 atg aat tct ttt gca gtc ttt cag gaa tgt gga ctc tgg gta ttg aca    2038
Met Asn Ser Phe Ala Val Phe Gln Glu Cys Gly Leu Trp Val Leu Thr
        630                 635                 640 gat gca aac ctc acg aag gat tat att gat ggt gtt tat gac aat gca    2086
Asp Ala Asn Leu Thr Lys Asp Tyr Ile Asp Gly Val Tyr Asp Asn Ala
    645                 650                 655 gaa tat gct gag agg ttt atg gag gaa aat gaa gga cat att gta gat    2134
Glu Tyr Ala Glu Arg Phe Met Glu Glu Asn Glu Gly His Ile Val Asp
660                 665                 670 att cat gac ttt tct ttg ggt agc agt cca cat gtc cga aag cat ttt    2182
Ile His Asp Phe Ser Leu Gly Ser Ser Pro His Val Arg Lys His Phe
675                 680                 685                 690 cca gag act tgg att tgg cta gac acc aac atg ggt tcc agg att tac    2230
Pro Glu Thr Trp Ile Trp Leu Asp Thr Asn Met Gly Ser Arg Ile Tyr
            695                 700                 705 caa gaa ttt gaa gta act gta cct gat tct atc act tct tgg gtg gct    2278
Gln Glu Phe Glu Val Thr Val Pro Asp Ser Ile Thr Ser Trp Val Ala
        710                 715                 720 act ggt ttt gtg atc tct gag gac ctg ggt ctt gga cta aca act act    2326
Thr Gly Phe Val Ile Ser Glu Asp Leu Gly Leu Gly Leu Thr Thr Thr
    725                 730                 735 cca gtg gag ctc caa gcc ttc caa cca ttt ttc att ttt ttg aat ctt    2374
Pro Val Glu Leu Gln Ala Phe Gln Pro Phe Phe Ile Phe Leu Asn Leu
740                 745                 750 ccc tac tct gtt atc aga ggt gaa gaa ttt gct ttg gaa ata act ata    2422
Pro Tyr Ser Val Ile Arg Gly Glu Glu Phe Ala Leu Glu Ile Thr Ile
755                 760                 765                 770 ttc aat tat ttg aaa gat gcc act gag gtt aag gta atc att gag aaa    2470
Phe Asn Tyr Leu Lys Asp Ala Thr Glu Val Lys Val Ile Ile Glu Lys
            775                 780                 785 agt gac aaa ttt gat att cta atg act tca aat gaa ata aat gcc aca    2518
Ser Asp Lys Phe Asp Ile Leu Met Thr Ser Asn Glu Ile Asn Ala Thr
        790                 795                 800 ggc cac cag cag acc ctt ctg gtt ccc agt gag gat ggg gca act gtt    2566
```

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| Gly | His | Gln | Gln | Thr | Leu | Leu | Val | Pro | Ser | Glu | Asp | Gly | Ala | Thr | Val |      |
|     |     | 805 |     |     |     |     | 810 |     |     |     |     | 815 |     |     |     |      |

```
ctt ttt ccc atc agg cca aca cat ctg gga gaa att cct atc aca gtc     2614
Leu Phe Pro Ile Arg Pro Thr His Leu Gly Glu Ile Pro Ile Thr Val
    820             825                 830 aca gct ctt tca ccc act gct tct gat gct gtc acc cag atg att tta     2662
Thr Ala Leu Ser Pro Thr Ala Ser Asp Ala Val Thr Gln Met Ile Leu
835             840                 845                 850 gta aag gct gaa gga ata gaa aaa tca tat tca caa tcc atc tta tta     2710
Val Lys Ala Glu Gly Ile Glu Lys Ser Tyr Ser Gln Ser Ile Leu Leu
                855                 860                 865 gac ttg act gac aat agg cta cag agt acc ctg aaa act ttg agt ttc     2758
Asp Leu Thr Asp Asn Arg Leu Gln Ser Thr Leu Lys Thr Leu Ser Phe
            870                 875                 880 tca ttt cct cct aat aca gtg act ggc agt gaa aga gtt cag atc act     2806
Ser Phe Pro Pro Asn Thr Val Thr Gly Ser Glu Arg Val Gln Ile Thr
        885                 890                 895 gca att gga gat gtt ctt ggt cct tcc atc aat ggc tta gcc tca ttg     2854
Ala Ile Gly Asp Val Leu Gly Pro Ser Ile Asn Gly Leu Ala Ser Leu
    900                 905                 910 att cgg atg cct tat ggc tgt ggt gaa cag aac atg ata aat ttt gct     2902
Ile Arg Met Pro Tyr Gly Cys Gly Glu Gln Asn Met Ile Asn Phe Ala
915                 920                 925                 930 cca aat att tac att ttg gat tat ctg act aaa aag aaa caa ctg aca     2950
Pro Asn Ile Tyr Ile Leu Asp Tyr Leu Thr Lys Lys Lys Gln Leu Thr
                935                 940                 945 gat aat ttg aaa gaa aaa gct ctt tca ttt atg agg caa ggt tac cag     2998
Asp Asn Leu Lys Glu Lys Ala Leu Ser Phe Met Arg Gln Gly Tyr Gln
            950                 955                 960 aga gaa ctt ctc tat cag agg gaa gat ggc tct ttc agt gct ttt ggg     3046
Arg Glu Leu Leu Tyr Gln Arg Glu Asp Gly Ser Phe Ser Ala Phe Gly
        965                 970                 975 aat tat gac cct tct ggg agc act tgg ttg tca gct ttt gtt tta aga     3094
Asn Tyr Asp Pro Ser Gly Ser Thr Trp Leu Ser Ala Phe Val Leu Arg
    980                 985                 990 tgt ttc ctt gaa gcc gat     cct tac ata gat att     gat cag aat gtg     3139
Cys Phe Leu Glu Ala Asp     Pro Tyr Ile Asp Ile     Asp Gln Asn Val
995                 1000                1005 tta cac aga aca tac act     tgg ctt aaa gga cat     cag aaa tcc aac     3184
Leu His Arg Thr Tyr Thr     Trp Leu Lys Gly His     Gln Lys Ser Asn
1010                1015                1020 ggt gaa ttt tgg gat cca     gga aga gtg att cat     agt gag ctt caa     3229
Gly Glu Phe Trp Asp Pro     Gly Arg Val Ile His     Ser Glu Leu Gln
1025                1030                1035 ggt ggc aat aaa agt cca     gta aca ctt aca gcc     tat att gta act     3274
Gly Gly Asn Lys Ser Pro     Val Thr Leu Thr Ala     Tyr Ile Val Thr
1040                1045                1050 tct ctc ctg gga tat aga     aag tat cag gta ttt     cgt att taa         3316
Ser Leu Leu Gly Tyr Arg     Lys Tyr Gln Val Phe     Arg Ile
1055                1060                1065 tttaataaat gatagatggg aaattcaagg aaggtaggtc ttaatgggtc aaatatgtgt     3376
gtggaaactt aacaagttgc agctttacaa cacatgtgaa atctgaattt gagtactctt     3436
ttgctttgca tttgcagcca tgttccaaaa tctgagaata aaacattacc cactctttca     3496
gataactaag agattctaaa aaaaaaaaaa aaaaaaaa                              3535
```

<210> SEQ ID NO 12
<211> LENGTH: 1067
<212> TYPE: PRT

<213> ORGANISM: HUMAN

<400> SEQUENCE: 12

```
Met Gln Gly Pro Pro Leu Leu Thr Ala Ala His Leu Leu Cys Val Cys
 1               5                  10                  15

Thr Ala Ala Leu Ala Val Ala Pro Gly Pro Arg Phe Leu Val Thr Ala
             20                  25                  30

Pro Gly Ile Ile Arg Pro Gly Gly Asn Val Thr Ile Gly Val Glu Leu
         35                  40                  45

Leu Glu His Cys Pro Ser Gln Val Thr Val Lys Ala Glu Leu Leu Lys
     50                  55                  60

Thr Ala Ser Asn Leu Thr Val Ser Val Leu Glu Ala Glu Gly Val Phe
 65                  70                  75                  80

Glu Lys Gly Ser Phe Lys Thr Leu Thr Leu Pro Ser Leu Pro Leu Asn
                 85                  90                  95

Ser Ala Asp Glu Ile Tyr Glu Leu Arg Val Thr Gly Arg Thr Gln Asp
            100                 105                 110

Glu Ile Leu Phe Ser Asn Ser Thr Arg Leu Ser Phe Glu Thr Lys Arg
        115                 120                 125

Ile Ser Val Phe Ile Gln Thr Asp Lys Ala Leu Tyr Lys Pro Lys Gln
    130                 135                 140

Glu Val Lys Phe Arg Ile Val Thr Leu Phe Ser Asp Phe Lys Pro Tyr
145                 150                 155                 160

Lys Thr Ser Leu Asn Ile Leu Ile Lys Asp Pro Lys Ser Asn Leu Ile
                165                 170                 175

Gln Gln Trp Leu Ser Gln Gln Ser Asp Leu Gly Val Ile Ser Lys Thr
            180                 185                 190

Phe Gln Leu Ser Ser His Pro Ile Leu Gly Asp Trp Ser Ile Gln Val
        195                 200                 205

Gln Val Asn Asp Gln Thr Tyr Tyr Gln Ser Phe Gln Val Ser Glu Tyr
    210                 215                 220

Val Leu Pro Lys Phe Glu Val Thr Leu Gln Thr Pro Leu Tyr Cys Ser
225                 230                 235                 240

Met Asn Ser Lys His Leu Asn Gly Thr Ile Thr Ala Lys Tyr Thr Tyr
                245                 250                 255

Gly Lys Pro Val Lys Gly Asp Val Thr Leu Thr Phe Leu Pro Leu Ser
            260                 265                 270

Phe Trp Gly Lys Lys Asn Ile Thr Lys Thr Phe Lys Ile Asn Gly
        275                 280                 285

Ser Ala Asn Phe Ser Phe Asn Asp Glu Glu Met Lys Asn Val Met Asp
    290                 295                 300

Ser Ser Asn Gly Leu Ser Glu Tyr Leu Asp Leu Ser Ser Pro Gly Pro
305                 310                 315                 320

Val Glu Ile Leu Thr Thr Val Thr Glu Ser Val Thr Gly Ile Ser Arg
                325                 330                 335

Asn Val Ser Thr Asn Val Phe Phe Lys Gln His Asp Tyr Ile Ile Glu
            340                 345                 350

Phe Phe Asp Tyr Thr Thr Val Leu Lys Pro Ser Leu Asn Phe Thr Ala
        355                 360                 365

Thr Val Lys Val Thr Arg Ala Asp Gly Asn Gln Leu Thr Leu Glu Glu
    370                 375                 380

Arg Arg Asn Asn Val Val Ile Thr Val Thr Gln Arg Asn Tyr Thr Glu
385                 390                 395                 400
```

-continued

```
Tyr Trp Ser Gly Ser Asn Ser Gly Asn Gln Lys Met Glu Ala Val Gln
                405                 410                 415

Lys Ile Asn Tyr Thr Val Pro Gln Ser Gly Thr Phe Lys Ile Glu Phe
            420                 425                 430

Pro Ile Leu Glu Asp Ser Ser Glu Leu Gln Leu Lys Ala Tyr Phe Leu
        435                 440                 445

Gly Ser Lys Ser Ser Met Ala Val His Ser Leu Phe Lys Ser Pro Ser
    450                 455                 460

Lys Thr Tyr Ile Gln Leu Lys Thr Arg Asp Glu Asn Ile Lys Val Gly
465                 470                 475                 480

Ser Pro Phe Glu Leu Val Val Ser Gly Asn Lys Arg Leu Lys Glu Leu
                485                 490                 495

Ser Tyr Met Val Val Ser Arg Gly Gln Leu Val Ala Val Gly Lys Gln
            500                 505                 510

Asn Ser Thr Met Phe Ser Leu Thr Pro Glu Asn Ser Trp Thr Pro Lys
        515                 520                 525

Ala Cys Val Ile Val Tyr Tyr Ile Glu Asp Asp Gly Glu Ile Ile Ser
    530                 535                 540

Asp Val Leu Lys Ile Pro Val Gln Leu Val Phe Lys Asn Lys Ile Lys
545                 550                 555                 560

Leu Tyr Trp Ser Lys Val Lys Ala Glu Pro Ser Glu Lys Val Ser Leu
                565                 570                 575

Arg Ile Ser Val Thr Gln Pro Asp Ser Ile Val Gly Ile Val Ala Val
            580                 585                 590

Asp Lys Ser Val Asn Leu Met Asn Ala Ser Asn Asp Ile Thr Met Glu
        595                 600                 605

Asn Val Val His Glu Leu Glu Leu Tyr Asn Thr Gly Tyr Tyr Leu Gly
    610                 615                 620

Met Phe Met Asn Ser Phe Ala Val Phe Gln Glu Cys Gly Leu Trp Val
625                 630                 635                 640

Leu Thr Asp Ala Asn Leu Thr Lys Asp Tyr Ile Asp Gly Val Tyr Asp
                645                 650                 655

Asn Ala Glu Tyr Ala Glu Arg Phe Met Glu Glu Asn Glu Gly His Ile
            660                 665                 670

Val Asp Ile His Asp Phe Ser Leu Gly Ser Ser Pro His Val Arg Lys
        675                 680                 685

His Phe Pro Glu Thr Trp Ile Trp Leu Asp Thr Asn Met Gly Ser Arg
    690                 695                 700

Ile Tyr Gln Glu Phe Glu Val Thr Val Pro Asp Ser Ile Thr Ser Trp
705                 710                 715                 720

Val Ala Thr Gly Phe Val Ile Ser Glu Asp Leu Gly Leu Gly Leu Thr
                725                 730                 735

Thr Thr Pro Val Glu Leu Gln Ala Phe Gln Pro Phe Phe Ile Phe Leu
            740                 745                 750

Asn Leu Pro Tyr Ser Val Ile Arg Gly Glu Glu Phe Ala Leu Glu Ile
        755                 760                 765

Thr Ile Phe Asn Tyr Leu Lys Asp Ala Thr Glu Val Lys Val Ile Ile
    770                 775                 780

Glu Lys Ser Asp Lys Phe Asp Ile Leu Met Thr Ser Asn Glu Ile Asn
785                 790                 795                 800

Ala Thr Gly His Gln Gln Thr Leu Leu Val Pro Ser Glu Asp Gly Ala
                805                 810                 815

Thr Val Leu Phe Pro Ile Arg Pro Thr His Leu Gly Glu Ile Pro Ile
```

-continued

```
                820                 825                 830
Thr Val Thr Ala Leu Ser Pro Thr Ala Ser Asp Ala Val Thr Gln Met
            835                 840                 845
Ile Leu Val Lys Ala Glu Gly Ile Glu Lys Ser Tyr Ser Gln Ser Ile
        850                 855                 860
Leu Leu Asp Leu Thr Asp Asn Arg Leu Gln Ser Thr Leu Lys Thr Leu
865                 870                 875                 880
Ser Phe Ser Phe Pro Pro Asn Thr Val Thr Gly Ser Glu Arg Val Gln
                885                 890                 895
Ile Thr Ala Ile Gly Asp Val Leu Gly Pro Ser Ile Asn Gly Leu Ala
            900                 905                 910
Ser Leu Ile Arg Met Pro Tyr Gly Cys Gly Glu Gln Asn Met Ile Asn
        915                 920                 925
Phe Ala Pro Asn Ile Tyr Ile Leu Asp Tyr Leu Thr Lys Lys Lys Gln
        930                 935                 940
Leu Thr Asp Asn Leu Lys Glu Lys Ala Leu Ser Phe Met Arg Gln Gly
945                 950                 955                 960
Tyr Gln Arg Glu Leu Leu Tyr Gln Arg Glu Asp Gly Ser Phe Ser Ala
                965                 970                 975
Phe Gly Asn Tyr Asp Pro Ser Gly Ser Thr Trp Leu Ser Ala Phe Val
            980                 985                 990
Leu Arg Cys Phe Leu Glu Ala Asp  Pro Tyr Ile Asp Ile  Asp Gln Asn
        995                1000                1005
Val Leu His Arg Thr Tyr Thr  Trp Leu Lys Gly His  Gln Lys Ser
        1010                1015                1020
Asn Gly  Glu Phe Trp Asp Pro  Gly Arg Val Ile His  Ser Glu Leu
        1025                1030                1035
Gln Gly  Gly Asn Lys Ser Pro  Val Thr Leu Thr Ala  Tyr Ile Val
        1040                1045                1050
Thr Ser  Leu Leu Gly Tyr Arg  Lys Tyr Gln Val Phe  Arg Ile
        1055                1060                1065

<210> SEQ ID NO 13
<211> LENGTH: 6
<212> TYPE: DNA
<213> ORGANISM: HUMAN
<220> FEATURE:
<221> NAME/KEY: polyA_signal
<222> LOCATION: (1)..(6)

<400> SEQUENCE: 13 aataaa                                                                 6

<210> SEQ ID NO 14
<211> LENGTH: 7
<212> TYPE: PRT
<213> ORGANISM: HUMAN
<220> FEATURE:
<221> NAME/KEY: THIOESTER
<222> LOCATION: (1)..(7)

<400> SEQUENCE: 14

Pro Tyr Gly Cys Gly Glu Gln
1               5

<210> SEQ ID NO 15
<211> LENGTH: 19
<212> TYPE: DNA
<213> ORGANISM: synthetic construct
```

```
<220> FEATURE:
<221> NAME/KEY: PRIMER
<222> LOCATION: (1)..(19)

<400> SEQUENCE: 15
sccctcagac agtggttca                                                        19

<210> SEQ ID NO 16
<211> LENGTH: 18
<212> TYPE: DNA
<213> ORGANISM: synthetic construct
<220> FEATURE:
<221> NAME/KEY: PRIMER
<222> LOCATION: (1)..(18)

<400> SEQUENCE: 16
cttcgaacct tcgaatcc                                                         18

<210> SEQ ID NO 17
<211> LENGTH: 22
<212> TYPE: DNA
<213> ORGANISM: synthetic construct
<220> FEATURE:
<221> NAME/KEY: PRIMER
<222> LOCATION: (1)..(22)

<400> SEQUENCE: 17
gtaatacgac tcactatagg gc                                                    22

<210> SEQ ID NO 18
<211> LENGTH: 20
<212> TYPE: DNA
<213> ORGANISM: synthetic construct
<220> FEATURE:
<221> NAME/KEY: PRIMER
<222> LOCATION: (1)..(20)

<400> SEQUENCE: 18
aattaaccct cactaaaggg                                                       20

<210> SEQ ID NO 19
<211> LENGTH: 20
<212> TYPE: DNA
<213> ORGANISM: synthetic construct
<220> FEATURE:
<221> NAME/KEY: PRIMER
<222> LOCATION: (1)..(20)

<400> SEQUENCE: 19
gaggatttgg aaagggtgtt                                                       20

<210> SEQ ID NO 20
<211> LENGTH: 20
<212> TYPE: DNA
<213> ORGANISM: synthetic construct
<220> FEATURE:
<221> NAME/KEY: PRIMER
<222> LOCATION: (1)..(20)

<400> SEQUENCE: 20
acaatagctc ttcagtctga                                                       20

<210> SEQ ID NO 21
<211> LENGTH: 24
<212> TYPE: DNA
<213> ORGANISM: synthetic construct
```

```
-continued

<400> SEQUENCE: 21
gtcacatgtg attgtatgtt ttcg                                      24

<210> SEQ ID NO 22
<211> LENGTH: 25
<212> TYPE: DNA
<213> ORGANISM: synthetic construct
<220> FEATURE:
<221> NAME/KEY: PRIMER
<222> LOCATION: (1)..(25)

<400> SEQUENCE: 22
ggggaaaata tagacacaca actgc                                     25
```